US012778883B2

(12) United States Patent
Kanasty et al.

(10) Patent No.: US 12,778,883 B2
(45) Date of Patent: Nov. 3, 2026

(54) GASTRIC RESIDENCE SYSTEMS FOR ADMINISTRATION OF ACTIVE AGENTS

(71) Applicant: Nortiva Bio, Inc., Lexington, MA (US)

(72) Inventors: Rosemary Kanasty, Somerville, MA (US); Tyler Grant, Arlington, MA (US); David Altreuter, Wayland, MA (US); Alisha Weight, Cambridge, MA (US); Saumya Moorthy, Medford, MA (US); Tammy Tai, Cambridge, MA (US); Juan Jaramillo Montezco, Cambridge, MA (US); Marlene Schwarz, Auburndale, MA (US); Jung Hoon Yang, Brookline, MA (US); Jeanne Tran, Brighton, MA (US); Michelle Duan, Wellesley, MA (US); Jie Jing, Watertown, MA (US); David C. Dufour, Watertown, MA (US); Erik Robert Waldemar Ryde, Watertown, MA (US); Nupura Bhise, Watertown, MA (US); Nicholas De La Torre, Boston, MA (US); Sonia Holar, Boston, MA (US); Estelle Beguin, Watertown, MA (US); Craig Simses, Quincy, MA (US); Erick Peeke, Cambridge, MA (US); Erica Lai, Somerville, MA (US)

(73) Assignee: Nortiva Bio, Inc., Lexington, MA (US)

( * ) Notice: Subject to any disclaimer, the term of this patent is extended or adjusted under 35 U.S.C. 154(b) by 933 days.

(21) Appl. No.: 17/774,132

(22) PCT Filed: Nov. 6, 2020

(86) PCT No.: PCT/US2020/059541

§ 371 (c)(1),
(2) Date: May 3, 2022

(87) PCT Pub. No.: WO2021/092491

PCT Pub. Date: May 14, 2021

(65) Prior Publication Data

US 2022/0387311 A1 Dec. 8, 2022

Related U.S. Application Data

(60) Provisional application No. 63/052,905, filed on Jul. 16, 2020, provisional application No. 62/992,075, filed on Mar. 19, 2020, provisional application No. 62/933,211, filed on Nov. 8, 2019, provisional application No. 62/933,313, filed on Nov. 8, 2019, provisional application No. 62/933,348, filed on Nov. 8, 2019, provisional application No. 62/933,226, filed on Nov. 8, 2019, provisional application No. 62/933,210, filed on Nov. 8, 2019.

(51) Int. Cl.

| | |
|---|---|
| *A61K 9/00* | (2006.01) |
| *A61K 31/13* | (2006.01) |
| *A61K 31/445* | (2006.01) |
| *A61K 31/519* | (2006.01) |
| *A61K 31/70* | (2006.01) |
| *A61K 47/34* | (2017.01) |
| *A61K 47/38* | (2006.01) |

(52) U.S. Cl.

CPC ............ *A61K 9/0065* (2013.01); *A61K 31/13* (2013.01); *A61K 31/445* (2013.01); *A61K 31/519* (2013.01); *A61K 31/70* (2013.01); *A61K 47/34* (2013.01); *A61K 47/38* (2013.01)

(58) Field of Classification Search

CPC .... A61K 9/0065; A61K 31/13; A61K 31/445; A61K 31/519; A61K 31/70; A61K 47/34; A61K 47/38

See application file for complete search history.

(56) References Cited

U.S. PATENT DOCUMENTS

| | | |
|---|---|---|
| 3,531,368 A | 9/1970 | Okamoto et al. |
| 3,716,614 A | 2/1973 | Watanabe et al. |
| 4,304,767 A | 12/1981 | Heller et al. |

(Continued)

FOREIGN PATENT DOCUMENTS

| | | |
|---|---|---|
| CN | 101400363 A | 4/2009 |
| CN | 106573999 A | 4/2017 |

(Continued)

OTHER PUBLICATIONS

International Preliminary Report on Patentability, issued May 10, 2022, for PCT Application No. PCT/US/2020/059533, filed Nov. 6, 2020, 7 pages.

(Continued)

*Primary Examiner* — Michael P Cohen

(74) *Attorney, Agent, or Firm* — MORRISON & FOERSTER LLP

(57) ABSTRACT

Gastric residence systems for administration of agents, such as drugs, are disclosed. Features which enhance gastric retention during the desired residence time and which allow for more precise control over residence time are disclosed, including circumferential filaments connecting the arms of a stellate gastric residence system; flexible arms for a gastric residence system; improved time-dependent and enteric disintegrating matrices (linkers); and release rate-modulating polymer coatings which are resistant to change in release rate properties during heat-assisted assembly or thermal cycling. Combinations of these features are also disclosed.

20 Claims, 72 Drawing Sheets

(56) References Cited

U.S. PATENT DOCUMENTS

| | | | | |
|---|---|---|---|---|
| 4,812,012 | A | 3/1989 | Terada et al. | |
| 5,002,772 | A | 3/1991 | Curatolo et al. | |
| 5,121,329 | A | 6/1992 | Crump | |
| 5,340,433 | A | 8/1994 | Crump | |
| 7,276,252 | B2 | 10/2007 | Payumo | |
| 9,884,022 | B2 * | 2/2018 | Deshmukh ........... | A61K 9/1652 |
| 10,182,985 | B2 | 1/2019 | Bellinger et al. | |
| 10,413,507 | B2 | 9/2019 | Zhang et al. | |
| 10,517,819 | B2 | 12/2019 | Bellinger et al. | |
| 10,517,820 | B2 | 12/2019 | Bellinger | |
| 10,532,027 | B2 | 1/2020 | Bellinger | |
| 10,596,110 | B2 | 3/2020 | Bellinger | |
| 10,610,482 | B2 | 4/2020 | Bellinger | |
| 10,716,751 | B2 | 7/2020 | Bellinger et al. | |
| 10,716,752 | B2 | 7/2020 | Bellinger et al. | |
| 10,849,853 | B2 | 12/2020 | Bellinger et al. | |
| 10,953,208 | B2 | 3/2021 | Zhang et al. | |
| 11,077,056 | B2 | 8/2021 | Bellinger et al. | |
| 11,083,690 | B2 | 8/2021 | Zhang et al. | |
| 11,246,829 | B2 | 2/2022 | Bellinger et al. | |
| 11,357,723 | B2 | 6/2022 | Bellinger et al. | |
| 11,389,399 | B2 | 7/2022 | Bellinger et al. | |
| 11,576,859 | B2 | 2/2023 | Kanasty et al. | |
| 11,576,866 | B2 | 2/2023 | Bellinger et al. | |
| 11,793,751 | B2 | 10/2023 | Grant et al. | |
| 11,992,552 | B2 | 5/2024 | Bellinger | |
| 12,023,406 | B2 | 7/2024 | Kanasty | |
| 12,109,305 | B2 | 10/2024 | Bellinger | |
| 12,142,158 | B2 | 11/2024 | Kanasty | |
| 2005/0249798 | A1 | 11/2005 | Mohammad | |
| 2007/0037792 | A1 * | 2/2007 | Lang ....................... | A61P 25/08<br>514/217 |
| 2007/0156248 | A1 | 7/2007 | Marco et al. | |
| 2007/0196416 | A1 | 8/2007 | Li et al. | |
| 2008/0131484 | A1 | 6/2008 | Robinson et al. | |
| 2010/0286628 | A1 | 11/2010 | Gross | |
| 2012/0269866 | A1 * | 10/2012 | Ali ....................... | A61K 9/0065<br>514/570 |
| 2013/0017264 | A1 | 1/2013 | Khandare et al. | |
| 2013/0225778 | A1 | 8/2013 | Goodrich et al. | |
| 2013/0273135 | A1 | 10/2013 | Brooks et al. | |
| 2016/0317453 | A1 | 11/2016 | Richey et al. | |
| 2016/0317796 | A1 | 11/2016 | Zhang et al. | |
| 2017/0105099 | A1 | 4/2017 | Liu et al. | |
| 2018/0311154 | A1 | 11/2018 | Kanasty | |
| 2019/0125667 | A1 | 5/2019 | Bellinger et al. | |
| 2019/0133936 | A1 | 5/2019 | Bellinger et al. | |
| 2019/0209090 | A1 | 7/2019 | Langer et al. | |
| 2019/0231697 | A1 | 8/2019 | Bellinger et al. | |
| 2019/0254966 | A1 | 8/2019 | Bellinger et al. | |
| 2019/0262265 | A1 | 8/2019 | Bellinger et al. | |
| 2020/0281851 | A1 | 9/2020 | Grant et al. | |
| 2021/0196627 | A1 | 7/2021 | Grant et al. | |
| 2022/0160642 | A1 | 5/2022 | Bhise et al. | |
| 2022/0192995 | A1 | 6/2022 | Kanasty et al. | |
| 2022/0387310 | A1 | 12/2022 | Altreuter et al. | |
| 2022/0387312 | A1 | 12/2022 | Kanasty et al. | |
| 2022/0409528 | A1 | 12/2022 | Kanasty et al. | |
| 2023/0039421 | A1 | 2/2023 | Bellinger et al. | |
| 2023/0190941 | A1 | 6/2023 | Montezco et al. | |
| 2024/0139102 | A1 | 5/2024 | Grant | |
| 2024/0252483 | A1 | 8/2024 | Bhise | |
| 2024/0335400 | A1 | 10/2024 | Beguin | |
| 2024/0342081 | A1 | 10/2024 | Bellinger | |
| 2024/0382418 | A1 | 11/2024 | Kanasty | |
| 2024/0390270 | A1 | 11/2024 | Kanasty | |
| 2024/0398701 | A1 | 12/2024 | Kanasty | |
| 2024/0423909 | A1 | 12/2024 | Bellinger | |

FOREIGN PATENT DOCUMENTS

| | | | | | |
|---|---|---|---|---|---|
| CN | 108472249 | A | | 8/2018 | |
| CN | 108697649 | A | | 10/2018 | |
| CN | 109310639 | A | | 2/2019 | |
| CN | 110022861 | A | | 7/2019 | |
| JP | 2017505817 | A | | 2/2017 | |
| JP | 2017524662 | A | | 8/2017 | |
| JP | 2018515476 | A | | 6/2018 | |
| JP | 2019501110 | A | | 1/2019 | |
| JP | 2019503347 | A | | 2/2019 | |
| JP | 2022553867 | A | | 12/2022 | |
| TW | 201902459 | A | | 1/2019 | |
| WO | 2015119653 | A1 | | 8/2015 | |
| WO | 2015191925 | A1 | | 12/2015 | |
| WO | WO-2015191920 | A1 | * | 12/2015 | .......... A61K 31/357 |
| WO | 2017070612 | A1 | | 4/2017 | |
| WO | WO-2017100367 | A1 | * | 6/2017 | ............ A61K 47/34 |
| WO | 2017205844 | A2 | | 11/2017 | |
| WO | 2018064630 | A1 | | 4/2018 | |
| WO | 2018102799 | A1 | | 6/2018 | |
| WO | 2018227147 | A1 | | 12/2018 | |
| WO | WO-2019060458 | A1 | * | 3/2019 | ............. A61J 3/071 |
| WO | 2021092483 | A1 | | 5/2021 | |
| WO | 2021092484 | A1 | | 5/2021 | |
| WO | 2021092486 | A1 | | 5/2021 | |
| WO | 2021092487 | A1 | | 5/2021 | |
| WO | 2023141524 | A2 | | 7/2023 | |
| WO | 2024031023 | A2 | | 2/2024 | |
| WO | 2024073752 | A2 | | 4/2024 | |

OTHER PUBLICATIONS

International Preliminary Report on Patentability, issued May 10, 2022, for PCT Application No. PCT/US/2020/059534, filed Nov. 6, 2020, 6 pages.

International Preliminary Report on Patentability, issued May 10, 2022, for PCT Application No. PCT/US/2020/059536, filed Nov. 6, 2020, 7 pages.

International Preliminary Report on Patentability, issued May 10, 2022, for PCT Application No. PCT/US/2020/059537, filed Nov. 6, 2020, 8 pages.

International Preliminary Report on Patentability, issued May 10, 2022, for PCT Application No. PCT/US/2020/059541, filed Nov. 6, 2020, 16 pages.

International Search Report and Written Opinion, mailed Feb. 2, 2021, for PCT Application No. PCT/US/2020/059534, filed Nov. 6, 2020, 8 pages.

International Search Report and Written Opinion, mailed Feb. 4, 2021, for PCT Application No. PCT/US/2020/059533, filed Nov. 6, 2020, 9 pages.

International Search Report and Written Opinion, mailed Feb. 4, 2021, for PCT Application No. PCT/US/2020/059541, filed Nov. 6, 2020, 19 pages.

International Search Report and Written Opinion, mailed Mar. 25, 2021, for PCT Application No. PCT/US/2020/059536, filed Nov. 6, 2020, 10 pages.

International Search Report and Written Opinion, mailed Mar. 25, 2021, for PCT Application No. PCT/US/2020/059537, filed Nov. 6, 2020, 11 pages.

Mukherji, G. et al. (2003). "Enteric Coating for Colonic Delivery," Chapter 18 in Modified-Release Drug Delivery Technology 126:223-232.

Singh, S.P. et al. (2011). "Measurement and Analysis of Vibration and Temperature Levels in Global Intermodal Container Shipments on Truck, Rail and Ship," Packaging Technol. Science, 12 pages.

U.S. Appl. No. 17/774, 128, filed May 3, 2022, Montezco et al. (Copy not submitted herewith pursuant to the waiver of 37 C.F.R. 1.98(a)(2)(iii) issued by the Office on Sep. 21, 2004).

Alhnan, M.A. et al. (Aug. 2016, e-published on May 18, 2016). "Emergence of 3D Printed Dosage Forms: Opportunities and Challenges," Pharm. Res. 33(8):1817-1832, 16 pages.

Burt, H.M. et al. (1999). "Development of Copolymers of Poly(D,L-lactide) and Methoxypolyethylene Glycol as Micellar Carriers of Paclitaxel," Colloids and Surfaces B: Biointerfaces 16(1-4):161-171.

CAS No. 112945-52-5 (2017). "Silicon Dioxide," 5 pages.

CAS No. 9003-11-6 (Dec. 21, 2022). "Polyethylene-Polyproylene Glycol," 2 pages.

(56) References Cited

OTHER PUBLICATIONS

European Examination Report, dated Jul. 15, 2025, for European Patent Application No. 20885040.4,6 pages.
Extended European Search Report, dated Jan. 17, 2024, for European Patent Application No. 20884024.9, 7 pages.
Extended European Search Report, dated Jan. 31, 2024, for European Patent Application No. 20885040.4, 13 pages.
Extended European Search Report, dated Jan. 9, 2024, for European Patent Application No. 20885272.3, 7 pages.
Extended European Search Report, dated Nov. 29, 2023, for European Patent Application No. 20884800.2, 7 pages.
Felix Lanao, R.P. et al. (Aug. 2013, E-pub Mar. 1, 2013). "Physicochemical Properties and Applications of Poly (Lactic-Co-Glycolic Acid) for Use in Bone Regeneration," Tissue Eng Part B Rev. 19(4):380-390.
Haslauer, C.M. et al. (Jul. 2015, e-pub. Jul. 1, 2016). "Translating Textiles To Tissue Engineering: Creation And Evaluation Of Microporous, Biocompatible, Degradable Scaffolds Using Industry Relevant Manufacturing Approaches And Human Adipose Derived Stem Cells," J. Biomed. Mater. Res. B Appl. Biomater. 103(5):1050-1058, 22 pages.
Khaled, S.A. et al. (2014). "Desktop 3D Printing of Controlled Release Pharmaceutical Bilayer Tablets," International Journal of Pharmaceutics, 17 pages.
Makadia, H.K. et al. (2011). "Poly Lactic-co-Glycolic Acid (PLGA) as Biodegradable Controlled Drug Delivery Carrier," Polymers 3:1377-1397.
Manna, S. et al. (2018). "Improved Design and Characterization of PLGA/PLA-Coated Chitosan Based Micro-Implants for Controlled Release of Hydrophilic Drugs," International Journal of Pharmaceutics 547(1-2):122-132.
Moroishi, H. et al. (2018). "PLA- and PLA/PLGA-Emulsion Composite Biomaterial Sheets for the Controllable Sustained Release of Hydrophilic Compounds," Materials 11(12)2588: 12 pages.
Partial Supplementary European Search Report, dated Nov. 6, 2023, for European Patent Application No. 20885040.4, 14 pages.
Poly(D, L-Lactide-co-glycolide), Poly(D, L-lactide-co-glycolide), 50:50, IV 0.40 dl/g, acid-terminated. (May 29, 2017). https://web.archive.org/web/20170529103446/https://www.polysciences.com/defau1Upoly-d-l-lactide-co-glycolide-50-50-iv-0-40-dl-g via wayback machine 2 pages.
Poly(D,L-lactic acid), IV 2.0 DUG. Poly(dl-lactic acid) i.v. 2.0 -2.8dl/g I Polysciences, Inc. (Aug. 24, 2016). https://web.archive.org/web/20160824222556/https://www.polysciences.com/defau1Upolydl-lactic-acid-iv-20-28dlg via wayback machine 3 pages.
Ursan, I.D. et al. (Mar.-Apr. 2013). "Three-Dimensional Drug Printing: A Structured Review," J. Am. Pharm. Assoc. 53(2):136-144.
Yu, D.G. et al. (Sep. 2008). "Three-Dimensional Printing in Pharmaceutics: Promises and Problems," J. Pharm. Sci. 97(9):3666-3690.
Evonik Industries. (Jul. 2015). "RESOMER Product Range" Evonik Industries 4 pages.
Martin, L.M. et al. (2014). "Applications of Polyethylene Oxide (POLYOX) in Hydrophilic Matrices," Chapter 5 in Hydrophilic Matrix Tablets for Oral Controlled Release, pp. 123-141.

* cited by examiner

Arm end slitting

Filament wrapping

Arm end forming

| Analyte (N=5) | $T_{max}$ (hr) | $C_{max}$ (ng/m) | $AUC_{inf}$ (hr*ng/mL)/D |
|---|---|---|---|
| **Memantine** | 120 (24-144) | 34.9 (57.9%) | 21.0 |
| **Donepezil** | 104 (24-192) | 5.47 (70.6%) | 7.8 |
| **Memantine (Namenda XR)** | 9.0 (6-12) | 64.9 (31.9%) | 31.5 |

| Analyte (N=8) | $T_{max}$ (hr) | $C_{max}$ (ng/mL) | $AUC_{inf}$ (hr*ng/mL)/D |
|---|---|---|---|
| **Memantine** | 63.5 (48-144) | 28.0 (25%) | 83.2 (23%) |
| **Donepezil** | 60.0 (48-144) | 20.3 (37%) | 60.05 (28%) |
| **Memantine (Namenda XR)** | 9.0 (6-16) | 166.1 (28%) | 109.21 |
| **Donepezil (Aricept)** | 6.13 (4-12) | 20.9 (23.9%) | 88.5 |

| Analyte (N=8) | $T_{max}$ (hr) | $C_{max}$ (hr) |
|---|---|---|
| Memantine | 63.5 (48-144) | 28.0 (25%) |
| Donepezil | 60.0 (48-144) | 20.3 (37%) |
| Memantine (Namenda XR®) | 9.0 (6-16) | 163.1 (28%) |
| Donepezil (Aricept®) | 3.19 (2-5) | 20.9 (23.9%) |

GASTRIC RESIDENCE SYSTEMS FOR ADMINISTRATION OF ACTIVE AGENTS

CROSS-REFERENCE TO RELATED APPLICATIONS

This application is a national stage application under 35 U.S.C. § 371 of International Application No. PCT/US2020/059541, filed internationally on Nov. 6, 2020 which claims priority benefit of U.S. Provisional Patent Application No. 62/933,348 filed on Nov. 8, 2019, U.S. Provisional Patent Application No. 62/933,211, filed Nov. 8, 2019, U.S. Provisional Patent Application No. 62/933,210, filed Nov. 8, 2019, U.S. Provisional Patent Application No. 62/933,313, filed Nov. 8, 2019, U.S. Provisional Patent Application No. 62/933,226, filed Nov. 8, 2019, U.S. Provisional Patent Application No. 62/992,075, filed Mar. 19, 2020, and U.S. Provisional Patent Application No. 63/052,905 filed on Jul. 16, 2020. The entire contents of those applications are hereby incorporated by reference herein.

STATEMENT REGARDING FEDERALLY SPONSORED RESEARCH OR DEVELOPMENT

This invention was made with government support under R01 AI131416 awarded by the National Institutes of Health. The government has certain rights in the invention.

FIELD OF THE INVENTION

The invention relates to gastric residence systems for sustained gastric release of active agents, such as drugs, and methods of use thereof.

BACKGROUND OF THE INVENTION

Gastric residence systems are delivery systems for agents which remain in the stomach for days to weeks, or even over longer periods, during which time drugs or other agents can elute from the systems for absorption in the gastrointestinal tract. Examples of such systems are described in U.S. Pat. No. 10,182,985, and in International Patent Application Nos. WO 2015/191920, WO 2015/191925, WO 2017/070612, WO 2017/100367, WO 2017/205844, and WO 2018/227147. Over the period of residence, the system releases an agent or agents, such as one or more drugs.

The current invention describes advancements in design, structure, and formulation of gastric residence systems, which provide improved control over residence time and release rate of agent.

SUMMARY OF THE INVENTION

Several features providing for more precise and consistent control of the desired residence time of gastric residence systems are disclosed. Improved release rate-modulating polymer films for the carrier polymer-agent arms or arm segments for gastric residence systems are also disclosed.

The following features are disclosed: I) a filament which is wrapped circumferentially around a gastric residence system and connecting the arms of the gastric residence system; II) use of arms with controlled stiffness; III) use of timed linkers and enteric linkers which permit higher precision in retention and passage of the gastric residence system; and IV) arms coated with release rate-modulating polymer films that are resistant to significant change in release rate properties after heat-assisted assembly or thermal cycling, as compared to the release rate properties of the arms prior to heat-assisted assembly. These features can be combined in any manner, e.g., I+II, II+III, III+IV, I+II+III, I+III+IV, II+III+IV, or I+II+III+IV.

The features of any of the embodiments recited above and herein are combinable with any of the other embodiments recited above and herein where appropriate and practical.

BRIEF DESCRIPTION OF THE DRAWINGS

FIG. 77A depicts Memantine Release Rate in Fed-State Gastric (mean±sd) and Fasted-State Intestinal Media (mean±sd) relative to release in FaSSGF (shaded area indicates 95% CI). FIG. 77B depicts Donepezil Release Rate in Fed-State Gastric (mean±sd) and Fasted-State Intestinal Media (mean±sd) relative to release in FaSSGF (shaded area indicates 95% CI). FIG. 77C depicts pre- and post-prandial plasma concentration of memantine in human subjects. Samples were taken one hour before and two hours after each meal on day 4 of the study (n=8 healthy volunteers, formulation of Example 1 dosed on day 1). FIG. 77D depicts pre- and post-prandial plasma concentration of donepezil in human subjects. Samples were taken one hour before and two hours after each meal on day 4 of the study (n=8 healthy volunteers, formulation of Example 1 dosed on day 1).

FIG. 22A shows the 3-point flexural modulus of timing linkers 1, 2, and 3 in fasted-state simulated gastric fluid. FIG. 22B shows the 3-point flexural modulus of enteric linkers 1, 2, and 3 in fasted-state simulated gastric fluid or fasted-state simulated intestinal fluid.

DETAILED DESCRIPTION OF THE INVENTION

Definitions

Figure 1:
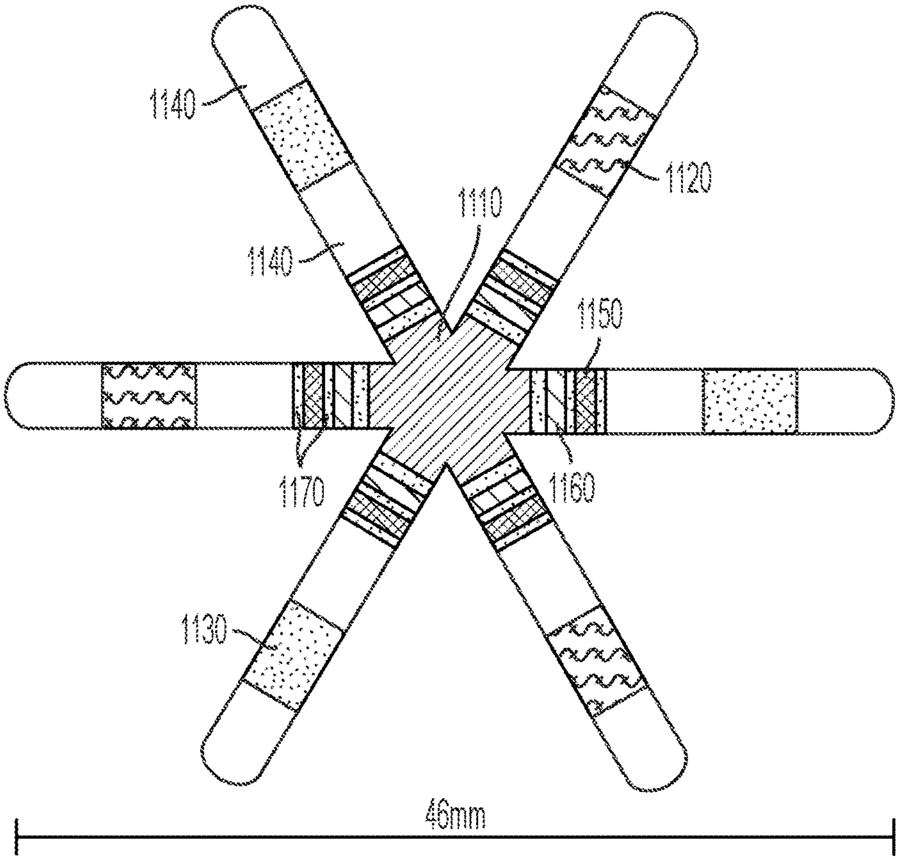
FIG. 1 shows the gastric residence system dosage form of Example 1.

A "carrier polymer" is a polymer suitable for blending with an agent, such as a drug, for use in a gastric residence system.

An "agent" is any substance intended for therapeutic, diagnostic, or nutritional use in a patient, individual, or subject. Agents include, but are not limited to, drugs, nutrients, vitamins, and minerals.

A "dispersant" is defined as a substance which aids in the minimization of particle size of agent and the dispersal of agent particles in the carrier polymer matrix. That is, the dispersant helps minimize or prevent aggregation or flocculation of particles during fabrication of the systems. Thus, the dispersant has anti-aggregant activity and anti-flocculant activity, and helps maintain an even distribution of agent particles in the carrier polymer matrix.

An "excipient" is any substance added to a formulation of an agent that is not the agent itself. Excipients include, but are not limited to, binders, coatings, diluents, disintegrants, emulsifiers, flavorings, glidants, lubricants, and preservatives. The specific category of dispersant falls within the more general category of excipient.

An "elastic polymer" or "elastomer" is a polymer that is capable of being deformed by an applied force from its original shape for a period of time, and which then substantially returns to its original shape once the applied force is removed.

"Approximately constant plasma level" refers to a plasma level that remains within a factor of two of the average plasma level (that is, between 50% and 200% of the average plasma level) measured over the period that the gastric residence system is resident in the stomach.

"Substantially constant plasma level" refers to a plasma level that remains within plus-or-minus 25% of the average plasma level measured over the period that the gastric residence system is resident in the stomach.

"Biocompatible," when used to describe a material or system, indicates that the material or system does not provoke an adverse reaction, or causes only minimal, tolerable adverse reactions, when in contact with an organism, such as a human. In the context of the gastric residence systems, biocompatibility is assessed in the environment of the gastrointestinal tract.

A "patient," "individual," or "subject" refers to a mammal, preferably a human or a domestic animal such as a dog or cat. In a most preferred embodiment, a patient, individual, or subject is a human.

The "diameter" of a particle as used herein refers to the longest dimension of a particle.

"Treating" a disease or disorder with the systems and methods disclosed herein is defined as administering one or more of the systems disclosed herein to a patient in need thereof, with or without additional agents, in order to reduce or eliminate either the disease or disorder, or one or more symptoms of the disease or disorder, or to retard the progression of the disease or disorder or of one or more symptoms of the disease or disorder, or to reduce the severity of the disease or disorder or of one or more symptoms of the disease or disorder. "Suppression" of a disease or disorder with the systems and methods disclosed herein is defined as administering one or more of the systems disclosed herein to a patient in need thereof, with or without additional agents, in order to inhibit the clinical manifestation of the disease or disorder, or to inhibit the manifestation of adverse symptoms of the disease or disorder. The distinction between treatment and suppression is that treatment occurs after adverse symptoms of the disease or disorder are manifest in a patient, while suppression occurs before adverse symptoms of the disease or disorder are manifest in a patient. Suppression may be partial, substantially total, or total. Because some diseases or disorders are inherited, genetic screening can be used to identify patients at risk of the disease or disorder. The systems and methods disclosed herein can then be used to treat asymptomatic patients at risk of developing the clinical symptoms of the disease or disorder, in order to suppress the appearance of any adverse symptoms.

"Therapeutic use" of the systems disclosed herein is defined as using one or more of the systems disclosed herein to treat a disease or disorder, as defined above. A "therapeutically effective amount" of a therapeutic agent, such as a drug, is an amount of the agent, which, when administered to a patient, is sufficient to reduce or eliminate either a disease or disorder or one or more symptoms of a disease or disorder, or to retard the progression of a disease or disorder or of one or more symptoms of a disease or disorder, or to reduce the severity of a disease or disorder or of one or more symptoms of a disease or disorder. A therapeutically effective amount can be administered to a patient as a single dose, or can be divided and administered as multiple doses.

"Prophylactic use" of the systems disclosed herein is defined as using one or more of the systems disclosed herein to suppress a disease or disorder, as defined above. A "prophylactically effective amount" of an agent is an amount of the agent, which, when administered to a patient, is sufficient to suppress the clinical manifestation of a disease or disorder, or to suppress the manifestation of adverse symptoms of a disease or disorder. A prophylactically effective amount can be administered to a patient as a single dose, or can be divided and administered as multiple doses.

A "flexural modulus" of a material is an intrinsic property of a material computed as the ratio of stress to strain in flexural deformation of the material as measured by a 3-point bending test. Although the linkers are described herein as being components of the gastric residence system, the flexural modulus of the material of the polymeric material may be measured in isolation. For example, the polymeric linker in the gastric residence system may be too short to measure the flexural modulus, but a longer sample of the same material may be used to accurately determine the flexural modulus. The longer sample used to measure the flexural modulus should have the same cross-sectional dimensions (shape and size) as the polymeric linker used in the gastric residence system. The flexural modulus is measured using a 3-point bending test in accordance with the ASTM standard 3-point bending test (ASTM D790) using a 10 mm distance between supports and further modified to accommodate materials with non-rectangular cross-sections. The longest line of symmetry for the cross section of the polymeric linker should be positioned vertically, and the flexural modulus should be measured by applying force downward. If the longest line of symmetry for the cross section of the polymeric linker is perpendicular to a single flat edge, the single flat edge should be positioned upward. If the cross-section of the polymeric linker is triangular, the apex of the triangle should be faced downward. As force is applied downward, force and displacement are measured, and the slope at the linear region is obtained to calculate the flexural modulus.

As used herein, the singular forms "a", "an", and "the" include plural references unless indicated otherwise or the context clearly dictates otherwise.

When numerical values are expressed herein using the term "about" or the term "approximately," it is understood that both the value specified, as well as values reasonably close to the value specified, are included. For example, the description "about 50° C." or "approximately 50° C." includes both the disclosure of 50° C. itself, as well as values close to 50° C. Thus, the phrases "about X" or "approximately X" include a description of the value X itself. If a range is indicated, such as "approximately 50° C. to 60° C." or "about 50° C. to 60° C.," it is understood that both the values specified by the endpoints are included, and that values close to each endpoint or both endpoints are included for each endpoint or both endpoints; that is, "approximately 50° C. to 60° C." (or "about 50° C. to 60° C.") is equivalent to reciting both "50° C. to 60° C." and "approximately 50° C. to approximately 60° C." (or "about 50° C. to 60° C.").

With respect to numerical ranges disclosed in the present description, any disclosed upper limit for a component may be combined with any disclosed lower limit for that component to provide a range (provided that the upper limit is greater than the lower limit with which it is to be combined). Each of these combinations of disclosed upper and lower limits are explicitly envisaged herein. For example, if ranges for the amount of a particular component are given as 10% to 30%, 10% to 12%, and 15% to 20%, the ranges 10% to 20% and 15% to 30% are also envisaged, whereas the combination of a 15% lower limit and a 12% upper limit is not possible and hence is not envisaged.

Unless otherwise specified, percentages of ingredients in compositions are expressed as weight percent, or weight/weight percent. It is understood that reference to relative weight percentages in a composition assumes that the combined total weight percentages of all components in the composition add up to 100. It is further understood that relative weight percentages of one or more components may be adjusted upwards or downwards such that the weight percent of the components in the composition combine to a total of 100, provided that the weight percent of any particular component does not fall outside the limits of the range specified for that component.

Some embodiments described herein are recited as "comprising" or "comprises" with respect to their various elements. In alternative embodiments, those elements can be recited with the transitional phrase "consisting essentially of" or "consists essentially of" as applied to those elements. In further alternative embodiments, those elements can be recited with the transitional phrase "consisting of" or "consists of" as applied to those elements. Thus, for example, if a composition or method is disclosed herein as comprising A and B, the alternative embodiment for that composition or method of "consisting essentially of A and B" and the alternative embodiment for that composition or method of "consisting of A and B" are also considered to have been disclosed herein. Likewise, embodiments recited as "consisting essentially of" or "consisting of" with respect to their various elements can also be recited as "comprising" as applied to those elements. Finally, embodiments recited as "consisting essentially of" with respect to their various elements can also be recited as "consisting of" as applied to those elements, and embodiments recited as "consisting of" with respect to their various elements can also be recited as "consisting essentially of" as applied to those elements.

When a composition or system is described as "consisting essentially of" the listed elements, the composition or system contains the elements expressly listed, and may contain other elements which do not materially affect the condition being treated (for compositions for treating conditions), or the properties of the described system (for compositions comprising a system). However, the composition or system either does not contain any other elements which do materially affect the condition being treated other than those elements expressly listed (for compositions for treating systems) or does not contain any other elements which do materially affect the properties of the system (for compositions comprising a system); or, if the composition or system does contain extra elements other than those listed which may materially affect the condition being treated or the properties of the system, the composition or system does not contain a sufficient concentration or amount of those extra elements to materially affect the condition being treated or the properties of the system. When a method is described as "consisting essentially of" the listed steps, the method contains the steps listed, and may contain other steps that do not materially affect the condition being treated by the method or the properties of the system produced by the method, but the method does not contain any other steps which materially affect the condition being treated or the system produced other than those steps expressly listed.

This disclosure provides several embodiments. It is contemplated that any features from any embodiment can be combined with any features from any other embodiment where possible. In this fashion, hybrid configurations of the disclosed features are within the scope of the present disclosure.

In addition to the embodiments and methods disclosed here, additional embodiments of gastric residence systems, and methods of making and using such systems, are disclosed in International Patent Application Nos. WO 2015/191920, WO 2015/191925, WO 2017/070612, WO 2017/100367, and PCT/US2017/034856, which are incorporated by reference herein in their entirety.

The following abbreviations for polymers and other components are used:

| Abbreviation | Component |
|---|---|
| PDL | poly(DL-lactide); inherent viscocity 1.6-2.4 dl/g ($CHCl_3$), $T_m$ 165-180° C. |
| PDL20 | PURASORB ® Poly-D,L-lactide; GMP grade copolymer of DL-lactide with an inherent viscosity midpoint of 2.0 dl/g |
| PCL HMW | polycaprolactone; MW(ave) 200,000 |
| PCL LMW | polycaprolactone; MW (ave) 15,000 |
| VA64 | copovidone; $T_m$ 140° C., $T_g$ 101° C. |
| Kollidon SR | Polyvinyl acetate/polyvinylpyrrolidone |
| K90F | povidone; $T_g$ 156° C. |
| PEG1 | polyethylene glycol; MW (ave) 1,000 |
| $PEO_{100K}$ | polyethylene glycol; MW (ave) 100,000 |
| L-31 | Pluronic ® L-31; PEG-PPG-PEG block co-polymer; MW (ave) 1,100 ($M_n$) |
| PPG | polypropylene glycol |
| PDLG | copolymer of DL-lactide and glycolide); inherent viscocity 1.6-2.4 dl/g ($CHCl_3$) |
| PCL triol | polycaprolactone triol; MW (ave) 900 ($M_n$) |
| Corbion PC17 | PURASORB ® Polycaprolactone; GMP grade homopolymer of ε-Caprolactone with an inherent viscosity midpoint of 1.7 dl/g |
| Corbion PC04 | PURASORB ® Polycaprolactone; GMP grade homopolymer of ε-Caprolactone with an inherent viscosity midpoint of 0.4 dl/g |
| F-108 | Pluronic ® F-108; PEG-PPG-PEG block co-polymer |
| PDL-PCL 25-75 | polyD-lactide-polycaprolactone co-polymer |
| PDL-PCL 80-20 | polyD-lactide-polycaprolactone co-polymer |
| PG | propylene glycol |
| PVPP | crospovidone |
| PVAc | polyvinylacetate |
| PEG10 | polyethylene glycol; MW (ave) 10,000 |
| Corbion 5004 | PURASORB ® 50/50 DL-lactide/glycolide copolymer; GMP grade copolymer of DL-lactide and Glycolide in a 50/50 molar ratio and with an inherent viscosity midpoint of 0.4 dl/g |
| Corbion 5004A | PURASORB ® 50/50 DL-lactide/glycolide copolymer; acid terminated GMP grade copolymer of DL-lactide and Glycolide in a 50/50 molar ratio and with an inherent viscosity midpoint of 0.4 dl/g |
| Corbion 5002A | PURASORB ® 50/50 DL-lactide/glycolide copolymer; acid terminated GMP grade copolymer of DL-lactide and Glycolide in a 50/50 molar ratio and with an inherent viscosity midpoint of 0.2 dl/g |
| HPMCAS | Synthetic polymer derived from cellulose |
| P407 | Poloxamer 407; PEG-PPG-PEG triblock co-polymer |
| E172 | Ferrosoferric Oxide |
| Span60 | Sorbitan monostearate |

PLURONIC® is a registered trademark of BASF Corporation for polyoxyalkylene ethers. In any formulation described herein using trade names, the trade name can be replaced by the generic name. For example, a formulation described as comprising 50% Corbion PC17 and 50% Corbion PC04 is understood to describe a formulation comprising 50% polycaprolactone of viscosity 1.7 dl/g and 50% polycaprolactone of viscosity 0.4 dl/g.

Gastric Residence System Description

Figure 7A:
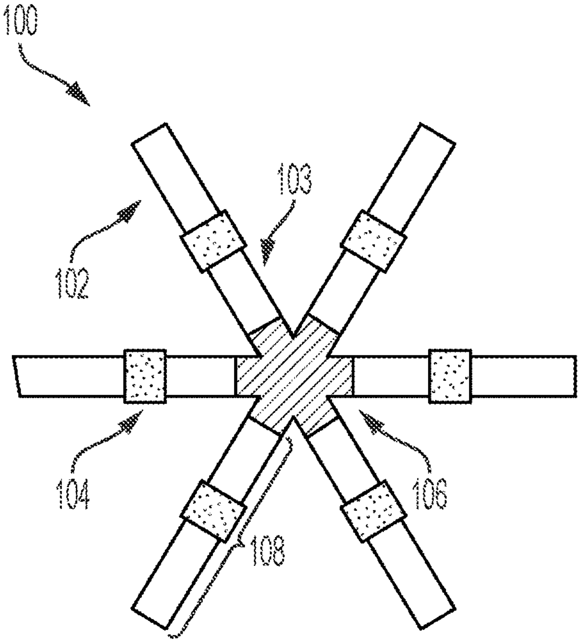
FIG. 7A, FIG. 7B, and FIG. 7C show various gastric residence system configurations, according to some embodiments.
Figure 7B:
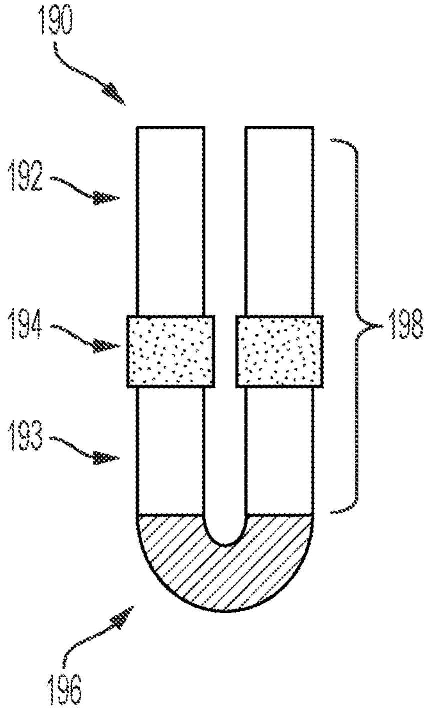

Gastric residence systems can be prepared in different configurations. The "stellate" configuration of a gastric residence system is also known as a "star" (or "asterisk") configuration. An example of a stellate system 100 is shown schematically in FIG. 7A. Multiple arms (only one such arm, 108, is labeled for clarity), are affixed to disk-shaped central elastomer 106. The arms depicted in FIG. 7A are comprised of segments 102 and 103, joined by a coupling polymer or linker region 104 (again, the components are only labeled in one arm for clarity) which serves as a linker region. This configuration permits the system to be folded or compacted at the central elastomer. FIG. 7B shows a folded configuration 190 of the gastric residence system of FIG. 7A (for clarity, only two arms are illustrated in FIG. 7B). Segments 192 and 193, linker region 194, elastomer 196, and arm 198 of FIG. 7B correspond to segments 102 and 103, linker region 104, elastomer 106, and arm 108 of FIG. 7A, respectively. When folded, the overall length of the system is reduced by approximately a factor of two, and the system can be conveniently placed in a container such as a capsule or other container suitable for oral administration. When the capsule reaches the stomach, the capsule dissolves, releasing the gastric residence system. The gastric residence system then unfolds into its uncompacted state, which is retained in the stomach for the desired residence period.

While the linker regions 104 are shown as slightly larger in diameter than the segments 102 and 103 in FIG. 7A, they can be the same diameter as the segments, so that the entire arm 102-104-103 has a smooth outer surface.

In some embodiments, the stellate system may have an arm composed of only one segment, which is attached to the central elastomer by a linker region. This corresponds to FIG. 7A with the segments 103 omitted. The single-segment arms comprising segments 102 are then directly attached to central elastomer 106 via the linkers 104. The linkers can comprise a coupling polymer or a disintegrating matrix.

A stellate system can be described as a gastric residence system for administration to the stomach of a patient, comprising an elastomer component, and a plurality of at least three carrier polymer-agent components comprising a carrier polymer and an agent or a salt thereof, attached to the elastomer component, wherein each of the plurality of carrier polymer-agent components is an arm comprising a proximal end, a distal end, and an outer surface therebetween; wherein the proximal end of each arm is attached to the elastomer component and projects radially from the elastomer component, each arm having its distal end not attached to the elastomer component and located at a larger radial distance from the elastomer component than the proximal end; wherein each arm independently comprises one or more segments, each segment comprising a proximal end, a distal end, and an outer surface therebetween. In some embodiments, when two or more segments are present in an arm, each segment is attached to an adjacent segment via a linker region. In some embodiments, when two or more segments are present in an arm, one segment is directly attached to the other segment, without using a linker region. The linker region can be a coupling polymer or a disintegrating matrix. The arms can be attached to the central elastomer via a coupling polymer or a disintegrating matrix, and can have intervening portions of interfacing polymers. For the plurality of at least three arms, or for a plurality of arms, a preferred number of arms is six, but three, four, five, seven, eight, nine, or ten arms can be used. The arms should be equally spaced around the central elastomer; if there are N arms, there will be an angle of about 360/N degrees between neighboring arms.

Figure 7C:
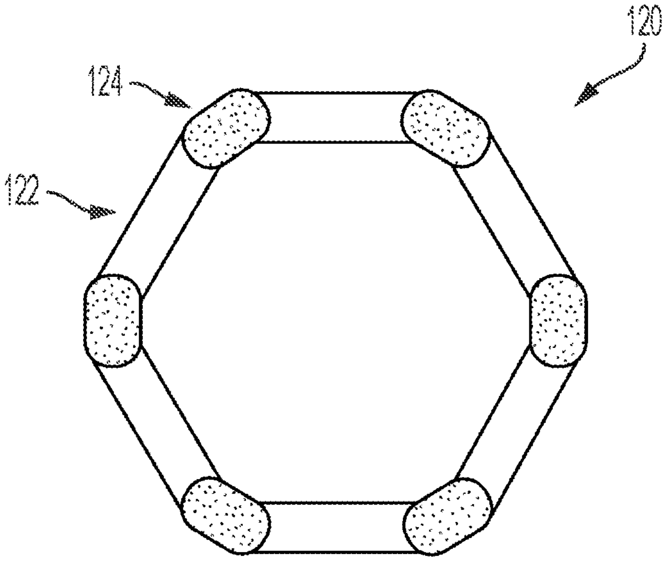

FIG. 7C shows another possible overall configuration 120 for a gastric residence system, which is a ring configuration. Segments 122 are joined by coupling polymer or linker region 124 (only one segment and one coupling linkage are labeled for clarity). The coupling polymer/linker region in this design must also function as an elastomer, to enable the ring to be twisted into a compacted state for placement in a container, such as a capsule.

In one embodiment of the stellate configuration, the segments 102 and 103 comprise a carrier polymer blended with an agent or drug. In one embodiment of the ring configuration, the segments 122 comprise a carrier polymer blended with an agent or drug.

The coupling polymers of the gastric residence system, which serve as linker regions, are designed to break down gradually in a controlled manner during the residence period of the system in the stomach. If the gastric residence system passes prematurely into the small intestine in an intact form, the system is designed to break down much more rapidly to avoid intestinal obstruction. This is readily accomplished by using enteric polymers as coupling polymers. Enteric polymers are relatively resistant to the acidic pH levels encountered in the stomach, but dissolve rapidly at the higher pH levels found in the duodenum. Use of enteric coupling polymers as safety elements protects against undesired passage of the intact gastric residence system into the small intestine. The use of enteric coupling polymers also provides a manner of removing the gastric residence system prior to its designed residence time; should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric coupling polymers. The gastric residence system will then break apart and be eliminated from the patient. In the system shown in FIG. 7A, at least the coupling polymer used for the couplings 104 are made from such enteric polymers.

In additional embodiments, a time-dependent coupling polymer or linker can be used. Such a time-dependent coupling polymer or linker degrades in a predictable, time-dependent manner. In some embodiments, the degradation of the time-dependent coupling polymer or linker may not be affected by the varying pH of the gastrointestinal system.

In additional embodiments, different types of linkers can be used in the gastric residence systems. That is, both enteric linkers (or enteric coupling polymers) and time-dependent linkers (or time-dependent coupling polymers) can be used. In some embodiments, a single multi-segment arm of a stellate system can use both an enteric linker at some linker regions between segments, and a time-dependent linker at other linker regions between segments.

Linker regions are typically about 100 microns to about 2 millimeter in width, such as about 200 um to about 2000 um, about 300 um to about 2000 um, about 400 um to about 2000 um, about 500 um to about 2000 um, about 600 um to about 2000 um, about 700 um to about 2000 um, about 800 um to about 2000 um, about 900 um to about 2000 um, about 1000 um to about 2000 um, about 1100 um to about 2000 um, about 1200 um to about 2000 um, about 1300 um to about 2000 um, about 1400 um to about 2000 um, about 1500 um to about 2000 um, about 1600 um to about 2000 um, about 1700 um to about 2000 um, about 1800 um to about 2000 um, or about 1900 um to about 2000 um; or about 100 um to about 1900 um, about 100 um to about 1800 um, about 100 um to about 1700 um, about 100 um to about 1600 um, about 100 um to about 1500 um, about 100 um to about 1400 um, about 100 to about 1300 um, about 100 um to about 1200 um, about 100 um to about 1100 um, about 100 um to about 1000 um, about 100 um to about 900 um, about 100 um to about 800 um, about 100 um to about 700 um, about 100 um to about 600 um, about 100 um to about 500 um, about 100 um to about 400 um, about 100 um to about 300 um, or about 100 um to about 200 um. Linker regions can be about 100 um, about 200 um, about 300 um, about 400 um, about 500 um, about 600 um, about 700 um, about 800 um, about 900 um, about 1000 um, about 1100 um, about 1200 um, about 1300 um, about 1400 um, about 1500 um, about 1600 um, about 1700 um, about 1800 um, about 1900 um, or about 200 o um in width, where each value can be plus or minus 50 um (±50 um).

The central elastomeric polymer of a stellate system is typically not an enteric polymer; however, the central elastomeric polymer can also be made from such an enteric polymer where desirable and practical.

The central elastomer should have a specific durometer and compression set. The durometer is important because it determines the folding force of the dosage form and whether it will remain in the stomach; a preferred range is from about 60 to about 90 A. The compression set should be as low as possible to avoid having permanent deformation of the gastric residence system when stored in the capsule in its compacted configuration. A preferred range is about 10% to about 20% range. Liquid silicone rubber is a useful material for the central elastomer. Examples of materials that fit these requirements are the QP1 range of liquid silicone rubbers from Dow Corning. In any embodiment with a central elastomer, the QP1-270 (70 A durometer) liquid silicone rubber can be used. In some embodiments, the central elastomer may comprise a 50 A or 60 A durometer liquid silicone rubber (Shin Etsu).

Segments and arms of the gastric residence systems can have cross-sections in the shape of a circle (in which case the segments are cylindrical), a polygon (such as segments with a triangular cross-section, rectangular cross-section, or square cross-section), or a pie-shaped cross-section (in which case the segments are cylindrical sections). Segments with polygon-shaped or pie-shaped cross-sections, and ends of cylindrically-shaped sections which will come into contact with gastric tissue, can have their sharp edges rounded off to provide rounded corners and edges, for enhanced safety in vivo. That is, instead of having a sharp transition between intersecting edges or planes, an arc is used to transition from one edge or plane to another edge or plane. Thus, a "triangular cross-section" includes cross-sections with an approximately triangular shape, such as a triangle with rounded corners. An arm with a triangular cross-section includes an arm where the edges are rounded, and the corners at the end of the arm are rounded. Rounded corners and edges are also referred to as fillet corners, filleted corners, fillet edges, or filleted edges.

Features for Improved Retention and Agent Release for Gastric Residence Systems

Retention of gastric residence systems for the desired residence period and agent release from gastric residence systems can be improved and made more consistent using the features described herein. In particular, the following features can be used: I) a filament which is wrapped circumferentially around a gastric residence system and connecting the arms of the gastric residence system; II) use of arms with controlled stiffness; III) use of timed linkers and enteric linkers which permit higher precision in retention and passage of the gastric residence system; and IV) arms coated with release rate-modulating polymer films that are resistant to significant change in release rate properties after heat-assisted assembly, as compared to the release rate properties of the arms prior to heat-assisted assembly.

I. Circumferential Filament

Provided in this Circumferential Filament disclosure are gastric residence systems comprising a filament for improved gastric residence and methods of preparing gastric residence forms having a filament. In particular, gastric residence systems having a filament described herein may help improve the gastric residence of the gastric residence system. Specifically, a filament can help provide a more consistent gastric residence time and/or a longer gastric residence time. Thus, gastric residence systems provided herein that include a filament may provide more predictable and/or controllable gastric residence times. Gastric residence systems having predictable and/or controllable gastric residence times can minimize the risk of the gastric residence system unfolding too early (e.g., in the esophagus) and causing an obstruction. Gastric residence systems having predictable and/or controllable gastric residence times can also minimize the possibility of the gastric residence system passing through the stomach and unfolding later in the gastrointestinal tract (i.e., intestine), or passing through the gastrointestinal tract without unfolding at all. In each of these possible scenarios, the therapeutic agent of the gastric residence dosage form is not delivered to the patient as intended.

However, it has been demonstrated that gastric residence systems of a stellate shape can bend into a configuration that allows for premature passage through the pylorus of a patient. Gastric residence systems that prematurely pass through the pylorus fail to deliver the therapeutic agent of the gastric residence system to the patient. Further, premature passage causes inconsistency, causes unreliability, and compromises the efficacy of the gastric residence system.

Figure 8:
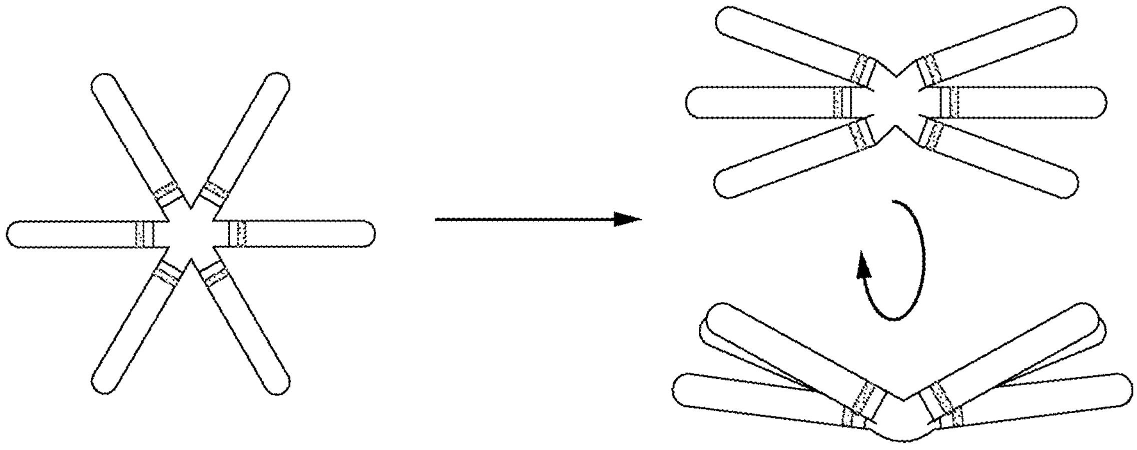
FIG. 8 shows a gastric residence system comprising a plurality of arms and the bent geometry a gastric residence can assume most easily when compressed by forces such as gastric contractions, according to some embodiments.

FIG. 8 shows a stellate-shaped gastric residence system having a plurality of arms. One example of a bended configuration is shown on the right side of the Figure. Due to forces in the stomach (e.g., peristaltic forces), gastric residence systems may bend into configurations, such as that shown in FIG. 8, that can allow for premature passage through the pylorus.

Figure 9A:
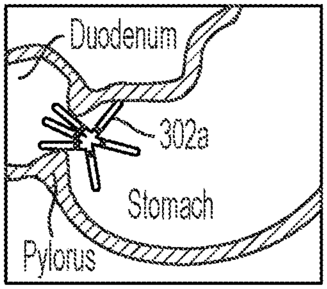
FIGS. 9A-9C show three different gastric residence systems having a plurality of arms and ways that it may bend to prematurely enter into the pylorus, according to some embodiments.
Figure 9B:
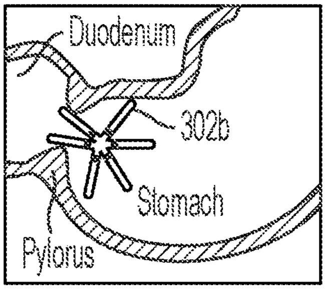
Figure 9C:
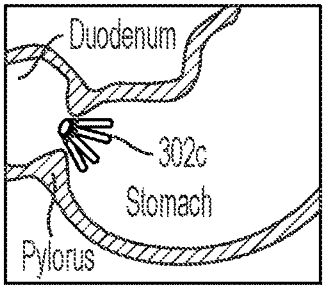

Other possible bended configurations are shown in FIGS. 9A-9C. Specifically, FIGS. 9A-9C show three different configurations that a gastric residence system may assume that can allow for premature passage through the pylorus. As shown in each Figure, the relatively stiff arms of the gastric residence system remain straight. However, because the core of each of the gastric residence systems has a higher flexibility than the arms, the core can bend. The bending of the core can allow gastric residence systems having relatively stiff arms to prematurely pass through the pylorus of a patient.

As shown in FIG. 9A, gastric residence system **302*a* is shown in a bended configuration having three arms leading through the pyloric opening. FIG. 9B shows gastric residence system 302*b* in a bended configuration having two arms leading through the pyloric opening. FIG. 9C shows gastric residence system 302*c*** in a bended configuration analogous to the shape of a shuttlecock and having the core leading through the pyloric opening.

Accordingly, described herein are gastric residence systems comprising a filament. A filament wrapped circumferentially around a gastric residence system and connecting the arms of the gastric residence system, for example, can help prevent premature passage through a patient's pylorus. Filaments and gastric residence systems comprising filaments are described in more detail with respect to the arms and coupling polymers of a gastric residence system.

Following is a description of gastric residence systems having a filament. As described in detail below, the filament of gastric residence systems having a filament may help prevent the gastric residence system from prematurely passing through a patient's pylorus. Accordingly, a filament and gastric residence systems having a filament described herein can help improve the efficacy and reliability of gastric residence systems.

Gastric residence systems with a filament can prevent the gastric residence system from prematurely passing through a patient's pylorus. Described herein are gastric residence systems having comprising a filament to help minimize the risk of the gastric residence system passing through the pylorus of a patient prematurely.

Figure 10A:
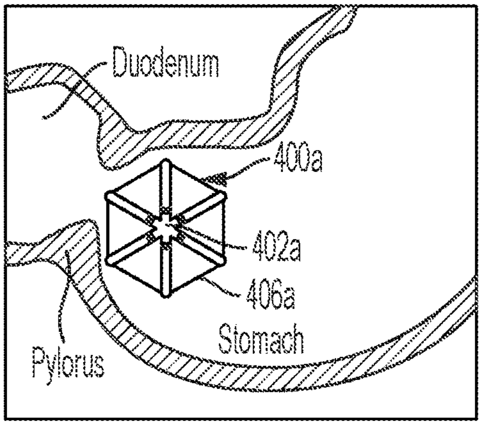
FIG. 10A and FIG. 10B show two different gastric residence systems having filament and how the filament may help prevent premature passage through the pylorus, according to some embodiments.
Figure 10B:
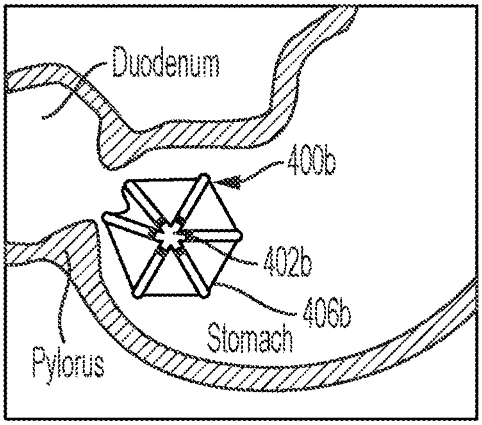

A filament may be attached to the distal ends of the arms of a gastric residence system. FIGS. 10A and 10B show how the inclusion of a filament affects the most common bending and passage modes of an intact gastric residence system through the pylorus. In particular, the filament can prevent one or two arms from prematurely entering the pylorus, for example. It also maintains the spacing of the arms, which changes the bending geometry and increases the force required to compress the gastric residence system to a configuration small enough to prematurely pass through the pylorus.

For example, gastric residence system 400*a* of FIG. 10A comprises a central core 402*a* and a plurality of arms. As shown, each arm 404*a* of the plurality of arms extends radially from the central core 402. Each arm 404 is attached to core 402*a* at a proximal end. Filament 406*a* is shown attached to the distal end of each arm 404*a*. FIG. 10A shows gastric residence system 400*a* in an open configuration. As shown, when gastric residence system 400*a* remains in an open configuration, filament 406*a* helps prevent gastric residence system 400*a* from passing prematurely through a pylorus.

FIG. 10B shows gastric residence system 400*b* in a bended configuration. Gastric residence system 400*b* comprises core 402*b*, arms 404*b*, and filament 406*b*. As shown, even if gastric residence system 400*b* bends into a configuration that might otherwise allow for premature passage through a patient's pylorus (see FIG. 9B), filament 408*b* can help prevent the device from passing. In particular, filament 408*b* is flexible and stretchable such that it can maintain its integrity despite gastric forces that may bend and contort gastric residence system 400*b*.

In some embodiments, a gastric residence system may comprise tips located at a distal end of one or more arms. The tips may comprise an enteric polymer composition. The filament may be connected to each arm by way of the tip at the distal end. The tips may be configured to separate from the rest of the arm when in a gastric environment. In particular, the tips may be configured to separate from the arms, allowing the filament to also separate from the gastric residence system. This separation may be fine-tuned such that the tips and filament separate once a predetermined gastric residence time approaches expiration, such that the gastric residence system separates and passes through a patient's pylorus at the expiration of the predetermined gastric residence time. If the tips and/or filament separate too early, the gastric residence system risks passing through the patient's pylorus prematurely.

In some embodiments, the arm tips may comprise one or more polymers, an enteric material, a plasticizer, and an acid. Suitable polymers may include polycaprolactone and/or thermoplastic polyurethanes (e.g. Pathway™ by Lubrizol). In some embodiments, the composition of an arm tip may be the same as the composition of a linker component. In some embodiments, the composition of an arm tip may be different than the composition of a linker component. In some embodiments, an arm tip may comprise from 10 to 50 wt. % polymer. In some embodiments, an arm tip may comprise less than 50 wt. %, less than 40 wt. %, less than 30 wt. %, or less than 20 wt. % polymer. In some embodiments, an arm tip may comprise more than 10 wt. %, more than 20 wt. %, more than 30 wt. %, or more than 40 wt. % polymer.

In some embodiments, the enteric material of the arm tips may comprise an enteric polymer. For example, suitable enteric polymers include Cellulose acetate phthalate, Hydroxypropyl methylcellulose phthalate 50, Hydroxypropyl methylcellulose phthalate 55, Polyvinylacetate phthalate, Methacrylic acid-methyl methacrylate copolymer (1:1), Methacrylic acid-methyl methacrylate copolymer (2:1), Methacrylic acid-ethyl acrylate copolymer (2:1), Shellac, Hydroxypropyl methylcellulose acetate succinate, Poly (methyl vinyl ether/maleic acid) monoethyl ester, or Poly (methyl vinyl ether/maleic acid) n-butyl ester. In some embodiments, an arm tip may comprise from 20 to 90 wt. % enteric material. In some embodiments, an arm tip may comprise less than 90 wt. %, less than 80 wt. %, less than 70 wt. %, less than 60 wt. %, less than 50 wt. %, less than 40 wt. %, or less than 30 wt. % enteric material. In some embodiments, an arm tip may comprise more than 20 wt. %, more than 30 wt. %, more than 40 wt. %, more than 50 wt. %, more than 60 wt. %, more than 70 wt. %, or more than 90 wt. % enteric material.

Suitable plasticizers may include propylene glycol, P407, triethyl citrate, triacetin, dibutyl sebacate, and/or polyethylene glycol. In some embodiments, an arm tip may comprise from 1 to 20 wt. % plasticizer. In some embodiments, an arm tip may comprise less than 20 wt. %, less than 15 wt. %, less than 10 wt. %, or less than 5 wt. % plasticizer. In some embodiments, an arm tip may comprise more than 1 wt. %, more than 5 wt. %, more than 10 wt. %, or more than 15 wt. % plasticizer.

Suitable acids can include stearic acid or other fatty acids. In some embodiments, an arm tip may comprise from 1 to 20 wt. % or from 1 to 10 wt. % acid. In some embodiments, an arm tip may comprise less than 20 wt. %, less than 15 wt. %, less than 10 wt. %, or less than 5 wt. % acid. In some embodiments, an arm tip may comprise more than 1 wt. %, more than 5 wt. %, more than 10 wt. %, or more than 15 wt. % acid.

Figure 11A:
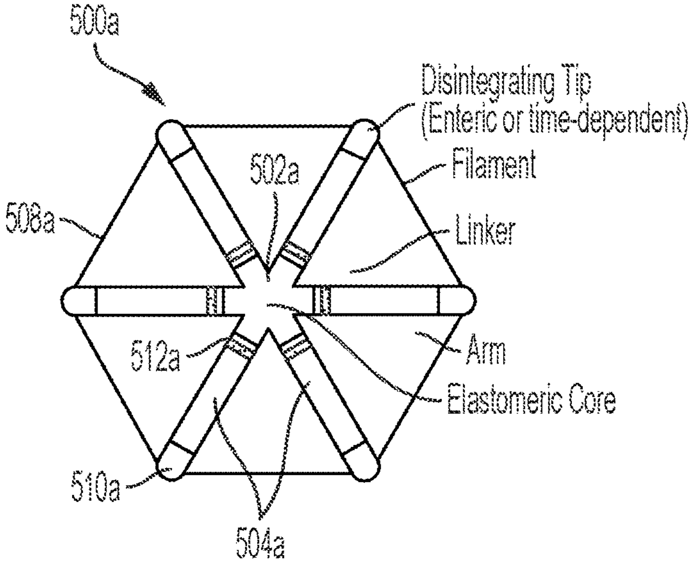
FIG. 11A and FIG. 11B show two different configurations of gastric residence systems comprising a filament, according to some embodiments.
Figure 11B:
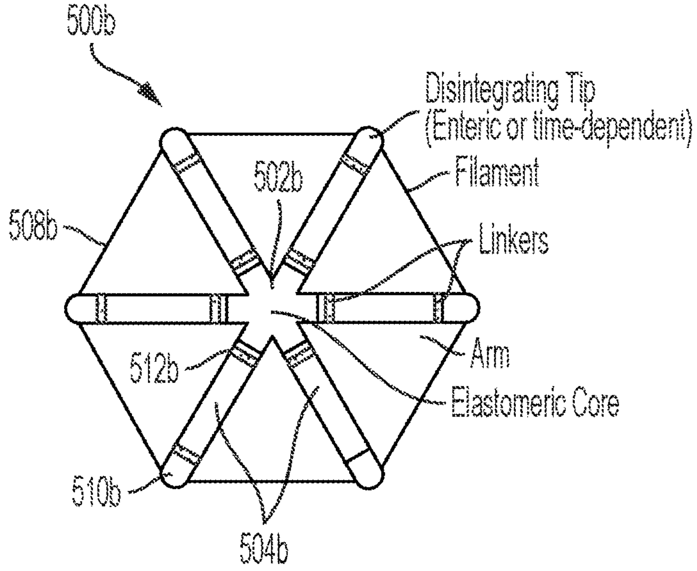

FIGS. 11A and 11B show two different configurations of a gastric residence system having a filament connected to tips at a distal end of each arm. In particular, FIG. 11A shows gastric residence system 500*a* comprising core 502*a* and six arms 504*a*. Each arm 504*a* comprises a tip 510*a* at a distal end. In some embodiments, each arm 504*a* may be connected to core 502*a* via a linker 512*a*. As shown, filament 508*a* connects each arm 504*a* at tip 510*a*. In some embodiments, a single filament 508*a* may wrap circumferentially around gastric residence system 500*a*, connecting to each arm at tip 510*a*. In some embodiments, multiple filaments 508*a* may connect each arm 504*a* of gastric residence system 500*a*.

FIG. 11B shows gastric residence system 500*b* having core 502*b*, six arms 504*b*, a tip 510*b* at a distal end of each arm 504*b*. Unlike gastric residence system 500*a* of FIG.

11A, gastric residence system 500*b* comprises a linker 512*b* connecting arm 504*b* to core 502*b*, as well as a linker 512*b* connecting two segments of arm 504*b*. As shown, filament 508*b* connects each arm 504*b* at tip 510*b*. In some embodiments, a single filament 508*b* may wrap circumferentially around gastric residence system 500*a*, connecting to each arm at tip 510*a*. In some embodiments, multiple filaments 508*b* may connect each arm 504*b* of gastric residence system 500*b*.

Filaments for improved gastric residence may include elastic polymers and/or bioresorbable polymers.

Suitable elastic polymers may include Polyurethanes (Lubrizol Pellethane, Pathways, Tecoflex, carbothane), polyamide-polyether block copolymers (Pebax), poly(ethylene-co-vinyl acetate) (PEVAc), polyvinyl acetate, silicones, and/or combinations thereof. In some embodiments, a filament may comprise 10-90 wt. %, 20-80%, or 30-70 wt. % elastic polymer. In some embodiments, a filament may comprise less than 90 wt. %, less than 80 wt. %, less than 70 wt. %, less than 60 wt. %, less than 50 wt. %, less than 40 wt. %, less than 30 wt. %, or less than 20 wt. % elastic polymer. In some embodiments, a filament my comprise more than 10 wt. %, more than 20 wt. %, more than 30 wt. %, more than 40 wt. %, more than 50 wt. %, more than 60 wt. %, more than 70 wt. %, or more than 80 wt. % elastic polymer.

Suitable bioresorbable polymers can include Poly(lactic-co-glycolic acid) (PLGA), polycaprolactone (PCL), poly (lactic acid) (PLA), PCL-PLA copolymers, polydioxanone, poly(trimethylene carbonate), PCL-poly(glycolic acid) copolymers, Poly(glycerol sebacate), Polyanhydrides, Polyphosphazenes, Poly(alkyl cyanoacrylate)s, poly(amino acids), Poly(propylene fumarate), and/or combinations thereof. In some embodiments, a filament may comprise 10-90 wt. %, 20-80%, or 30-70 wt. % bioresorbable polymer. In some embodiments, a filament may comprise less than 90 wt. %, less than 80 wt. %, less than 70 wt. %, less than 60 wt. %, less than 50 wt. %, less than 40 wt. %, less than 30 wt. %, or less than 20 wt. % bioresorbable polymer. In some embodiments, a filament my comprise more than 10 wt. %, more than 20 wt. %, more than 30 wt. %, more than 40 wt. %, more than 50 wt. %, more than 60 wt. %, more than 70 wt. %, or more than 80 wt. % bioresorbable polymer.

In some embodiments, a filament may include a plasticizer. For example, suitable plasticizers can include propylene glycol, polyethylene glycol-polypropylene glycol-polyethylene glycol (PEG-PPG-PEG) block copolymers such as P407, triethyl citrate, triacetin, dibutyl sebacate, and/or polyethylene glycol. In some embodiments, a filament may include 0.1 to 20 wt. % plasticizer or 1 to 10 wt. % plasticizer. In some embodiments, a filament may comprise less than 20 wt. %, less than 15 wt. %, less than 10 wt. %, less than 5 wt. %, or less than 1 wt. % plasticizer. In some embodiments, a filament may comprise more than 0.1 wt. %, more than 1 wt. %, more than 5 wt. %, more than 10 wt. %, or more than 15 wt. % plasticizer.

A length of the filament can be measured as a length between each arm, or, for embodiments comprising a single filament wrapping the circumference of the gastric residence system, the entire length of said circumferentially-wrapped filament. Either way, the length of a filament depends on the size of the gastric residence system and the number of arms. For example, for a stellate-shape gastric residence system comprise six arms, the length of a circumferentially-wrapped single filament may be 100-150 mm, 110-140 mm, or 120-130 mm in length. The length of the filament between any two adjacent arms of the six arms may be 18-24 mm or 20-22 mm.

In some embodiments, filaments made from thermoplastic polyurethane (TPU) tubes, such as aromatic polyether TPU tubes or aromatic polyester TPU tubes, such as Pellethane tubes may be stretched between two adjacent arms to create tension in the filament between the arms. For a stellate-shape gastric residence system comprise six arms, the length of a circumferentially-wrapped single filament comprising thermoplastic polyurethane (TPU) tubes, such as aromatic polyether TPU tubes or aromatic polyester TPU tubes, such as Pellethane tubes may be 90-130 mm or 100-120 mm in length. The length of the filament between any two adjacent arms of the six arms may be 18-22 mm. In some embodiments, filaments made from Pellethane tubes may be stretched between two adjacent arms to create tension in the filament between the arms. For a stellate-shape gastric residence system comprise six arms, the length of a circumferentially-wrapped single filament comprising Pellethane tubes may be 90-130 mm or 100-120 mm in length. The length of the filament between any two adjacent arms of the six arms may be 18-22 mm.

The cross-sectional shape of a filament may be any of a variety of shapes including, but not limited to: a circle, an oval, a rectangle, or an annulus. The thickness or diameter of a filament may be 100-1000 microns, preferably 200 to 400 microns. In some embodiments, the thickness or diameter of a filament may be less than 1000 microns, less than 800 microns, less than 600 microns, less than 400 microns, or less than 200 microns. In some embodiments, the thickness or diameter of a filament may be more than 100 microns, more than 200 microns, more than 400 microns, more than 600 microns, or more than 800 microns.

In embodiments comprising a filament having a rectangular cross-section, the width of the filament (i.e., longer side of the rectangular cross-sectional measurement) may be 1-4 mm. In some embodiments, the width may be less than 4 mm, less than 3 mm, or less than 2 mm. In some embodiments, the width may be more than 2 mm, more than 3 mm, or more than 4 mm.

The force required to compress a gastric residence system having a filament may be quantified using a radial compression test, described in detail in the "Testing Methods" section, below. In some embodiments, the force required to compress a gastric residence system having a filament may be 1.25 to 5 times the force required to compress a gastric residence system without a filament to the same compressed diameter. In some embodiments, the force required to compress a gastric residence system having a filament may be less than 5 times, less than 4 times, less than 3 times, or less than 2 times the force required to compress a gastric residence system without a filament to the same compressed diameter. In some embodiments, the force required to compress a gastric residence system having a filament may be more than 1.25 times, more than 2 times, more than 3 times, or more than 4 times the force required to compress a gastric residence system without a filament to the same compressed diameter.

The force required to separate a filament from an arm tip may be quantified using a pullout force test, described in detail in the "Testing Methods" section, below. In some embodiments, the force required to separate a filament from its corresponding arm tip may be 0.5 to 10N or 2 to 6N. In some embodiments, the force required to separate a filament from its corresponding arm tip may be less than 10N, less than 9N, less than 8N, less than 7N, less than 6N, less than 5N, less than 4N, less than 3N, less than 2N, or less than 1N. In some embodiments, the force required to separate a filament from its corresponding arm tip may be more than 0.5N, more than 1N, more than 2N, more than 3N, more than 4N, more than 5N, more than 6N, more than 7N, more than 8N, or more than 9N. In some embodiments, the force required to separate a filament from its corresponding arm tip may decrease the longer the gastric residence system stays in a gastric environment.

In some embodiments, the force required to separate a filament from its corresponding arm tip may depend on the method used to secure the ends of the filament (i.e., knotted, heated, or no secured end). In some embodiments, the force required to separate a filament having knotted ends from its corresponding arm tip may be greater than the force required to separate a filament having heated ends from its corresponding arm tip. In some embodiments, the force required to separate a filament having knotted ends and the force required to separate a filament having heated ends from its corresponding arm tip may be greater than the force required to separate an unmodified filament (i.e., unsecured) from its corresponding arm tip.

As described, a filament of a gastric residence system may be connected to a tip of an arm of the gastric residence system. If not properly connected, the arm may translate along the filament when the gastric residence system is compressed/bent, which may compromise the ability of the filament to help prevent premature passage of the gastric residence system through the pylorus. Thus, following is a description of methods of manufacturing gastric residence systems having a filament.

Figure 12A:
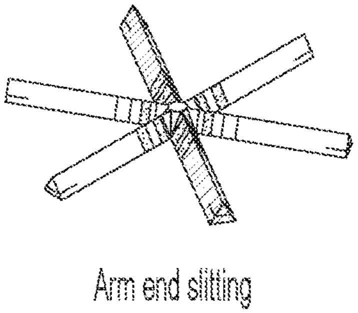
FIG. 12A, FIG. 12B, and FIG. 12C show stages of preparing a gastric residence system with filament, according to some embodiments.
Figure 12B:
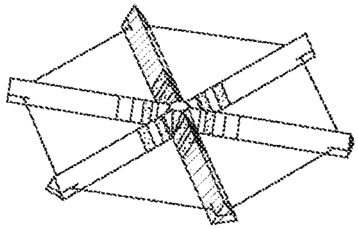
Figure 12C:
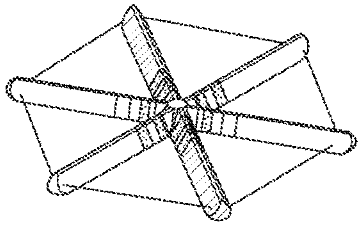

In some embodiments, a filament may be attached to the arms of pre-assembled gastric residence systems by notching, wrapping, and end forming. The gastric residence systems may be assembled with specially-formulated tips at each distal end of each arm. Each tip of each arm may be notched with a razor blade or circular saw to form a notch in the tip, as shown in FIG. 12A. FIG. 12B shows a filament that has been wrapped circumferentially around the arms of the gastric residence system and fed through each notch. In some embodiments, the filament may be wrapped using a winding fixture with controlled tension. FIG. 12C shows notches that have been closed and rounded to secure the filament. In some embodiments, the notches may be closed using a fixture that applies heat and pressure to the end of each arm through a heated die, leaving a rounded surface at the end of the arm.

Figure 13:
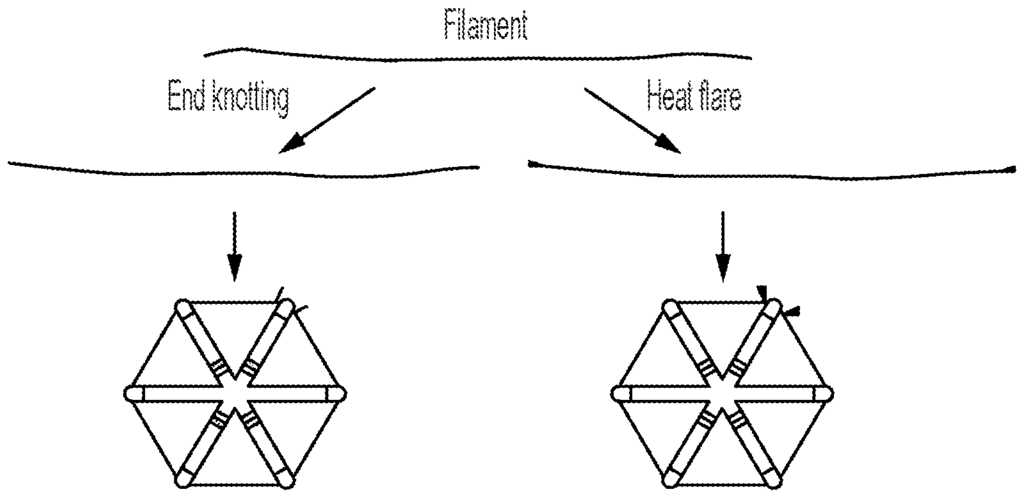
FIG. 13 shows two methods of securing the filament, according to some embodiments.

After wrapping a filament to connect two or more arms, the ends of the filament can be secured. FIG. 13 shows two different methods of securing the ends of a filament. The two ends of the filament may be secured first by overlapping them within the notch of a single arm. As the gastric residence system bends within the stomach during gastric residence, tension is applied to the filament and the two free filament ends may slip through the notch and detach from the arm. Thus, to better secure the filament ends, the filament ends can be enlarged by knotting and/or heat flaring. In some embodiments, the ends of the filament may be knotted and/or heated prior to attaching to the gastric residence system.

Figure 14:
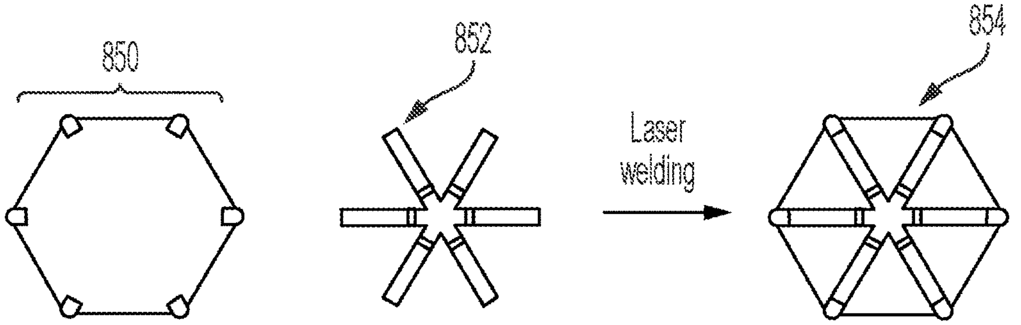
FIG. 14 shows a method of manufacturing a gastric residence system, according to some embodiments.

In some embodiments, the filament may be attached to a plurality of arm tips prior to attaching the arm tips to the rest of the gastric residence system. For example, the filament and arm tips may be manufactured by injection molding or insert molding (e.g., overmolding the tips onto an existing filament). FIG. 14 shows an example of a manufacturing process that includes forming the filament and arm tips by injection molding. As shown, gastric residence system 852 may be inserted into the injection molded filament and arm tips (850). Gastric residence system 852 maybe welded to the filament and arm tips 850 to form a completed gastric residence system having a filament 854.

II. Controlled Stiffness

This feature II, Controlled Stiffness, provides gastric residence systems having optimized arm stiffness and methods of preparing gastric residence dosage forms having optimized arm stiffness. In particular, gastric residence dosage forms having optimally stiff arms described herein may help improve the gastric residence of the gastric residence forms. By controlling the stiffness of the arms of a gastric residence system, the gastric residence of the gastric residence system may be better controlled. Specifically, flexible arms can help provide a more consistent gastric residence time and/or a longer gastric residence time. Thus, gastric residence systems including arms having a controlled stiffness provided herein may provide more predictable and/or controllable gastric residence times. Gastric residence systems having predictable and/or controllable gastric residence times can increase the reliability and efficacy of the gastric residence system to help ensure that the therapeutic agent is delivered to the patient as intended.

Conversely, gastric residence systems having relatively stiff arms and a relatively flexible core have been shown to bend into configurations (due to gastric waves/forces) small enough to prematurely pass through the pylorus. When the relatively stiff arms are subjected to compression forces, the compression forces are transferred to the relatively flexible core. Thus, configuring gastric residence systems with relatively stiff arms and relatively flexible cores may contribute to variability in gastric residence.

Accordingly, provided herein are gastric residence systems having controlled stiffness that can resist premature passage through a pylorus. The flexible arms may comprise a relatively stiff, or first, portion at a proximal end and a relatively flexible, or second, portion at a distal end, wherein the arms of a gastric residence system extend radially outwards from a proximal end. When subjected to compression forces, the second segment of the arms absorbs some of the force. This allows the second segment to bend, but the first segment can maintain its shape without bending (depending on the magnitude of the force), allowing the gastric residence system to maintain a configuration too large to prematurely mass through a patient's pylorus. Accordingly, gastric residence systems comprising flexible arms disclosed herein may be more able to provide consistent and accurate residence times, improving the reliability and efficacy of the gastric residence system.

Provided herein are arms of gastric residence systems and segments for use in gastric residence systems, in which the arms and segments of the arms have controlled stiffness to help prevent early passage of the gastric residence system through the pylorus.

It has been determined that some gastric residence systems having relatively stiff arms can bend into configurations that allow for premature passage through the pylorus of a patient. Gastric residence systems that prematurely pass through the pylorus fail to deliver the therapeutic agent of the gastric residence system to the patient as intended. Further, premature passage can cause inconsistency, causes unreliability, and compromises the efficacy of the gastric residence system. FIGS. 24 and 25A-25C, described below, illustrate the issues posed by gastric residence systems having relatively stiff arms.

Figure 24:
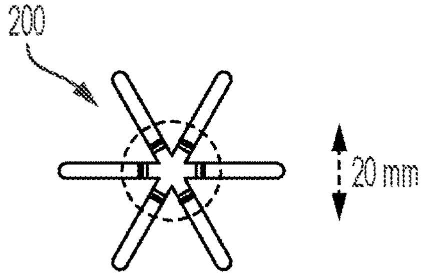
FIG. 24 shows a gastric residence system in an open configuration, according to some embodiments.

FIG. 24 shows gastric residence system 200 having relatively stiff arms. As shown, gastric residence system 200 comprises a central core and a plurality of arms extending radially from the central core. The dashed circle shown encircling the central core represents the approximate maximum opening size of the pylorus in an adult human (i.e., 20 mm). Gastric residence system 200 is designed to prevent premature passage through the pylorus when in an open configuration. As shown, the width (or diameter) of gastric residence system 200, as measured from the distal end of one arm, passing through the central core, and to the distal end of another arm, is at least twice that of the diameter of the pyloric opening.

Figure 25A:
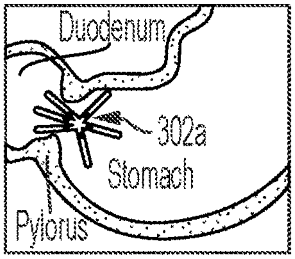
FIG. 25A, FIG. 25B, and FIG. 25C show various methods by which a gastric residence system may pass through a pylorus prior to dissolving, according to some embodiments.

Though the gastric residence system of FIG. 24 is sufficiently larger than the pyloric opening, it has been shown that it can bend into configurations small enough to prematurely pass through the pylorus. FIGS. 25A-3C show three different configurations that a gastric residence system may assume that can allow for premature passage through the pylorus. As shown in each Figure, the stiff arms of the gastric residence system remain straight. However, because the core of each of the gastric residence systems has a greater flexibility/elasticity than the stiff arms, the core can bend. The length of the stiff arm provides a lever arm that transfers forces of stomach contractions to the core. Longer stiff arms provide greater mechanical advantage and allow the core to bend under less force. The bending of the core can allow gastric residence systems having stiff arms to prematurely pass through the pylorus of a patient.

Figure 25B:
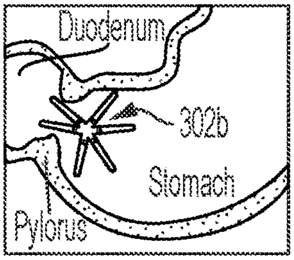
Figure 25C:
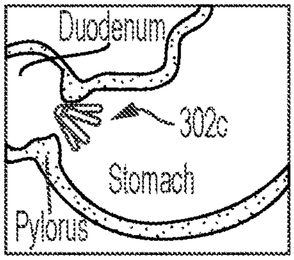

As shown in FIG. 25A, gastric residence system 302*a* is shown in a bended configuration having three stiff arms leading through the pyloric opening. FIG. 25B shows gastric residence system 302*b* in a bending configuration having two stiff arms leading through the pyloric opening. FIG. 25C shows gastric residence system 302*c* in a bended configuration analogous to the shape of a shuttlecock and having the core leading through the pyloric opening.

When a force is applied to an arm of a gastric residence system comprising relatively stiff material throughout the length of each arm, the force is transferred to the core of the gastric residence system. Because the core of the gastric residence system has a greater flexibility than the relatively stiff arms, the core bends or contorts under the force.

Accordingly, described herein are gastric residence systems comprising segments of arms having controlled stiffness. A gastric residence system comprising a first segment that is relatively stiffer than a second segment may help prevent gastric forces from being able to compress the gastric residence system into a configuration that may allow for premature passage through the pylorus. Arms, segments of arms, and gastric residence systems comprising arms and segments of arms are described in more detail with respect to the arms and coupling polymers of a gastric residence system.

In some embodiments, a gastric residence system may comprise arms that have both a first segment and a second segment. For example, the first segment may be located at a proximal end of an arm (i.e., proximate to the core of the gastric residence system) and the second segment may be located at a distal end of an arm. In some embodiments, the first segment may have a stiffness that is greater than a stiffness of a second segment. In some embodiments, an entire arm may comprise a single material of different durometers. For example, the arm material at the proximal end may comprise a higher durometer than the arm material at the distal end of the arm. In some embodiments, the stiff portion of an arm may comprise a first material, and the flexible portion of the arm may comprise a second material, wherein the first material has a higher durometer than the second material. In some embodiments, an arm of a gastric residence dosage form may comprise a single material having a constant stiffness throughout the length of the arm. In some embodiments, the thickness of an arm, or the cross-sectional area of the arm, may be less towards a distal end of the arm as compared to the proximal end of the arm.

As described herein, flexible arms for gastric residence systems having flexible arms may comprise two portions—a first segment comprising a first polymer composition and a second segment comprising a second polymer composition.

In some embodiments, the first segment may be welded to the second segment. In some embodiments, the arm may be extruded or prepared using injection molding.

Described herein are gastric residence systems having controlled stiffness. By controlling the stiffness of an element of a gastric residence system that widens/enlarges the device to its open configuration (such as an arm), the risk of premature passage of the gastric residence system through the pylorus may be minimized. Accordingly, gastric residence systems having arms of controlled stiffness described herein can help improve the efficacy and reliability of gastric residence systems. Additionally, gastric residence systems having arms of controlled stiffness as described herein can help prevent the gastric residence system from bending into configurations that allow for premature passage through the pylorus.

Gastric residence systems having arms of controlled stiffness require more force for the gastric residence system to bend into configurations suitable for premature passage through the pylorus. Described herein are gastric residence systems having controlled stiffness of any member that can widen or enlarge the gastric residence system into its open configuration (such as an arm) to help minimize the risk of the gastric residence system passing through the pylorus of a patient prematurely.

As described herein, a gastric residence system having arms of a controlled stiffness is defined as a system comprising one or more arms having at least a portion of the arm made of a flexible material. In some embodiments, one or more arms may include a first segment comprising a first polymer composition and a second segment comprising a second polymer composition, wherein the second segment is more flexible than the first segment.

In some embodiments, the one or more arms extend radially. A proximal end of the one or more arms may be connected to a core. In some embodiments, a gastric residence system may include a plurality of arms extending radially. In some embodiments, a gastric residence system may include a plurality of arms connected to a core at the proximal end of each arm, the plurality of arms extending radially from the core. In some embodiments, a gastric residence system may comprise a plurality of arms, each arm comprising a first segment and a second segment.

The first polymer composition of a flexible arm of a gastric residence system disclosed herein may comprise a relatively stiff polymer. For example, suitable polymers may include polycaprolactone, polylactic acid, poly(lactic-co-glycolic acid), HPMCAS, high durometer TPU, and/or combinations thereof. Other examples may include hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly (vinyl pyrrolidone), ethylene/vinyl alcohol copolymer, poly (vinyl alcohol), carboxyvinyl polymer (Carbomer), Carbopol® acidic carboxy polymer, polycarbophil, poly (ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), polymethacrylates/polyethacrylates such as poly(methacrylic acid), methylmethacrylates, and ethyl acrylates, polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly (ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. In some embodiments, the first segment may also comprise one or more therapeutic agent or active pharmaceutical ingredients (APIs).

In some embodiments, the first polymer composition may comprise 10-90 wt. % or 50-70 wt. % polycaprolactone. In some embodiments, the first polymer composition may comprise less than 90 wt. %, less than 80 wt. %, less than 70 wt. %, less than 60 wt. %, less than 50 wt. %, less than 40 wt. %, less than 30 wt. %, or less than 20 wt. % polycaprolactone. In some embodiments, the first polymer composition may include more than 20 wt. %, more than 30 wt. %, more than 40 wt. %, more than 50 wt. %, more than 60 wt. %, more than 70 wt. %, or more than 80 wt. % polycaprolactone.

In some embodiments, the first polymer composition may comprise 10-90 wt. % or 30-70 wt. % therapeutic agent or API. In some embodiments, the first polymer composition may comprise less than 90 wt. %, less than 80 wt. %, less than 70 wt. %, less than 60 wt. %, less than 50 wt. %, less than 40 wt. %, less than 30 wt. %, or less than 20 wt. % therapeutic agent or API. In some embodiments, the first polymer composition may include more than 20 wt. %, more than 30 wt. %, more than 40 wt. %, more than 50 wt. %, more than 60 wt. %, more than 70 wt. %, or more than 80 wt. % therapeutic agent or API.

The second polymer composition of an arm of a gastric residence system disclosed herein may comprise a primary polymer that is flexible relative to the polymer of the first polymer composition. For example, suitable relatively "flexible" polymers may include one or more of a polyurethane, a polyether-polyamide copolymer, a thermoplastic elastomer, a thermoplastic polyurethane, polycaprolactone polylactic acid copolymer, a poly(trimethylene carbonate), a polyglycerol sebacate, a polyethylene-co-vinyl acetate, and a silicone. In some embodiments, the second polymer composition of an arm may actually comprise the same primary polymer as the first polymer composition. For example, the second polymer composition may comprise polycaprolactone. However, unlike the first polymer composition, the second polymer composition may additionally comprise a soluble material (e.g., copovidone, poloxamers). Thus, upon hydration (e.g., within the stomach), the second polymer composition will soften such that the stiffness of the second polymer composition of the second segment is less than the first polymer composition of the first segment. Suitable polymers may include customizable thermoplastic polyurethanes with durometer range from 62 A to 83 D, such as Pathway™ TPU polymers (The Lubrizol Corporation); aliphatic polyether-based thermoplastic polyurethanes, such as Tecoflex™ (The Lubrizol Corporation); aliphatic, hydrophilic polyether-based resin, such as Tecophilic™ (The Lubrizol Corporation); aliphatic and aromatic, polycarbonate-based thermoplastic polyurethanes, such as Carbothane™ (The Lubrizol Corporation); hard and high flexural modulus polyurethane engineering resins, such as Isoplast® (The Lubrizol Corporation); elastomers, such as block copolymers made up of rigid polyamide blocks and soft polyether blocks, such as Pebax® (Arkema); thermoplastic polyurethanes with hardness from 60 A to 85 D, such as Texin® (Covestro); biodurable aromatic polycarbonate-based thermoplastic urethanes, such as Chronoflex (AdvanSource Biomaterials); translucent, ultra-soft polyether or polyester-based TPU blends, such as NEUSoft™ (PolyOne); thermoplastic polyurethanes with hardness from 30 to 90 Shore A, such as Medalist® TPEs (Teknor Apex). Suitable commercially-available polymers may include Pathway™ TPU polymers (The Lubrizol Corporation), Tecoflex™ (The Lubrizol Corporation), Tecophilic™ (The Lubrizol Corporation), Carbothane™ (The Lubrizol Corporation), Isoplast® (The Lubrizol Corporation), Pebax® (Arkema), Texin® (Covestro), Chronoflex (AdvanSource Biomaterials), NEUSoft™ (PolyOne), and Medalist® TPEs (Teknor Apex). Additional polymers include thermoplastic polyurethanes, polyether polyamides, vinyl acetates, styrenics, thermoplastic silicone copolymers, thermoplastic vulcanizates, liquid silicone rubber, poly(ethylene-co-vinyl acetate), and bioresorbable polymers. Bioresorbable polymers include, but are not limited to, polycaprolactone-polygylicolide copolymer, poly(glycerol sebacate), and poly(glycerol sebacate) polyurethane.

In some embodiments, the second polymer composition may comprise 10-90 wt. % or 40-70 wt. % primary polymer. In some embodiments, the second polymer composition may comprise less than 90 wt. %, less than 80 wt. %, less than 70 wt. %, less than 60 wt. %, less than 50 wt. %, less than 40 wt. %, less than 30 wt. %, or less than 20 wt. % primary polymer. In some embodiments, the second polymer composition may include more than 20 wt. %, more than 30 wt. %, more than 40 wt. %, more than 50 wt. %, more than 60 wt. %, more than 70 wt. %, or more than 80 wt. % primary polymer.

In some embodiments, the second polymer composition may additionally include one or more water-soluble excipients (which may include one or more polymers to the primary polymer described previously). For example, suitable water-soluble excipients may include a copovidone, a poloxamer, and/or a polyethylene oxide. Suitable commercially-available water-soluble excipients can include Kolliphor P407 (poloxamer 407, poly(ethylene glycol)-block-poly(propylene glycol)-block-poly(ethylene glycol)), PEG-PCL, SIF (FaSSIF/FaSSGF powder from BioRelevant), EPO (dimethylaminoethyl methacrylate-butyl methacrylate-methyl methacrylate copolymer), Kollidon VA64 (vinylpyrrolidone-vinyl acetate copolymer in a ratio of 6:4 by mass), polyvinyl pyrrolidine.

The second polymer composition may comprise 5-70 wt. % or 10-40 wt. % water-soluble excipients. In some embodiments, the second polymer composition may comprise less than 70 wt. %, less than 60 wt. %, less than 50 wt. %, less than 40 wt. %, less than 30 wt. %, less than 20 wt. %, or less than 10 wt. % water-soluble excipients. In some embodiments, the second polymer composition may comprise more than 5 wt. %, more than 10 wt. %, more than 20 wt. %, more than 30 wt. %, more than 40 wt. %, more than 50 wt. %, or more than 60 wt. % water-soluble excipients.

In some embodiments, the second polymer composition may comprise additional excipients. For example, the second polymer composition may comprise bismuth subcarbonate, silica, vitamin E succinate, iron oxide, a polyethylene glycol, polyvinyl acetate and polyvinylcaprolactame-based graft copolymer (Soluplus®), sodium starch glycolate, and/or hydroxypropyl cellulose. In some embodiments, the second polymer composition may comprise 10-70 wt. % or 20-50 wt. % excipients. In some embodiments, the second polymer composition may comprise less than 70 wt. %, less than 60 wt. %, less than 50 wt. %, less than 40 wt. %, less than 30 wt. %, or less than 20 wt. % excipients. In some embodiments, the second polymer composition may comprise more than 10 wt. %, more than 20 wt. %, more than 30 wt. %, more than 40 wt. %, more than 50 wt. %, or more than 60 wt. % excipients.

In some embodiments, the second polymer composition may additionally comprise a therapeutic agent or API. The second polymer composition may comprise 20-80 wt. % or 40-60 wt. % Therapeutic agent or API. In some embodiments, the second polymer composition may comprise less than 80 wt. %, less than 70 wt. %, less than 60 wt. %, less than 50 wt. %, less than 40 wt. %, or less than 30 wt. % therapeutic agent or API. In some embodiments, the second polymer composition may comprise more than 20 wt. %, more than 30 wt. %, more than 40 wt. %, more than 50 wt. %, more than 60 wt. %, or more than 70 wt. % therapeutic agent or API.

Some polymer materials that are useful for creating arms of controlled stiffness may have an added advantage in thermal stability. For example, gastric residence systems may experience temperature variation during shipping and distribution. Shipping data suggest that cargo temperature extremes may approach 60° C. in some climates (Singh et al, Packag. Technol. Sci. 2012; 25: 149-160). The polymers that comprise gastric residence systems should be physically stable at this temperature if they are to be shipped without cold chain packaging and storage.

Polycaprolactone is a preferred polymer for relatively stiff arms (or stiff/first segments), and thermoplastic polyurethane is a preferred polymer for creating arms of controlled stiffness (i.e., second segments). Polycaprolactone-based arms are physically stable when exposed to temperatures as high as 55° C., but melt if they reach 60° C. When stored in a capsule, arms that begin to melt can adhere to one another and prevent the gastric residence system from unfolding in the stomach. Suitable polymers may include customizable thermoplastic polyurethanes with durometer range from 62 A to 83 D, such as Pathway™ TPU polymers (The Lubrizol Corporation). Thermoplastic polyurethanes such as Pathway PY-PT72AE provide improved thermal stability. Pathway PY-PT72AE is an amorphous material that does not undergo a clear melt transition but does soften at elevated temperatures.

Figure 26A:
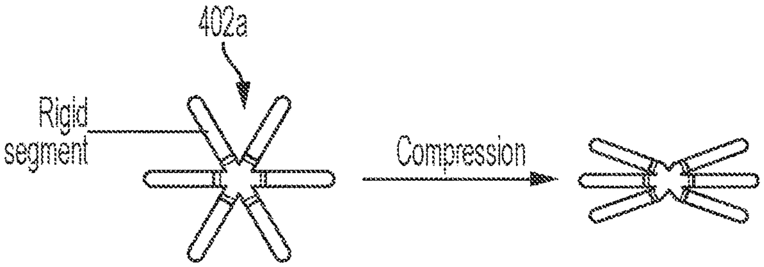
FIG. 26A and FIG. 26B show how the bending profile of a gastric residence system can be altered by modifying the stiffness of the arms of a gastric residence system, according to some embodiments.
Figure 26B:
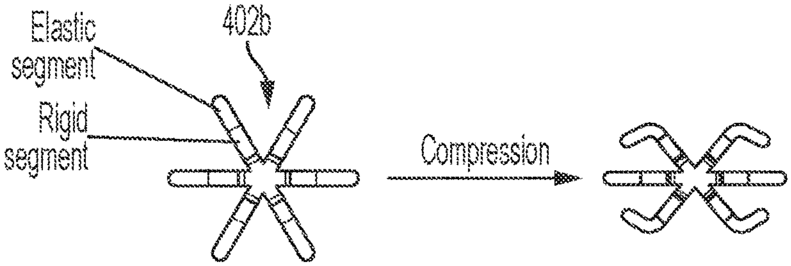

FIGS. 26A and 26B show the response of a gastric residence system comprising relatively stiff arms compared to a gastric residence system comprising relatively flexible arms (as disclosed herein) when subjected to a radial force compression test. Gastric residence system 402*a* comprises relatively stiff arms. When compressed, the compression force is transferred to the more flexible core of gastric residence system 402*a*, resulting in a gastric residence system in a bended configuration that is capable of passing through the pylorus of a patient (i.e., an opening having a diameter of 20 mm).

Conversely, FIG. 26B shows the behavior of gastric residence system 402*b* (having relatively flexible arms) when subjected to a radial force compression test. First segment 404, at a proximal end, is stiffer than second segment 406, at a distal end, of each arm. As shown in the figure, when compressed, second segment 406 absorbs some of the compression force. Thus, the compression forces are not transferred to the core of gastric residence system 402*b* as is the case with gastric residence system 402*a* of FIG. 26A. To compress the stiff inner segments of the arms to pyloric size, greater force is required due to the shorter lever arm attached to the flexible core. This can mean that gastric residence system 402*b* requires a greater compression force to bend it into a configuration small enough to pass through the pylorus of a patient (i.e., an opening having a diameter of 20 mm). Accordingly, gastric residence system 402*b* can more easily resist premature passage through the pylorus of a patient than gastric residence system 402*a*.

Figure 27A:
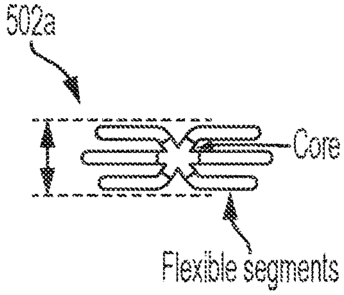
FIG. 27A, FIG. 27B, and FIG. 27C shows various gastric residence system bending profiles, according to some embodiments.
Figure 27B:
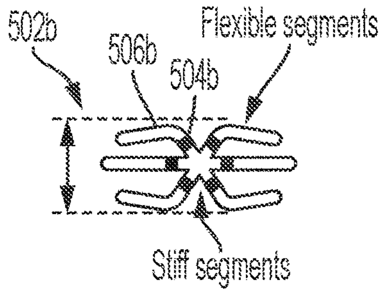
Figure 27C:
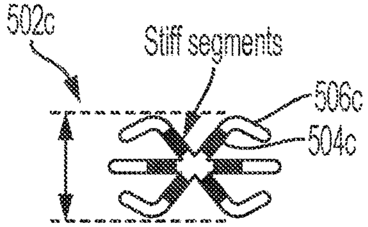

FIGS. 27A-27C show various configurations of gastric residence systems described herein. In particular, the relative sizes of the first segment compared to the second segment of a flexible arm may be varied. As shown in the figures, as the second segment increases, so too does the compression force required to compress the gastric residence system into a bended configuration small enough to pass through a pylorus (i.e., an opening having a diameter of 20 mm). (As long as the size of the stiff inner portion and the core is still larger than the diameter of the pylorus.) It may be assumed that the compression force applied to each gastric residence system of FIGS. 27A, 27B, and 27C is the same.

FIG. 27A shows gastric residence system 502*a* having arms comprising relatively flexible material the full length of each arm (e.g., arms comprising only a second segment, and no first segment). As shown, the compression force applied to gastric residence system 502*a* compresses the system to the shortest height of the three gastric residence systems depicted in FIGS. 27A-27C. Gastric residence system 502*a* will more easily pass through the pylorus than a stellate with fully stiff arms (i.e., comprising only a first segment). Thus, arms having only a second, flexible material are not effective at preventing premature passage through the pylorus.

The benefit of the second, relatively flexible, portion comes in when the innermost sections of the arms are relatively stiff. The second segment of the arms bends relatively easily, but more force is required to compress the inner first segments. If the stiff sections are too short, the bending of the second segments will make the gastric residence system small enough to pass through the pylorus.

FIG. 27B shows gastric residence system 502*b* having a first segment 504*b* and a second segment 506*b*. As shown, the second segment is larger than the first segment. The second segment is able to absorb some of the compression force applied to gastric residence system 502*a*, and more force is required to compress the first portion of the arms, preventing it from bending to the extent gastric residence system 502*a* bends in FIG. 27A.

FIG. 27C shows gastric residence system 502*c* having a first segment 504*c* and a second segment 506*c*. As shown, second segment 506*c* is smaller than second segment 506*b* of FIG. 5B. Thus, first segment 506*c* is larger than first segment 506*b* of FIG. 27B. Like gastric residence system 502*b* of FIG. 27B, second segment 504*c* absorbs some of the compression forces applied to gastric residence system 502*c*, preventing it from bending to the extent gastric residence system 502*a* bends in FIG. 27A. Additionally, gastric residence system 502*c* is compressed less than gastric residence system 502*b* of FIG. 27B.

The ratio of the first segment of a relatively flexible arm to the second segment of the arm may vary. If the first segment is too large in comparison to the second segment, the compression forces may transfer to the core of a gastric residence system too early, allowing the compression forces to compress the gastric residence system into a bended configuration small enough to prematurely pass through a pylorus. If the second segment is too large compared to the first segment, the second segment may too easily bend under the compression forces, allowing the forces to compress the gastric residence system into a bended configuration small enough to prematurely pass through a pylorus. Both scenarios result in a gastric residence system that is not as effective at resisting premature passage through the pylorus as desired.

An effective ratio of the first segment to the second segment of a flexible arm of a gastric residence system may vary. In some embodiments, the first segment may comprise from 10-90% of a length of an arm (as measured from the proximal end to the distal end). In some embodiments, the first segment may comprise less than 90%, less than 80%, less than 70%, less than 60%, less than 50%, less than 40%, less than 30%, or less than 20% of a length of an arm. In some embodiments, the first segment may comprise more than 10%, more than 20%, more than 30%, more than 40%, more than 50%, more than 60%, more than 70%, or more than 80% of a length of an arm. In some embodiments, the second segment may comprise from 10-90% of a length of an arm (as measured from the proximal end to the distal end). In some embodiments, the second segment may comprise less than 90%, less than 80%, less than 70%, less than 60%, less than 50%, less than 40%, less than 30%, or less than 20% of a length of an arm. In some embodiments, the second segment may comprise more than 10%, more than 20%, more than 30%, more than 40%, more than 50%, more than 60%, more than 70%, or more than 80% of a length of an arm.

Exemplary formulations of a flexible carrier polymer-agent arm segment are provided in the table below (provided as approximate weight percentages, with the understanding that the sum of all components equals 100%). These formulations can be used with any of the agents disclosed herein, such as dapagliflozin.

| Component | Formulation 1 | Formulation 2 | Formulation 3 |
|---|---|---|---|
| Agent | 10-30 | 15-25 | 20 |
| TPU | 40-60 | 45-55 | 49 |
| Copovidone | 10-30 | 15-25 | 20 |
| Poly-D,L-lactide | 5-15 | 7.5-12.5 | 10 |
| Vitamin E succinate | 0.1-2 | 0.3-0.7 | 0.5 |
| Colloidal $SiO_2$ | 0.1-2 | 0.3-0.7 | 0.5 |

III. Timed Linkers and Enteric Linkers

The timed linkers and enteric linkers in this Feature III of the disclosure provide precise control over the residence time of the gastric residence systems.

Figure 41A:
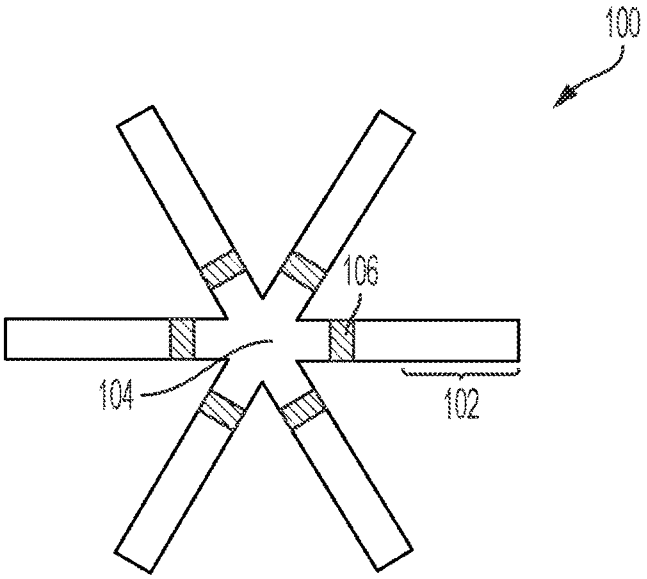
FIG. 41A shows an exemplary stellate configuration of a gastric residence system described herein.

Gastric residence systems can be prepared in different configurations. The "stellate" configuration of a gastric residence system is also known as a "star" (or "asterisk") configuration. An example of a stellate system 100 is shown schematically in FIG. 41A. Multiple arms (which may also be referred to as "elongate members") (only one such arms, 102, is labeled for clarity), are affixed to a second structural member, namely a central elastomer 104. The arms 102 are joined to the central elastomer 104 through a polymeric linker 106 (again, only one polymeric linker is labeled for clarity) which serves as a linker region. The polymeric linkers 106 may be enteric linkers or time-dependent linkers, or may have both properties (i.e., are both time-dependent and enteric). This configuration permits the system to be folded or compacted at the central elastomer. When folded, the overall length of the system is reduced by approximately a factor of two, and the system can be conveniently placed in a container such as a capsule or other container suitable for oral administration. When the capsule reaches the stomach, the capsule dissolves, releasing the gastric residence system. The gastric residence system then unfolds into its uncompacted state, which is retained in the stomach for the desired residence period.

Figure 41B:
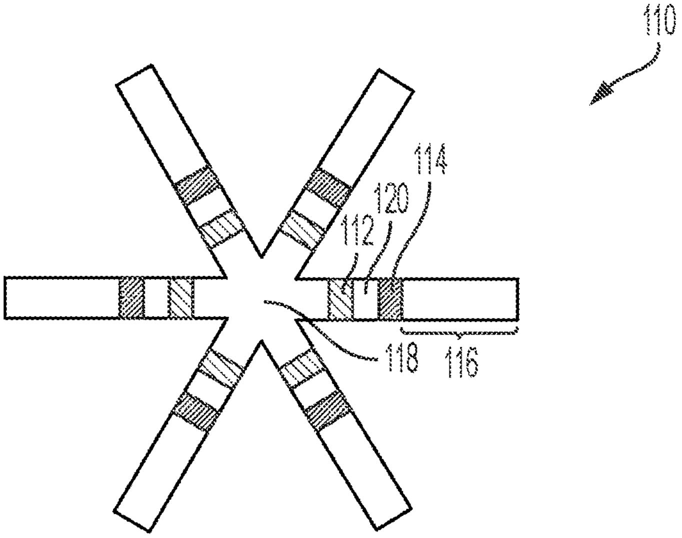
FIG. 41B shows another exemplary stellate configuration of a gastric residence system described herein.

FIG. 41B shows another embodiment of a stellate system 110 with two polymeric linkers 112 and 114 joining the arms 116 to the central member 118. The two polymeric linkers may be directly joined together, or may each be directly joined to a coupling member 120 separating the first polymeric linker 112 and the second polymeric linker 114, as shown. A first polymeric linker 112 proximal to the central member 118 may be an enteric linker, and the second polymeric linker 114 distal from the central member 118 may be a time-dependent linker. Alternatively, the first polymeric linker 112 proximal to the central member 118 may be a time-dependent linker, and the second polymeric linker 114 distal from the central member 118 may be an enteric linker. Multiple arms are affixed to and radially project from a central structural member 118.

A stellate system can be described as a gastric residence system for administration to the stomach of a patient, comprising an elastomer component, and a plurality of at least three carrier polymer-agent components (i.e., "arms" or "elongate members") comprising a carrier polymer and an agent or a salt thereof, attached to the elastomer component, wherein each of the plurality of carrier polymer-agent components is an arm comprising a proximal end and a distal end; wherein the proximal end of each arm is attached to the elastomer component through one or more polymeric linkers and projects radially from the elastomer component, each arm having its distal end not attached to the elastomer component and located at a larger radial distance from the elastomer component than the proximal end. The polymeric linker may be an enteric linker or a time-dependent linker. The arm can be attached to the central elastomer via a one or the polymeric linker or through an additional interfacing polymeric segment. In the stellate configuration, the gastric residence system may have two, three, four, five, six seven, eight, nine, or ten, or more arms. The arms may be equally spaced around the central elastomer; if there are N arms, there will be an angle of about 360/N degrees between neighboring arms.

Figure 41C:
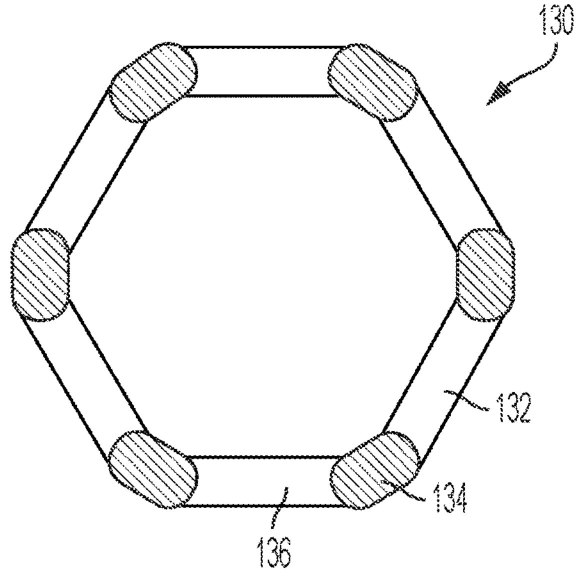
FIG. 41C shows an exemplary ring configuration of a gastric residence system described herein.

FIG. 41C shows another possible overall configuration for a gastric residence system 130 in a ring configuration. A first arm 132 is joined to a second elongate segment 136 through a polymeric linkers 134. The second arm may be, for example, an elastomeric member, which allows the ring-shaped system to be configured in a compacted state.

Figure 41D:
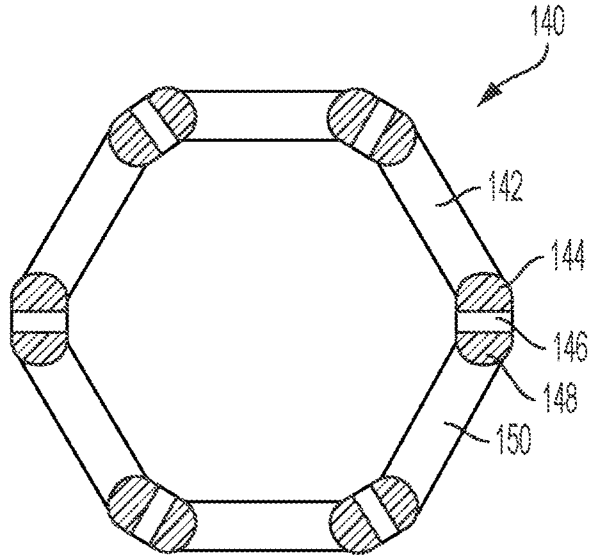
FIG. 41D shows another exemplary ring configuration of a gastric residence system described herein.

FIG. 41D shows another gastric residence system 140 in a ring configuration. The system 140 includes an arm 142 attached to another arm 150 (and so forth around the ring structure), through a first polymeric linker 144 and a second polymeric linker 148. The first polymeric linker 144 and the second polymeric linker 148 may be directly joined to each other, or may be joined through a coupling member 146. Arm 150 may be the same as arm 142, or may be different. For example, arm 142 may include a carrier polymer and an agent, while arm 150 is an elastomeric member that allows the ring to be configured in a compacted state. In another example, the coupling member 146 may be an elastomeric member, which allows the ring to be configured in a compacted state.

Figure 42A:
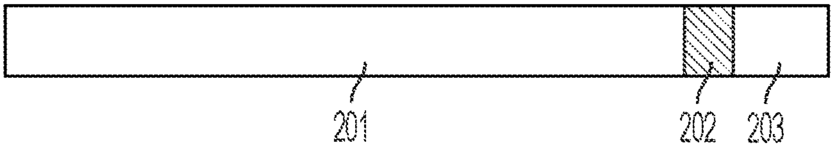
FIG. 42A shows a portion of a gastric residence system that includes an exemplary configuration of a structural member attached to a second structural member through a polymeric linker.

FIGS. 42A-2K illustrate exemplary configurations for attaching a first structural member (such as an arm, which may include an agent and a carrier polymer) to a second structural member (for example, an elastomeric member, such as a central member in a stellate configuration). As further described, the exemplary configurations may include one or two polymeric linkers, and may include zero, one, two, or three coupling members. Further, the arm may include one or more segments, which may include active segments or inactive segments.

FIG. 42A shows a portion of a gastric residence system that includes an arm 201, which is directly attached to polymeric linker 202 (which may be an enteric linker, a time-dependent linker, or a dual time-dependent and enteric linker), which is directly attached to a second structural member 203 (such as a central member or central elastomeric member). The arm 201 can include a carrier polymer and an agent. In some embodiments, the polymeric linker 202 includes the same carrier polymer or same type of carrier polymer as the arm 201.

Figure 42B:
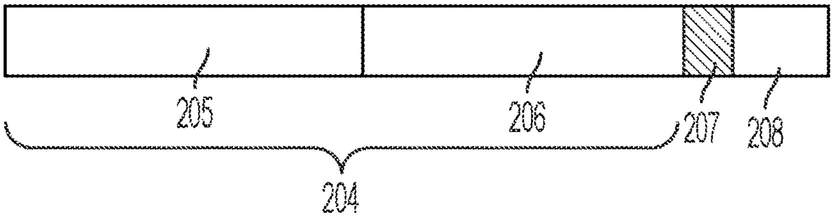
FIG. 42B shows a portion of a gastric residence system that includes another exemplary configuration of a structural member attached to a second structural member through a polymeric linker.

FIG. 42B shows a portion of a gastric residence system that includes an arm 204, which includes an active segment 205 containing an agent and a carrier polymer and an inactive segment 206 containing the carrier polymer but is substantially free of the agent. The arm 204 is attached to a second structural member 208 (such as a central member, or central elastomeric member) through a polymeric linker 207 (which may be an enteric linker, a time-dependent linker, or a dual time-dependent and enteric linker). The active segment 205 is distal to the polymeric linker 207, and the inactive segment 206 is proximal to and directly attached to the polymeric linker 207, and the polymeric linker 207 is directly attached to the second structural member 208. In some embodiments, the polymeric linker 207 includes the same carrier polymer or same type of carrier polymer as the inactive segment 206.

Figure 42C:
FIG. 42C shows a portion of a gastric residence system that includes another exemplary configuration of a structural member attached to a second structural member through a polymeric linker.

FIG. 42C shows a portion of a gastric residence system that includes an arm 209, which is directly attached to polymeric linker 210 (which may be an enteric linker, a time-dependent linker, or a dual time-dependent and enteric linker), which is directly attached to a coupling member 211, which is directly attached to second structural member 212 (such as a central member or central elastomeric member). The arm 209 can include a carrier polymer and an agent. In some embodiments, the polymeric linker 210 includes the same carrier polymer or same type of carrier polymer as the arm 209. In some embodiments, the coupling member 211 and the polymeric linker 210 include the same carrier polymer or the same type of carrier polymer as the arm 209.

Figure 42D:
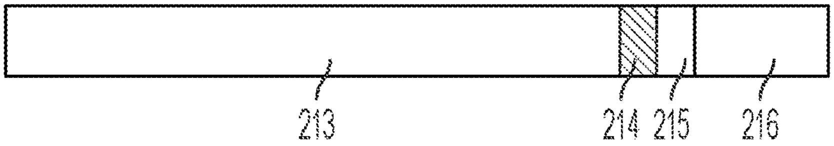
FIG. 42D shows a portion of a gastric residence system that includes an exemplary configuration of a structural member attached to a second structural member through two polymeric linkers.

FIG. 42D shows a portion of a gastric residence system that includes an arm 213, which is directly attached to a first polymeric linker 214 (which may be an enteric linker or a time-dependent linker), which is directly attached to a second polymeric linker 215 (which is an enteric linker if first polymeric linker 214 is a time-dependent linker, or a time-dependent linker if first polymeric linker 214 is an enteric linker), which is directly attached to second structural member 216 (such as a central member or central elastomeric member). The arm 213 can include a carrier polymer and an agent. In some embodiments, the first polymeric linker 214 includes the same carrier polymer or same type of carrier polymer as the arm 213. In some embodiments, the first polymeric linker 214 and the second polymeric linker 215 include the same carrier polymer or the same type of carrier polymer as the arm 213.

Figure 42E:
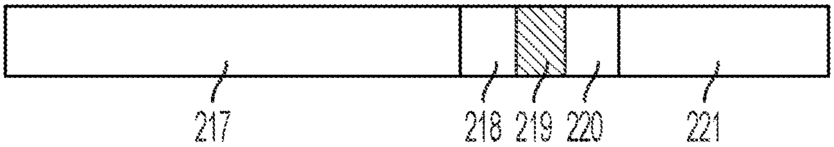
FIG. 42E shows a portion of a gastric residence system that includes another exemplary configuration of a structural member attached to a second structural member through two polymeric linkers.

FIG. 42E shows a portion of a gastric residence system that includes an arm 217, which is directly attached to a coupling member 218, which is directly attached to a first polymeric linker 219, which is directly attached to a second polymeric linker 220, which his directly attached to a second structural member 221. The arm 217 includes a carrier polymer and an agent. The first polymeric linker 219 may be an enteric linker or a time-dependent linker, and the second polymeric linker 220 may be a time-dependent linker (if the first polymeric linker 219 is an enteric linker) or an enteric linker (if the first polymeric linker 219 is a time-dependent linker). The second structural member 221 may be, for example, a central member (such as a central elastomeric member) of the gastric residence system. The coupling member 218 can include a carrier polymer (which may be the same or same type of carrier polymer in the arm 217), and the first polymeric linker 219 and/or the second polymeric linker 220 may include the same or same type of carrier polymer.

Figure 42F:
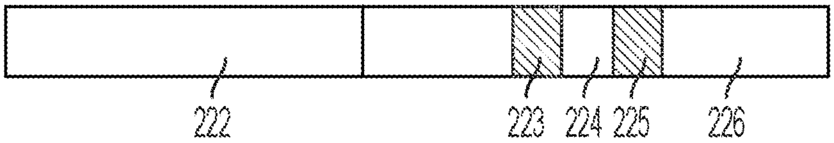
FIG. 42F shows a portion of a gastric residence system that includes another exemplary configuration of a structural member attached to a second structural member through two polymeric linkers.

FIG. 42F shows a portion of a gastric residence system that includes an arm 222, which is directly attached to a first polymeric linker 223, which is directly attached to a coupling member 224, which is directly attached to a second polymeric linker 225, which his directly attached to a second structural member 226. The arm 222 includes a carrier polymer and an agent. The first polymeric linker 223 may be an enteric linker or a time-dependent linker, and the second polymeric linker 225 may be a time-dependent linker (if the first polymeric linker 223 is an enteric linker) or an enteric linker (if the first polymeric linker 223 is a time-dependent linker). The second structural member 226 may be, for example, a central member (such as a central elastomeric member) of the gastric residence system. In some embodiments, the first polymeric linker 223 includes the same or same type of carrier polymer present in the arm 222. The coupling member 224 positioned between the first polymeric linker 223 and the second polymeric linker 225 can include a carrier polymer (which may be the same or same type of carrier polymer in the arm 222), and the first polymeric linker 223 and/or the second polymeric linker 225 may include the same or same type of carrier polymer as the coupling member 224.

Figure 42G:
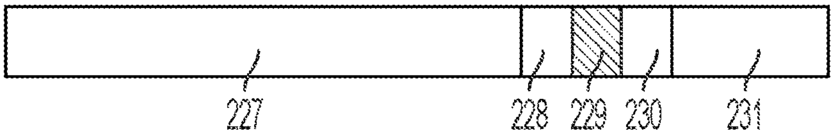
FIG. 42G shows a portion of a gastric residence system that includes another exemplary configuration of a structural member attached to a second structural member through two polymeric linkers.

FIG. 42G shows a portion of a gastric residence system that includes an arm 227, which is directly attached to a first polymeric linker 228, which is directly attached to a second polymeric linker 229, which is directly attached to a coupling member 230, which his directly attached to a second structural member 231. The arm 227 includes a carrier polymer and an agent. The first polymeric linker 228 may be an enteric linker or a time-dependent linker, and the second polymeric linker 229 may be a time-dependent linker (if the first polymeric linker 228 is an enteric linker) or an enteric linker (if the first polymeric linker 228 is a time-dependent linker). The second structural member 231 may be, for example, a central member (such as a central elastomeric member) of the gastric residence system. In some embodiments, the first polymeric linker 228 includes the same or same type of carrier polymer in the arm 227. The coupling member 230 can include a carrier polymer (which may be the same or same type of carrier polymer in the arm 227), and the first polymeric linker 228 and/or the second polymeric linker 229 may include the same or same type of carrier polymer as the coupling member 230.

Figure 42H:
FIG. 42H shows a portion of a gastric residence system that includes another exemplary configuration of a structural member attached to a second structural member through two polymeric linkers.

FIG. 42H shows a portion of a gastric residence system that includes an arm 232, which is directly attached to a first coupling member 233, which is directly attached to a first polymeric linker 234, which is directly attached to a second coupling member 235, which is directly attached to a second polymeric linker 236, which his directly attached to a second structural member 237. The arm 232 includes a carrier polymer and an agent. The first polymeric linker 234 may be an enteric linker or a time-dependent linker, and the second polymeric linker 236 may be a time-dependent linker (if the first polymeric linker 234 is an enteric linker) or an enteric linker (if the first polymeric linker 234 is a time-dependent linker). The second structural member 237 may be, for example, a central member (such as a central elastomeric member) of the gastric residence system. In some embodiments, the first polymeric linker 234 and/or the second polymeric linker 236 includes the same or same type of carrier polymer in the arm 232. In some embodiments, the first coupling member 233 and/or the second coupling member 235 can include a carrier polymer (which may be the same or same type of carrier polymer in the arm 232), and the first polymeric linker 234 and/or the second polymeric linker 236 may include the same or same type of carrier polymer as the first coupling member 233 and/or the second coupling member 235.

Figure 42I:
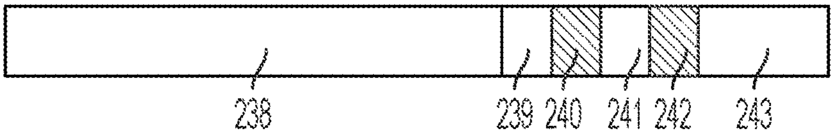
FIG. 42I shows a portion of a gastric residence system that includes another exemplary configuration of a structural member attached to a second structural member through two polymeric linkers.

FIG. 42I shows a portion of a gastric residence system that includes an arm 238, which is directly attached to a first coupling member 239, which is directly attached to a first polymeric linker 240, which is directly attached to a second polymeric linker 241, which is directly attached to a second coupling member 242, which his directly attached to a second structural member 243. The arm 238 includes a carrier polymer and an agent. The first polymeric linker 240 may be an enteric linker or a time-dependent linker, and the second polymeric linker 241 may be a time-dependent linker (if the first polymeric linker 240 is an enteric linker) or an enteric linker (if the first polymeric linker 240 is a time-dependent linker). The second structural member 243 may be, for example, a central member (such as a central elastomeric member) of the gastric residence system. In some embodiments, the first polymeric linker 240 and/or the second polymeric linker 241 includes the same or same type of carrier polymer in the arm 238. In some embodiments, the first coupling member 239 and/or the second coupling member 242 can include a carrier polymer (which may be the same or same type of carrier polymer in the arm 238), and the first polymeric linker 240 and/or the second polymeric linker 241 may include the same or same type of carrier polymer as the first coupling member 239 and/or the second coupling member 242.

Figure 42J:
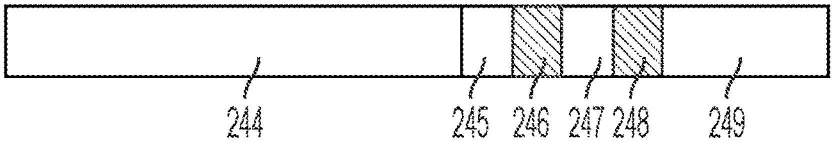
FIG. 42J shows a portion of a gastric residence system that includes another exemplary configuration of a structural member attached to a second structural member through two polymeric linkers.

FIG. 42J shows a portion of a gastric residence system that includes an arm 244, which is directly attached to a first polymeric linker 245, which is directly attached to a first coupling member 246, which is directly attached to a second polymeric linker 247, which is directly attached to a second coupling member 248, which his directly attached to a second structural member 249. The arm 244 includes a carrier polymer and an agent. The first polymeric linker 245 may be an enteric linker or a time-dependent linker, and the second polymeric linker 247 may be a time-dependent linker (if the first polymeric linker 245 is an enteric linker) or an enteric linker (if the first polymeric linker 245 is a time-dependent linker). The second structural member 249 may be, for example, a central member (such as a central elastomeric member) of the gastric residence system. In some embodiments, the first polymeric linker 245 and/or the second polymeric linker 247 includes the same or same type of carrier polymer in the arm 244. In some embodiments, the first coupling member 246 and/or the second coupling member 248 can include a carrier polymer (which may be the same or same type of carrier polymer in the arm 244), and the first polymeric linker 245 and/or the second polymeric linker 247 may include the same or same type of carrier polymer as the first coupling member 246 and/or the second coupling member 248.

Figure 42K:
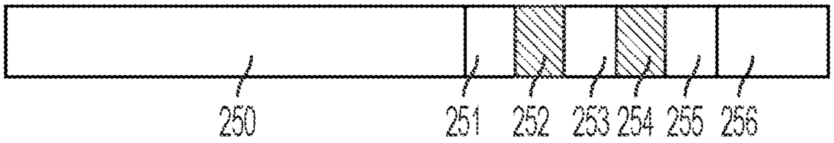
FIG. 42K shows a portion of a gastric residence system that includes another exemplary configuration of a structural member attached to a second structural member through two polymeric linkers.

FIG. 42K shows a portion of a gastric residence system that includes an arm 250, which is directly attached to a first coupling member 251, which is directly attached to a first polymeric linker 252, which is directly attached to a second coupling member 253, which is directly attached to a second polymeric linker 254, which is directly attached to a third coupling member 255, which his directly attached to a second structural member 256. The arm 250 includes a carrier polymer and an agent. The first polymeric linker 252 may be an enteric linker or a time-dependent linker, and the second polymeric linker 254 may be a time-dependent linker (if the first polymeric linker 252 is an enteric linker) or an enteric linker (if the first polymeric linker 252 is a time-dependent linker). The second structural member 256 may be, for example, a central member (such as a central elastomeric member) of the gastric residence system. In some embodiments, the first polymeric linker 252 and/or the second polymeric linker 254 includes the same or same type of carrier polymer in the arm 250. In some embodiments, the first coupling member 251 and/or the second coupling member 253 and/or the third coupling member 255 can include a carrier polymer (which may be the same or same type of carrier polymer in the arm 250), and the first polymeric linker 252 and/or the second polymeric linker 254 may include the same or same type of carrier polymer as the first coupling member 251 and/or the second coupling member 253 and/or the third coupling member 255.

Polymeric Linkers

The agent-containing structural members are attached to a second structural member (such as a central member, which may be an elastic central member) through one or more linkers. A polymeric linker may directly interface with the agent-containing structural member, or may interface with the agent-containing structural member through a coupling member. Similarly, the polymeric linker may interface directly with the second structural member, or may interface through a coupling member. In an embodiment wherein the agent-containing structural member is connected to the second structural member through two or more polymeric linkers, the polymeric linkers may directly interface with each other, or may interface through a coupling member. One or both of an enteric linker and a time-dependent linkers may be used, or a polymeric linker may function as both an enteric linker and a time-dependent linker.

The polymeric linkers are typically about 100 microns to about 3 millimeter in width, such as about 200 um to about 3000 um, about 300 um to about 3000 um, about 400 um to about 3000 um, about 500 um to about 3000 um, about 600 um to about 3000 um, about 700 um to about 3000 um, about 800 um to about 3000 um, about 900 um to about 3000 um, about 1000 um to about 3000 um, about 1100 um to about 3000 um, about 1200 um to about 3000 um, about 1300 um to about 3000 um, about 1400 um to about 3000 um, about 1500 um to about 3000 um, about 1600 um to about 3000 um, about 1700 um to about 3000 um, about 1800 um to about 3000 um, about 1900 um to about 3000 um, about 2000 um to about 3000 um, about 2100 um to about 3000 um, about 2200 um to about 3000 um, about 2300 um to about 3000 um, about 2400 um to about 3000 um, about 2500 um to about 3000 um, about 2600 um to about 3000 um, about 2700 um to about 3000 um, about 2800 um to about 3000 um, or about 2900 um to about 3000 um; or about 100 um to about 200 um, about 200 um to about 300 um, about 300 um to about 400 um, about 400 um to about 500 um, about 500 um to about 600 um, about 600 um to about 700 um, about 700 um to about 800 um, about 800 um to about 900 um, about 900 um to about 1000 um, about 1000 um to about 1100 um, about 1100 um to about 1200 um, about 1200 um to about 1300 um, about 1300 um to about 1400 um, about 1400 um to about 1500 um, about 1500 um to about 1600 um, about 1600 um to about 1700 um, about 1700 um to about 1800 um, about 1800 um to about 1900 um, about 1900 um to about 2000 um, about 2000 um to about 2100 um, about 2100 um to about 2200 um, about 2200 um to about 2300 um, about 2300 um to about 2400 um, about 2400 um to about 2500 um, about 2500 um to about 2600 um, about 2600 um to about 2700 um, about 2700 um to about 2800 um, about 2800 um to about 2900 um, about 2900 um to about 3000 um. Polymeric linkers can be about 100 um, about 200 um, about 300 um, about 400 um, about 500 um, about 600 um, about 700 um, about 800 um, about 900 um, about 1000 um, about 1100 um, about 1200 um, about 1300 um, about 1400 um, about 1500 um, about 1600 um, about 1700 um, about 1800 um, about 1900 um, about 2000 um, about 2100 um, about 2200 um, about 2300 um, about 2400 um, about 2500 um, about 2600 um, about 2700 um, about 2800 um, about 2900 um, about 3000 um in width, where each value can be plus or minus 50 um (±50 um).

The cross section of the polymeric linker may be round (i.e., circular), elliptical, triangular, square, rectangular, pentagonal, hexagonal, or any other polymeric shape. In some embodiments, the cross-section of the polymeric linker is the same shape as the cross-section of an agent-containing structural member attached to the polymeric linker. In some embodiments, the cross-section of the polymeric linker has a larger area than the cross-section of the agent-containing structural member, a smaller area than the cross-section of the agent-containing structural member, or approximately the same area as the cross-section of the attached agent-containing structural member.

Time-Dependent Disintegrating Matrices (Time-Dependent Linkers)

A time-dependent linker degrades in a predictable, time-dependent manner under aqueous conditions, such as when the gastric residence system is deployed in the stomach of an individual. The time-dependent polymeric linkers control the residence time of the gastric residence system in the stomach. The time-dependent polymeric linkers are designed to degrade, dissolve, mechanically weaken, or break gradually over time. After the desired residence period, the time-dependent polymeric linker has degraded, dissolved, disassociated, or mechanically weakened, or has broken, to the point where the gastric residence system can pass through the pyloric valve, exiting the gastric environment and entering the small intestine, for eventual elimination from the body.

The time-dependent polymeric linker preferably comprises a pH-independent degradable polymer, which degrades under aqueous conditions in a pH-independent or approximately pH-independent manner. Exemplary pH-independent degradable polymer include PLGA, PLA, PCL, polydioxanone, cellulose, or blends or copolymers thereof. In some embodiments, the pH-independent degradable polymer is PLGA. A pH-independent degradable polymer may be, for example, a polymer that has a flexural modulus after incubation in an aqueous solution, such as fasted state intestinal fluid (FaSSIF), at pH 6.5 for 3 days at 37° C. that is within 30%, within 20%, within 15%, within 10%, or within 5% of the flexural modulus after incubation in an aqueous solution, such as FaSSGF, at pH 1.6 for 3 days at 37° C. In some embodiments, the pH-independent degradable polymer has a flexural modulus after incubation in an aqueous solution, such as fasted state intestinal fluid (FaSSIF), at pH 6.5 for 5 days at 37° C. that is within 30%, within 20%, within 15%, within 10%, or within 5% of the flexural modulus after incubation in an aqueous solution, such as FaSSGF, at pH 1.6 for 5 days at 37° C. In some embodiments, the pH-independent degradable polymer has a flexural modulus after incubation in an aqueous solution, such as fasted state intestinal fluid (FaSSIF), at pH 6.5 for 7 days at 37° C. that is within 30%, within 20%, within 15%, within 10%, or within 5% of the flexural modulus after incubation in an aqueous solution, such as FaSSGF, at pH 1.6 for 7 days at 37° C. In some embodiments, the pH-independent degradable polymer has a flexural modulus after incubation in an aqueous solution, such as fasted state intestinal fluid (FaSSIF), at pH 6.5 for 10 days at 37° C. that is within 30%, within 20%, within 15%, within 10%, or within 5% of the flexural modulus after incubation in an aqueous solution, such as FaSSGF, at pH 1.6 for 10 days at 37° C. In some embodiments, the pH-independent degradable polymer has a flexural modulus after incubation in an aqueous solution, such as fasted state intestinal fluid (FaSSIF), at pH 6.5 for 14 days at 37° C. that is within 30%, within 20%, within 15%, within 10%, or within 5% of the flexural modulus after incubation in an aqueous solution, such as FaSSGF, at pH 1.6 for 14 days at 37° C. In some embodiments, the pH-independent degradable polymer has a flexural modulus after incubation in an aqueous solution, such as fasted state intestinal fluid (FaSSIF), at pH 6.5 for 18 days at 37° C. that is within 30%, within 20%, within 15%, within 10%, or within 5% of the flexural modulus after incubation in an aqueous solution, such as FaSSGF, at pH 1.6 for 18 days at 37° C. In some embodiments, the pH-independent degradable polymer has a flexural modulus after incubation in an aqueous solution, such as fasted state intestinal fluid (FaSSIF), at pH 6.5 for 18 days at 37° C. that is within 30%, within 20%, within 15%, within 10%, or within 5% of the flexural modulus after incubation in an aqueous solution, such as FaSSGF, at pH 1.6 for 21 days at 37° C. In some embodiments, the pH-independent degradable polymer has a flexural modulus after incubation in an aqueous solution, such as fasted state intestinal fluid (FaSSIF), at pH 6.5 for 18 days at 37° C. that is within 30%, within 20%, within 15%, within 10%, or within 5% of the flexural modulus after incubation in an aqueous solution, such as FaSSGF, at pH 1.6 for 28 days at 37° C.

Weakening or degradation of the time-dependent polymeric linker may be measured in references to a loss of the flexural modulus or breakage of the polymeric linker under a given condition (e.g., enteric conditions or gastric conditions). The time-dependent linkers weaken in the gastric environment over a selected gastric residence period, and become sufficiently weak or break such that the gastric residence system can exit the stomach. Stomach conditions may be simulated using an aqueous solution, such as a fasted state simulated gastric fluid (FaSSGF), at a pH of 1.6 and at 37° C. For example, in some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 3 days at 37° C. In some embodiments, the polymeric linker loses a about 60% or more, about 70% or more, about 80% or more, about 90% or more, about 95% or more, or about 99% or more of its flexural modulus or breaks after incubation in an aqueous solution, such as FaSSGF, at pH 1.6 for 5 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 7 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 10 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 14 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 18 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 21 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 24 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 30 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 45 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSGF, at pH 1.6 for 60 days at 37° C.

In certain gastric residence systems, sustained gastric retention is desired, and quick degradation of the time-dependent polymeric linker is less preferred. Accordingly, in some embodiments, the polymeric linker loses about 80% or less, about 70% or less, about 60% or less, about 50% or less, about 40% or less, or about 30% or less of its flexural modulus after incubation in an aqueous solution, such as FaSSGF, at pH 1.6 for 3 days at 37° C. In some embodiments, the polymeric linker loses about 80% or less, about 70% or less, about 60% or less, about 50% or less, about 40% or less, or about 30% or less or less of its flexural modulus after incubation in an aqueous solution, such as FaSSGF, at pH 1.6 for 5 days at 37° C. In some embodiments, the polymeric linker loses about 80% or less, about 70% or less, about 60% or less, about 50% or less, about 40% or less, or about 30% or less of its flexural modulus after incubation in an aqueous solution, such as FaSSGF, at pH 1.6 for 7 days at 37° C. In some embodiments, the polymeric linker loses about 80% or less, about 70% or less, about 60% or less, about 50% or less, about 40% or less, or about 30% or less of its flexural modulus after incubation in an aqueous solution, such as FaSSGF, at pH 1.6 for 10 days at 37° C. In some embodiments, the polymeric linker loses about 80% or less, about 70% or less, about 60% or less, about 50% or less, about 40% or less, or about 30% or less of its flexural modulus after incubation in an aqueous solution, such as FaSSGF, at pH 1.6 for 14 days at 37° C.

The degradation profile of the time-dependent polymeric linker may be configured based on the amount of time-dependent degradable polymer in the time-dependent polymeric linker. For example, a greater amount of poly(lactic-co-glycolide) (PLGA) may result in a greater loss of flexural modulus over an extended gastric residence period, but may retain sufficient structural integrity over a short period of time to retain the gastric residence system in the stomach. By way of example, in some embodiments, the polymeric linker loses about 80% or less, about 70% or less, about 60% or less, about 50% or less, about 40% or less, or about 30% or less of its flexural modulus after incubation in an aqueous solution, such as FaSSGF, at pH 1.6 for 3 days at 37° C., and loses about 60% or more, about 70% or more, about 80% or more, about 90% or more, about 95% or more, or about 99% or more of its flexural modulus or breaks after incubation in an aqueous solution, such as FaSSGF, at pH 1.6 for 7 days at 37° C.

In some embodiments, time-dependent polymeric linkers are pH-independent; that is, the polymeric linker degrades under aqueous conditions in a pH-independent or approximately pH-independent manner. A pH-independent time-dependent polymeric linker may be, for example a time-dependent polymeric linker that has a flexural modulus after incubation in an aqueous solution, such as fasted state intestinal fluid (FaSSIF), at pH 6.5 for 3 days at 37° C. that is within 30%, within 20%, within 15%, within 10%, or within 5% of the flexural modulus after incubation in an aqueous solution, such as FaSSGF, at pH 1.6 for 3 days at 37° C. In some embodiments, the pH-independent time-dependent polymeric linker has a flexural modulus after incubation in an aqueous solution, such as fasted state intestinal fluid (FaSSIF), at pH 6.5 for 5 days at 37° C. that is within 30%, within 20%, within 15%, within 10%, or within 5% of the flexural modulus after incubation in an aqueous solution, such as FaSSGF, at pH 1.6 for 5 days at 37° C. In some embodiments, the pH-independent time-dependent polymeric linker has a flexural modulus after incubation in an aqueous solution, such as fasted state intestinal fluid (FaSSIF), at pH 6.5 for 7 days at 37° C. that is within 30%, within 20%, within 15%, within 10%, or within 5% of the flexural modulus after incubation in an aqueous solution, such as FaSSGF, at pH 1.6 for 7 days at 37° C. In some embodiments, the pH-independent time-dependent polymeric linker has a flexural modulus after incubation in an aqueous solution, such as fasted state intestinal fluid (FaSSIF), at pH 6.5 for 10 days at 37° C. that is within 30%, within 20%, within 15%, within 10%, or within 5% of the flexural modulus after incubation in an aqueous solution, such as FaSSGF, at pH 1.6 for 10 days at 37° C. In some embodiments, the pH-independent time-dependent polymeric linker has a flexural modulus after incubation in an aqueous solution, such as fasted state intestinal fluid (FaSSIF), at pH 6.5 for 14 days at 37° C. that is within 30%, within 20%, within 15%, within 10%, or within 5% of the flexural modulus after incubation in an aqueous solution, such as FaSSGF, at pH 1.6 for 14 days at 37° C. In some embodiments, the pH-independent time-dependent polymeric linker has a flexural modulus after incubation in an aqueous solution, such as fasted state intestinal fluid (FaSSIF), at pH 6.5 for 18 days at 37° C. that is within 30%, within 20%, within 15%, within 10%, or within 5% of the flexural modulus after incubation in an aqueous solution, such as FaSSGF, at pH 1.6 for 18 days at 37° C.

In some embodiments, the time-dependent polymeric linker has an initial flexural modulus of about 100 MPa to about 2500 MPa, such as about 100 MPa to about 2500 MPa, such as about 100 MPa to about 250 MPa, about 250 MPa to about 500 MPa, about 500 mPa to about 750 MPa, about 750 MPa to about 1000 MPa, about 1000 MPa to about 1250 MPa, about 1250 MPa to about 1500 MPa, about 1500 MPa to about 2000 MPa, or about 2000 MPa to about 2500 MPa.

The time-dependent polymeric linker can include poly (lactic-co-glycolide) (PLGA) and at least one additional linker polymer, preferably homogenously mixed together. For example, the PLGA and the additional linker polymer may be homogenously blended together before the mixture is extruded, and the extruded material being cut to a desired size for the polymeric linker. As PLGA is degradable in an aqueous environment, the amount of PLGA in the polymeric linker can affect the time-dependent degradation profile of the polymeric linker, and thus the gastric residence period of the gastric residence system. A higher weight percentage of PLGA in the polymeric linker generally results in faster weakening or degradation of the polymeric linker in an aqueous (e.g., gastric) environment. Similarly, a lower weight percentage of PLGA results in a slower weakening or degradation of the polymeric linker in the aqueous environment. Any amount of PLGA may be used in the polymeric linker, with the amount selected based on the desired degradation profile. For example, in some embodiments, the time-dependent polymeric linker includes about 99% or less, about 98% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less (by weight) PLGA. In some embodiments, the time-dependent polymeric linker includes about 99% or more, about 98% or more, about 95% or more, about 90% or more, about 85% or more, about 80% or more, about 75% or more, about 70% or more, about 65% or more, about 60% or more, about 55% or more, about 50% or more, about 40% or more, about 30% or more, about 20% or more, or about 10% or more (by weight) PLGA. In some embodiments, the time-dependent polymeric linker includes about 0.1% to about 10% PLGA, about 10% to about 20% PLGA, about 20% to about 30% PLGA, about 30% to about 40% PLGA, about 40% to about 50% PLGA, about 50% to about 60% PLGA, about 60% to about 70% PLGA, about 70% to about 80% PLGA, about 80% to about 90% PLGA, or about 90% to about 99.9% PLGA. In some embodiments, the time-dependent polymeric linker includes about 30% PLGA or less. In some embodiments, the time-dependent polymer linker includes about 70% PLGA or more. In some embodiments, the time-dependent polymeric liker includes about 30% to about 70% PLGA.

The PLGA in the polymeric linker may include poly(D, L-lactic-co-glycolide) (PDLG), poly(D-lactic-co-glycolide), and/or poly(L-lactic-co-glycolide), although PDLG is preferred. The ratio of lactide monomers to glycolide monomers in the copolymer may range from about 5:95 to about 95:5, such as about 5:95 to about 10:90, about 10:90 to about 20:80, about 20:80 to about 35:65, about 35:65 to about 50:50, about 50:50 to about 65:35, about 65:35 to about 80:20, about 80:20 to about 90:10, or about 90:10 to about 95:5.

The molecular weight of the PLGA also affects the rate of polymer degradation, and thus the rate of loss of the flexural modulus, with higher molecular weight polymers degrading (and thus losing flexural modulus) more slowly. In some embodiments, the mass-weighted molecular weight ($M_w$) of the PLGA is about 5,000 Da to about 250,000 Da, such as about 5,000 Da to about 10,000 Da, about 10,000 to about 20,000 Da, about 20,000 Da to about 30,000 Da, about 30,000 Da to about 50,000 Da, about 50,000 Da to about 100,000 Da, about 100,000 Da to about 150,000 Da, about 150,000 Da to about 200,000 Da, or about 200,000 Da to about 250,000 Da. In some embodiments, the inherent viscosity (as measured in $CHCl_3$ at 25° C.) of the PLGA is between about 0.1 dl/g to about 1.5 dl/g, such as about 0.1 dl/g to about 0.15 dl/g, about 0.15 dl/g to about 0.25 dl/g, about 0.25 dl/g to about 0.5 dl/g, about 0.5 dl/g to about 0.75 dl/g, about 0.75 dl/g to about 1.0 dl/g, about 1.0 dl/g to about 1.25 dl/g, or about 1.25 dl/g to about 1.5 dl/g.

The amount or ratio of acid-terminated PLGA to ester-terminated PLGA may also affect the degradation or weakening speed of the time-dependent polymeric linker, with a higher proportion of acid-terminated PLGA resulting in a faster degradation or weakening speed compared to a higher proportion of ester-terminated PLGA. In some embodiments, the PLGA comprises, consists essentially of, or consists of acid-terminated PLGA. In some embodiments, the PLGA comprises, consists essentially of, or consists of ester-terminated PLGA. In some embodiments, the PLGA comprises a blend of acid-terminated PLGA and ester-terminated PLGA. For example, in some embodiments, the PLGA comprises a blend of acid-terminated PLGA and ester-terminated PLGA at a ratio of about 1:9 to about 9:1 (such as about 1:9 to about 1:8, about 1:8 to about 1:7, about 1:7 to about 1:6, about 1:6 to about 1:5, about 1:5 to about 1:4, about 1:4 to about 1:3, about 1:3 to about 1:2, about 1:2 to about 1:1, about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, about 8:1 to about 9:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, or about 1:9. In some embodiments, the PLGA comprises a blend of acid-terminated PLGA and ester-terminated PLGA at a ratio of about 1:1.

In some embodiments, the PLGA of the time-dependent polymeric linker comprises acid-terminated poly(D,L-lactic-co-glycolide) with a ratio of lactide monomers to glycolide monomers of about 50:50 and an inherent viscosity between 0.16 dl/g and 0.24 dl/g (such as the PLGA sold under the tradename Purasorb® PDLG 5002 A or Purasorb®

PDLG 5002 A Y, each available from Corbion). In some embodiments, the PLGA of the time-dependent polymeric linker comprises poly(D,L-lactic-co-glycolide) with a ratio of lactide monomers to glycolide monomers of about 50:50 and an inherent viscosity between 0.16 dl/g and 0.24 dl/g (such as the PLGA sold under the tradename Purasorb® PDLG 5002, available from Corbion). In some embodiments, the PLGA of the time-dependent polymeric linker comprises poly(D,L-lactic-co-glycolide) with a ratio of lactide monomers to glycolide monomers of about 50:50 (such as the PLGA sold under the tradename Purasorb® PDLG 5004, available from Corbion). In some embodiments, the PLGA of the time-dependent polymeric linker comprises an acid-terminated poly(D,L-lactic-co-glycolide) with a ratio of lactide monomers to glycolide monomers of about 50:50 (such as the PLGA sold under the tradename Purasorb® PDLG 5004 A, available from Corbion). In some embodiments, the PLGA of the time-dependent polymeric linker comprises poly(D,L-lactic-co-glycolide) with a ratio of lactide monomers to glycolide monomers of about 50:50 and an inherent viscosity between 0.8 dl/g and 1.2 dl/g (such as the PLGA sold under the tradename Purasorb® PDLG 5010, available from Corbion). In some embodiments, the PLGA of the time-dependent polymeric linker comprises poly(D,L-lactic-co-glycolide) with a ratio of lactide monomers to glycolide monomers of about 55:45 and an inherent viscosity between 0.4 dl/g and 0.6 dl/g (such as the PLGA sold under the tradename Purasorb® PDLG 5505G, available from Corbion). In some embodiments, the PLGA of the time-dependent polymeric linker comprises acid-terminated poly(D,L-lactic-co-glycolide) with a ratio of lactide monomers to glycolide monomers of about 75:25 and an inherent viscosity between 0.16 dl/g and 0.24 dl/g (such as the PLGA sold under the tradename Purasorb® PDLG 7502 A, available from Corbion). In some embodiments, the PLGA of the time-dependent polymeric linker comprises poly(D,L-lactic-co-glycolide) with a ratio of lactide monomers to glycolide monomers of about 75:25 and an inherent viscosity between 0.16 dl/g and 0.24 dl/g (such as the PLGA sold under the tradename Purasorb® PDLG 7502, available from Corbion). In some embodiments, the PLGA of the time-dependent polymeric linker comprises a poly(D,L-lactic-co-glycolide) with a ratio of lactide monomers to glycolide monomers of about 75:25 and an inherent viscosity between 0.65 dl/g and 0.95 dl/g (such as the PLGA sold under the tradename Purasorb® PDLG 7507 Y, available from Corbion). In some embodiments, the PLGA of the time-dependent polymeric linker comprises a poly(D,L-lactic-co-glycolide) with a ratio of lactide monomers to glycolide monomers of about 75:25 and an inherent viscosity between 0.56 dl/g and 0.84 dl/g (such as the PLGA sold under the tradename Purasorb® PDLG 7507, available from Corbion). In some embodiments, the PLGA of the time-dependent polymeric linker comprises a poly(D,L-lactic-co-glycolide) with a ratio of lactide monomers to glycolide monomers of about 75:25 and an inherent viscosity between 0.85 dl/g and 1.05 dl/g (such as the PLGA sold under the tradename Purasorb® PDLG 7510, available from Corbion). In some embodiments, the PLGA of the time-dependent polymeric linker comprises a poly(D,L-lactic-co-glycolide) with a ratio of lactide monomers to glycolide monomers of about 65:35 and an inherent viscosity between 0.32 dl/g and 0.44 dl/g (such as the PLGA sold under the tradename Resomer® RG 653 H, available from Evonik). In some embodiments, the PLGA of the time-dependent polymeric linker comprises a mixture of two or more of the above PDLG polymers. By way of example, in some embodiments, the PLGA of the time-dependent polymeric linker comprises a mixture of (a) poly(D,L-lactic-co-glycolide) with a ratio of lactide monomers to glycolide monomers of about 50:50 (such as the PLGA sold under the tradename Purasorb® PDLG 5004, available from Corbion), and (b) acid-terminated poly(D,L-lactic-co-glycolide) with a ratio of lactide monomers to glycolide monomers of about 50:50 (such as the PLGA sold under the tradename Purasorb® PDLG 5004 A, available from Corbion).

The one or more additional linker polymers included in the polymer linker is preferably homogenously mixed with the PLGA. In some embodiments, the one or more additional linker polymers are miscible with the PLGA. The one or more additional linker polymers may be a non-degradable polymer (that is, not degradable or in the gastric or enteric environment, or an aqueous solution of pH 1.6 (representing the gastric environment) or pH 6.5 (representing the enteric environment), and is optionally present in the time-dependent polymeric linker is an amount such that the time-dependent polymeric linker does not break during the gastric residence period.

Bonding of the polymeric linker to a directly adjacent member may be improved if at least one polymer is common to both the adjacent member and the time-dependent polymeric linker. That is, one of the one or more additional linker polymers in the time-dependent linker may be the same (or the same polymer type) as at least one polymer in a directly adjacent component (or, optionally, both directly adjacent components) of the gastric residence system. For example, if the time-dependent polymeric linker is bonded directly to a structural member comprising a carrier polymer, in some embodiments the one or more additional linker polymers also includes the carrier polymer (in addition to the PLGA in the time-dependent polymeric linker) at the same or different concentration. Exemplary carrier polymers include, but are not limited to, polylactic acid (PLA), polycaprolactone (PCL), and a thermoplastic polyurethane (TPU), among others described herein.

In some embodiments, the one or more additional linker polymers is PLA, for example a PLA as described herein in reference to carrier polymers. In some embodiments, the time-dependent polymeric linker includes about 99% or less, about 98% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less (by weight) PLA. In some embodiments, the time-dependent polymeric linker includes about 99% or more, about 98% or more, about 95% or more, about 90% or more, about 85% or more, about 80% or more, about 75% or more, about 70% or more, about 65% or more, about 60% or more, about 55% or more, about 50% or more, about 40% or more, about 30% or more, about 20% or more, or about 10% or more (by weight) PLA. In some embodiments, the time-dependent polymeric linker includes about 0.1% to about 10% PLA, about 10% to about 20% PLA, about 20% to about 30% PLA, about 30% to about 40% PLA about 40% to about 50% PLA, about 50% to about 60% PLA, about 60% to about 70% PLA, about 70% to about 80% PLA, about 80% to about 90% PLA, or about 90% to about 99.9% PLA. In some embodiments, the time-dependent polymeric linker includes about 30% PLA or less. In some embodiments, the time-dependent polymer linker includes about 70% PLA or more. In some embodiments, the time-dependent polymeric liker includes about 30% to about 70% PLA. The PLGA may be further included with the PLA, and can make up to the balance of the time-dependent polymeric linker, although additional agents (such as a plasticizer, a coloring agent, or other agent may be further included).

In some embodiments, the time-dependent polymeric linker includes 10 to 90%, 20 to 80%, 30 to 70%, 40 to 60%, 45 to 55%, 48 to 52%, or 50% (by weight) PLA. In some embodiments, the time-dependent polymeric linker includes 10 to 50%, 20 to 40%, 25 to 35%, 28 to 32%, or 30% (by weight) PLA. In some embodiments, the time-dependent polymeric linker includes 10 to 40%, 15 to 35%, 20 to 28%, 22 to 26%, or 24% (by weight) PLA. The In some embodiments, the one or more additional linker polymers comprises a PCL. The time-dependent polymeric linker may be directly joined or bonded to another member of the gastric residence system (such as the structural member comprising the drug and the carrier polymer, a coupling member, the enteric polymeric linker, or a central structural member), which may also include a PCL, which may be the same PCL in the time-dependent polymeric linker or a different PCL as the one in the polymeric linker, and which may be at the same concentration or a different concentration. A different PCL in the time-dependent polymeric linker and the other member directly joined or bonded to the time-dependent linker may differ, for example, in the weight-average molecular weight of the PCL, the inherent viscosity of the PCL, or the proportions of PCL (for example, when a blend of two or more PCL polymers are used).

In some embodiments, the time-dependent polymeric linker includes about 99% or less, about 98% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less (by weight) PCL. In some embodiments, the time-dependent polymeric linker includes about 99% or more, about 98% or more, about 95% or more, about 90% or more, about 85% or more, about 80% or more, about 75% or more, about 70% or more, about 65% or more, about 60% or more, about 55% or more, about 50% or more, about 40% or more, about 30% or more, about 20% or more, or about 10% or more (by weight) PCL. In some embodiments, the time-dependent polymeric linker includes about 0.1% to about 10% PCL, about 10% to about 20% PCL, about 20% to about 30% PCL, about 30% to about 40% PCL about 40% to about 50% PCL, about 50% to about 60% PCL, about 60% to about 70% PCL, about 70% to about 80% PCL, about 80% to about 90% PCL, or about 90% to about 99.9% PCL. In some embodiments, the time-dependent polymeric linker includes about 30% PLA or less. In some embodiments, the time-dependent polymer linker includes about 70% PLA or more. In some embodiments, the time-dependent polymeric liker includes about 30% to about 70% PCL. The PLGA may be further included with the PCL, and can make up to the balance of the time-dependent polymeric linker, although additional agents (such as a plasticizer, a coloring agent, or other agent may be further included).

In some embodiments, the one or more additional linker polymers comprises a TPU. The time-dependent polymeric linker may be directly joined or bonded to another member of the gastric residence system (such as the structural member comprising the drug and the carrier polymer, a coupling member, the enteric polymeric linker, or a central structural member), which may also include a TPU, which may be the same TPU in the time-dependent polymeric linker or a different TPU as the one in the polymeric linker, and which may be at the same concentration or a different concentration. A different TPU in the time-dependent polymeric linker and the other member directly joined or bonded to the time-dependent linker may differ, for example, in the weight-average molecular weight of the TPU, the inherent viscosity of the TPU, or the proportions of TPU (for example, when a blend of two or more TPU polymers are used). Suitable polymers may include customizable thermoplastic polyurethanes with durometer range from 62 A to 83 D, such as Pathway™ TPU polymers (The Lubrizol Corporation); aliphatic polyether-based thermoplastic polyurethanes, such as Tecoflex™ (The Lubrizol Corporation); aliphatic, hydrophilic polyether-based resin, such as Tecophilic™ (The Lubrizol Corporation); aliphatic and aromatic, polycarbonate-based thermoplastic polyurethanes, such as Carbothane™ (The Lubrizol Corporation); thermoplastic polyurethanes with hardness from 60 A to 85 D, such as Texin® (Covestro); translucent, ultra-soft polyether or polyester-based TPU blends, such as NEUSoft™ (PolyOne). Suitable commercially-available TPU polymers may include Pathway™ TPU polymers (The Lubrizol Corporation), Tecoflex™ (The Lubrizol Corporation), Tecophilic™ (The Lubrizol Corporation), Carbothane™ (The Lubrizol Corporation), Texin® (Covestro), and NEUSoft™ (PolyOne).

In some embodiments, the time-dependent polymeric linker includes about 99% or less, about 98% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less (by weight) TPU. In some embodiments, the time-dependent polymeric linker includes about 99% or more, about 98% or more, about 95% or more, about 90% or more, about 85% or more, about 80% or more, about 75% or more, about 70% or more, about 65% or more, about 60% or more, about 55% or more, about 50% or more, about 40% or more, about 30% or more, about 20% or more, or about 10% or more (by weight) TPU. In some embodiments, the time-dependent polymeric linker includes about 0.1% to about 10% TPU, about 10% to about 20% TPU, about 20% to about 30% TPU, about 30% to about 40% TPU about 40% to about 50% TPU, about 50% to about 60% TPU, about 60% to about 70% TPU, about 70% to about 80% TPU, about 80% to about 90% TPU, or about 90% to about 99.9% TPU. In some embodiments, the time-dependent polymeric linker includes about 30% TPU or less. In some embodiments, the time-dependent polymer linker includes about 70% TPU or more. In some embodiments, the time-dependent polymeric liker includes about 30% to about 70% TPU. In some embodiments, the time-dependent polymeric liker includes about 30% to about 70% PLA. The PLGA may be further included with the TPU, and can make up to the balance of the time-dependent polymeric linker, although additional agents (such as a plasticizer, a color-absorbing dye, or other agent may be further included).

The time-dependent polymeric linker may further include one or more plasticizers, which can aid in cutting an extruded polymeric linker material to a desired size and aid in bonding or attaching the time-dependent polymeric linker to other components of the gastric residence system. Exemplary plasticizers include, but are not limited to, propylene glycol, polyethylene glycol (PEG), triethyl butyl citrate (TBC), dibutyl sebacate (DBS), triacetin, triethyl citrate (TEC), a poloxamer (e.g., Poloxamer 407, or "P407"), or D-α-tocopheryl polyethylene glycol succinate. The term "polyethylene glycol" is used interchangeably herein with the terms "polyethylene oxide" and "PEO." In some embodiments, the molecular weight of the polyethylene glycol is about 200 Da to about 8,000,000 Da (also referred to as 8000K or 8000 kDa), for example, about 200 Da to about 400 Da, about 400 Da to about 800 Da, about 800 Da to about 1600 Da, about 1600 Da to about 2500 Da, about 2500 Da to about 5000 Da, about 5000 Da to about 10K, about 10K to about 20K, about 20K to about 50K, about 50K to about 100K, about 100K to about 200K, about 200K to about 400K, about 400K to about 800K, about 800K to about 1000K, about 1000K to about 2000K, about 2000K to about 4000K, about 4000K to about 6000K, or about 6000K to about 8000K. In some embodiments, the polymeric linker comprises up to 20% plasticizer, such as up to 18% plasticizer, up to 15% plasticizer, up to 12% plasticizer, up to 10% plasticizer, up to 8% plasticizer, up to 6% plasticizer, up to 4% plasticizer, up to 3% plasticizer, up to 2% plasticizer, or up to 1% plasticizer. In some embodiments, the polymeric linker comprises about 0.5% to about 20% plasticizer, such as about 0.5% to about 1%, about 1% to about 2%, about 2% to about 3%, about 3% to about 5%, about 5% to about 7%, about 7% to about 10%, about 10% to about 12%, about 12% to about 15% plasticizer, about 15% to about 18% plasticizer, or about 18% to about 20% plasticizer.

In some embodiments, the time-dependent polymeric linker includes a color-absorbing dyes (also referred to as a colorant or a pigment). A color-absorbing dye may be included to enhance bonding or attachment of the polymeric linker to other gastric residence system components. Color-absorbing dyes can absorb heat during the laser-welding, infrared welding, or other heat-induced attachment, which increases the tensile strength of the resulting bond. Exemplary color-absorbing dyes include iron oxide and carbon black. The time-dependent polymeric linker may include the color-absorbing dye in an amount of up to about 5%, such as up to about 4%, up to about 3%, up to about 2%, up to about 1%, up to about 0.5%, up to about 0.3%, up to about 0.2%, or up to about 0.1%.

The time-dependent polymeric linker optionally includes one or more additional excipients. For example, the time-dependent polymeric linker may include a porogen, such as a sugar (e.g., lactose, sucrose, glucose, etc.), a salt (e.g., NaCl), sodium starch glycolate (SSG), or any other suitable substance. The porogen may quickly dissolve in the aqueous environment, which allows the aqueous solution to accelerate contact with the inner portions of the polymeric linker. Other excipients may include a flow aid, such as vitamin E succinate or silicified silicon dioxide (e.g., Cab-O-Sil), which may be included in the polymer blend for easier handling of the material prior to extrusion.

In one example of a time-dependent polymeric linker, the polymeric linker comprises about 75% to about 90% PLGA and about 10% to about 25% PLA (for example, about 85% PLGA and about 15% PLA). The PLA may be, for example, PLDL or PDL. The PLGA may be, for example, poly(D,L-lactic-co-glycolide) with a lactide monomer to glycolide monomer ratio of about 50:50 to about 75:25 (such as about 65:35) and/or have an inherent viscosity between about 0.1 dl/g and about 0.7 dl/g (such as about 0.3 dl/g to about 0.5 dl/g).

In another example of a time-dependent polymeric linker, the polymeric linker comprises about 40% to about 70% PLGA and about 30% to about 60% carrier polymer (for example, about 55% PLGA and about 45% PLA). The carrier polymer may be, for example, a TPU or a PCL. The PLGA may be, for example, (1) poly(D,L-lactic-co-glycolide) with a lactide monomer to glycolide monomer ratio of about 65:35 to about 95:5 (such as about 75:25) and/or have an inherent viscosity between about 0.1 dl/g and about 0.5 dl/g (such as about 0.15 dl/g to about 0.25 dl/g); (2) poly(D,L-lactic-co-glycolide) with a lactide monomer to glycolide monomer ratio of about 25:75 to about 75:25 (such as about 50:50) and/or have an inherent viscosity between about 0.5 dl/g and about 1.5 dl/g (such as about 0.8 dl/g to about 1.2 dl/g); or (3) poly(D,L-lactic-co-glycolide) with a lactide monomer to glycolide monomer ratio of about 65:35 to about 95:5 (such as about 75:25) and/or have an inherent viscosity between about 0.3 dl/g and about 1.2 dl/g (such as about 0.5 dl/g to about 0.9 dl/g).

In another example of a time-dependent polymeric linker, the polymeric linker comprises about 35% to about 65% (such as about 50%) carrier polymer, about 35% to about 65% (such as about 53%) PDLG, and about 2% polyethylene glycol (such as polyethylene glycol 100K), and optionally further comprises about iron oxide (such as about 0.01% to about 0.25% iron oxide). The carrier polymer may be, for example, a TPU or a PCL.

In another example of a time-dependent polymeric linker, the polymeric linker comprises about 35% to about 45% (such as about 40%) carrier polymer (such as a TPU or a PCL), and about 55% to about 65% (such as about 60%) PLGA. The PLGA may be, for example acid-terminated PLGA In another example of a time-dependent polymeric linker, the polymeric linker comprises about 40% to about 50% (such as about 45%) carrier polymer (such as a TPU or a PCL), about 48% to about 58% (such as about 53%) PLGA, and about 1% to about 3% (such as about 2%) polyethylene glycol (such as about polyethylene glycol 100K). The PLGA may be, for example acid-terminated PLGA.

In another example of a time-dependent polymeric linker, the polymeric linker comprises about 40% to about 50% (such as about 45%) carrier polymer (such as a TPU or a PCL), about 48% to about 58% (such as about 53%) PLGA, wherein the PLGA comprises acid-terminated PLGA and ester-terminated PLAG at a ratio of about 4:1 to about 1:1, such as about 2:1. Optionally, the polymeric linker comprises about 1% to about 3% (such as about 2%) polyethylene glycol (such as about polyethylene glycol 100K) and/or iron oxide (for example at about 0.01% to about 0.2%, such as about 0.05% to about 0.1%).

In another example of a time-dependent polymeric linker, the polymeric linker comprises about 45% to about 55% (such as about 50%) carrier polymer (such as a TPU or a PCL), and about 45% to about 55% (such as about 50%) PLGA. The PLGA may be, for example acid-terminated PLGA.

In another example of a time-dependent polymeric linker, the polymeric linker comprises about 45% to about 55% (such as about 50%) carrier polymer (such as a TPU or a PCL), about 40% to about 50% (such as about 45%) PLGA, and about 2% to about 7% (such as about 5%) polyethylene oxide (such as polyethylene glycol 100K). The PLGA may be, for example acid-terminated PLGA.

In some embodiments, a time-dependent polymeric linker may comprise about 10% or more, about 20% or more, about 30% or more, about 40% or more, about 50% or more, about 60% or more, about 70% or more, or about 80% or more (by weight) PLGA. In some embodiments, a time-dependent polymeric linker may comprise about 90% or less, about 80% or less, about 70% or less, about 60% or less, about 50% or less, about 40% or less, about 30 or less, or about 20% or less (by weight) PLGA.

In some embodiments, a time-dependent polymeric linker may comprise 50 to 90%, 60 to 80%, 65 to 75%, 68 to 72%, or 70% (by weight) PLGA. In some embodiments, a time-dependent polymeric linker may comprise 40 to 72%, 45 to 67%, 50 to 62%, 54 to 58%, or 56% (by weight) PLGA. In some embodiments, a time-dependent polymeric linker may comprise 30 to 70%, 40 to 60%, 45 to 55%, 48 to 52%, or 50% (by weight) PLGA. In some embodiments, a time-dependent polymeric linker may comprise 20 to 60%, 30 to 50%, 35 to 45%, 38 to 42%, or 40% (by weight) PLGA.

In some embodiments, a time-dependent polymeric linker comprising PLGA may include a lactic acid to glycolic acid ratio of 5:95, 10:90, 15:85, 20:80, 25:75, 30:70, 35:65, 40:60, 45:55, 50:50, 55:45, 6-:40, 65:35, 70:30, 75:25, 80:20, 85:15, 90:10, or 95:5.

Gastric Residence Time

The gastric residence time of the system is controlled by the degradation or weakening, or breakage, rate of the time-dependent polymeric linker in the gastric residence system. Faster degradation or weakening, or breakage of the time-dependent polymeric linker results in faster passage of the system from the stomach. The residence time of the gastric residence system is defined as the time between administration of the system to the stomach and exit of the system from the stomach. In one embodiment, the gastric residence system has a residence time of about 24 hours, or up to about 24 hours. In one embodiment, the gastric residence system has a residence time of about 48 hours, or up to about 48 hours. In one embodiment, the gastric residence system has a residence time of about 72 hours, or up to about 72 hours. In one embodiment, the gastric residence system has a residence time of about 96 hours, or up to about 96 hours. In one embodiment, the gastric residence system has a residence time of about 5 days, or up to about 5 days. In one embodiment, the gastric residence system has a residence time of about 6 days, or up to about 6 days. In one embodiment, the gastric residence system has a residence time of about 7 days (about one week), or up to about 7 days (about one week). In one embodiment, the gastric residence system has a residence time of about 10 days, or up to about 10 days. In one embodiment, the gastric residence system has a residence time of about 14 days (about two weeks), or up to about 14 days (about two weeks).

In one embodiment, the gastric residence system has a residence time between about 24 hours and about 7 days. In one embodiment, the gastric residence system has a residence time between about 48 hours and about 7 days. In one embodiment, the gastric residence system has a residence time between about 72 hours and about 7 days. In one embodiment, the gastric residence system has a residence time between about 96 hours and about 7 days. In one embodiment, the gastric residence system has a residence time between about 5 days and about 7 days. In one embodiment, the gastric residence system has a residence time between about 6 days and about 7 days.

In one embodiment, the gastric residence system has a residence time between about 24 hours and about 10 days. In one embodiment, the gastric residence system has a residence time between about 48 hours and about 10 days. In one embodiment, the gastric residence system has a residence time between about 72 hours and about 10 days. In one embodiment, the gastric residence system has a residence time between about 96 hours and about 10 days. In one embodiment, the gastric residence system has a residence time between about 5 days and about 10 days. In one embodiment, the gastric residence system has a residence time between about 6 days and about 10 days. In one embodiment, the gastric residence system has a residence time between about 7 days and about 10 days.

In one embodiment, the gastric residence system has a residence time between about 24 hours and about 14 days. In one embodiment, the gastric residence system has a residence time between about 48 hours and about 14 days. In one embodiment, the gastric residence system has a residence time between about 72 hours and about 14 days. In one embodiment, the gastric residence system has a residence time between about 96 hours and about 14 days. In one embodiment, the gastric residence system has a residence time between about 5 days and about 14 days. In one embodiment, the gastric residence system has a residence time between about 6 days and about 14 days. In one embodiment, the gastric residence system has a residence time between about 7 days and about 14 days. In one embodiment, the gastric residence system has a residence time between about 10 days and about 14 days.

The gastric residence system releases a therapeutically effective amount of agent (or salt thereof) during at least a portion of the residence time or residence period during which the system resides in the stomach. In one embodiment, the system releases a therapeutically effective amount of agent (or salt thereof) during at least about 25% of the residence time. In one embodiment, the system releases a therapeutically effective amount of agent (or salt thereof) during at least about 50% of the residence time. In one embodiment, the system releases a therapeutically effective amount of agent (or salt thereof) during at least about 60% of the residence time. In one embodiment, the system releases a therapeutically effective amount of agent (or salt thereof) during at least about 70% of the residence time. In one embodiment, the system releases a therapeutically effective amount of agent (or salt thereof) during at least about 75% of the residence time. In one embodiment, the system releases a therapeutically effective amount of agent (or salt thereof) during at least about 80% of the residence time. In one embodiment, the system releases a therapeutically effective amount of agent (or salt thereof) during at least about 85% of the residence time. In one embodiment, the system releases a therapeutically effective amount of agent (or salt thereof) during at least about 90% of the residence time. In one embodiment, the system releases a therapeutically effective amount of agent (or salt thereof) during at least about 95% of the residence time. In one embodiment, the system releases a therapeutically effective amount of agent (or salt thereof) during at least about 98% of the residence time. In one embodiment, the system releases a therapeutically effective amount of agent (or salt thereof) during at least about 99% of the residence time.

Enteric Disintegrating Matrices (Enteric Linkers)

If the gastric residence system passes prematurely into the small intestine in an intact form, the system may be designed to break down much more rapidly to avoid intestinal obstruction. This is readily accomplished by using an enteric polymeric linker that includes an enteric polymer in addition to an additional linker polymer (such as a carrier polymer), which weakens or degrades within the intestinal environment. Enteric polymers are relatively resistant to the acidic pH levels encountered in the stomach, but dissolve rapidly at the higher pH levels found in the duodenum. Use of enteric polymeric linkers as safety elements protects against undesired passage of the intact gastric residence system into the small intestine. The use of enteric polymeric linker also provides a manner of removing the gastric residence system prior to its designed residence time; should the system need to be removed, the patient can drink a mildly alkaline solution, such as a sodium bicarbonate solution, or take an antacid preparation such as hydrated magnesium hydroxide (milk of magnesia) or calcium carbonate, which will raise the pH level in the stomach and cause rapid degradation of the enteric polymeric linker.

Weakening or degradation of the enteric polymeric linker may be measured in references to a loss of the flexural modulus or breakage of the polymeric linker under a given condition (e.g., enteric conditions or gastric conditions). The enteric linkers weaken, degrade, or break in the intestinal environment relatively quickly, while retain much of their flexural modulus in the gastric environment. Stomach conditions may be simulated using an aqueous solution, such FaSSGF, at a pH of 1.6 and at 37° C., and intestinal conditions may be simulated using an aqueous solution, such as FaSSIF, at a pH 6.5 at 37° C. For example, in some embodiments, the enteric polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 12 hours at 37° C. In some embodiments, the enteric polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 24 hours at 37° C. In some embodiments, the enteric polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 2 days at 37° C. In some embodiments, the enteric polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 3 days at 37° C. In some embodiments, the enteric polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 4 days at 37° C. In some embodiments, the enteric polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 5 days at 37° C.

In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 3 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 5 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 7 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 10 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 14 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 18 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 21 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 24 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 30 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 45 days at 37° C. In some embodiments, the enteric polymeric linker retains about 60% or more, about 70% or more, about 80% or more, about 90% or more, about 95% or more, or about 99% or more of its flexural modulus after incubation in an aqueous solution, such as FaSSGF, at pH 1.6 for 60 days at 37° C.

In some embodiments, the enteric polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 3 days at 37° C.; and the enteric polymeric linker retains about 60% or more, about 70% or more, about 80% or more, about 90% or more, about 95% or more, or about 99% or more of its flexural modulus or breaks after incubation in an aqueous solution, such as FaSSGF, at pH 1.6 for 7 days at 37° C.

The enteric polymeric linker weakens faster or to a greater extent in enteric conditions than in gastric conditions. For example, in some embodiments, the enteric polymeric linker loses its flexural modulus after incubation in an aqueous solution, such as FaSSIF, at pH 6.5 for 12 hours by more than about 5%, more than about 10%, more than about 15%, more than about 20%, more than about 25%, more than about 30%, more than about 35%, more than about 40%, more than about 50%, more than about 55%, more than about 60%, more than about 65%, more than about 70%, more than about 75%, more than about 80%, more than about 85%, more than about 90%, more than about 95%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, or about 90% to about 95%, or any consecutive combination of such ranges, of the loss of its flexural modulus after incubation an aqueous solution, such as FaSSGF, at pH 1.6 for 12 hours. In some embodiments, the enteric polymeric linker loses its flexural modulus after incubation in an aqueous solution, such as FaSSIF, at pH 6.5 for 12 hours by more than about 5%, more than about 10%, more than about 15%, more than about 20%, more than about 25%, more than about 30%, more than about 35%, more than about 40%, more than about 50%, more than about 55%, more than about 60%, more than about 65%, more than about 70%, more than about 75%, more than about 80%, more than about 85%, more than about 90%, more than about 95%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, or about 90% to about 95%, or any consecutive combination of such ranges, of the loss of its flexural modulus after incubation an aqueous solution, such as FaSSGF, at pH 1.6 for 24 hours. In some embodiments, the enteric polymeric linker loses its flexural modulus after incubation in an aqueous solution, such as FaSSIF, at pH 6.5 for 12 hours by more than about 5%, more than about 10%, more than about 15%, more than about 20%, more than about 25%, more than about 30%, more than about 35%, more than about 40%, more than about 50%, more than about 55%, more than about 60%, more than about 65%, more than about 70%, more than about 75%, more than about 80%, more than about 85%, more than about 90%, more than about 95%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, or about 90% to about 95%, or any consecutive combination of such ranges, of the loss of its flexural modulus after incubation an aqueous solution, such as FaSSGF, at pH 1.6 for 36 hours. In some embodiments, the enteric polymeric linker loses its flexural modulus after incubation in an aqueous solution, such as FaSSIF, at pH 6.5 for 12 hours by more than about 5%, more than about 10%, more than about 15%, more than about 20%, more than about 25%, more than about 30%, more than about 35%, more than about 40%, more than about 50%, more than about 55%, more than about 60%, more than about 65%, more than about 70%, more than about 75%, more than about 80%, more than about 85%, more than about 90%, more than about 95%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, or about 90% to about 95%, or any consecutive combination of such ranges, of the loss of its flexural modulus after incubation an aqueous solution, such as FaSSGF, at pH 1.6 for 2 days. In some embodiments, the enteric polymeric linker loses its flexural modulus after incubation in an aqueous solution, such as FaSSIF, at pH 6.5 for 12 hours by more than about 5%, more than about 10%, more than about 15%, more than about 20%, more than about 25%, more than about 30%, more than about 35%, more than about 40%, more than about 50%, more than about 55%, more than about 60%, more than about 65%, more than about 70%, more than about 75%, more than about 80%, more than about 85%, more than about 90%, more than about 95%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, or about 90% to about 95%, or any consecutive combination of such ranges, of the loss of its flexural modulus after incubation an aqueous solution, such as FaSSGF, at pH 1.6 for 3 days. In some embodiments, the enteric polymeric linker loses its flexural modulus after incubation in an aqueous solution, such as FaSSIF, at pH 6.5 for 12 hours by more than about 5%, more than about 10%, more than about 15%, more than about 20%, more than about 25%, more than about 30%, more than about 35%, more than about 40%, more than about 50%, more than about 55%, more than about 60%, more than about 65%, more than about 70%, more than about 75%, more than about 80%, more than about 85%, more than about 90%, more than about 95%, about 5% to about 10%, about 10% to about 15%, about 15% to about 20%, about 20% to about 25%, about 25% to about 30%, about 30% to about 35%, about 35% to about 40%, about 40% to about 45%, about 45% to about 50%, about 50% to about 55%, about 55% to about 60%, about 60% to about 65%, about 65% to about 70%, about 70% to about 75%, about 75% to about 80%, about 80% to about 85%, about 85% to about 90%, or about 90% to about 95%, or any consecutive combination of such ranges, of the loss of its flexural modulus after incubation an aqueous solution, such as FaSSGF, at pH 1.6 for 4 days.

In some embodiments, the enteric polymeric linker has an initial flexural modulus of about 100 MPa to about 2500 MPa, such as about 100 MPa to about 250 MPa, about 250 MPa to about 500 MPa, about 500 mPa to about 750 MPa, about 750 MPa to about 1000 MPa, about 1000 MPa to about 1250 MPa, about 1250 MPa to about 1500 MPa, about 1500 MPa to about 2000 MPa, or about 2000 MPa to about 2500 MPa.

Exemplary enteric polymers that can be used in the invention are listed in the Enteric Polymer Table (Table 1), along with their dissolution pH. (See Mukherji, Gour and Clive G. Wilson, "Enteric Coating for Colonic Delivery," Chapter 18 of Modified-Release Drug Delivery Technology (editors Michael J. Rathbone, Jonathan Hadgraft, Michael S. Roberts), Drugs and the Pharmaceutical Sciences Volume 126, New York: Marcel Dekker, 2002.) Preferably, enteric polymers that dissolve at a pH of no greater than about 5 or about 5.5 are used. Poly(methacrylic acid-co-ethyl acrylate) (sold under the trade name EUDRAGIT L 100-55; EUDRAGIT is a registered trademark of Evonik Rohm GmbH, Darmstadt, Germany) is a preferred enteric polymer. Another preferred enteric polymer is hydroxypropylmethylcellulose acetate succinate (hypromellose acetate succinate or HPMCAS; Ashland, Inc., Covington, Kentucky, USA), which has a tunable pH cutoff from about 5.5 to about 7.0. Cellulose acetate phthalate, cellulose acetate succinate, and hydroxypropyl methylcellulose phthalate are also suitable enteric polymers.

TABLE 1

| Enteric Polymer Table | |
|---|---|
| Polymer | Dissolution pH |
| Cellulose acetate phthalate | 6.0-6.4 |
| Hydroxypropyl methylcellulose phthalate 50 | 4.8 |
| Hydroxypropyl methylcellulose phthalate 55 | 5.2 |
| Polyvinylacetate phthalate | 5.0 |
| Methacrylic acid-methyl methacrylate copolymer (1:1) | 6.0 |
| Methacrylic acid-methyl methacrylate copolymer (2:1) | 6.5-7.5 |
| Methacrylic acid-ethyl acrylate copolymer (2:1) | 5.5 |
| Shellac | 7.0 |
| Hydroxypropyl methylcellulose acetate succinate | 7.0 |
| Poly (methyl vinyl ether/maleic acid) monoethyl ester | 4.5-5.0 |
| Poly (methyl vinyl ether/maleic acid) n-butyl ester | 5.4 |

The amount of enteric polymer included in the enteric polymeric linker can be selected based on the desired linker weakening or degradation profile. For example, the polymeric linker may include about 1% to about 99% enteric polymer, such as about 1% to about 5% enteric polymer, about 5% to about 10% enteric polymer, about 10% to about 20% enteric polymer, about 20% to about 30% enteric polymer, about 30% to about 40% enteric polymer, about 40% to about 50% enteric polymer, about 50% to about 60% enteric polymer, about 60% to about 70% enteric polymer, about 70% to about 80% enteric polymer, about 80% to about 90% enteric polymer, or about 90% to about 99% enteric polymer. In some embodiments, the enteric polymeric linker comprises less than 20% enteric polymer. In some embodiments, the enteric polymeric linker comprises less than 15% enteric polymer. In some embodiments, the enteric clinker comprises less than 10% enteric polymer. In some embodiments, the enteric linker comprises more than 80% enteric polymer. In some embodiments, the enteric linker comprises more than 85% enteric polymer. In some embodiments, the enteric linker comprises more than 90% enteric polymer. In some embodiments, the enteric linker comprises about 20% to about 80% enteric polymer.

In some embodiments, the enteric polymer comprises hydroxypropyl methylcellulose acetate succinate (HPMCAS). For example, in some embodiments, the polymeric linker includes about 1% to about 99% HPMCAS, such as about 1% to about 5% HPMCAS, about 5% to about 10% HPMCAS, about 10% to about 20% HPMCAS, about 20% to about 30% HPMCAS, about 30% to about 40% HPMCAS, about 40% to about 50% HPMCAS, about 50% to about 60% HPMCAS, about 60% to about 70% HPMCAS, about 70% to about 80% HPMCAS, about 80% to about 90% HPMCAS, or about 90% to about 99% HPMCAS. In some embodiments, the enteric polymeric linker comprises less than 20% HPMCAS. In some embodiments, the enteric polymeric linker comprises less than 15% HPMCAS. In some embodiments, the enteric clinker comprises less than 10% HPMCAS. In some embodiments, the enteric linker comprises more than 80% HPMCAS. In some embodiments, the enteric linker comprises more than 85% HPMCAS. In some embodiments, the enteric linker comprises more than 90% HPMCAS. In some embodiments, the enteric linker comprises about 20% to about 80% HPMCAS.

The enteric polymer is combined with one or more additional polymers (such as one or more carrier polymers) in the enteric linker, preferably in a homogenous mixture. For example, the enteric polymer and the additional linker polymer may be homogenously blended together before the mixture is extruded, and the extruded material being cut to a desired size for the polymeric linker. In some embodiments, the one or more additional linker polymers are miscible with the enteric polymer. The one or more additional linker polymers may be a non-degradable polymer (that is, not degradable or in the gastric or enteric environment, or an aqueous solution of pH 1.6 (representing the gastric environment) or pH 6.5 (representing the enteric environment).

Bonding of the polymeric linker to a directly adjacent member may be improved if at least one polymer is common to both the adjacent member and the enteric polymeric linker. That is, one of the one or more additional linker polymers in the enteric linker may be the same (or the same polymer type) as at least one polymer in a directly adjacent component (or, optionally, both directly adjacent components) of the gastric residence system. For example, if the enteric polymeric linker is bonded directly to a structural member comprising a carrier polymer, in some embodiments the one or more additional linker polymers also includes the carrier polymer (in addition to the PLGA in the time-dependent polymeric linker) at the same or different concentration. Exemplary carrier polymers include, but are not limited to, polylactic acid (PLA), polycaprolactone (PCL), and a thermoplastic polyurethane (TPU), among others described herein.

In some embodiments, the one or more additional linker polymers in the enteric polymeric linker is PLA, for example a PLA as described herein in reference to carrier polymers. In some embodiments, the enteric polymeric linker includes about 99% or less, about 98% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less (by weight) PLA. In some embodiments, the enteric polymeric linker includes about 99% or more, about 98% or more, about 95% or more, about 90% or more, about 85% or more, about 80% or more, about 75% or more, about 70% or more, about 65% or more, about 60% or more, about 55% or more, about 50% or more, about 40% or more, about 30% or more, about 20% or more, or about 10% or more (by weight) PLA. In some embodiments, the enteric polymeric linker includes about 0.1% to about 10% PLA, about 10% to about 20% PLA, about 20% to about 30% PLA, about 30% to about 40% PLA about 40% to about 50% PLA, about 50% to about 60% PLA, about 60% to about 70% PLA, about 70% to about 80% PLA, about 80% to about 90% PLA, or about 90% to about 99.9% PLA. In some embodiments, the enteric polymeric linker includes about 30% PLA or less. In some embodiments, the enteric polymeric linker includes about 70% PLA or more. In some embodiments, the enteric polymeric liker includes about 30% to about 70% PLA. The enteric polymer (such as HPMCAS) is further included with the PLA, and can make up to the balance of the enteric polymeric linker, although additional agents (such as a plasticizer, a coloring agent, or other agent may be further included).

In some embodiments, the one or more additional linker polymers in the enteric linker comprises a PCL. The enteric polymeric linker may be directly joined or bonded to another member of the gastric residence system (such as the structural member comprising the drug and the carrier polymer, a coupling member, the time-dependent polymeric linker, or a central structural member), which may also include a PCL, which may be the same PCL in the enteric polymeric linker or a different PCL as the one in the enteric polymeric linker, and which may be at the same concentration or a different concentration. A different PCL in the enteric polymeric linker and the other member directly joined or bonded to the enteric linker may differ, for example, in the weight-average molecular weight of the PCL, the inherent viscosity of the PCL, or the proportions of PCL (for example, when a blend of two or more PCL polymers are used).

In some embodiments, the enteric polymeric linker includes about 99% or less, about 98% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less (by weight) PCL. In some embodiments, the enteric polymeric linker includes about 99% or more, about 98% or more, about 95% or more, about 90% or more, about 85% or more, about 80% or more, about 75% or more, about 70% or more, about 65% or more, about 60% or more, about 55% or more, about 50% or more, about 40% or more, about 30% or more, about 20% or more, or about 10% or more (by weight) PCL. In some embodiments, the enteric polymeric linker includes about 0.1% to about 10% PCL, about 10% to about 20% PCL, about 20% to about 30% PCL, about 30% to about 40% PCL about 40% to about 50% PCL, about 50% to about 60% PCL, about 60% to about 70% PCL, about 70% to about 80% PCL, about 80% to about 90% PCL, or about 90% to about 99.9% PCL. In some embodiments, the enteric polymeric linker includes about 30% PLA or less. In some embodiments, the enteric polymer linker includes about 70% PLA or more. In some embodiments, the enteric polymeric liker includes about 30% to about 70% PCL. The enteric polymer (such as HPMCAS) is further included with the PCL, and can make up to the balance of the enteric polymeric linker, although additional agents (such as a plasticizer, a coloring agent, or other agent may be further included).

In some embodiments, the one or more additional linker polymers in the enteric polymeric linker comprises a TPU. The enteric polymeric linker may be directly joined or bonded to another member of the gastric residence system (such as the structural member comprising the drug and the carrier polymer, a coupling member, the time-dependent polymeric linker, or a central structural member), which may also include a TPU, which may be the same TPU in the enteric polymeric linker or a different TPU as the one in the enteric polymeric linker, and which may be at the same concentration or a different concentration. A different TPU in the enteric polymeric linker and the other member directly joined or bonded to the enteric linker may differ, for example, in the weight-average molecular weight of the TPU, the inherent viscosity of the TPU, or the proportions of TPU (for example, when a blend of two or more TPU polymers are used). Suitable polymers may include customizable thermoplastic polyurethanes with durometer range from 62 A to 83 D, such as Pathway™ TPU polymers (The Lubrizol Corporation); aliphatic polyether-based thermoplastic polyurethanes, such as Tecoflex™ (The Lubrizol Corporation); aliphatic, hydrophilic polyether-based resin, such as Tecophilic™ (The Lubrizol Corporation); aliphatic and aromatic, polycarbonate-based thermoplastic polyurethanes, such as Carbothane™ (The Lubrizol Corporation); thermoplastic polyurethanes with hardness from 60 A to 85 D, such as Texin® (Covestro); translucent, ultra-soft polyether or polyester-based TPU blends, such as NEU-Soft™ (PolyOne). Suitable commercially-available TPU polymers may include Pathway™ TPU polymers (The Lubrizol Corporation), Tecoflex™ (The Lubrizol Corporation), Tecophilic™ (The Lubrizol Corporation), Carbothane™ (The Lubrizol Corporation), Texin® (Covestro), and NEU-Soft™ (PolyOne). Additionally, suitable types of TPU polymers for the polymeric linker can include aliphatic TPUs, aliphatic polyether TPUs, aromatic TPUs, polycarbonate polyurethanes, and the like.

In some embodiments, the enteric polymeric linker includes about 99% or less, about 98% or less, about 95% or less, about 90% or less, about 85% or less, about 80% or less, about 75% or less, about 70% or less, about 65% or less, about 60% or less, about 55% or less, about 50% or less, about 40% or less, about 30% or less, about 20% or less, or about 10% or less (by weight) TPU. In some embodiments, the enteric polymeric linker includes about 99% or more, about 98% or more, about 95% or more, about 90% or more, about 85% or more, about 80% or more, about 75% or more, about 70% or more, about 65% or more, about 60% or more, about 55% or more, about 50% or more, about 40% or more, about 30% or more, about 20% or more, or about 10% or more (by weight) TPU. In some embodiments, the enteric polymeric linker includes about 0.1% to about 10% TPU, about 10% to about 20% TPU, about 20% to about 30% TPU, about 30% to about 40% TPU about 40% to about 50% TPU, about 50% to about 60% TPU, about 60% to about 70% TPU, about 70% to about 80% TPU, about 80% to about 90% TPU, or about 90% to about 99.9% TPU. In some embodiments, the enteric polymeric linker includes about 30% TPU or less. In some embodiments, the enteric polymer linker includes about 70% TPU or more. In some embodiments, the enteric polymeric liker includes about 30% to about 70% TPU. In some embodiments, the enteric polymeric liker includes about 30% to about 70% PLA. The enteric polymer (such as HMPCAS) may be further included with the TPU, and can make up to the balance of the enteric polymeric linker, although additional agents (such as a plasticizer, a color-absorbing dye, or other agent may be further included).

In some embodiments, an enteric polymeric linker may include 1 to 40%, 5 to 35%, 10 to 30%, 15 to 25%, 18 to 22%, or 20% (by weight) TPU.

The enteric polymeric linker may further include one or more plasticizers, which can aid in cutting an extruded polymeric linker material to a desired size and aid in bonding or attaching the enteric polymeric linker to other components of the gastric residence system. Exemplary plasticizers include, but are not limited to, propylene glycol, polyethylene glycol (PEG), triethyl butyl citrate (TBC), dibutyl sebacate (DBS), triacetin, triethyl citrate (TEC), a poloxamer (e.g., Poloxamer 407, or "P407"), or D-α-tocopheryl polyethylene glycol succinate. In some embodiments, the molecular weight of the polyethylene glycol is about 200 Da to about 8,000,000 Da (also referred to as 8000K or 8000 kDa), for example, about 200 Da to about 400 Da, about 400 Da to about 800 Da, about 800 Da to about 1600 Da, about 1600 Da to about 2500 Da, about 2500 Da to about 5000 Da, about 5000 Da to about 10K, about 10K to about 20K, about 20K to about 50K, about 50K to about 100K, about 100K to about 200K, about 200K to about 400K, about 400K to about 800K, about 800K to about 1000K, about 1000K to about 2000K, about 2000K to about 4000K, about 4000K to about 6000K, or about 6000K to about 8000K. In some embodiments, the polymeric linker comprises up to 20% plasticizer, such as up to 18% plasticizer, up to 15% plasticizer, up to 12% plasticizer, up to 10% plasticizer, up to 8% plasticizer, up to 6% plasticizer, up to 4% plasticizer, up to 3% plasticizer, up to 2% plasticizer, or up to 1% plasticizer. In some embodiments, the polymeric linker comprises about 0.5% to about 15% plasticizer, such as about 0.5% to about 1%, about 1% to about 2%, about 2% to about 3%, about 3% to about 5%, about 5% to about 7%, about 7% to about 10%, about 10% to about 12%, about 12% to about 15% plasticizer, about 15% to about 18% plasticizer, or about 18% to about 20% plasticizer.

In some embodiments, the enteric polymeric linker includes a color-absorbing dyes (also referred to as a colorant or a pigment). A color-absorbing dye may be included to enhance bonding or attachment of the polymeric linker to other gastric residence system components. Color-absorbing dyes can absorb heat during the laser-welding, infrared welding, or other heat-induced attachment, which increases the tensile strength of the resulting bond. Exemplary color-absorbing dyes include iron oxide and carbon black. The enteric polymeric linker may include the color-absorbing dye in an amount of up to about 5%, such as up to about 4%, up to about 3%, up to about 2%, up to about 1%, up to about 0.5%, up to about 0.3%, up to about 0.2%, or up to about 0.1%.

The enteric polymeric linker optionally includes one or more additional excipients. For example, the enteric polymeric linker may include a porogen, such as a sugar (e.g., lactose, sucrose, glucose, etc.), a salt (e.g., NaCl), sodium starch glycolate (SSG), or any other suitable substance. The porogen may quickly dissolve in the aqueous environment, which allows the aqueous solution to accelerate contact with the inner portions of the polymeric linker. Other excipients may include a flow aid, such as vitamin E succinate or silicified silicon dioxide (e.g., Cab-O-Sil), which may be included in the polymer blend for easier handling of the material prior to extrusion.

In some embodiments, the enteric polymeric linker comprises about 30% to about 80% HPMCAS and about 20% to about 70% carrier polymer (such as a TPU or a PCL). Optionally, the enteric polymeric linker further comprises propylene glycol (for example, about 10% to about 14% propylene glycol).

In some embodiments, the enteric polymeric linker comprises about 55% to about 65% (such as about 60%) HPMCAS and about 35% to about 45% (such as about 40%) carrier polymer (such as a TPU or a PCL).

In some embodiments, the enteric polymeric linker comprises about 35% to about 45% (such as about 40%) HPMCAS, about 45% to about 55% (such as about 50%) carrier polymer (such as a TPU or a PCL), and propylene glycol (for example, about 8% to about 12% propylene glycol, such as about 10% propylene glycol).

In some embodiments, the enteric polymeric linker comprises about 43% to about 53% (such as about 48%) HPMCAS, about 35% to about 45% (such as about 40%) carrier polymer (such as a TPU or a PCL), and propylene glycol (for example, about 10% to about 14% propylene glycol, such as about 12% propylene glycol).

In some embodiments, the enteric polymeric linker comprises about 51% to about 61% (such as about 56%) HPMCAS, about 25% to about 35% (such as about 30%) carrier polymer (such as a TPU or a PCL), and propylene glycol (for example, about 12% to about 16% propylene glycol, such as about 14% propylene glycol).

In some embodiments, the enteric polymeric linker comprises about 52% to about 62% (such as about 57%) HPMCAS, about 35% to about 45% (such as about 40%) carrier polymer (such as a TPU or a PCL), and propylene glycol (for example, about 1% to about 5% propylene glycol, such as about 3% propylene glycol).

In some embodiments, the enteric polymeric linker comprises about 49% to about 59% (such as about 54%) HPMCAS, about 35% to about 45% (such as about 40%) carrier polymer (such as a TPU or a PCL), and propylene glycol (for example, about 4% to about 8% propylene glycol, such as about 6% propylene glycol).

In some embodiments, the enteric polymeric linker comprises about 45% to about 55% (such as about 50%) HPMCAS and about 45% to about 55% (such as about 55%) carrier polymer (such as a TPU or a PCL). Optionally, the enteric polymeric linker further comprises iron oxide, for example about 0.01% to about 0.2% (such as about 0.05% to about 0.1%) iron oxide.

In some embodiments, the enteric polymeric linker comprises about 55% to about 65% (such as about 60%) HPMCAS and about 35% to about 45% (such as about 40%) carrier polymer (such as a TPU or a PCL). Optionally, the enteric polymeric linker further comprises iron oxide, for example about 0.01% to about 0.2% (such as about 0.05% to about 0.1%) iron oxide.

In some embodiments, the enteric polymeric linker comprises about 53% to about 63% (such as about 58%) HPMCAS and about 33% to about 43% (such as about 38%) carrier polymer (such as a TPU or a PCL), and about 2% to about 6% (such as about 4%) polyethylene glycol (such as polyethylene glycol 100K). Optionally, the enteric polymeric linker further comprises iron oxide, for example about 0.01% to about 0.2% (such as about 0.05% to about 0.1%) iron oxide.

In some embodiments, the enteric polymeric linker comprises about 31% to about 41% (such as about 36%) HPMCAS and about 31% to about 41% (such as about 36%) carrier polymer (such as a TPU or a PCL), and about 23% to about 33% (such as about 28%) TEC. Optionally, the enteric polymeric linker further comprises iron oxide, for example about 0.01% to about 0.2% (such as about 0.05% to about 0.1%) iron oxide.

In some embodiments, the enteric polymeric linker comprises about 59% to about 69% (such as about 64%) HPMCAS and about 29% to about 39% (such as about 34%) carrier polymer (such as a TPU or a PCL), and about 1% to about 3% (such as about 2%) poloxamer (such as P407). Optionally, the enteric polymeric linker further comprises iron oxide, for example about 0.01% to about 0.2% (such as about 0.05% to about 0.1%) iron oxide.

In some embodiments, the enteric polymeric linker comprises about 59% to about 69% (such as about 64%) HPMCAS and about 29% to about 39% (such as about 34%) carrier polymer (such as a TPU or a PCL), and about 1% to about 3% (such as about 2%) polyethylene glycol (such as polyethylene glycol 100K). Optionally, the enteric polymeric linker further comprises iron oxide, for example about 0.01% to about 0.2% (such as about 0.05% to about 0.1%) iron oxide.

In some embodiments, the enteric polymeric linker comprises about 65% to about 75% (such as about 70%) HPMCAS and about 25% to about 35% (such as about 30%) carrier polymer (such as a TPU or a PCL). Optionally, the enteric polymeric linker further comprises iron oxide, for example about 0.01% to about 0.2% (such as about 0.05% to about 0.1%) iron oxide.

In some embodiments, the enteric polymeric linker comprises about 79% to about 89% (such as about 84%) HPMCAS and about 9% to about 19% (such as about 14%) carrier polymer (such as a TPU or a PCL), and about 1% to about 3% (such as about 2%) polyethylene glycol (such as polyethylene glycol 100K). Optionally, the enteric polymeric linker further comprises iron oxide, for example about 0.01% to about 0.2% (such as about 0.05% to about 0.1%) iron oxide.

In some embodiments, the enteric polymeric linker comprises about 70% to about 80% (such as about 75%) HPMCAS and about 10% to about 20% (such as about 15%) carrier polymer (such as a TPU or a PCL), and about 5% to about 15% (such as about 10%) TEC. Optionally, the enteric polymeric linker further comprises iron oxide, for example about 0.01% to about 0.2% (such as about 0.05% to about 0.1%) iron oxide.

Dual Time Dependent and Enteric Linkers

In some embodiments, the gastric residence system includes a polymeric linker that includes both time-dependent and enteric functionalities. That is, the dual time-dependent and enteric polymeric linker weakens or degrades in both the gastric and intestinal environments, although weakening and degradation of the linker is faster in the intestinal environment than the gastric environment. This type of linker may be obtained, for example, by including a mixture of a pH-independent degradable polymer, such as PLGA, with an enteric polymer, such as HPMCAS.

For example, in some embodiments, the polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 12 hours at 37° C., retains about 60% or more, about 70% or more, about 80% or more, about 90% or more, about 95% or more, or about 99% or more of its flexural modulus after incubation in an aqueous solution, such as FaSSGF, at pH 1.6 for 12 hours at 37° C., and loses about 60% or more, about 70% or more, about 80% or more, about 90% or more, about 95% or more, or about 99% or more of its flexural modulus after incubation in an aqueous solution, such as FaSSGF, at pH 1.6 for 7 days at 37° C. In some embodiments, the polymeric linker loses about 60% or more, about 70% or more, about 80% or more, about 90% or more, about 95% or more, or about 99% or more of its flexural modulus or breaks after incubation in an aqueous solution, such as FaSSIF, at pH 6.5 for 24 hours at 37° C., retains about 60% or more, about 70% or more, about 80% or more, about 90% or more, about 95% or more, or about 99% or more of its flexural modulus after incubation in an aqueous solution, such as FaSSGF, at pH 1.6 for 24 hours at 37° C., and loses about 60% or more, about 70% or more, about 80% or more, about 90% or more, about 95% or more, or about 99% or more of its flexural modulus after incubation in an aqueous solution, such as FaSSGF, at pH 1.6 for 7 days at 37° C.

In some embodiments, the dual time-dependent polymeric linker has an initial flexural modulus of about 100 MPa to about 2500 MPa, such as about 100 MPa to about 2500 MPa, such as about 100 MPa to about 250 MPa, about 250 MPa to about 500 MPa, about 500 mPa to about 750 MPa, about 750 MPa to about 1000 MPa, about 1000 MPa to about 1250 MPa, about 1250 MPa to about 1500 MPa, about 1500 MPa to about 2000 MPa, or about 2000 MPa to about 2500 MPa.

In some embodiments, the dual time-dependent and enteric polymeric linker comprises PLGA. Examples of PLGA that may be included in the dual time-dependent and enteric polymeric linker is discussed above in reference to the time-dependent polymeric linker. In some embodiments, the dual time-dependent and enteric polymeric linker includes about 60% or less, about 55% or less, about 50% or less, about 40% or less, about 30% or less, about 20% or less, or about 10% or less (by weight) PLGA. In some embodiments, the dual time-dependent and enteric polymeric linker includes about 50% or more, about 40% or more, about 30% or more, about 20% or more, or about 10% or more (by weight) PLGA. In some embodiments, the dual time-dependent and enteric polymeric linker includes about 5% to about 60% PLGA, such as about 5% to about 10% PLGA, about 10% to about 20% PLGA, about 20% to about 30% PLGA, about 30% to about 40% PLGA, about 40% to about 50% PLGA, or about 50% to about 60% PLGA.

In some embodiments, the dual time-dependent and enteric polymeric linker includes about 60% or less, about 55% or less, about 50% or less, about 40% or less, about 30% or less, about 20% or less, or about 10% or less (by weight) enteric polymer, such as HPMCAS. In some embodiments, the dual time-dependent and enteric polymeric linker includes about 50% or more, about 40% or more, about 30% or more, about 20% or more, or about 10% or more (by weight) PLGA. In some embodiments, the dual time-dependent and enteric polymeric linker includes about 5% to about 60% enteric polymer, such as HPMCAS, such as about 5% to about 10%, about 10% to about 20%, about 20% to about 30%, about 30% to about 40%, about 40% to about 50%, or about 50% to about 60% enteric polymer, such as HPMCAS.

In some embodiments, the dual time-dependent and enteric polymeric linker comprise about 40% to about 80% HPMCAS and about 20% to about 60% PLGA. Optionally, the polymeric linker further comprises a carrier polymer (such as PLA, TPU, or PCL), for example at about 5% to about 40%.

Components of the gastric residence system may attached directly or through one or more coupling members. The coupling members may be inactive (i.e., free or substantially free of an agent), but can contain a carrier polymer, which may be the same (or same type) as the carrier polymer contained in an adjacent member (or segment) or a different (or different type) of carrier polymer as the carrier polymer contained in an adjacent member (or segment).

In some embodiments, a coupling member separates a first segment of an arm from a second segment of an arm. For example, in some embodiments, the coupling member separates an active segment of an arm from an inactive segment from an arm. The coupling member separating the two segments may directly interface with the two segments. In some embodiments, the first segment, the second segment, and the coupling member separating the two segments (such as directly interfacing with the two segments) comprises the same carrier polymer, such as PCL, TPU, PLA, or other carrier polymer described herein.

In some embodiments, a coupling member separates an arm from a polymeric linker (such as a time-dependent polymeric linker, an enteric polymeric linker, or a dual time-dependent and enteric polymeric linker). The coupling member separating the polymeric linker from the arm may directly interface with the arm and the polymeric linker. In some embodiments, the coupling member comprises the same (or same type) of carrier polymer as the arm at the interface junction, and/or comprises the same (or same type) of carrier polymer as the polymeric linker (i.e., one or more of the one or more additional polymers in the polymeric linker may be the common carrier polymer or common carrier polymer type). For example, in some embodiments, the arm, the polymeric linker and the coupling member between the arm comprise a PCL. In some embodiments, the arm, the polymeric linker and the coupling member between the arm comprise a TPU. In some embodiments, the arm, the polymeric linker and the coupling member between the arm comprise a PLA.

In some embodiments, a coupling member separates a first polymeric linker from a second polymer linker. The coupling member separating the first polymeric linker from the second polymeric linker may directly interface with both polymeric linkers. In some embodiments, the first and second polymeric linkers and the coupling member between the polymeric linkers have a common polymer (or common type of polymer), such as a PCL, a TPU, or a PLA.

In some embodiments, a coupling member separates a polymeric linker from a second structural member (such as a central elastomeric member). The coupling member may interface directly with both the second structural member and the polymeric linker, for example.

Exemplary Gastric Residence Systems

The following gastric residence systems are exemplary to better illustrate certain embodiments of the system described herein. As these examples are only exemplary, they are not intended to limit the gastric residence system described herein. One skilled in the art, in view of the provided disclosure, would be able to contemplate additional configurations of the gastric residence system.

In one example of a gastric residence system, the system includes a plurality of structural members comprising an active segment comprising a carrier polymer homogenously mixed with a drug, the arms attached to and radially extending from a central elastomeric member through a time-dependent polymeric linker comprising a pH-independent degradable polymer (such as PLGA) and at least one additional polymer (such as PLA or the carrier polymer), wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising a carrier polymer homogenously mixed with a drug, the arms attached to and radially extending from a central elastomeric member through a time-dependent polymeric linker comprising a pH-independent degradable polymer (such as PLGA) and the carrier polymer; wherein the time-dependent polymeric linker is directly bonded to the segment of the structural member comprising the carrier polymer homogenously mixed with the drug; wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising a coupling member and an active segment comprising a carrier polymer homogenously mixed with a drug, the arms attached to and radially extending from a central elastomeric member through a time-dependent polymeric linker comprising a pH-independent degradable polymer (such as PLGA) and the carrier polymer; wherein the time-dependent polymeric linker is directly bonded to the coupling member; wherein the coupling member separates the active segment from the time-dependent polymeric linker; wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising PCL polymer homogenously mixed with a drug, the arms attached to and radially extending from a central elastomeric member through a time-dependent polymeric linker comprising a pH-independent degradable polymer (such as PLGA) and PCL, wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising PCL homogenously mixed with a drug, the arms attached to and radially extending from a central elastomeric member through a time-dependent polymeric linker comprising a pH-independent degradable polymer (such as PLGA) and PCL; wherein the time-dependent polymeric linker is directly bonded to the segment of the structural member comprising the PCL homogenously mixed with the drug; wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising a coupling member comprising PCL and an active segment comprising a carrier polymer homogenously mixed with a drug, the arms attached to and radially extending from a central elastomeric member through a time-dependent polymeric linker comprising a pH-independent degradable polymer (such as PLGA) and PCL; wherein the time-dependent polymeric linker is directly bonded to the coupling member of the structural member; wherein the coupling member separates the active segment from the time-dependent polymeric linker; wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising TPU polymer homogenously mixed with a drug, the arms attached to and radially extending from a central elastomeric member through a time-dependent polymeric linker comprising a pH-independent degradable polymer (such as PLGA) and TPU, wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising TPU homogenously mixed with a drug, the arms attached to and radially extending from a central elastomeric member through a time-dependent polymeric linker comprising a pH-independent degradable polymer (such as PLGA) and TPU; wherein the time-dependent polymeric linker is directly bonded to the segment of the structural member comprising the TPU homogenously mixed with the drug; wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising a coupling member comprising TPU and an active segment comprising a carrier polymer homogenously mixed with a drug, the arms attached to and radially extending from a central elastomeric member through a time-dependent polymeric linker comprising a pH-independent degradable polymer (such as PLGA) and TPU; wherein the time-dependent polymeric linker is directly bonded to the coupling member of the structural member; wherein the coupling member separates the active segment from the time-dependent polymeric linker; wherein the time-dependent polymeric linker loses 80% or more of its flexural modulus or breaks after incubation in an aqueous solution at pH 1.6 for 14 days at 37° C.; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising a carrier polymer homogenously mixed with a drug, the arms attached to and radially extending from a central elastomeric member through a time-dependent polymeric linker comprising a pH-independent degradable polymer (such as PLGA) and PLA; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising PCL homogenously mixed with a drug, the arms attached to and radially extending from a central elastomeric member through a time-dependent polymeric linker comprising a pH-independent degradable polymer (such as PLGA) and PCL; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising TPU homogenously mixed with a drug, the arms attached to and radially extending from a central elastomeric member through a time-dependent polymeric linker comprising a pH-independent degradable polymer (such as PLGA) and TPU; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising a carrier polymer homogenously mixed with a drug, the arms attached to and radially extending from a central elastomeric member through a time-dependent polymeric linker comprising a pH-independent degradable polymer (such as PLGA) and PLA; wherein the time-dependent polymeric linker is directly bonded to the segment of the structural member comprising the carrier polymer homogenously mixed with the drug; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising PCL homogenously mixed with a drug, the arms attached to and radially extending from a central elastomeric member through a time-dependent polymeric linker comprising a pH-independent degradable polymer (such as PLGA) and PCL; wherein the time-dependent polymeric linker is directly bonded to the segment of the structural member comprising the PCL homogenously mixed with the drug; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising TPU homogenously mixed with a drug, the arms attached to and radially extending from a central elastomeric member through a time-dependent polymeric linker comprising a pH-independent degradable polymer (such as PLGA) and TPU; wherein the time-dependent polymeric linker is directly bonded to the segment of the structural member comprising the TPU homogenously mixed with the drug; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising a coupling member and an active segment comprising a carrier polymer homogenously mixed with a drug, the arms attached to and radially extending from a central elastomeric member through a time-dependent polymeric linker comprising a pH-independent degradable polymer (such as PLGA) and PLA; wherein the time-dependent polymeric linker is directly bonded to the coupling member; wherein the coupling member separates the active segment from the time-dependent polymeric linker; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising a coupling member comprising PCL and an active segment comprising a carrier polymer homogenously mixed with a drug, the arms attached to and radially extending from a central elastomeric member through a time-dependent polymeric linker comprising a pH-independent degradable polymer (such as PLGA) and PCL; wherein the time-dependent polymeric linker is directly bonded to the coupling member; wherein the coupling member separates the active segment from the time-dependent polymeric linker; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising a coupling member comprising TPU and an active segment comprising a carrier polymer homogenously mixed with a drug, the arms attached to and radially extending from a central elastomeric member through a time-dependent polymeric linker comprising a pH-independent degradable polymer (such as PLGA) and TPU; wherein the time-dependent polymeric linker is directly bonded to the coupling member; wherein the coupling member separates the active segment from the time-dependent polymeric linker; and wherein the gastric residence system is retained in the stomach for a period of at least 24 hours. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the time-dependent polymeric linker comprises a plasticizer, such as about 0.5% to about 20% plasticizer (such as about 0.5% to about 12% plasticizer).

In another example of a gastric residence system, the system includes a plurality of structural members comprising an active segment comprising TPU homogenously mixed with a drug, the arms attached to and radially extending from a central elastomeric member through an enteric polymeric linker comprising an enteric polymer and TPU, wherein the polymeric linker loses 80% or more of its flexural modulus or breaks after incubation in an aqueous solution at pH 6.5 for 3 days at 37° C.; and wherein the gastric residence system is retained in the stomach for a period of at least 24 hours. In some embodiments, the enteric polymer is HMPCAS. Optionally, the enteric polymeric linker comprises a plasticizer, such as about 0.5% to about 20% plasticizer (such as about 0.5% to about 12% plasticizer).

In another example of a gastric residence system, the system includes a plurality of structural members comprising an active segment comprising TPU homogenously mixed with a drug, the arms attached to and radially extending from a central elastomeric member through an enteric polymeric linker comprising an enteric polymer and TPU; wherein the enteric polymeric linker is directly bonded to the active segment comprising TPU; wherein the polymeric linker loses 80% or more of its flexural modulus or breaks after incubation in an aqueous solution at pH 6.5 for 3 days at 37° C.; and wherein the gastric residence system is retained in the stomach for a period of at least 24 hours. In some embodiments, the enteric polymer is HMPCAS. Optionally, the enteric polymeric linker comprises a plasticizer, such as about 0.5% to about 20% plasticizer (such as about 0.5% to about 12% plasticizer).

In another example of a gastric residence system, the system includes a plurality of structural members comprising a coupling member comprising TPU and an active segment comprising a carrier polymer homogenously mixed with a drug, the arms attached to and radially extending from a central elastomeric member through an enteric polymeric linker comprising an enteric polymer and TPU; wherein the enteric polymeric linker is directly bonded to the coupling member; wherein the polymeric linker loses 80% or more of its flexural modulus or breaks after incubation in an aqueous solution at pH 6.5 for 3 days at 37° C.; and wherein the gastric residence system is retained in the stomach for a period of at least 24 hours. In some embodiments, the enteric polymer is HMPCAS. Optionally, the enteric polymeric linker comprises a plasticizer, such as about 0.5% to about 20% plasticizer (such as about 0.5% to about 12% plasticizer).

In another example of a gastric residence system, the system includes a plurality of structural members comprising an active segment comprising a carrier polymer homogenously mixed with a drug, the arms attached to and radially extending from a central elastomeric member through an enteric polymeric linker comprising an enteric polymer and PLGA, wherein the polymeric linker loses 80% or more of its flexural modulus or breaks after incubation in an aqueous solution at pH 6.5 for 3 days at 37° C.; and wherein the gastric residence system is retained in the stomach for a period of at least 24 hours. In some embodiments, the enteric polymeric linker comprises the carrier polymer. In some embodiments, the carrier polymer is PCL and the enteric polymeric linker comprise PCL. In some embodiments, the carrier polymer is TPU and the enteric polymeric linker comprise TPU. In some embodiments, the enteric polymer is HMPCAS. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the enteric polymeric linker comprises a plasticizer, such as about 0.5% to about 20% plasticizer (such as about 0.5% to about 12% plasticizer).

In another example of a gastric residence system, the system includes a plurality of structural members comprising an active segment comprising a carrier polymer homogenously mixed with a drug, the arms attached to and radially extending from a central elastomeric member through an enteric polymeric linker comprising an enteric polymer and PLGA; wherein the enteric polymeric linker is directly bonded to the active segment comprising the carrier polymer; wherein the polymeric linker loses 80% or more of its flexural modulus or breaks after incubation in an aqueous solution at pH 6.5 for 3 days at 37° C.; and wherein the gastric residence system is retained in the stomach for a period of at least 24 hours. In some embodiments, the enteric polymer is HMPCAS. In some embodiments, the enteric polymeric linker comprises the carrier polymer. In some embodiments, the carrier polymer is PCL and the enteric polymeric linker comprise PCL. In some embodiments, the carrier polymer is TPU and the enteric polymeric linker comprise TPU. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the enteric polymeric linker comprises a plasticizer, such as about 0.5% to about 20% plasticizer (such as about 0.5% to about 12% plasticizer).

In another example of a gastric residence system, the system includes a plurality of structural members comprising a coupling member and an active segment comprising a carrier polymer homogenously mixed with a drug, the arms attached to and radially extending from a central elastomeric member through an enteric polymeric linker comprising an enteric polymer and PLGA; wherein the enteric polymeric linker is directly bonded to the coupling member; wherein the polymeric linker loses 80% or more of its flexural modulus or breaks after incubation in an aqueous solution at pH 6.5 for 3 days at 37° C.; and wherein the gastric residence system is retained in the stomach for a period of at least 24 hours. In some embodiments, the enteric polymer is HMPCAS. In some embodiments, the coupling member and the enteric polymeric linker comprise a carrier polymer. In some embodiments, the coupling member and the enteric polymeric linker comprise PCL. In some embodiments, the coupling member and the enteric polymeric linker comprise TPU. In some embodiments, the pH-independent degradable polymer comprises acid-terminated PLGA, ester-terminated PLGA, or a mixture thereof. In some embodiments, the polymeric linker comprises 70% or less PLGA (such as about 30% to about 70% PLGA). Optionally, the enteric polymeric linker comprises a plasticizer, such as about 0.5% to about 20% plasticizer (such as about 0.5% to about 12% plasticizer).

Assembly of System Components, Including Linkers

The various components of the gastric residence system or polymer assemblies can be attached to each other by various methods. One convenient method for attachment is heat welding, which involves heating a first surface on a first component at a first temperature to provide a first heated surface, heating a second surface on a second component at a second temperature to provide a second heated surface, and then contacting the first heated surface with the second heated surface (or equivalently, contacting the second heated surface with the first heated surface). The first temperature may be the same as the second temperature, or the first temperature and the second temperature may be different, depending on the properties of the first and second components to be welded together. Heating of the first surface or of the second surface can be performed by contacting the respective surface with a metal platen (a flat metal plate) at the respective temperature. For ease of manufacture, a dual-temperature platen can be used where a first end of the platen is at the first temperature and a second end of the platen is at the second temperature; the first surface can be pressed against the first end of the platen, the second surface can be pressed against the second end of the platen, and then the platen can be removed and the resulting first heated surface can be contacted with the resulting second heated surface. The contacting heated surfaces are pressed together with some degree of force or pressure to ensure adherence after cooling (the applied force or pressure is optionally maintained during the cooling process). Heat welding is also referred to as heat fusion.

Another method for attachment of the various components of the gastric residence systems, or polymer assemblies, is infrared welding. Infrared welding is performed by contacting a first surface on a first component with a second surface on a second component, and irradiating the region of the contacting surfaces with infrared radiation, while applying force or pressure to maintain the contact between the two surfaces, followed by cooling of the attached components (the applied force or pressure is optionally maintained during the cooling process).

After each welding step, an annealing step can optionally be used to increase the strength of the weld. The welded first and second components can be heat annealed by placing the welded components in an oven set to a third temperature (if the components were welded by heat welding, the third temperature can be the same as the first temperature, the same as the second temperature, or different from the first temperature and second temperature used in heat welding). The welded first and second components can be infrared annealed by irradiating the welded region with infrared radiation. Infrared annealing has the advantage that a localized area can be irradiated, unlike heat annealing in an oven where all of the first and second components will be heated.

Any combination of welding and annealing can be used. Heat welding of components can be followed by heat annealing in an oven of the heat weld; heat welding of components can be followed by infrared annealing of the heat weld; infrared welding of components can be followed by heat annealing in an oven of the infrared weld; or infrared welding of components can be followed by infrared annealing of the infrared weld.

Figure 43:
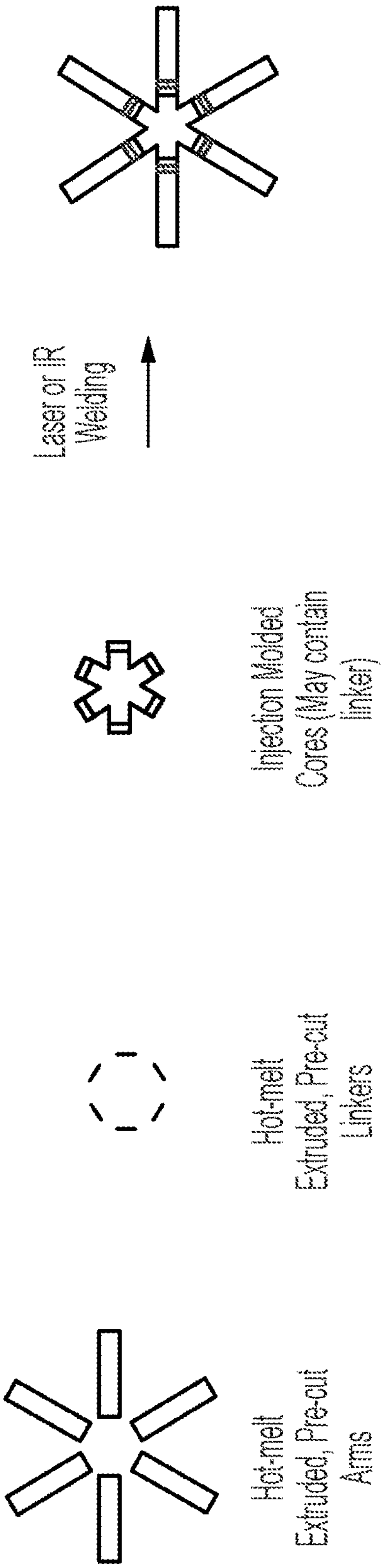
FIG. 43 shows an exemplary method of bonding components together to form a gastric residence system.
Figure 44:
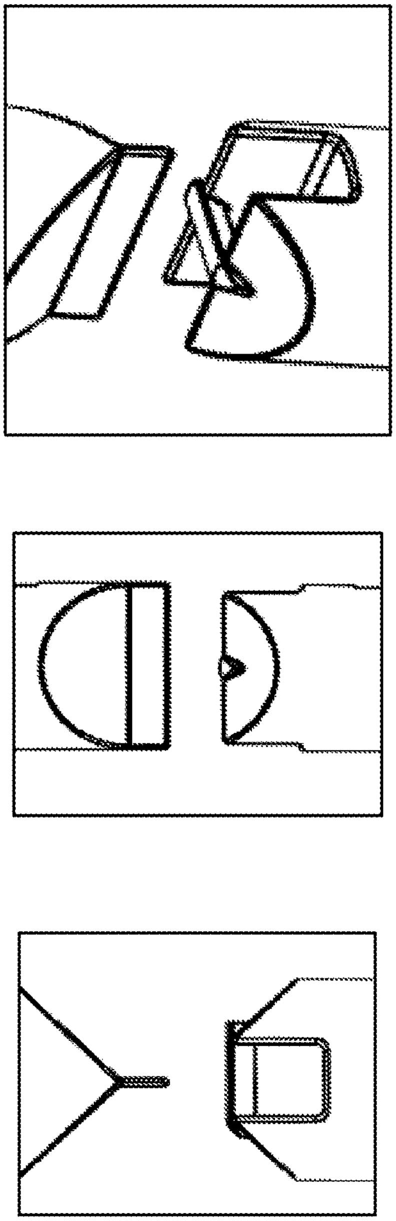
FIG. 44 shows how the flexural modulus of a material may be tested using the three-point bending test.

FIG. 43 shows an exemplary method of bonding components together to form a gastric residence system. A pre-cut polymeric linker (such as an enteric linker or a time-dependent linker) is laser or IR welded to an elastomeric central member. The polymeric linker may be formed, for example, by hot melt extruding a material and cutting it to the desired length. Hot melt extruded arms containing a carrier polymer mixed with an agent are then laser or IR welded to the polymeric linkers, thereby forming the stellate structure of the gastric residence system.

Strong attachment of gastric residence system components to each other allows for optimal system performance when deployed in the stomach of an individual. Poor welding or other attachments of system components may cause the interfaces between system components to sever, which can cause some or all of the system to pass through the pyloric valve into the intestine prior completion of the desired gastric residence period. Several features have been identified to enhance attachment of system components, any one or more of which may be utilized in any of the gastric system components, such as the polymeric linkers (e.g., the time-dependent polymeric linker and/or the enteric polymeric linker) described herein.

The inclusion of a plasticizer in a system component may enhance attachment (such as welding) of that component to an immediately adjacent component. For example, a plasticizer may be included in a polymeric linker (such as a time-dependent linker, an enteric linker, or a dual time-dependent and enteric linker) to strengthen the welded interface between the polymeric linker and an immediately adjacent component (such as a structural member comprising a carrier polymer and an agent (or an active or inactive segment thereof), a coupling member, another polymeric linker, or a second structural member (such as an elastomeric central member)). In certain embodiments, too much plasticizer may result in a weaker welded interface compared to a lower amount of plasticizer. Therefore, in some embodiments, the plasticizer in the system component (such as the polymeric linker) is included in an amount of up to 20% plasticizer, such as up to 18% plasticizer, up to 15% plasticizer, up to 12% plasticizer, up to 10% plasticizer, up to 8% plasticizer, up to 6% plasticizer, up to 4% plasticizer, up to 3% plasticizer, up to 2% plasticizer, or up to 1% plasticizer. In some embodiments, the system component (such as the polymeric linker) includes about 0.5% to about 15% plasticizer, such as about 0.5% to about 1%, about 1% to about 2%, about 2% to about 3%, about 3% to about 5%, about 5% to about 7%, about 7% to about 10%, about 10% to about 12%, about 12% to about 15%, about 15% to about 18%, or about 18% to about 20% plasticizer. Exemplary plasticizers include propylene glycol, polyethylene glycol (PEG), triethyl butyl citrate (TBC), dibutyl sebacate (DBS), triacetin, triethyl citrate (TEC), a poloxamer (e.g., Poloxamer 407, or "P407"), and D-α-tocopheryl polyethylene glycol succinate, among others. In some embodiments, the molecular weight of the polyethylene glycol is about 200 Da to about 8,000,000 Da (also referred to as 8000K or 8000 kDa), for example, about 200 Da to about 400 Da, about 400 Da to about 800 Da, about 800 Da to about 1600 Da, about 1600 Da to about 2500 Da, about 2500 Da to about 5000 Da, about 5000 Da to about 10K, about 10K to about 20K, about 20K to about 50K, about 50K to about 100K, about 100K to about 200K, about 200K to about 400K, about 400K to about 800K, about 800K to about 1000K, about 1000K to about 2000K, about 2000K to about 4000K, about 4000K to about 6000K, or about 6000K to about 8000K.

The inclusion of a color-absorbing agent in a system component may enhance attachment (such as welding) of a system component to an immediately adjacent component. The welding includes heading a component, such as using infrared energy. The color-absorbing agent can absorb heat and act as a black body radiation to evenly distribute head to the welded joint, thus enhancing the strength and durability of the weld. Exemplary color-absorbing agents include iron oxide and carbon black.

The inclusion of a common polymer (such as a common carrier polymer) or a common type of polymer (such as a common type of carrier polymer) between joined components of the gastric residence system can enhance the strength of the welded joint between directly adjacent components. By way of example, in some embodiments, a polymeric linker (such as a time-dependent linker, an enteric polymeric linker, or a dual time-dependent and enteric polymeric linker) includes a common polymer or type of polymer with a directly adjacent component (such as a structural member comprising a carrier polymer and an agent (or an active or inactive segment thereof), a coupling member, another polymeric linker, or a second structural member (such as an elastomeric central member)). The common polymer may be, for example, PCL or a type of PCL, a TPU or a type of TPU, or PLA or a type of PLA.

Directly adjacent or welded components may have similar melt flow index at the welding temperature, which can enhance the weld between the joined gastric residence system components. The melt flow index is a measurement of viscosity determined by the grams of material that flow through a capillary in 10 minutes at a set temperature and set load. The melt flow index may be measured, for example, in accordance with the method described in ASTM D1238, using a 2.16 kg load. In some embodiments, the melt flow index of two gastric residence system components welded together differ by no more than 50%, no more than 40%, no more than 30%, no more than 20%, or no more than 10%, relative to the lower melt flow index of the two components. In some embodiments, the weld temperature of the two components is between about 120° C. and about 200° C., such as about 120° C. to about 140° C., about 140° C. to about 160° C., about 160° C. to about 180° C., or about 180° C. to about 200° C.

IV. Release Rate-Modulating Polymer Films

The following abbreviations for polymers are used:

| Abbreviation | Polymer |
|---|---|
| PDL | poly(DL-lactide); inherent viscosity 1.6-2.4 dl/g ($CHCl_3$), $T_m$ 165-180° C. |
| PCL HMW | polycaprolactone; MW (ave) 200,000 |
| PCL LMW | polycaprolactone; MW (ave) 15,000 |
| VA64 | copovidone; $T_m$ 140° C., $T_g$ 101° C. |
| K90F | povidone; $T_g$ 156° C. |
| PEG1 | polyethylene glycol; MW (ave) 1,000 |
| L-31 | Pluronic ® L-31; PEG-PPG-PEG block co-polymer; MW (ave) 1,100 ($M_n$) |
| PPG | polypropylene glycol |
| PDLG | copolymer of DL-lactide and glycolide); inherent viscosity 1.6-2.4 dl/g ($CHCl_3$) |
| PCL triol | polycaprolactone triol; MW (ave) 900 ($M_n$) |
| F-108 | Pluronic ® F-108; PEG-PPG-PEG block co-polymer |
| PDL-PCL 25-75 | poly-D-lactide-polycaprolactone co-polymer |
| PDL-PCL 80-20 | poly-D-lactide-polycaprolactone co-polymer |
| PG | propylene glycol |
| PVPP | crospovidone |
| PVAc | polyvinylacetate |
| PEG10 | polyethylene glycol; MW (ave) 10,000 |

PLURONIC® is a registered trademark of BASF Corporation for polyoxyalkylene ethers.

Release Rate-Modulating Polymer Films

In this section IV, the current disclosure provides release-rate modulating polymer films which can be coated onto components of gastric residence systems which release agents, such as drugs. Components coated with the release-rate modulating polymer films disclosed herein have substantially the same release-rate properties before and after exposure to heat which occurs during heat-assisted assembly of a gastric residence system. The current disclosure also provides, inter alia, gastric residence systems, arms (elongate members) of gastric residence systems, and segments for use in gastric residence systems and arms of gastric residence systems, which are coated with such release rate-modulating films.

In some embodiments, the release rate modulating film of any of the gastric residence systems disclosed herein does not cover the enteric linkers, time-dependent linkers, disintegrating matrices, or other linkers of the gastric residence system. If a release-rate modulating polymer film is coated on the surface of an arm which comprises one or more linkers, such as a coupling polymer, enteric polymer, enteric linker, time-dependent linker, disintegrating polymer, disintegrating matrix, or other linker, the film does not cover or coat the linkers. This is readily accomplished by applying a release rate-modulating film to segments which will comprise an arm, and then linking the coated segments together with linkers or disintegrating matrices to form an arm; the segments comprising carrier polymer-agent (or agent salt) will thus be coated with the release rate-modulating film, but the linkers or disintegrating matrices will not be coated with the release rate-modulating film.

Figure 70A:
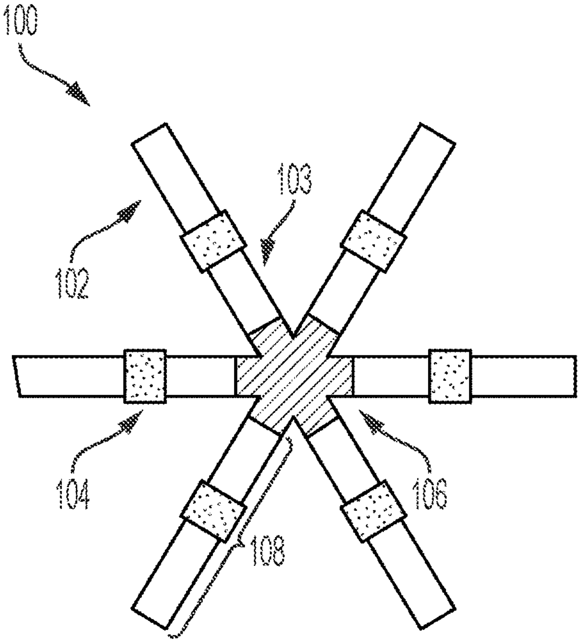
FIG. 70A shows a stellate design of a gastric residence system in its uncompacted state.
Figure 70B:
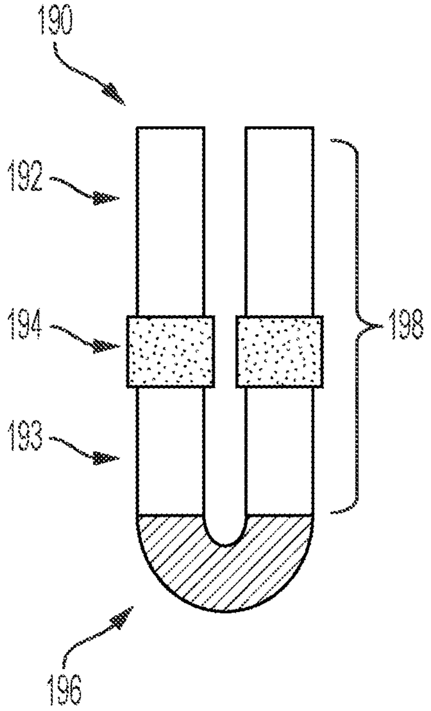
FIG. 70B shows a stellate design of a gastric residence system in a compacted or folded state.
Figure 70C:
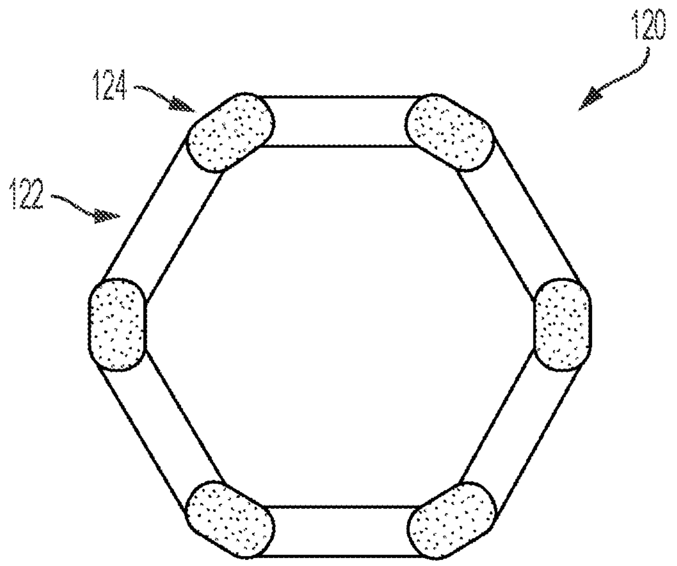
FIG. 70C shows a ring design of a gastric residence system in an uncompacted state.

The films are typically applied to segments of the gastric residence systems. The films can also be applied to multi-segment arms prior to attachment of the multi-segment arms to a central elastomer. The films can also be applied to non-segmented arms (that is, arms which comprise only one segment) prior to attachment of the non-segmented arms to a central elastomer. The non-segmented arm can be attached to the central elastomer either directly or via a linker, such as a disintegrating matrix or coupling polymer. An example of segments of a gastric residence system is shown in FIG. 70A, where segment 102 and segment 103 are linked by linker 104, and attached to a central elastomer 106. The segments 102 and 104 comprise carrier polymer and agent (such as a drug). Using a release rate-modulating polymer film on the segments of the gastric residence system provides the advantageous characteristics described herein.

Several parameters of the films can be adjusted in order to generate desired agent release characteristics, and are discussed below.

Chemical Composition of Release Rate-Modulating Polymer Films

Various polymers can be used to form the release-rate modulating polymer films, including PCL, PDL, PDLG, PDL-PCL copolymer, and PVAc. Mixtures of these polymers can also be used. Additional polymers or other compounds can be blended with the base polymer, such as one or more of copovidone, povidone, polyethylene glycol, Pluronic L-31 (PEG-PPG-PEG block co-polymer), polypropylene glycol, polycaprolactone triol, Pluronic F-108 (PEG-PPG-PEG block co-polymer), poly-D-lactide-polycaprolactone co-polymer (25:75), poly-D-lactide-polycaprolactone co-polymer (80:20), propylene glycol, crospovidone, and polyvinylacetate. Ratios of polymers below are expressed in terms of weight (that is, weight/weight; w/w).

Polymers can be characterized by their number-average molecular weight, $M_n$. For example, where a high molecular weight polycaprolactone is desired, polycaprolactone having a number-average molecular weight of about 150,000 to about 250,000, about 175,000 to about 225,000, or about 200,000 can be used. Where a low molecular weight polycaprolactone is desired, polycaprolactone having a number-average molecular weight of about 10,000 to about 30,000, about 15,000 to about 30,000, about 10,000 to about 25,000, about 10,000 to about 20,000, about 12,000 to about 18,000, or about 15,000 can be used.

Polymers can also be characterized by their intrinsic viscosity, which is correlated to molecular weight by the Mark-Houwink equation. For example, polycaprolactone having an intrinsic viscosity of about 1.0 dL/g to about 2.5 dL/g or about 1.5 dL/g to about 2.1 dL/g can be used. The intrinsic viscosity can be measured in $CHCl_3$ at 25° C. For applications where a high molecular weight PCL is desired, the intrinsic viscosity can be about 1.5 dL/g to about 1.9 dL/g, or the intrinsic viscosity can have a midpoint of about 1.7 dL/g. For applications where a low molecular weight PCL is desired, the intrinsic viscosity can be about 0.2 dL/g to about 0.4 dL/g, or the intrinsic viscosity can have a midpoint of about 0.2 dL/g or 0.4 dL/g.

Poly-D,L-lactide (PDL) is a useful polymer, either alone or in combination with one or more other polymers. In one embodiment, PDL having an intrinsic viscosity of about 1 dl/g to about 3 dl/g can be used. In one embodiment, PDL having an intrinsic viscosity of about 1.6 dl/g to about 2.4 dl/g can be used. In another embodiment, PDL having an intrinsic viscosity midpoint of about 2.0 dl/g can be used. In one embodiment, PDL having an intrinsic viscosity of about 1.3 dl/g to about 1.7 dl/g can be used. In another embodiment, PDL having an intrinsic viscosity midpoint of about 1.5 dl/g can be used.

Polymers that can be combined with PDL include poly-D,L-lactide/glycolide (PDLG). In one embodiment, PDLG having an intrinsic viscosity of about 0.1 dl/g to about 0.5 dl/g is used in combination with PDL. A PDL:PDLG ratio of about 9:1 to about 1:3 can be used, such as about 2:1 to about 1:2, about 1.25:1 to about 1:1.25; or about 1:1.

Another polymer that can be combined with PDL includes polycaprolactone (PCL), for example, PCL of molecular weight about $M_n$ 75,000 to about $M_n$ 250,000.

Another polymer that can be combined with PDL is polyethylene glycol (PEG), such as PEG of molecular weight about $M_n$ 800 to about $M_n$ 10,000.

Yet another polymer that can be combined with PDL is polypropylene glycol (PPG), such as PPG of about $M_n$ 2,500 to about $M_n$ 6,000.

Both PCL and PEG can be combined with PDL, to form a PDL:PCL:PEG film. In one embodiment, the PDL can comprise between about 15% to about 80% of the release rate-modulating film, the PCL can comprise between about 15% to about 75% of the release rate-modulating film, and the PEG can comprise between about 5% to about 15% of the release rate-modulating film, by weight. Exemplary ratios include a PDL:PCL:PEG ratio of about 9:27:4 (w/w/w) and a PDL:PCL:PEG ratio of about 36:9:5 (w/w/w).

PDL:PEG:PPG combinations can also be used. In one embodiment, the PDL can comprise between about 75% to about 95% of the release rate-modulating film, the PEG can comprise between about 3% to about 10% of the release rate-modulating film, and the PPG can comprise between about 1% to about 7% of the release rate-modulating film, by weight.

PDL can also be combined with a polyethylene glycol-polypropylene glycol-polyethylene glycol (PEG-PPG-PEG) block copolymer, for example, a PEG-PPG-PEG block copolymer which comprises about 75% to about 90% ethylene glycol. In one embodiment, the PEG-PPG-PEG block copolymer can have a molecular weight $M_n$ of about 14,000 to about 15,000.

Exemplary ratios of this combination include a (PDL):(PEG-PPG-PEG block copolymer) ratio of between about 85:15 to about 95:5 (w/w), and a (PDL):(PEG-PPG-PEG block copolymer) ratio of about 9:1 (w/w).

A PDL-PCL copolymer, that is, poly-D-lactide-polycaprolactone co-polymer, can also be used as a release rate-modulating polymer film. The relative composition of the copolymer can range widely, from about 15% PDL monomer and 85% PCL monomer to about 90% PDL monomer and 10% PCL monomer in the copolymer. Other ranges, such as PDL monomer:PCL monomer of about 15:85 to about 35:65, or about 25:75 and PDL monomer:PCL monomer of about 70:30 to about 90:10, or about 80:20, can be used. The PDL-PCL copolymer can have an intrinsic viscosity of about 0.4 dl/g to about 1.2 dl/g, such as about 0.6 dl/g to about 1 dl/g.

PEG can also be combined with the PDL-PCL copolymer, to form a release rate-modulating polymer film comprising (PDL-PCL copolymer):PEG. The PDL-PCL copolymer can comprise about 75% to about 95% of the release rate modulating film by weight and the PEG can comprise about 5% to about 25% of the release rate modulating film by weight, such as PDL-PCL copolymer comprising about 90% of the release rate modulating film by weight and the PEG comprising about 10% of the release rate modulating film by weight.

Polycaprolactone can be used as a release-rate modulating film. One such formulation comprises both high molecular weight polycaprolactone (PCL-HMW) and low molecular weight polycaprolactone (PCL-LMW). The PCL-HMW can comprise PCL of about $M_n$ 75,000 to about $M_n$ 250,000; or PCL having an intrinsic viscosity of about 1.6 dl/g to about 2.4 dl/g. The PCL-LMW can comprise PCL of about $M_n$ 10,000 to about $M_n$ 20,000; or PCL having an intrinsic viscosity of about 0.1 dl/g to about 0.8 dl/g. Ratios of (PCL-HMW):(PCL-LMW) ratio can range from about 1:4 to about 95:5, about 2:3 to about 95:5, about 3:1 to about 95:5, or about 9:1.

Advantage of Uniform Release-Rate Modulating Polymer Films During Thermal Processing Gastric residence systems are often assembled by heating individual components, such as arms and linkers, and pressing the heated components together. Techniques such as infrared welding or contact with a heated platen can be used to heat individual components, which can then be pressed together to join the components.

In some embodiments, release-rate modulating polymer films are applied to gastric residence systems after all heat-assisted assembly steps have been completed. Applying the film after all heat-assisted assembly steps prevents disruption of the film during the heating process. In other embodiments, however, release-rate modulating polymer films are applied to components of gastric residence systems before the all heat-assisted assembly steps have been completed. In these embodiments, it is important that the use of heat during the heat-assisted assembly steps do not change the release-rate properties of the release-rate modulating polymer films.

One aspect of the current disclosure is the use of uniform release-rate modulating polymer films. Uniform films may comprise a single polymer or may comprise multiple polymers, along with other additives such as plasticizers, permeable components, or anti-tack agents. However, all of the ingredients in the film are blended together into a uniform mixture, so that the film, after coating onto any component of the gastric residence system, is essentially uniform. Use of such uniform films is advantageous, as it significantly reduces or prevents alteration of the release rate properties of the release-rate modulating polymer film by any heat-assisted assembly steps.

In some embodiments, the release rate of agent from a coated segment or arm as disclosed herein changes by less than about 20% after heat-assisted assembly, as compared to the release rate of agent from the coated segment or arm before heat-assisted assembly. In some embodiments, the release rate of agent from a coated segment or arm as disclosed herein changes by less than about 15% after heat-assisted assembly, as compared to the release rate of agent from the coated segment or arm before heat-assisted assembly. In some embodiments, the release rate of agent from a coated segment or arm as disclosed herein changes by less than about 10% after heat-assisted assembly, as compared to the release rate of agent from the coated segment or arm before heat-assisted assembly. In some embodiments, the release rate of agent from a coated segment or arm as disclosed herein changes by less than about 5% after heat-assisted assembly, as compared to the release rate of agent from the coated segment or arm before heat-assisted assembly. Comparative release rates can be measured by incubating the coated segment or coated arm in FaSSGF at 37° C., and measuring cumulative release of agent at about day 1, at about day 4, or at about day 7; or at any two of about day 1, about day 4, and about day 7; or at all three of about day 1, about day 4, and about day 7.

Thermal cycling is exposure of an arm, such as an arm coated with a release rate-modulating polymer film, to heat, such as heat-assisted assembly, heat welding, IR welding, or using conditions similar to heat-assisted assembly, heat welding, or IR welding, followed by cooling of the arm. Comparative release rates can be measured as indicated above and in the examples before and after thermal cycling.

Some release-rate modulating polymer films disclosed in WO 2018/227147 contain porogens, which are additives in particle form that dissolve out of the release rate-modulating polymer films, creating pores in the films. Examples of porogens include sodium chloride, sucrose, or water-soluble polymeric materials in particulate form. Use of porogens results in non-uniform (non-homogeneous) release-rate modulating films, where small porogen particles are embedded in the release-rate modulating polymer film. Such porogen-containing films may be disrupted during heat-assisted assembly steps. Accordingly, in one embodiment, the release-rate modulating polymer films of the current disclosure do not comprise porogens.

Plasticizers and Other Additives to Release Rate-Modulating Polymer Films

Plasticizers can also be added to further tune the properties of the release rate-modulating polymer films. Plasticizers that can be used include the classes of phthalates, phosphates, citrates, tartrates, adipates, sebacates, sulfonamides, succinates, glycolates, glycerolates, benzoates, myristates, and halogenated phenyls. Specific plasticizers that can be used include triacetin, triethyl citrate, PEG, poloxamer, tributyl citrate, and dibutyl sebacate. Triacetin and triethyl citrate (TEC) are particularly useful.

Plasticizers can be added to make up about 1% to about 35%, about 1% to about 30%, about 1% to about 25%, about 1% to about 20%, about 1% to about 15%, about 1% to about 10%, about 1% to about 8%, about 1% to about 5%, about 1% to about 3%, about 5% to about 40%, about 10% to about 40%, about 15% to about 40%, about 20% to about 40%, about 25% to about 40%, about 30% to about 40%, about 10% to about 30%, about 15% to about 30%, about 20% to about 30%, about 25% to about 30%, or about 10%, about 15%, about 20%, about 25%, about 30%, about 35%, or about 40% by weight of the release rate-modulating polymer film. A preferred range of plasticizer is about 5% to about 20%, more preferably about 10% to about 20%, by weight of the release rate-modulating polymer film.

Processing aids can also be added to release rate-modulating polymer films. Anti-tack agents, such as magnesium stearate, talc, or glycerol monostearate can be added to aid in processing of the films. Such anti-tack agents can be added in amounts of about 0.5% to about 5%, about 1% to about 3%, or about 2%.

Film Thickness

The release-rate modulating polymer films should be very thin in comparison to the carrier polymer-agent segment of the gastric residence system that they cover. This allows for diffusion of water into the carrier polymer-agent segment, and diffusion of agent out of the segment.

The thickness of the release-rate modulating polymer films can be between about 1 micrometer to about 40 micrometers, between about 1 micrometer to about 30 micrometers, or between about 1 micrometer to about 25 micrometers. The films are typically between about 1 micrometer to about 20 micrometers, such as between about 1 micrometer to about 20 micrometers, about 1 micrometer to about 15 micrometers, about 1 micrometer to about 10 micrometers, about 1 micrometer to about 5 micrometers, about 1 micrometer to about 4 micrometers, about 1 micrometer to about 3 micrometers, about 1 micrometer to about 2 micrometers, about 2 micrometers to about 10 micrometers, about 5 micrometers to about 20 micrometers, about 5 micrometer to about 10 micrometers, about 10 micrometer to about 15 micrometers, or about 15 micrometers to about 20 micrometers.

In further embodiments, the release-rate modulating polymer film does not add substantially to the strength of the carrier polymer-agent segment that it covers. In further embodiments, the release-rate modulating polymer film adds less than about 20%, less than about 10%, less than about 5%, or less than about 1% to the strength of the segment. The strength of the segment can be measured by the four-point bending flexural test (ASTM D790) described in Example 18 of WO 2017/070612 and Example 13 of WO 2017/100367.

Film Weight

The release-rate modulating polymer films can be coated onto the carrier polymer-agent arm or arm segment of the gastric residence system in amounts from about 0.1% to 20% of the weight of the carrier polymer-agent arm or arm segment prior to coating; or in amounts from about 0.1% to 15%, of about 0.1% to 10%, about 0.1% to about 8%, about 0.1% to about 5%, about 0.1% to about 4%, about 0.1% to about 3%, about 0.1% to about 2%, about 0.1% to about 1%, about 0.5% to about 10%, about 0.5% to about 8%, about 0.5% to about 5%, about 0.5% to about 4%, about 0.5% to about 3%, about 0.5% to about 2%, about 0.5% to about 1%, about 1% to about 10%, about 1% to about 8%, about 1% to about 5%, about 1% to about 4%, about 1% to about 3%, or about 1% to about 2% of the weight of the carrier polymer-agent arm or arm segment prior to coating. The films can be applied in amounts of about 1% to about 20% of the weight of the carrier polymer-agent arm or arm segment of the gastric residence system prior to coating, such as in amounts of about 1% to about 10%, about 1% to about 7%, about 1% to about 5%, or about 2% to about 5%, for example, in amounts of 1%, 1.5%, 2%, 2.5%, 3%, 3.5%, 4%, 4.5%, 5%, 6%, 7%, 8%, 9%, or 10% of the weight of the carrier polymer-agent arm or arm segment prior to coating.

Exemplary Embodiments of Release Rate-Modulating Films for Combination with Other Features The release rate-modulating films described below can be used with any of the arms, arm segments, or gastric residence systems, and in any combination with the other features described herein, such as filaments, arms of varying stiffness, and improved time-dependent and enteric linkers.

In some embodiments, provided are release rate-modulating films comprising poly-D,L-lactide (PDL) and poly-D,L-lactide/glycolide (PDLG). In some embodiments, the PDL comprises PDL having an intrinsic viscosity of about 1 dl/g to about 4 dl/g. In some embodiments, the PDLG comprises PDLG having an intrinsic viscosity of about 0.1 dl/g to about 3 dl/g; 0.1 dl/g to about 1.5 dl/g; or 0.1 dl/g to about 0.5 dl/g. In some embodiments, the PDL:PDLG ratio is between about 2:1 to about 1:2 (weight/weight). In some embodiments, the PDL:PDLG ratio is between about 1.25:1 to about 1:1.25 (w/w). In some embodiments, the PDL:PDLG ratio is about 1:1 (w/w). In some embodiments according to any one of the release rate-modulating films described herein, the release rate-modulating film is substantially free of porogen. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

In some embodiments, provided are release rate-modulating films comprising high molecular weight polycaprolactone (PCL-HMW) and low molecular weight polycaprolactone (PCL-LMW). In some embodiments, the PCL-HMW comprises PCL of about $M_n$ 75,000 to about $M_n$ 250,000; or PCL having an intrinsic viscosity of about 1.0 dl/g to about 2.4 dl/g; or PCL having an intrinsic viscosity of about 1.2 dl/g to about 2.4 dl/g; or PCL having an intrinsic viscosity of about 1.6 dl/g to about 2.4 dl/g. In some embodiments, the PCL-LMW comprises PCL of about $M_n$ 10,000 to about $M_n$ 20,000; or PCL having an intrinsic viscosity of about 0.1 dl/g to about 0.8 dl/g. In some embodiments, the PCL-HMW comprises PCL of about $M_n$ 75,000 to about $M_n$ 250,000, or PCL having an intrinsic viscosity of about 1.0 dl/g to about 2.4 dl/g, or PCL having an intrinsic viscosity of about 1.2 dl/g to about 2.4 dl/g, or PCL having an intrinsic viscosity of about 1.6 dl/g to about 2.4 dl/g; and the PCL-LMW comprises PCL of about $M_n$ 10,000 to about $M_n$ 20,000, or PCL having an intrinsic viscosity of about 0.1 dl/g to about 0.8 dl/g. In some embodiments, the (PCL-HMW):(PCL-LMW) ratio is between about 1:4 to about 95:5 (weight/weight). In some embodiments, the (PCL-HMW):(PCL-LMW) ratio is between about 2:3 to about 95:5 (weight/weight). In some embodiments, the (PCL-HMW):(PCL-LMW) ratio is between about 3:1 to about 95:5 (weight/weight). In some embodiments, the (PCL-HMW):(PCL-LMW) ratio is about 9:1 (w/w). In some embodiments, the (PCL-HMW):(PCL-LMW) ratio is about 1:3 (w/w). In some embodiments, wherein the (PCL-HMW):(PCL-LMW) ratio is about 4:6 (w/w); or wherein the (PCL-HMW):(PCL-LMW) ratio is about 6:4 (w/w). In some embodiments, the (PCL-HMW):(PCL-LMW) ratio is about 1:1 (w/w). In some embodiments, the (PCL-HMW):(PCL-LMW) ratio is about 3:1 (w/w). In some embodiments, the (PCL-HMW):(PCL-LMW) ratio is about 85:15 (w/w). In some embodiments, the release rate-modulating film is substantially free of porogen. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

In some embodiments, provided are release rate-modulating films comprising poly-D,L-lactide (PDL). In some embodiments, the PDL comprises PDL having an intrinsic viscosity of about 1 dl/g to about 5 dl/g, or about 1.6 dl/g to about 2.4 dl/g. In some embodiments, the release rate-modulating film further comprises polycaprolactone (PCL). In some embodiments, the release rate-modulating film further comprises polycaprolactone (PCL) and polyethylene glycol (PEG). In some embodiments, the release rate-modulating film further comprises polycaprolactone (PCL), polyethylene glycol (PEG) and polypropylene glycol (PPG). In some embodiments, the PCL comprises PCL of about $M_n$ 75,000 to about $M_n$ 250,000. In some embodiments, the PEG comprises PEG of about $M_n$ 800 to about $M_n$ 20,000. In some embodiments, the PPG comprises PPG having $M_n$ of at least about 2,500. In some embodiments, the PPG comprises PPG of about $M_n$ 2,500 to about $M_n$ 6,000. In some embodiments, the PDL:PCL ratio is about 9:27 (w/w). In some embodiments, the PDL:PCL ratio is about 36:9 (w/w). In some embodiments, the PDL:PCL:PEG ratio is about 9:27:4 (w/w/w). In some embodiments, the PDL:PCL:PEG ratio is about 36:9:5 (w/w/w). In some embodiments, the release rate-modulating film is substantially free of porogen. In some embodiments, the increase in the weight of the arm, the arm segment, or the gastric residence system due to addition of the release rate-modulating film is about 2% to about 6% of the weight of the uncoated arm, arm segment or gastric resident system. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

In some embodiments, provided are release rate-modulating films comprising polycaprolactone (PCL). In some embodiments, the PCL comprises PCL of about $M_n$ 75,000 to about $M_n$ 250,000. In some embodiments, the release rate-modulating film further comprises polyethylene glycol (PEG). In some embodiments, the release rate-modulating film further comprises polyethylene glycol (PEG) and polypropylene glycol (PPG). In some embodiments, the PEG comprises PEG of $M_n$ about 800 to about 1,200. In some embodiments, the PPG comprises PPG of about $M_n$ 2,500 to about $M_n$ 6,000. In some embodiments, the PCL comprises between about 15% to about 80% of the release rate-modulating film, the PEG comprises between about 5% to about 15% of the release rate-modulating film, and/or the PPG comprises between about 5% to about 15% of the release rate-modulating film by weight. In some embodiments, the release rate-modulating film is substantially free of porogen. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

In some embodiments, provided are release rate-modulating films comprising high molecular weight poly-D,L-lactide (PDL-HMW) and low molecular weight poly-D,L-lactide (PDL-LMW). In some embodiments, the PDL-HMW comprises PDL of inherent viscosity of about 1.6 dl/g to about 2.4 dl/g. In some embodiments, the PDL-LMW comprises PDL of inherent viscosity of about 0.5 dl/g to about 1.5 dl/g. In some embodiments, the PDL-HMW comprises PDL having an intrinsic viscosity midpoint of about 2 dl/g and the PDL-LMW comprises PDL having an intrinsic viscosity midpoint of about 1.5 dl/g. In some embodiments, the (PDL-HMW):(PDL-LMW) ratio is between about 5:95 to about 95:5 (weight/weight). In some embodiments, the (PDL-HMW):(PDL-LMW) ratio is between about 2:3 to about 95:5 (weight/weight). In some embodiments, the (PDL-HMW):(PDL-LMW) ratio is between about 3:1 to about 95:5 (weight/weight). In some embodiments, the (PDL-HMW):(PDL-LMW) ratio is about 9:1 (w/w). In some embodiments, the release rate-modulating film further comprises polycaprolactone (PCL) and polyethylene glycol (PEG). In some embodiments, the PCL comprises PCL of about $M_n$ 80,000 to about $M_n$ 200,000. In some embodiments, the (PDL-HMW+PDL-LMW) comprises between about 15% to about 80% of the release rate-modulating film, the PCL comprises between about 15% to about 75% of the release rate-modulating film, and the PEG comprises between about 5% to about 15% of the release rate-modulating film, by weight. In some embodiments, the (PDL-HMW+PDL-LMW):PCL:PEG ratio is about 9:27:4 (w/w/w). In some embodiments, the (PDL-HMW+PDL-LMW):PCL:PEG ratio is about 36:9:5 (w/w/w). In some embodiments, the release rate-modulating film is substantially free of porogen. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

In some embodiments according to any one of the release rate-modulating films described herein, the release rate-modulating film further comprises a polyethylene glycol-polypropylene glycol-polyethylene glycol (PEG-PPG-PEG) block copolymer. In some embodiments, the PEG-PPG-PEG block copolymer comprises PEG-PPG-PEG block copolymer of $M_n$ about 14,000 to about 15,000. In some embodiments, the PEG-PPG-PEG block copolymer comprises about 75% to about 90% ethylene glycol. In some embodiments wherein the release rate-modulating film comprises PDL and PEG-PPG-PEG block copolymer, the (PDL):(PEG-PPG-PEG block copolymer) ratio is between about 85:15 to about 95:5 (w/w). In some embodiments wherein the release rate-modulating film comprises PDL-HMW+PDL-LMW and PEG-PPG-PEG block copolymer, the (PDL-HMW+PDL-LMW):(PEG-PPG-PEG block copolymer) ratio is between about 85:15 to about 95:5 (w/w). In some embodiments wherein the release rate-modulating film comprises PCL and PEG-PPG-PEG block copolymer, the (PCL):(PEG-PPG-PEG block copolymer) ratio is between about 85:15 to about 95:5 (w/w). In some embodiments wherein the release rate-modulating film comprises PDL and PEG-PPG-PEG block copolymer, the (PDL):(PEG-PPG-PEG block copolymer) ratio is about 9:1 (w/w). In some embodiments wherein the release rate-modulating film comprises PDL-HMW+PDL-LMW and PEG-PPG-PEG block copolymer, the (PDL-HMW+PDL-LMW):(PEG-PPG-PEG block copolymer) ratio is about 9:1 (w/w). In some embodiments wherein the release rate-modulating film comprises PCL and PEG-PPG-PEG block copolymer, the (PCL):(PEG-PPG-PEG block copolymer) ratio is about 9:1 (w/w). In some embodiments, the release rate-modulating film is substantially free of porogen. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

In some embodiments according to any one of the release rate-modulating films described herein, the release rate-modulating film further comprises polyethylene glycol (PEG). In some embodiments according to any one of the release rate-modulating films described herein, the release rate-modulating film further comprises polypropylene glycol (PPG). In some embodiments according to any one of the release rate-modulating films described herein, the release rate-modulating film further comprises polyethylene glycol (PEG) and polypropylene glycol (PPG). In some embodiments, wherein the release rate-modulating comprises PDL, PEG and PPG, the PDL comprises between about 75% to about 95% of the release rate-modulating film, the PEG comprises between about 3% to about 10% of the release rate-modulating film, and the PPG comprises between about 1% to about 7% of the release rate-modulating film, by weight. In some embodiments, wherein the release rate-modulating film comprises PDL, PEG, and PPG, the (PDL):(PEG):(PPG) ratio is about 90:(six and two-thirds):(three and one-third) by weight. In some embodiments, wherein the release rate-modulating film comprises PDL, PEG, PPG, the (PDL):(PEG):(PPG) ratio is about 27:2:1 by weight. In some embodiments, wherein the release rate-modulating film comprises PCL, PEG, PPG, the (PCL):(PEG):(PPG) ratio is about 27:2:1 by weight. In some embodiments, wherein the release rate-modulating film comprises (PDL-HMW+PDL-LMW), PEG, PPG, the (PDL-HMW+PDL-LMW):(PEG):(PPG) ratio is about 27:2:1 by weight. In some embodiments, the PEG comprises PEG of $M_n$ about 800 to about 1,200. In some embodiments, the PPG comprises PPG of about $M_n$ 2,500 to about $M_n$ 6,000. In some embodiments, the release rate-modulating film is substantially free of porogen. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

In some embodiments, provided are release rate-modulating film comprises poly-D-lactide-polycaprolactone copolymer (PDL-PCL copolymer). In some embodiments, PDL comprises between about 15% to about 90% of the PDL-PCL copolymer. In some embodiments, PDL comprises between about 15% to about 35% of the PDL-PCL copolymer. In some embodiments, PDL comprises between about 70% to about 90% of the PDL-PCL copolymer. In some embodiments, the PDL-PCL copolymer comprises PDL-PCL copolymer having intrinsic viscosity of about 0.6 dl/g to about 4 dl/g, preferably about 0.6 dl/g to about 2 dl/g. In some embodiments, the release rate-modulating film further comprises PEG. In some embodiments, the PEG comprises PEG of average molecular weight between about 800 and about 1,200. In some embodiments, the PDL-PCL copolymer comprises about 75% to about 95% of the release rate modulating film by weight and the PEG comprises about 5% to about 25% of the release rate modulating film by weight. In some embodiments, the PDL-PCL copolymer comprises about 90% of the release rate modulating film by weight and the PEG comprises about 10% of the release rate modulating film by weight. In some embodiments, PDL comprises about 25% of the PDL-PCL copolymer. In some embodiments, PDL comprises about 80% of the PDL-PCL copolymer. In some embodiments, the release rate-modulating film is substantially free of porogen. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

In some embodiments according to any one of the release rate-modulating films described herein, wherein the release rate-modulating film comprises PDL-PCL copolymer, the release rate-modulating film further comprises a polyethylene glycol-polypropylene glycol-polyethylene glycol (PEG-PPG-PEG) block copolymer. In some embodiments, the PEG-PPG-PEG block copolymer comprises PEG-PPG-PEG block copolymer of $M_n$ about 14,000 to about 15,000. In some embodiments, the PEG-PPG-PEG block copolymer comprises about 75% to about 90% ethylene glycol. In some embodiments, the (PDL-PCL copolymer):(PEG-PPG-PEG block copolymer) ratio is between about 85:15 to about 95:5 (w/w). In some embodiments, the (PDL-PCL copolymer):(PEG-PPG-PEG block copolymer) ratio is about 9:1 (w/w). IN some embodiments, PDL comprises about 25% of the PDL-PCL copolymer. In some embodiments, PDL comprises about 80% to about 90% of the PDL-PCL copolymer. In some embodiments, the release rate-modulating film is substantially free of porogen. The release rate-modulating films described above can be used with any of the arms, arm segments, or gastric residence systems, and in any combination with the other features described herein, such as filaments, arms of varying stiffness, and improved time-dependent and enteric linkers. In some embodiments, the increase in the weight of the arm, the arm segment, or the gastric residence system due to addition of the release rate-modulating film is about 2% to about 6% of the weight of the uncoated arm, uncoated arm segment or uncoated gastric resident system respectively. In some embodiments, the release rate of agent from the arm, the arm segment, or the gastric resident system in aqueous media is substantially linear over at least a 96-hour period. In some embodiments, the release rate of agent from the arm, the arm segment, or the gastric resident system is substantially the same before and after thermal cycling or heat-assisted assembly.

The release rate-modulating films described above can be used with any of the arms, arm segments, or gastric residence systems, and in any combination with the other features described herein, such as filaments, arms of varying stiffness, and improved time-dependent and enteric linkers. In some embodiments according to any one of the arms, arm segments, or gastric residence systems described herein, the release rate-modulating film is applied by pan coating. In some embodiments according to any one of the arms, arm segments, or gastric residence systems described herein, the release rate-modulating film is applied by dip coating. In some embodiments, the arm, arm segment or gastric residence system comprises at least one agent or a pharmaceutically acceptable salt thereof comprising one or more of drug, a pro-drug, a biologic, a statin, rosuvastatin, a non-steroidal anti-inflammatory drug (NSAID), meloxicam, a selective serotonin reuptake inhibitor (SSRs), escitalopram, citalopram, a blood thinner, clopidogrel, a steroid, prednisone, an antipsychotic, aripiprazole, risperidone, an analgesic, buprenorphine, an opioid antagonist, naloxone, an anti-asthmatic, montelukast, an anti-dementia drug, memantine, a cardiac glycoside, digoxin, an alpha blocker, tamsulosin, a cholesterol absorption inhibitor, ezetimibe, an anti-gout treatment, colchicine, an antihistamine, loratadine, cetirizine, an opioid, loperamide, a proton-pump inhibitor, omeprazole, an antiviral agent, entecavir, an antibiotic, doxycycline, ciprofloxacin, azithromycin, an anti-malarial agent, levothyroxine, a substance abuse treatment, methadone, varenicline, a contraceptive, a stimulant, caffeine, a nutrient, folic acid, calcium, iodine, iron, zinc, thiamine, niacin, vitamin C, vitamin D, biotin, a plant extract, a phytohormone, a vitamin, a mineral, a protein, a polypeptide, a polynucleotide, a hormone, an anti-inflammatory drug, an antipyretic, an antidepressant, an antiepileptic, an antipsychotic agent, a neuroprotective agent, an anti-proliferative, an anti-cancer agent, an antimigraine drug, a prostaglandin, an antimicrobial, an antifungals, an antiparasitic, an anti-muscarinic, an anxiolytic, a bacteriostatic, an immunosuppressant agent, a sedative, a hypnotic, a bronchodilator, a cardiovascular drug, an anesthetic, an anti-coagulant, an enzyme inhibitor, a corticosteroid, a dopaminergic, an electrolyte, a gastro-intestinal drug, a muscle relaxant, a parasympathomimetic, an anorectic, an anti-narcoleptics, quinine, lumefantrine, chloroquine, amodiaquine, pyrimethamine, proguanil, chlorproguanil-dapsone, a sulfonamide, sulfadoxine, sulfamethoxypyridazine, mefloquine, atovaquone, primaquine, halofantrine, doxycycline, clindamycin, artemisinin, an artemisinin derivative, artemether, dihydroartemisinin, arteether, or artesunate. In some embodiments, the at least one agent or a pharmaceutically acceptable salt thereof comprises memantine. In some embodiments, the at least one agent or a pharmaceutically acceptable salt thereof comprises donepezil. In some embodiments, the at least one agent or a pharmaceutically acceptable salt thereof comprises memantine and donepezil. In some embodiments, the at least one agent or a pharmaceutically acceptable salt thereof comprises risperidone. In some embodiments, the at least one agent or a pharmaceutically acceptable salt thereof comprises dapagliflozin.

In any of the embodiments disclosed herein which uses poly-D,L-lactide, poly-L-lactide can be used in place of the poly-D,L-lactide.

In any of the embodiments disclosed herein which uses poly-D,L-lactide, poly-D-lactide can be used in place of the poly-D,L-lactide.

Application of Release Rate-Modulating Polymer Films onto Segments for Use in Gastric Residence Systems The release rate-modulating polymer films can be applied to segments for use in gastric residence systems using various techniques. Several of the techniques involve coating a segment, comprising a carrier polymer and agent, with a solution of a formulation of a release rate-modulating polymer film, producing a film-coated segment. The film-coated segment is then dried.

Various methods of coating films onto objects are known in the art, and include dip coating, pan coating, spray coating, and fluidized bed coating. Fluidized bed coating is also known as Wurster coating or air suspension coating. For these coating methods, a formulation of a release-rate modulating polymer film, including the polymer, and any plasticizers if present, is prepared as a solution. The solvent used for the solution of the polymer film formulation is typically an organic solvent, such as ethyl acetate, dichloromethane, acetone, methanol, ethanol, isopropanol, or any combination thereof. Preferably, Class 3 solvents as listed in the guidance from the United States Food and Drug Administration at URL www.fda.gov/downloads/drugs/guidances/ucm073395.pdf (which include ethanol, acetone, and ethyl acetate) are used; however, Class 2 solvents (which include dichloromethane and methanol) can be used if necessary for the formulation. Class 1 and Class 4 solvents should be used only when the formulation cannot be prepared with a suitable Class 3 or Class 2 solvent.

Release rate-modulating polymer films can also be integrated onto segments by co-extrusion, where the segment formulation is co-extruded with a surrounding thin layer of the release rate-modulating polymer film.

The Examples below illustrate the use of some of these coating techniques for preparation of segments with a release rate-modulating polymer film.

Evaluation of Release Characteristics

The release characteristics of agent from segments, arms, and gastric residence systems can be evaluated by various assays. Assays for agent release are described in detail in the examples. Release of agent in vitro from segments, arms, and gastric residence systems can be measured by immersing a segment, arm, or gastric residence system in a liquid, such as distilled water, 0.1 N HCl, buffered solutions, fasted state simulated gastric fluid (FaSSGF), or fed state simulated gastric fluid (FeSSGF). Fasted state simulated gastric fluid (FaSSGF) is a preferred aqueous medium for release assays. Simulated gastric fluid indicates either fasted state simulated gastric fluid (FaSSGF) or fed state simulated gastric fluid (FeSSGF); when a limitation is specified as being measured in simulated gastric fluid (SGF), the limitation is met if the limitation holds in either fasted state simulated gastric fluid (FaSSGF) or fed state simulated gastric fluid (FeSSGF). For example, if a segment is indicated as releasing at least 10% of an agent over the first 24 hours in simulated gastric fluid, the limitation is met if the segment releases at least 10% of the agent over the first 24 hours in fasted state simulated gastric fluid, or if the segment releases at least 10% of the agent over the first 24 hours in fed state simulated gastric fluid.). Release rates can be measured at any desired temperature, which will typically be in a range from about 35° C. to about 40° C., such as normal body temperature of 37° C. Release rates can be measured for any desired period of time, for example, about 30 minutes, about 1, 2, 3, 4, 5, 6, 10, 12, 15, 18, 20, or 24 hours; about 1, 2, 3, 4, 5, 6, or 7 days; about 1, 2, 3, or 4 weeks; or about 1 month. When in vitro tests are done to compare release rates, the comparison solutions are kept at the same temperature, such as room temperature, 25° C., or 37° C. Room temperature (ambient temperature) is a preferred temperature for measurements or comparisons; in one embodiment, the ambient temperature does not drop below 20° C. or exceed 25° C. (although it may fluctuate between 20° C. and 25° C.). Normal human body temperature (37° C.) is another preferred temperature for measurements or comparisons.

Release rates can also be measured in environments designed to test specific conditions, such as an environment designed to simulate consumption of alcoholic beverages. Such environments can comprise a mixture of any one of the aqueous solutions described herein and ethanol, for example, a mixture of about 60% of any one of the aqueous solutions described herein and about 40% ethanol. Sequential exposure to different aqueous media (that is, different environments) can also be used to measure release rates.

Fasted state simulated gastric fluid (FaSSGF) is typically prepared using Biorelevant powders (biorelevant.com; Biorelevant.com Ltd., London, United Kingdom). When FaSSGF is prepared according to the Biorelevant "recipe," it is an aqueous solution at pH 1.6 with taurocholate (0.08 mM), phospholipids (0.02 mM), sodium (34 mM), and chloride (59 mM).

In vivo tests can be performed in animals such as dogs (for example, beagle dogs or hound dogs) and swine. For in vivo tests, a gastric residence system is used, since an individual segment or arm would not be retained in the stomach of the animal. Blood samples can be obtained at appropriate time points, and, if desired, gastric contents can be sampled by cannula or other technique.

Clinical trials in humans, conducted in accordance with appropriate laws, regulations, and institutional guidelines, also provide in vivo data.

Release Profiles

The increased linearity profiles of the segments with release rate-modulating polymer films provides advantageous release characteristics over a segment with the same carrier polymer-agent composition, but lacking the release rate-modulating polymer films. For example, a segment of a gastric residence system comprising a carrier polymer, an agent or a salt thereof, and a release-rate modulating polymer film configured to control the release rate of the agent, can have a release profile where the release-rate modulating polymer film is configured such that, over a seven-day incubation in simulated gastric fluid, the amount of the agent or salt thereof released during day 5 is at least about 40% of the amount of agent or salt thereof released during day 2. That is, over the seven day incubation period, the amount of the agent or salt thereof released from hours 96-120 (day 5) is at least about 40% of the amount of agent or salt released during hours 24-48 (day 2) of the incubation. In some embodiments, release over day 5 is at least about 50%, at least about 60%, at least about 70%, at least about 80%, or at least about 90% of the amount of agent or salt released over day 2. In some embodiments, release over day 5 is at least about 40% to about 90%, at least about 50% to about 90%, at least about 60% to about 90%, at least about 70% to about 90%, at least about 80% to about 90%, or at least about 40% to about 100%, of the amount of agent or salt released over day 2. In any of these embodiments, at least about 5% of the total amount of agent is released on day 2 and at least about 5% of the total amount of agent is released on day 5, at least about 5% of the total amount of agent is released on day 2 and at least about 7% of the total amount of agent is released on day 5, or at least about 7% of the total amount of agent is released on day 2 and at least about 7% of the total amount of agent is released on day 5. “Total amount of agent” refers to the amount of agent originally present in the segment.

In another embodiment, a segment of a gastric residence system comprising a carrier polymer, an agent or a salt thereof, and a release-rate modulating polymer film configured to control the release rate of the agent, can have a release profile where the release-rate modulating polymer film is configured such that, over a seven-day incubation in simulated gastric fluid, the amount of the agent or salt thereof released during day 7 is at least about 20% of the amount of agent or salt thereof released during day 1. That is, over the seven day incubation period, the amount of the agent or salt thereof released from hours 144-168 (day 7) is at least about 20% of the amount of agent or salt released during hours 0-24 (day 1) of the incubation. In some embodiments, release over day 7 is at least about 30%, at least about 40%, at least about 50%, at least about 60%, or at least about 70% of the amount of agent or salt released over day 1. In some embodiments, release over day 7 is at least about 20% to about 70%, at least about 30% to about 70%, at least about 40% to about 70%, at least about 50% to about 70%, at least about 60% to about 70%, or at least about 20% to about 100%, of the amount of agent or salt released over day 1. In any of these embodiments, at least about 7% of the total amount of agent is released on day 1 and at least about 4% of the total amount of agent is released on day 7, at least about 4% of the total amount of agent is released on day 1 and at least about 4% of the total amount of agent is released on day 7, or at least about 7% of the total amount of agent is released on day 1 and at least about 7% of the total amount of agent is released on day 7. “Total amount of agent” refers to the amount of agent originally present in the segment.

Segments with release rate-modulating polymer films as disclosed herein also have lower burst release when initially immersed in simulated gastric fluid. In one embodiment, a segment of a gastric residence system comprising a carrier polymer and an agent or a salt thereof, where the segment has a release-rate modulating polymer film configured to control the release rate of the agent, can have a release profile where the release-rate modulating polymer film is configured such that the release of agent from the segment in simulated gastric fluid over an initial 24 hour period is at least about 40% lower than the release of agent from a second segment in simulated gastric fluid over an initial 6 hour period, where the second segment comprises the same combination of carrier polymer and agent or salt thereof, but lacks the release-rate modulating polymer film; and wherein the release of agent from the segment with the polymer film in simulated gastric fluid over a seven-day period is either i) at least about 60% of the release of agent from the second segment lacking the polymer film over a seven-day period, or ii) at least 60% of the total amount of agent originally present in the segment. In further embodiments, the release of agent from the segment with the film in simulated gastric fluid over an initial 24 hour period is at least about 40% lower, about 40% to about 50% lower, about 40% to about 60% lower, or about 40% to about 70% lower than the release of agent from a second segment without the film in simulated gastric fluid over an initial 6 hour period, while the release of agent from the segment with the film in simulated gastric fluid over a seven day period is either i) at least about 60%, at least about 70%, at least about 80%, or about 60% to about 80% of the release of agent from the second segment in simulated gastric fluid lacking the polymer film over a seven-day period, or ii) at least about 60%, at least about 70%, at least about 80%, or about 60% to about 80% of the total amount of agent originally present in the segment. In further embodiments, the release of agent from the segment with the film in simulated gastric fluid over a seven-day period is either i) at least about 60%, at least about 70%, at least about 75%, or at least about 80% (such as about 60% to about 70%, about 60% to about 80%, about 60% to about 90%, or about 60% to about 99%) of the release of agent from the second segment without the film in simulated gastric fluid over a seven-day period, or ii) at least about 60%, at least about 70%, at least about 75%, or at least about 80% (such as about 60% to about 70%, about 60% to about 80%, about 60% to about 90%, or about 60% to about 99%) of the total amount of agent originally present in the segment.

Linearity of release of agent from segments having a release rate-modulating polymer film coating is also improved. In one embodiment, a segment of a gastric residence system comprising a carrier polymer and an agent or a salt thereof, where the segment has a release-rate modulating polymer film configured to control the release rate of the agent, can have a release profile where the release-rate modulating polymer film is configured such that a best-fit linear regression model of the release rate of agent has a coefficient of determination $R^2$ of at least about 0.8, at least about 0.85, or at least about 0.9 over an initial period of seven days in simulated gastric fluid (where the initial period of seven days is measured from the start time when the segment is initially immersed in simulated gastric fluid; that is, the period of seven days includes the time at t=0 or origin point of the release profile); and wherein the segment releases about 30% to about 70% of the agent or salt thereof within a time of about 40% to about 60% of the seven-day period.

In one embodiment, a segment of a gastric residence system comprising a carrier polymer and an agent or a salt thereof, where the segment has a release-rate modulating polymer film configured to control the release rate of the agent, can have a release profile where the release-rate modulating polymer film is configured such that the release rate over any one of the seven days varies by no more than about 50%, no more than about 40%, no more than about 30%, no more than about 25%, no more than about 20%, or no more than about 10% from the average daily total release over the seven days.

Carrier Polymers for Segments and Arms (Carrier Polymer-Agent Component)

Exemplary carrier polymers suitable for use in the release-rate modulating polymer films disclosed herein include, but are not limited to, hydrophilic cellulose derivatives (such as hydroxypropylmethyl cellulose, hydroxypropyl cellulose, hydroxymethyl cellulose, hydroxyethyl cellulose, carboxymethylcellulose, sodium-carboxymethylcellulose), cellulose acetate phthalate, poly (vinyl pyrrolidone), ethylene/vinyl alcohol copolymer, poly (vinyl alcohol), carboxyvinyl polymer (Carbomer), Carbopol® acidic carboxy polymer, polycarbophil, poly (ethyleneoxide) (Polyox WSR), polysaccharides and their derivatives, polyalkylene oxides, polyethylene glycols, chitosan, alginates, pectins, acacia, tragacanth, guar gum, locust bean gum, vinylpyrrolidonevinyl acetate copolymer, dextrans, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, gellan, hyaluronic acid, pullulan, scleroglucan, xanthan, xyloglucan, maleic anhydride copolymers, ethylenemaleic anhydride copolymer, poly(hydroxyethyl methacrylate), ammoniomethacrylate copolymers (such as Eudragit RL or Eudragit RS), poly(ethylacrylate-methylmethacrylate) (Eudragit NE), Eudragit E (cationic copolymer based on dimethylamino ethyl methylacrylate and neutral methylacrylic acid esters), poly(acrylic acid), polymethacrylates/polyethacrylates such as poly(methacrylic acid), methylmethacrylates, and ethyl acrylates, polylactones such as poly(caprolactone), polyanhydrides such as poly[bis-(p-carboxyphenoxy)-propane anhydride], poly(terephthalic acid anhydride), polypeptides such as polylysine, polyglutamic acid, poly(ortho esters) such as copolymers of DETOSU with diols such as hexane diol, decane diol, cyclohexanedimethanol, ethylene glycol, polyethylene glycol and incorporated herein by reference those poly(ortho) esters described and disclosed in U.S. Pat. No. 4,304,767, starch, in particular pregelatinized starch, and starch-based polymers, carbomer, maltodextrins, amylomaltodextrins, dextrans, poly(2-ethyl-2-oxazoline), poly (ethyleneimine), polyurethane, poly(lactic acid), poly(glycolic acid), poly(lactic-co-glycolic acid) (PLGA), polyhydroxyalkanoates, polyhydroxybutyrate, and copolymers, mixtures, blends and combinations thereof. Polycaprolactone (PCL) is a useful carrier polymer. In another embodiment, polydioxanone is used as the carrier polymer. In any of the embodiments of the gastric residence system, the carrier polymer used in the gastric residence system can comprise polycaprolactone, such as linear polycaprolactone with a number-average molecular weight ($M_n$) range between about 60 kiloDalton (kDa) to about 100 kDa; 75 kDa to 85 kDa; or about 80 kDa; or between about 45 kDa to about 55 kDa; or between about 50 kDa to about 110,000 kDa, or between about 80 kDa to about 110,000 kDa.

Other excipients can be added to the carrier polymers to modulate the release of agent. Such excipients can be added in amounts from about 1% to 15%, preferably from about 5% to 10%, more preferably about 5% or about 10%. Examples of such excipients include Poloxamer 407 (poly (ethylene glycol)-block-poly(propylene glycol)-block-poly (ethylene glycol), CAS No. 9003-11-6; H—(OCH2CH2)x-(O—CH(CH3)CH2)y-(OCH2CH2)z-OH where x and z are about 101 and y is about 56); Pluronic P407; Eudragit E, dimethylaminoethyl methacrylate-butyl methacrylate-methyl methacrylate copolymer; hypromellose (available from Sigma, Cat #H3785), Kolliphor RH40 (available from Sigma, Cat #07076), polyvinyl caprolactam, polyvinyl acetate (PVAc), polyvinylpyrrolidone (PVP), polyvinyl alcohol (PVA), polyethylene glycol (PEG), PDO (polydioxanone), copovidone; vinylpyrrolidone-vinyl acetate copolymer in a ratio of 6:4 by mass, and copolymers of polyvinyl caprolactam, polyvinyl acetate, and polyethylene glycol. Preferred soluble excipients include Eudragit E, polyethylene glycol (PEG), polyvinylpyrrolidone (PVP), polyvinyl acetate (PVAc), and polyvinyl alcohol (PVA). Preferred insoluble excipients include Eudragit RS and Eudragit RL. Further examples of such excipients include Poloxamer 407 (available as Kolliphor P407, Sigma Cat #62035), poly (ethylene glycol)-block-poly(propylene glycol)-block-poly (ethylene glycol), CAS No. 9003-11-6; H—(OCH2CH2)x-(O—CH(CH3)CH2)y-(OCH2CH2)z-OH where x and z are about 101 and y is about 56); Pluronic P407; Eudragit E, Eudragit EPO (dimethylaminoethyl methacrylate-butyl methacrylate-methyl methacrylate copolymer; available from Evonik); hypromellose (available from Sigma, Cat #H3785), Kolliphor RH40 (available from Sigma, Cat #07076), polyvinyl caprolactam, polyvinyl acetate (PVAc), polyvinylpyrrolidone (PVP), polyvinyl alcohol (PVA), polyethylene glycol (PEG), PDO (polydioxanone), Kollidon VA64 (copovidone; vinylpyrrolidone-vinyl acetate copolymer in a ratio of 6:4 by mass), and Soluplus (available from BASF; a copolymer of polyvinyl caprolactam, polyvinyl acetate, and polyethylene glycol). Preferred soluble excipients include Eudragit E, polyethylene glycol (PEG), polyvinylpyrrolidone (PVP), polyvinyl acetate (PVAc), and polyvinyl alcohol (PVA). Preferred insoluble excipients include Eudragit RS and Eudragit RL. Preferred insoluble, swellable excipients include crospovidone, croscarmellose, hypromellose acetate succinate (HPMCAS), and carbopol. EUDRAGIT RS and EUDRAGIT RL are registered trademarks of Evonik (Darmstadt, Germany) for copolymers of ethyl acrylate, methyl methacrylate and methacrylic acid ester with quaternary ammonium groups (trimethylammonioethyl methacrylate chloride), having a molar ratio of ethyl acrylate, methyl methacrylate and trimethylammonioethyl methacrylate of about 1:2:0.2 in Eudragit® RL and about 1:2:0.1 in Eudragit® RS. Preferred insoluble, swellable excipients include crospovidone, croscarmellose, hypromellose acetate succinate (HPMCAS), carbopol, and linear block copolymers of dioxanone and ethylene glycol; linear block copolymers of lactide and ethylene glycol; linear block copolymers of lactide, ethylene glycol, trimethyl carbonate, and caprolactone; linear block copolymers of lactide, glycolide, and ethylene glycol; linear block copolymers of glycolide, polyethylene glycol, and ethylene glycol; such as linear block copolymers of dioxanone (80%) and ethylene glycol (20%); linear block copolymers of lactide (60%) and ethylene glycol (40%); linear block copolymers of lactide (68%), ethylene glycol (20%), trimethyl carbonate (10%), and caprolactone (2%); linear block copolymers of lactide (88%), glycolide (8%), and ethylene glycol (4%); linear block copolymers of glycolide (67%), polyethylene glycol (28%), and ethylene glycol (5%).

Excipients can be added to the carrier polymers to modulate the release of agent. Such excipients can be added in amounts from about 1% to 15%, preferably from about 5% to 10%, more preferably about 5% or about 10%. Examples of such excipients include poly(ethylene glycol)-block-poly (propylene glycol)-block-poly(ethylene glycol) polymers, such as H—(OCH2CH2)x-(O—CH(CH3)CH2)y-(OCH2CH2)z-OH where x and z are about 101 and y is about 56, such as Poloxamer 407 (such as commercially available Pluronic P407); polyvinylpyrrolidones, such as a dimethylaminoethyl methacrylate-butyl methacrylate-methyl methacrylate copolymer, such as Eudragit E; hypromellose, a nonionic solubilizer and emulsifying agent obtained by reacting 1 mole of hydrogenated castor oil with 40 moles of ethylene oxide, with glycerol polyethylene glycol hydroxy-stearate as the main constituent, such as Kolliphor RH40 (available from Sigma, Cat #07076), polyvinyl caprolactam, polyvinyl acetate (PVAc), polyvinylpyrrolidone (PVP), polyvinyl alcohol (PVA), polyethylene glycol (PEG), PDO (polydioxanone), copovidone; vinylpyrrolidone-vinyl acetate copolymer in a ratio of 6:4 by mass, and copolymers of polyvinyl caprolactam, polyvinyl acetate, and polyethylene glycol. Preferred soluble excipients include Eudragit E, polyethylene glycol (PEG), polyvinylpyrrolidone (PVP), polyvinyl acetate (PVAc), and polyvinyl alcohol (PVA). Preferred insoluble excipients include acrylate co-polymers, such as copolymers of ethyl acrylate, methyl methacrylate and methacrylic acid ester with quaternary ammonium groups (trimethylammonioethyl methacrylate chloride), such as a copolymer having a molar ratio of ethyl acrylate, methyl methacrylate and trimethylammonioethyl methacrylate of about 1:2:0.2, such as Eudragit RL; or such as a copolymer having a molar ratio of ethyl acrylate, methyl methacrylate and trimethylammonioethyl methacrylate of about 1:2:0.1, such as Eudragit RS.

Further examples of excipients that can be used in the segments of the gastric residence system are listed in the Excipient Table below.

Excipient Table

| Function | General examples | Specific examples |
|---|---|---|
| Polymeric and non-polymeric solubilizers | Polyalkylene oxides<br>Polyethoxylated castor oil<br>Detergents | Kolliphor RH, Kolliphor P407, Soluplus, Cremophor, SDS |
| Release-enhancing excipient (wicking agent) | Acrylate polymers<br>Acrylate co-polymers<br>Polyvinylpyrrolidone | Eudragit RL<br>Eudragit RS<br>Eudragit E<br>Linear block copolymer of dioxanone and ethylene glycol (e.g., 80:20 ratio) |
| Dispersant | porous inorganic material<br>polar inorganic material<br>non-toxic metal oxides<br>amphiphilic organic molecules<br>polysaccharides, cellulose, cellulose derivatives<br>Tatty acids<br>detergents | silica, hydrophilic-fumed silica, hydrophobic colloidal silica, magnesium aluminum silicate, stearate salts, calcium stearate, magnesium stearate, microcrystalline cellulose, carboxymethylcellulose, hypromellose, phospholipids, polyoxyethylene stearates, zinc acetate, alginic acid, lecithin, sodium lauryl sulfate, aluminum oxide |
| Stabilizer/Preservative agent | Anti-oxidants<br>Anti-microbial agents<br>Buffering substances/pH stabilizers | Tocopherols<br>Alpha-tocopherol<br>Ascorbic acid; ascorbate salts<br>Carotenes<br>Butylated hydroxytoluene (BHT)<br>Butylated hydroxyanisole (BHA)<br>Fumaric acid<br>calcium carbonate<br>calcium lactate<br>calcium phosphate<br>sodium phosphate<br>sodium bicarbonate |

Agents for Use in Gastric Residence Systems

Agents which can be administered to or via the gastrointestinal tract can be used in the gastric residence systems as disclosed herein. The agent is blended with the carrier polymer, and any other excipients or other additives to the carrier polymer, and formed into a segment for use in a gastric residence system. Agents include, but are not limited to, drugs, pro-drugs, biologics, and any other substance which can be administered to produce a beneficial effect on an illness or injury. Agents that can be used in the gastric residence systems as disclosed herein include statins, such as rosuvastatin; nonsteroidal anti-inflammatory drugs (NSAIDs) such as meloxicam; selective serotonin reuptake inhibitors (SSRIs) such as escitalopram and citalopram; blood thinners, such as clopidogrel; steroids, such as prednisone; antipsychotics, such as aripiprazole and risperidone; analgesics, such as buprenorphine; opioid antagonists, such as naloxone; anti-asthmatics such as montelukast; anti-dementia drugs, such as memantine; cardiac glycosides such as digoxin; alpha blockers such as tamsulosin; cholesterol absorption inhibitors such as ezetimibe; anti-gout treatments, such as colchicine; antihistamines, such as loratadine and cetirizine, opioids, such as loperamide; proton-pump inhibitors, such as omeprazole; antiviral agents, such as entecavir; antibiotics, such as doxycycline, ciprofloxacin, and azithromycin; anti-malarial agents; levothyroxine; substance abuse treatments, such as methadone and varenicline; contraceptives; stimulants, such as caffeine; and nutrients such as folic acid, calcium, iodine, iron, zinc, thiamine, niacin, vitamin C, vitamin D, biotin, plant extracts, phytohormones, and other vitamins or minerals. Biologics that can be used as agents in the gastric residence systems disclosed herein include proteins, polypeptides, polynucleotides, and hormones. Exemplary classes of agents include, but are not limited to, analgesics; anti-analgesics; anti-inflammatory drugs; antipyretics; antidepressants; antiepileptics; antipsychotic agents; neuroprotective agents; anti-proliferatives, such as anti-cancer agents; antihistamines; antimigraine drugs; hormones; prostaglandins; antimicrobials, such as antibiotics, antifungals, antivirals, and antiparasitics; antimuscarinics; anxiolytics; bacteriostatics; immunosuppressant agents; sedatives; hypnotics; antipsychotics; bronchodilators; anti-asthma drugs; cardiovascular drugs; anesthetics; anti-coagulants; enzyme inhibitors; steroidal agents; steroidal or non-steroidal anti-inflammatory agents; corticosteroids; dopaminergics; electrolytes; gastro-intestinal drugs; muscle relaxants; nutritional agents; vitamins; parasympathomimetics; stimulants; anorectics; anti-narcoleptics; and antimalarial drugs, such as quinine, lumefantrine, chloroquine, amodiaquine, pyrimethamine, proguanil, chlorproguanil-dapsone, sulfonamides (such as sulfadoxine and sulfamethoxypyridazine), mefloquine, atovaquone, primaquine, halofantrine, doxycycline, clindamycin, artemisinin, and artemisinin derivatives (such as artemether, dihydroartemisinin, arteether and artesunate). The term "agent" includes salts, solvates, polymorphs, and co-crystals of the aforementioned substances. In certain embodiments, the agent is selected from the group consisting of cetirizine, rosuvastatin, escitalopram, citalopram, risperidone, olanzapine, donepezil, and ivermectin. In another embodiment, the agent is one that is used to treat a neuropsychiatric disorder, such as an anti-psychotic agent, or an anti-dementia drug such as memantine.

Agent Loading of Arms and Segments

The arms, or segments of which the arms are comprised, comprise agent or a pharmaceutically acceptable salt thereof. In some embodiments, the agent or salt thereof (for example, a drug) makes up about 10% to about 40% by weight of the arm or segment, and thus the carrier polymer and any other components of the arm or segment blended into the carrier polymer together make up the remainder of the weight of the arm or segment. In some embodiments, the agent or salt thereof makes up about 10% to about 35%, about 10% to about 30%, about 10% to about 25%, about 10% to about 20%, about 10% to about 15%, about 15% to about 40%, about 20% to about 40%, about 25% to about 40%, about 30% to about 40%, about 35% to about 40%, about 15% to about 35%, about 20% to about 35%, or about 25% to about 40% by weight of the arm or segment.

In some embodiments, the amount of agent by weight in the arms, or segments of which the arms are comprised, can comprise about 20% to about 60%, about 25% to about 60%, about 30% to about 60%, about 35% to about 60%, about 20% to about 50%, about 20% to about 40%, or about 25% to about 50%.

In some embodiments, the amount of agent by weight in the arms, or segments of which the arms are comprised, can comprise at least about 40%, at least about 45%, at least about 50%, at least about 55%, or about 60%. In some embodiments, the amount of agent by weight in the arms, or segments of which the arms are comprised, can comprise about 40% to about 60%, about 45% to about 60%, about 50% to about 60%, about 55% to about 60%, about 40% to about 55%, about 40% to about 50%, or about 40% to about 45%. In some embodiments, the amount of agent by weight in the arms, or segments of which the arms are comprised, can comprise about 25% to about 60%, about 30% to about 60%, or about 35% to about 60%. In some embodiments, the amount of agent by weight in the arms, or segments of which the arms are comprised, can comprise about 51% to about 60%, about 52% to about 60%, about 53% to about 60%, about 54% to about 60%, about 55% to about 60%, about 56% to about 60%, or about 57% to about 60%. In some embodiments, the agent or pharmaceutically acceptable salt thereof is present in an amount by weight of between about 67% and about 150% of the weight of the carrier polymer.

Dispersants for Use in Gastric Residence Systems

Dispersants can be used in the gastric residence systems in order to improve distribution of agent in the carrier polymer-agent arms and provide more consistent release characteristics. Examples of dispersants that can be used include silicon dioxide (silica, $SiO_2$) (including hydrophilic fumed silica); stearate salts, such as calcium stearate and magnesium stearate; microcrystalline cellulose; carboxymethylcellulose; hydrophobic colloidal silica; hypromellose; magnesium aluminum silicate; phospholipids; polyoxyethylene stearates; zinc acetate; alginic acid; lecithin; fatty acids; sodium lauryl sulfate; and non-toxic metal oxides such as aluminum oxide. Porous inorganic materials and polar inorganic materials can be used. Hydrophilic-fumed silicon dioxide is a preferred dispersant. One particularly useful silicon dioxide is sold by Cabot Corporation (Boston, Massachusetts, USA) under the registered trademark CAB-O-SIL® M-5P (CAS #112945-52-5), which is hydrophilic-fumed silicon dioxide having a BET surface area of about 200 m2/g±15 m2/g The mesh residue for this product on a 45 micron sieve is less than about 0.02%. The typical primary aggregate size is about 150 to about 300 nm, while individual particle sizes may range from about 5 nm to about 50 nm.

The weight/weight ratio of dispersant to agent substance can be about 0.1% to about 5%, about 0.1% to about 4%, about 0.1% to about 3%, about 0.1% to about 2%, about 0.1% to about 1%, about 1% to about 5%, about 1% to about 4%, about 1% to about 3%, about 1% to about 2%, about 2% to about 4%, about 2% to about 3%, about 3% to about 4%, about 4% to about 5%, or about 0.1%, about 0.5%, about 1%, about 2%, about 3%, about 4% or about 5%.

Dispersants can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%.

Stabilizers for Use in Gastric Residence Systems

Many agents are prone to oxidative degradation when exposed to reactive oxygen species, which can be present in the stomach. An agent contained in the system may thus oxidize due to the prolonged residence in the stomach of the system, and the extended release period of agent from the system. Accordingly, it is desirable to include stabilizers, such as anti-oxidants including tocopherols, alpha-tocopherol, ascorbic acid, ascorbyl palmitate, butylated hydroxytoluene, butylated hydroxyanisole, and fumaric acid, in the systems, in amounts of about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%. Vitamin E, a tocopherol, a Vitamin E ester, a tocopherol ester, ascorbic acid, or a carotene, such as alpha-tocopherol, Vitamin E succinate, alpha-tocopherol succinate, Vitamin E acetate, alpha-tocopherol acetate, Vitamin E nicotinate, alpha-tocopherol nicotinate, Vitamin E linoleate, or alpha-tocopherol linoleate can be used as anti-oxidant stabilizers.

Buffering or pH-stabilizer compounds that can be included in the systems to reduce or prevent degradation of pH-sensitive agents at low pH include calcium carbonate, calcium lactate, calcium phosphate, sodium phosphate, and sodium bicarbonate. They are typically used in an amount of up to about 2% w/w. The buffering or pH-stabilizer compounds can comprise about 0.1% to about 4% of the carrier polymer-agent components, such as about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, or about 0.2% to about 0.8%. The anti-oxidant stabilizers, pH stabilizers, and/or other stabilizer compounds can be blended into the carrier polymer, the agent, or the carrier polymer-agent mixture, resulting in the presence of the anti-oxidant stabilizers, pH stabilizers, and/or other stabilizer compounds in the final segment or arm.

Manufacture/Assembly of System Using Heat-Assisted Assembly and Infrared Welding Components of the gastric residence systems can be manufactured by various methods, such as co-extrusion or three-dimensional printing, as disclosed in U.S. Pat. No. 10,182,985, and published patent applications US 2018/0311154 A1, US 2019/0262265 A1, US 2019/0231697 A1, US 2019/0254966 A1, and WO 2018/227147.

Figure 69:
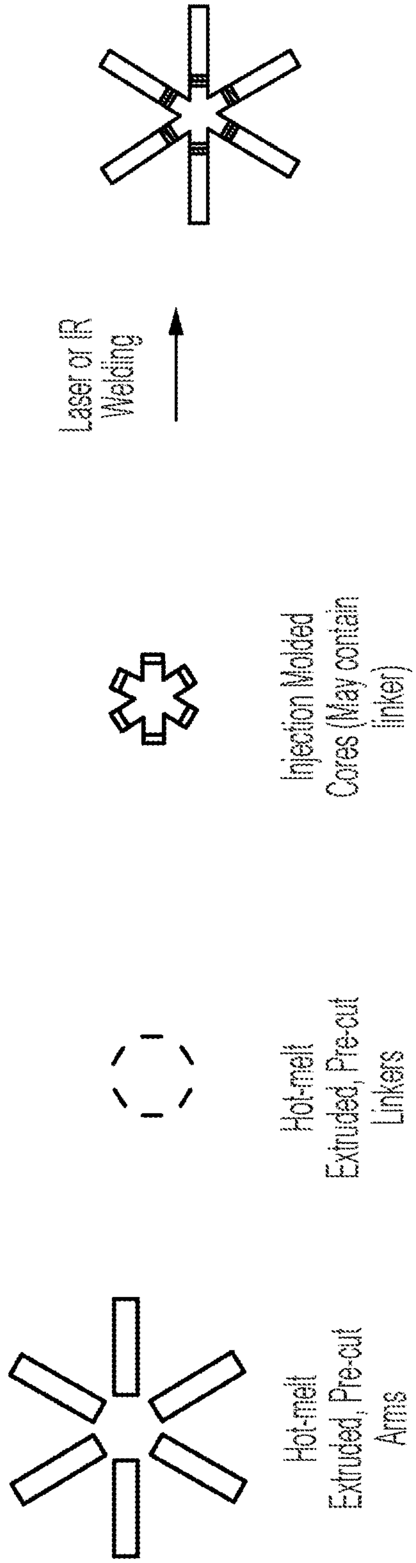
FIG. 69 shows an exemplary method of bonding components together to form a gastric residence system.

FIG. 69 shows an exemplary method of bonding components together to form a gastric residence system. A pre-cut polymeric linker (such as an enteric linker or a time-dependent linker) is laser or IR welded to an elastomeric central member. The polymeric linker may be formed, for example, by hot melt extruding a material and cutting it to the desired length. Hot melt extruded arms (elongate members) containing a carrier polymer mixed with an agent are then laser or IR welded to the polymeric linkers, thereby forming the stellate structure of the gastric residence system.

Heat-assisted assembly can be accomplished by contacting the surfaces to be joined with a heated platen, by using an infrared radiation source such as an infrared lamp, by using an infrared laser, or by using other heat-producing, heat-emitting, or heat-transferring devices. Examples 12-14 of US 2019/0262265 A1 describe modalities for heating components of gastric residence system, such as by using a hot plate or an infrared lamp. The heated surfaces are then pressed together, followed by cooling.

Infrared welding can be performed by contacting a first surface on a first component with a second surface on a second component, and irradiating the region of the contacting surfaces with infrared radiation, while applying force or pressure to maintain the contact between the two surfaces, followed by cooling of the attached components (the applied force or pressure is optionally maintained during the cooling process).

Specific Drug Dosage Forms

Carrier Polymer Agent Segments (Drug-Eluting Segments)

The carrier polymer-agent segments, or drug-eluting segments, release an agent in a controlled manner during the period that the gastric residence system resides in the stomach. The carrier polymer is blended with the agent, and formed into segments which are then assembled with the other components described herein to manufacture the gastric residence system. The composition of such carrier polymer-agent blends is provided below for specific drug formulations, including memantine and donepezil; risperidone; and dapagliflozin.

In some embodiments, a dosage form for administration of memantine and donepezil comprises a gastric residence system comprising about 30 mg to about 50 mg of memantine HCl and about 30 mg to about 50 mg of donepezil HCl. In some embodiments, a dosage form for administration of memantine and donepezil comprises a gastric residence system comprising about 40 mg of memantine HCl and about 38 mg of donepezil HCl. In some embodiments, the dosage form comprises a gastric residence system, wherein the gastric residence system comprises a first drug-eluting segment comprising about 30 mg to about 50 mg of memantine HCl and a second drug-eluting segment comprising about 30 mg to about 50 mg of donepezil HCl. In some embodiments, the dosage form comprises a gastric residence system, wherein the gastric residence system comprises a first drug-eluting segment comprising about 40 mg of memantine HCl and a second drug-eluting segment comprising about 38 mg of donepezil HCl. In some embodiments, the first drug-eluting segment comprises about 40 wt % to about 50 wt % of memantine HCl, about 35 wt % to about 45 wt % of Corbion PC17, about 5 wt % to about 15 wt % of PDL 20, about 1 wt % to about 3 wt % of P407, about 0.2 wt % to about 0.8 wt % of Vitamin E succinate, about 0.2 wt % to about 0.8 wt % of $SiO_2$, and about 0.05 wt % to about 0.2 wt % of Sunset yellow. In some embodiments, the first drug-eluting segment comprises about 45.0 wt % of memantine HCl, about 41.9 wt % of Corbion PC17, about 10.0 wt % of PDL 20, about 2.0 wt % of P407, about 0.5 wt % of Vitamin E succinate, about 0.5 wt % of $SiO_2$, and about 0.1 wt % of Sunset yellow. In some embodiments, the second drug-eluting segment comprises about 30 wt % to about 50 wt % of donepezil HCl, about 40 wt % to about 50 wt % of Corbion PC17, about 5 wt % to about 15 wt % of PDL 20, about 2 wt % to about 8 wt % of P407, about 0.2 wt % to about 0.8 wt % of Vitamin E succinate, and about 0.2 wt % to about 0.8 wt % of $SiO_2$. In some embodiments, the second drug-eluting segment comprises about 40.0 wt % of donepezil HCl, about 44.0 wt % of Corbion PC17, about 10.0 wt % of PDL 20, about 5.0 wt % of P407, about 0.5 wt % of Vitamin E succinate, and about 0.5 wt % of $SiO_2$.

In some embodiments, a dosage form for administration of memantine and donepezil comprises a gastric residence system comprising about 150 mg to about 200 mg of memantine HCl and about 50 to about 90 mg of donepezil HCl. In some embodiments, a dosage form for administration of memantine and donepezil comprises a gastric residence system comprising about 170 mg of memantine HCl and about 70 mg of donepezil HCl. In some embodiments, the dosage form comprises a gastric residence system, wherein the gastric residence system comprises a drug-eluting segment comprising about 150 mg to about 200 mg of memantine HCl and about 50 to about 90 mg of donepezil HCl. In some embodiments, the dosage form comprises a gastric residence system, wherein the gastric residence system comprises a drug-eluting segment comprising about 170 mg of memantine HCl and about 70 mg of donepezil HCl. In some embodiments, the drug-eluting segment comprises about 30 wt % to about 40 wt % of memantine HCl, about 10 wt % to about 20 wt % of donepezil HCl, about 40 wt % to about 50 wt % of Corbion PC17, about 2 wt % to about 8 wt % of Kollidon SR, about 0.2 wt % to about 0.8 wt % of Vitamin E succinate, about 0.2 wt % to about 0.8 wt % of $SiO_2$, and about 0.01 wt % to about 0.05 wt % of Sunset yellow. In some embodiments, the drug-eluting segment comprises about 35.5 wt % of memantine HCl, about 14.5 wt % of donepezil HCl, about 43.97 wt % of Corbion PC17, about 5.0 wt % of Kollidon SR, about 0.5 wt % of Vitamin E succinate, about 0.5 wt % of $SiO_2$, and about 0.03 wt % of Sunset yellow.

In some embodiments, a dosage form for administration of memantine and donepezil comprises a gastric residence system comprising about 150 mg to about 200 mg of memantine or a salt thereof and about 50 to about 90 mg of donepezil or a salt thereof. In some embodiments, a dosage form for administration of memantine and donepezil comprises a gastric residence system comprising about 150 mg to about 200 mg of memantine HCl and about 50 to about 90 mg of donepezil HCl. In some embodiments, a dosage form for administration of memantine and donepezil comprises a gastric residence system comprising about 170 mg of memantine or a salt thereof and about 70 mg of donepezil or a salt thereof. In some embodiments, a dosage form for administration of memantine and donepezil comprises a gastric residence system comprising about 170 mg of memantine HCl and about 70 mg of donepezil HCl. In any of the foregoing embodiments, the dosage form comprises a gastric residence system, wherein the gastric residence system comprises arms with drug-eluting segments comprising memantine or a salt thereof and donepezil or a salt thereof. In any of the foregoing embodiments, the arms are attached to a central elastomer. In some embodiments, the central elastomer comprises silicone rubber, such as silicone rubber having a durometer between about 40 A to about 70 A, or between about 45 A to about 65 A, or between about 50 A and about 60 A, or of about 40 A, about 45 A, about 50 A, about 55 A, about 60 A, about 65 A, or about 70 A, e.g., about 50 A or about 60 A. In some embodiments, the drug-eluting segments comprise about 30 wt % to about 40 wt % of memantine or a salt thereof, such as memantine HCl; and about 10 wt % to about 20 wt % of donepezil or a salt thereof, such as donepezil HCl. In further embodiments, the drug-eluting segments further comprise about 40 wt % to about 50 wt % of polycaprolactone (PCL), such as PCL having a viscosity midpoint between about 1.5 dl/g to about 2.1 dl/g, such as Corbion PC17. In further embodiments, the drug-eluting segments further comprise about 2 wt % to about 8 wt % of a polyvinyl acetate-povidone mixture, such as about a 3:1 to 5:1 polyvinyl acetate-povidone mixture, such as a 4:1 polyvinyl acetate-povidone mixture, where the polyvinyl acetate-povidone mixture can optionally comprise about 0.5% to 1.5% sodium lauryl sulfate and 0.1% to 0.4% $SiO_2$, such as a polyvinyl acetate-povidone mixture containing approximately 80% polyvinyl acetate, 19% povidone, 0.8% sodium lauryl sulfate, and 0.2% $SiO_2$, such as Kollidon SR. In further embodiments, the drug-eluting segments further comprise about 0.2 wt % to about 0.8 wt % of Vitamin E or an ester thereof, such as Vitamin E succinate. In some embodiments, the drug-eluting segments further comprise about 0.2 wt % to about 0.8 wt % of $SiO_2$. In some embodiments, the drug-eluting segments further comprise about 0.01 wt % to about 0.05 wt % of a coloring agent, such as Sunset Yellow. In some embodiments, the drug-eluting segments further comprise a coating comprising a release rate-modulating polymer film. In some embodiments, the release rate-modulating polymer film comprises polycaprolactone (PCL). In some embodiments, the release rate-modulating polymer film comprises PCL having a viscosity between about 1.5 dl/g to about 2.1 dl/g. In some embodiments, the release rate-modulating polymer film comprises at least two PCL polymers having different viscosities; the polymers are blended together before application of the polymer blend to the drug-eluting segments. In some embodiments, the at least two PCL polymers having different viscosities comprise PCL having a viscosity between about 1.5 dl/g to about 2.1 dl/g and PCL having a viscosity between about 0.2 dl/g to about 0.6 dl/g, such as PCL having a viscosity of about 1.7 dl/g and PCL having a viscosity of about 0.4 dl/g. In any embodiment where the release rate-modulating polymer film comprises two PCL polymers having different viscosities, they can be in a ratio of about 6:1 to 12:1 of the higher viscosity:lower viscosity PCLs, such as about 9:1 (PCL having a viscosity between about 1.5 dl/g to about 2.1 dl/g):(PCL having a viscosity between about 0.2 dl/g to about 0.6 dl/g) or 9:1 (PCL having a viscosity of about 1.7 dl/g):(PCL having a viscosity of about 0.4 dl/g). In some embodiments, the release rate-modulating polymer film can further comprise an anti-tack agent, such as magnesium stearate, talc, or glycerol monostearate, in an amount of about 0.5% to about 5%, about 1% to about 3%, or about 2%; the anti-tack agent is blended with the polymer or polymers comprising the release rate-modulating polymer film before application of the polymer/anti-tack agent blend to the drug-eluting segments. In some embodiments, the release rate-modulating polymer film can further comprise magnesium stearate in an amount of about 0.5% to about 5%, or about 1% to about 3%, such as about 2%. In some embodiments, the release rate-modulating polymer film can comprise about 85% to about 90% PCL having a viscosity of about 1.7 dl/g, about 5% to about 15% PCL having a viscosity of about 0.4 dl/g, and about 0.5% to about 5% of magnesium stearate, such as about 88.2% PCL having a viscosity of about 1.7 dl/g, about 9.8% PCL having a viscosity of about 0.4 dl/g, and about 2% magnesium stearate. In any of the embodiments of the release rate-modulating film, the film can be applied to the drug-eluting segment in an amount of about 2% to about 8% of the weight of the segment after coating, such as about 4% to about 6%, or about 5%.

In some embodiments, a dosage form for administration of risperidone comprises a gastric residence system comprising about 10 mg to about 20 mg of risperidone. In some embodiments, a dosage form for administration of risperidone comprises a gastric residence system comprising about 14 mg of risperidone. In some embodiments, the dosage form comprises a gastric residence system, wherein the gastric residence system comprises a drug-eluting segment comprising about 10 mg to about 20 mg of risperidone. In some embodiments, the dosage form comprises a gastric residence system, wherein the gastric residence system comprises a drug-eluting segment comprising about 14 mg of risperidone. In some embodiments, wherein the drug-eluting segment comprises about 30 wt % to about 40 wt % of risperidone, the drug-eluting segment comprises about 50 wt % to about 60 wt % of polycaprolactone (PCL), such as PCL having a viscosity midpoint between about 1.5 dl/g to about 2.1 dl/g, such as Corbion PC17. In some embodiments, the drug-eluting segment comprises about 2 wt % to about 5 wt % of vinylpyrrolidone-vinyl acetate copolymer, such as Kollidon VA64. In some embodiments, the drug-eluting segment comprises about 1 wt % to about 5 wt % of poly(ethylene glycol)-block-poly(propylene glycol)-block-poly(ethylene glycol) polymers, such as H—(OCH2CH2)x-(O—CH(CH3)CH2)y-(OCH2CH2)z-OH where x and z are about 101 and y is about 56, such as Poloxamer 407. In some embodiments, the drug-eluting segment comprises about 0.2 wt % to about 0.8 wt % of Vitamin E succinate. In some embodiments, the drug-eluting segment comprises about 0.2 wt % to about 0.8 wt % of colloidal silicon dioxide ($SiO_2$). In some embodiments, the drug-eluting segment comprises about 0.05 wt % to about 0.15 wt % of pigment.

In some embodiments, wherein the drug-eluting segment comprises about 35 wt % of risperidone, the drug-eluting segment comprises about 55.9 wt % of polycaprolactone (PCL), such as PCL having a viscosity midpoint between about 1.5 dl/g to about 2.1 dl/g, such as Corbion PC17. In some embodiments, the drug-eluting segment comprises about 5.0 wt % of vinylpyrrolidone-vinyl acetate copolymer, such as Kollidon VA64. In some embodiments, the drug-eluting segment comprises about 3.0 wt % of poly(ethylene glycol)-block-poly(propylene glycol)-block-poly(ethylene glycol) polymers, such as H—(OCH2CH2)x-(O—CH(CH3) CH2)y-(OCH2CH2)z-OH where x and z are about 101 and y is about 56, such as Poloxamer 407. In some embodiments, the drug-eluting segment comprises about 0.5 wt % of Vitamin E succinate. In some embodiments, the drug-eluting segment comprises about 0.5 wt % of colloidal silicon dioxide ($SiO_2$). In some embodiments, the drug-eluting segment comprises about 0.1 wt % of pigment. In some embodiments, the pigment comprises Aluminium, 4,5-dihydro-5-oxo-1-(4-sulfophenyl)-4-((4-sulfophenyl)azo)-1H-pyrazole-3-carboxylic acid complex, such as FD&C Yellow 5 Aluminum lake, in the amount of about 0.05 wt % of the total weight of the drug-eluting segment and Benzenemethanaminium, N-ethyl-N-(4-((4-(ethyl((3-sulfophenyl) methyl)amino)phenyl)(2-sulfophenyl)methylene)-2,5-cyclohexadi, such as FD&C Blue 1 Aluminum lake, in the amount of 0.05 wt % of the total weight of the drug-eluting segment. FD&C Yellow 5 Aluminum lake and FD&C Blue 1 Aluminum lake are approved food-coloring additives. In some embodiments, the amount of dye in FD&C Yellow 5 Aluminum lake is about 14-16% by weight. In some embodiments, the amount of dye in FD&C Blue 1 Aluminum lake is about 11-13% by weight.

In some embodiments, the drug-eluting segment comprises about 30 wt % to about 40 wt % of risperidone, about 50 wt % to about 60 wt % of Corbion PC17, about 2 wt % to about 5 wt % of VA64, about 1 wt % to about 5 wt % of P407, about 0.2 wt % to about 0.8 wt % of Vitamin E succinate, about 0.2 wt % to about 0.8 wt % of $SiO_2$, and about 0.05 wt % to about 0.15 wt % of pigment. In some embodiments, the drug-eluting segment comprises about 35.0 wt % of risperidone, about 55.9 wt % of Corbion PC17, about 5.0 wt % of VA64, about 3.0 wt % of P407, about 0.5 wt % of Vitamin E succinate, about 0.5 wt % of $SiO_2$, and about 0.1 wt % of pigment. In some embodiments, the pigment comprises FD&C Yellow 5 Aluminum lake in the amount of about 0.05 wt % of the total weight of the drug-eluting segment and FD&C Blue 1 Aluminum lake in the amount of 0.05 wt % of the total weight of the drug-eluting segment. FD&C Yellow 5 Aluminum lake and FD&C Blue 1 Aluminum lake are approved food-coloring additives. In some embodiments, the amount of dye in FD&C Yellow 5 Aluminum lake is about 14-16% by weight. In some embodiments, the amount of dye in FD&C Blue 1 Aluminum lake is about 11-13% by weight.

In some embodiments, a dosage form for administration of dapagliflozin comprises a gastric residence system comprising about 20 mg to about 50 mg of dapagliflozin. In some embodiments, a dosage form for administration of dapagliflozin comprises a gastric residence system comprising about 35 mg of dapagliflozin. In some embodiments, the dosage form comprises a gastric residence system, wherein the gastric residence system comprises a drug-eluting segment comprising about 20 mg to about 50 mg of dapagliflozin. In some embodiments, the dosage form comprises a gastric residence system, wherein the gastric residence system comprises a drug-eluting segment comprising about 35 mg of dapagliflozin. In some embodiments, wherein the drug-eluting segment comprises about 10 wt % to about 30 wt % of dapagliflozin (amorphous), the drug-eluting segment comprises about 20 wt % to about 50 wt % of polycaprolactone (PCL), such as PCL having a viscosity midpoint between about 1.5 dl/g to about 2.1 dl/g, such as Corbion PC17. In some embodiments, the drug-eluting segment comprises about 20 wt % to about 40 wt % of vinylpyrrolidone-vinyl acetate copolymer, such as Kollidon VA64. In some embodiments, the drug-eluting segment comprises about 5 wt % to about 15 wt % of poly(DL-lactide) (PDL), such as a PDL having 2.0 dl/g intrinsic viscosity (range 1.6 dl/g to 2.4 dl/g), such as PDL20. In some embodiments, the drug-eluting segment comprises about 2 wt % to about 8 wt % of non-ionic detergent, such as sorbitane monostearate, such as Span60. In some embodiments, the drug-eluting segment comprises about 0.2 wt % to about 0.8 wt % of Vitamin E succinate. In some embodiments, the drug-eluting segment comprises about 0.2 wt % to about 0.8 wt % of colloidal silicon dioxide. In some embodiments, the drug-eluting segment comprises about 0.005 wt % to about 0.015 wt % of pigment.

In some embodiments, wherein the drug-eluting segment comprises about 20 wt % of dapagliflozin (amorphous), the drug-eluting segment comprises about 33.99 wt % of polycaprolactone (PCL), such as PCL having a viscosity midpoint between about 1.5 dl/g to about 2.1 dl/g, such as Corbion PC17. In some embodiments, the drug-eluting segment comprises about 30 wt % of vinylpyrrolidone-vinyl acetate copolymer, such as Kollidon VA64. In some embodiments, the drug-eluting segment comprises about 10 wt % of poly(DL-lactide) (PDL), such as a PDL having 2.0 dl/g intrinsic viscosity (range 1.6 dl/g to 2.4 dl/g), such as PDL20. In some embodiments, the drug-eluting segment comprises about 5 wt % of non-ionic detergent, such as sorbitane monostearate, such as Span60. In some embodiments, the drug-eluting segment comprises about 0.5 wt % of Vitamin E succinate. In some embodiments, the drug-eluting segment comprises about 0.5 wt % of colloidal silicon dioxide. In some embodiments, the drug-eluting segment comprises 0.01 wt % of pigment. In some embodiments, the pigment comprises tartazine, such as FD&C Yellow 5 Aluminum lake. In some embodiments, the amount of dye in FD&C Yellow 5 Aluminum lake is about 17% by weight.

In some embodiments, the drug-eluting segment comprises about 10 wt % to about 30 wt % of dapagliflozin (amorphous), about 20 wt % to about 50 wt % of Corbion PC17, about 20 wt % to about 40 wt % of Kollidon VA64, about 5 wt % to about 15 wt % of PDL20, about 2 wt % to about 8 wt % of Span60, about 0.2 wt % to about 0.8 wt % of Vitamin E succinate, about 0.2 wt % to about 0.8 wt % of colloidal silicon dioxide, and about 0.005 wt % to about 0.015 wt % of pigment. In some embodiments, the drug-eluting segment comprises about 20 wt % of dapagliflozin (amorphous), about 33.99 wt % of Corbion PC17, about 30 wt % of Kollidon VA64, about 10 wt % of PDL20, about 5 wt % of Span60, about 0.5 wt % of Vitamin E succinate, about 0.5 wt % of colloidal silicon dioxide, and about 0.01 wt % of pigment. In some embodiments, the pigment comprises FD&C Yellow 5 Aluminum lake. In some embodiments, the amount of dye in FD&C Yellow 5 Aluminum lake is about 17% by weight.

In some embodiments, a stellate-shaped dosage form for administration of rosuvastatin can comprise arms, which arms in turn comprise 1) a carrier polymer-agent arm segment; 2) an inactive arm segment; 3) one or more enteric linkers; 4) one or more time-dependent linkers; 5) release rate-modulating films; and 6) other optional spacers. The arms are connected to an elastomeric core in a stellate device arrangement. Typically, six arms are used for a stellate dosage form.

The carrier polymer-agent arm segments of the rosuvastatin dosage form can comprise rosuvastatin (or a pharmaceutically acceptable salt thereof), polycaprolactone, poloxamer 407 (P407), polyethylene oxide (PEO), silica ($SiO_2$), vitamin E succinate (vitE), and optionally coloring. The calcium salt of rosuvastatin can be used in the carrier polymer-agent arm segment. The polycaprolactone used can be from about 1.5 dL/g to about 1.9 dL/g viscosity, such as about 1.7 dL/g. The polyethylene oxide used can be from about 60,000 MW to about 125,000 MW, such as about 80,000 MW to 110,000 MW, or about 100,000 MW. Any pharmaceutically acceptable coloring agent can be used. Examples of coloring that can be used include FD&C Red 40 Aluminum lake, FD&C Yellow 5 Aluminum lake, or an approximately equal blend of the two. As noted, typically six arms are used for a stellate dosage form, so typically the total amount of agent contained in the dosage form is six times the amount of agent contained in a single arm. The total amount of weight of rosuvastatin, pharmaceutically acceptable salt of rosuvastatin, or calcium salt of rosuvastatin in the stellate dosage form can range from about 20 mg to about 350 mg, such as about 35 mg to about 350 mg, or about 50 mg to about 350 mg, or about 100 mg to about 350 mg, or about 150 mg to about 350 mg, or about 200 mg to about 350 mg, or about 250 mg to about 350 mg, or about 50 mg to about 300 mg, or about 100 mg to about 300 mg, or about 150 mg to about 300 mg, or about 150 mg to about 250 mg, or about 200 mg to about 300 mg, or about 50 mg to about 150 mg.

The inactive arm segments of the rosuvastatin dosage form can comprise polycaprolactone (PCL), poly(D,L-lactide) (PDL), a radiopaque substance, and optionally coloring. The polycaprolactone used can be from about 1.5 dL/g to about 1.9 dL/g viscosity, such as about 1.7 dL/g. The poly(D,L-lactide) used can be from about 1.5 dL/g to about 1.9 dL/g viscosity, such as about 1.7 dL/g. The radiopaque substance can be barium sulfate. Any pharmaceutically acceptable coloring agent can be used. An example of coloring that can be used includes FD&C Blue #5.

The enteric disintegrating matrices of the rosuvastatin dosage form can comprise polycaprolactone (PCL), hydroxypropyl methyl cellulose acetate succinate (HPMCAS), poloxamer 407 (P407), and optionally coloring. The polycaprolactone used can be from about 1.5 dL/g to about 1.9 dL/g viscosity, such as about 1.7 dL/g. The HPMCAS used can be MG grade (M grade: about 7-11% acetyl content, about 10-14% succinoyl content, about 21-25% methoxyl content, about 5-9% hydroxypropoxy content; G grade: granular). Any pharmaceutically acceptable coloring agent can be used. An example of coloring that can be used includes ferrosoferric oxide.

The time dependent disintegrating matrices of the rosuvastatin dosage form can comprise poly(D,L-lactide-co-glycolide) (PLGA), a co-polymer of L-lactide and DL-lactide (PLDL), and optionally coloring. The poly(D,L-lactide-co-glycolide) can be in about a 75:25 lactide:glycolide molar ratio with a viscosity range of about 0.32-0.44 dL/g. The co-polymer of L-lactide and DL-lactide can be in about a 70/30 molar ratio and with a viscosity midpoint of about 2.4 dl/g.

The release rate-modulating film of the rosuvastatin dosage form can comprise polycaprolactone (PCL), copovidone (such as VA64) and magnesium stearate. The polycaprolactone used can be from about 1.5 dL/g to about 1.9 dL/g viscosity, such as about 1.7 dL/g.

The central elastomer of the rosuvastatin dosage form can be of about 40 A to about 60 A durometer, such as about 45 A to about 55 A durometer, or about 50 A durometer. The central elastomer can be made from liquid silicone rubber; e.g., the central elastomer can comprise cured liquid silicone rubber.

Exemplary amounts for the various components of the rosuvastatin dosage form are provided in the table below. The amounts are given in approximate weight percent, with the understanding that when ranges are provided, the amounts are chosen so as to add up to 100%.

| | Formulation 1 | Formulation 2 | Formulation 3 |
|---|---|---|---|
| Carrier polymer-arm segment | | | |
| rosuvastatin (or pharm. accept, salt) | 25-45 | 30-40 | 35.4 |
| PCL | 30-50 | 35-45 | 40 |
| P407 | 5-10 | 6-9 | 8 |
| PEO | 10-20 | 12-18 | 15 |
| $SiO_2$ | 0.1-1 | 0.2-0.8 | 0.5 |
| vitE | 0.1-1 | 0.2-0.8 | 0.5 |
| coloring (optional) | 0.1-1 | 0.3-0.9 | 0.6 (e.g., 0.3 red, 0.3 yellow) |
| Inactive spacer | | | |
| PCL | 20-40 | 25-35 | 30 |
| PDL | 20-40 | 25-35 | 30 |
| barium sulfate | 30-50 | 35-45 | 39.9 |
| coloring (optional) | 0.01-0.5 | 0.05-0.15 | 0.1 |
| Enteric disintegrating matrix | | | |
| PCL | 25-45 | 30-40 | 33.95 |
| HPMCAS | 50-75 | 60-70 | 63.95 |
| P407 | 0.5-5 | 1-3 | 2 |
| coloring (optional) | 0.01-0.5 | 0.05-0.15 | 0.1 |
| Time-dependent disintegrating matrix | | | |
| PLGA | 25-75 | 40-60 | 50 |
| PLDL | 25-75 | 40-60 | 50 |
| Release rate-modulating film | | | |
| PCL | 60-80 | 65-75 | 68.6 |
| VA64 | 20-40 | 25-35 | 29.4 |
| Mg stearate | 0.5-5 | 1-3 | 2.0 |

The assembled arms comprising 1) a carrier polymer-agent arm segment; 2) an inactive arm segment; 3) one or more enteric linkers; 4) one or more time-dependent linkers; and 5) other optional spacers attached to the central elastomer can be arranged in various orders. One such order is (carrier polymer-agent segment)-(inactive arm segment)-(enteric disintegrating matrix segment)-(inactive arm segment)-(time-dependent disintegrating matrix segment). Approximate dimensions for the length of the segments on each arm are provided below. Optional PCL spacers of about 1-2 mm width, such as about 1.5 mm width, can be inserted between any two components below, or added to the outer tip of the assembled arm, or between the inner tip of the assembled arm and the elastomeric core.

| Component | Dimension set 1 | Dimension set 2 | Dimension set 3 |
|---|---|---|---|
| Carrier polymer-agent segment | 6-14 mm | 8-12 mm | 9.5 mm |
| Inactive segment | 2-6 mm | 3-5 mm | 4 mm |
| Enteric DM | 0.5-3 mm | 1-2 mm | 1.5 mm |
| Inactive segment | 0.5-3 mm | 1-2 mm | 1.5 mm |
| Timed DM | 0.5-3 mm | 1-2 mm | 1.5 mm |

Release Rate-Modulating Films on the Carrier Polymer Agent Segments (Coatings on the Drug-Eluting Segments)

Additional control of the release rate of agent from the carrier polymer-agent segments (drug-eluting segments) can be accomplished by coating the surface of the carrier polymer-agent segments with a release rate-modulating polymer film. Appropriate release rate-modulating films provide a more linear release of agent over the residence time in the stomach, reduce variations in release rate due to changes in gastric pH, and provide enhanced resistance against ethanol dumping if alcoholic beverages are consumed.

In some embodiments, a dosage form for administration of memantine and donepezil comprises a gastric residence system, wherein the gastric residence system further comprises a release rate-modulating film comprising about 73.5 wt % of polycaprolactone (PCL), such as PCL having a viscosity midpoint between about 1.5 dl/g to about 2.1 dl/g, such as Corbion PC17. In some embodiments, the release rate-modulating film comprises about 24.5 wt % of copovidone, such as VA64. In some embodiments, the release rate-modulating film comprises about 2.0 wt % of Mg stearate. In some embodiments, a dosage form for administration of memantine and donepezil comprises a gastric residence system, wherein the gastric residence system further comprises a release rate-modulating film comprising about 73.5 wt % of Corbion PC17, about 24.5 wt % of VA 64, and about 2.0 wt % of Mg stearate.

In some embodiments, a dosage form for administration of memantine and donepezil comprises a gastric residence system, wherein the gastric residence system further comprises a release rate-modulating film comprising about 88.2 wt % of polycaprolactone (PCL), such as PCL having a viscosity midpoint between about 1.5 dl/g to about 2.1 dl/g, such as Corbion PC17. In some embodiments, the release rate-modulating film further comprises 9.8 wt % of polycaprolactone (PCL), such as a low molecular weight PCL with an inherent viscosity midpoint between about 0.35 dl/g to about 0.43 dl/g, such as Corbion PC04. In some embodiments, the release rate-modulating film comprises about 2.0 wt % of Mg stearate. In some embodiments, a dosage form for administration of memantine and donepezil comprises a gastric residence system, wherein the gastric residence system further comprises a release rate-modulating film comprising about 88.2 wt % of Corbion PC17, about 9.8 wt % of Corbion PC04, and about 2.0 wt % of Mg stearate. In some embodiments, the release rate-modulating film accounts for about 5 wt % of the total weight of the drug-eluting segment.

In some embodiments, a dosage form for administration of risperidone comprises a gastric residence system, wherein the gastric residence system further comprises a release rate-modulating film comprising about 73.5 wt % of polycaprolactone (PCL), such as PCL having a viscosity midpoint between about 1.5 dl/g to about 2.1 dl/g, such as Corbion PC17. In some the release rate-modulating film comprises about 24.5 wt % of copovidone, such as VA64. In some embodiments, the gastric residence system further comprises a release rate-modulating film comprising about 2.0 wt % of Mg stearate. In some embodiments, a dosage form for administration of risperidone comprises a gastric residence system, wherein the gastric residence system further comprises a release rate-modulating film comprising about 73.5 wt % of Corbion PC17, about 24.5 wt % of VA64, and about 2.0 wt % of Mg stearate.

In some embodiments, a dosage form for administration of dapagliflozin comprises a gastric residence system, wherein the gastric residence system further comprises a release rate-modulating film comprising about 49 wt % of poly(DL-lactide) (PDL), such as a PDL having 2.0 dl/g intrinsic viscosity (range 1.6 dl/g to 2.4 dl/g), such as PDL20. In some embodiments, the release rate-modulating film comprises about 49 wt % of an acid terminated copolymer of DL-lactide and glycolide (50/50 molar ratio), such as an acid terminated copolymer of DL-lactide and glycolide (50/50 molar ratio) having an inherent viscosity midpoint of about 0.16 dl/g to about 0.24 dl/g, such as Corbion 5002 A. In some embodiments, the release rate-modulating film comprises about 2.0 wt % of Mg stearate. In some embodiments, a dosage form for administration of dapagliflozin comprises a gastric residence system, wherein the gastric residence system further comprises a release rate-modulating film comprising about 49 wt % of PDL20, about 49 wt % of Corbion 5002 A, and about 2 wt % of Mg stearate. In some embodiments, the release rate-modulating film accounts for about 2 wt % of the total weight of the drug-eluting segment and inactive segments.

Time-Dependent Disintegrating Matrices (Time-Dependent Linkers)

The time-dependent disintegrating matrices control the residence time of the gastric residence system in the stomach. The time-dependent disintegrating matrices are designed to degrade, dissolve, or mechanically weaken gradually over time. After the desired residence period, the time-dependent disintegrating matrices have degraded, dissolved, disassociated, or mechanically weakened to the point where the gastric residence system can pass through the pyloric valve, exiting the gastric environment and entering the small intestine, for eventual elimination from the body.

In some embodiments, a dosage form for administration of one or more agents comprises a gastric residence system, wherein the gastric residence system comprises a time-dependent disintegrating matrix comprising about 44.95 wt % of polycaprolactone (PCL), such as PCL having a viscosity midpoint between about 1.5 dl/g to about 2.1 dl/g, such as Corbion PC17. In some embodiments, the gastric residence system comprises a time-dependent disintegrating matrix comprising about 35.0 wt % of an acid terminated copolymer of DL-lactide and glycolide (50/50 molar ratio) having a viscosity midpoint between about 0.32 dl/g to about 0.48 dl/g (such as about 0.4 dl/g), such as PDLG 5004 A. In some embodiments, the gastric residence system comprises a time-dependent disintegrating matrix comprising about 18.0 wt % of a copolymer of DL-lactide and glycolide (50/50 molar ratio) having a viscosity midpoint between about 0.32 dl/g to about 0.48 dl/g (such as about 0.4 dl/g), such as PDLG 5004. In some embodiments, the gastric residence system comprises a time-dependent disintegrating matrix comprising about 2.0 wt % of polyethylene glycol, such as polyethylene glycol with average molecular weight of 100,000, such as $PEO_{100K}$. In some embodiments, the gastric residence system comprises a time-dependent disintegrating matrix comprising about 0.05 wt % of iron oxide, such as E172. In some embodiments, a dosage form for administration of one or more agents comprises a gastric residence system, wherein the gastric residence system comprises a time-dependent disintegrating matrix comprising about 44.95 wt % of Corbion PC17, about 35.0 wt % of PDLG 5004 A, about 18.0 wt % of PDLG 5004, about 2.0 wt % of $PEO_{100K}$, and about 0.05 wt % of E172.

pH-Dependent Disintegrating Matrices (Enteric Linkers)

The pH-dependent disintegrating matrices provide a safety mechanism for the gastric residence systems. If the system exits the stomach prematurely, that is, with all of the time-dependent disintegrating matrices intact, the pH-dependent disintegrating matrices will degrade, dissolve, disassociate, or mechanically weaken in the high pH environment of the small intestine, permitting the gastric residence system to pass readily through the small intestine. In addition, after passage of the gastric residence system once the time-dependent disintegrating matrices degrade, dissolve, disassociate, or mechanically weaken in the gastric environment, exposure of the pH-dependent disintegrating matrices to the high pH of the small intestine will provide further weakening and/or break-up of the system, for ready passage through the small intestine.

In some embodiments, a dosage form for administration of one or more agents comprises a gastric residence system, wherein the gastric residence system comprises a pH-dependent disintegrating matrix comprising about 33.95 wt % of polycaprolactone (PCL), such as PCL having a viscosity midpoint between about 1.5 dl/g to about 2.1 dl/g, such as Corbion PC17. In some embodiments, the gastric residence system comprises a pH-dependent disintegrating matrix comprising about 63.95 wt % of hypromellose acetate succinate, such as HPMCAS-MG. In some embodiments, the gastric residence system comprises a pH-dependent disintegrating matrix comprising about 2.0 wt % of poly (ethylene glycol)-block-poly(propylene glycol)-block-poly (ethylene glycol) polymers, such as H—(OCH2CH2)x-(O—CH(CH3)CH2)y-(OCH2CH2)z-OH where x and z are about 101 and y is about 56, such as Poloxamer 407 (P407, a poly(ethylene glycol)-block-poly(propylene glycol)-block-poly(ethylene glycol) polymer with a polyoxypropylene molecular mass of about 4000 and about 70% polyoxyethylene content). In some embodiments, the gastric residence system comprises a pH-dependent disintegrating matrix comprising about 0.1 wt % of iron oxide, such as E172. In some embodiments, a dosage form for administration of one or more agents comprises a gastric residence system, wherein the gastric residence system comprises a pH-dependent disintegrating matrix comprising about 33.95 wt % of Corbion PC17, about 63.95 wt % of HPMCAS-MG, about 2.0 wt % of P407, and about 0.1 wt % of E172.

Central Elastomer

The central elastomer provides the gastric residence system with the ability to be compacted into a compressed configuration, which can be placed in a capsule or other suitable containing structure for administration to a subject.

In some embodiments, a dosage form for administration of one or more agents comprises a gastric residence system, wherein the gastric residence system comprises a central elastomer comprising a liquid silicone rubber (LSR). In some embodiments, the LSR has a hardness of 60 durometer.

In some embodiments, a dosage form for administration of one or more agents comprises a gastric residence system, wherein the gastric residence system comprises a central elastomer comprising a liquid silicone rubber (LSR). In some embodiments, the LSR has a hardness of 50 durometer.

In some embodiments, the dosage form for administration of memantine and donepezil comprises a gastric residence system. In some embodiments, the gastric residence system comprises an inactive layer comprising about 66.495 wt % of polycaprolactone (PCL), such as PCL having a viscosity midpoint between about 1.5 dl/g to about 2.1 dl/g, such as Corbion PC17. In some embodiments, the gastric residence system comprises an inactive layer comprising about, about 32.0 wt % of copovidone, such as VA64. In some embodiments, the gastric residence system comprises an inactive layer comprising about 1.5 wt % of poly(ethylene glycol)-block-poly(propylene glycol)-block-poly(ethylene glycol) polymers, such as H—(OCH2CH2)x-(O—CH(CH3)CH2)y-(OCH2CH2)z-OH where x and z are about 101 and y is about 56, such as Poloxamer 407 (P407). In some embodiments, the gastric residence system comprises an inactive layer comprising about 0.005 wt % of iron oxide, such as E172. In some embodiments, the dosage form for administration of memantine and donepezil comprises a gastric residence system, wherein the gastric residence system comprises an inactive layer comprising about 66.495 wt % of Corbion PC17, about 32.0 wt % of VA 64, about 1.5 wt % of P407 and about 0.005 wt % of E172.

In some embodiments, the dosage form for administration of risperidone comprises a gastric residence system, wherein the gastric residence system comprises one or two inactive layers. In some embodiments, the gastric residence system comprises a first inactive layer comprising about 66.495 wt % of polycaprolactone (PCL), such as PCL having a viscosity midpoint between about 1.5 dl/g to about 2.1 dl/g, such as Corbion PC17. In some embodiments, the gastric residence system comprises a first inactive layer comprising about, about 32.0 wt % of copovidone, such as VA64. In some embodiments, the gastric residence system comprises a first inactive comprising about 1.5 wt % of poly(ethylene glycol)-block-poly(propylene glycol)-block-poly(ethylene glycol) polymers, such as H—(OCH2CH2)x-(O—CH(CH3)CH2)y-(OCH2CH2)z-OH where x and z are about 101 and y is about 56, such as Poloxamer 407 (P407). In some embodiments, the gastric residence system comprises a first inactive layer comprising about 0.005 wt % of iron oxide, such as E172. In some embodiments, the gastric residence system comprises a second inactive layer comprising about 39.995 wt % of polycaprolactone (PCL), such as PCL having a viscosity midpoint between about 1.5 dl/g to about 2.1 dl/g, such as Corbion PC17. In some embodiments, the gastric residence system comprises a second inactive layer comprising about, about 42.0 wt % of copovidone, such as VA64. In some embodiments, the gastric residence system comprises a second inactive comprising about 15.0 wt % of polyethylene glycol, such as polyethylene glycol with average molecular weight of 100,000, such as $PEO_{100K}$. In some embodiments, the gastric residence system comprises a second inactive comprising about 3.0 wt % of poly(ethylene glycol)-block-poly(propylene glycol)-block-poly(ethylene glycol) polymers, such as H—(OCH2CH2)x-(O—CH(CH3)CH2)y-(OCH2CH2)z-OH where x and z are about 101 and y is about 56, such as Poloxamer 407 (P407). In some embodiments, the gastric residence system comprises a second inactive layer comprising about 0.005 wt % of iron oxide, such as E172. In some embodiments, the dosage form for administration of risperidone comprises a gastric residence system, wherein the gastric residence system comprises one or two inactive layers. In some embodiments, the gastric residence system comprises a first inactive layer comprising about 66.45 wt % of Corbion PC17, about 32.0 wt % of VA 64, about 1.5 wt % of P407 and about 0.05 wt % of FD&C Blue 1 Aluminum lake. In some embodiments, the gastric residence system comprises a second inactive layer comprising about 39.995 wt % of Corbion PC17, about 42.0 wt % of VA 64, about 15.0 wt % of $PEO_{100K}$, about 3.0 wt % of P407 and about 0.005 wt % of E172.

In some embodiments, the dosage form for administration of dapagliflozin comprises a gastric residence system, wherein the gastric residence system comprises one or two inactive layers. In some embodiments, the gastric residence system comprises a first inactive layer comprising about 39.9 wt % of polycaprolactone (PCL), such as PCL having a viscosity midpoint between about 1.5 dl/g to about 2.1 dl/g, such as Corbion PC17. In some embodiments, the gastric residence system comprises a first inactive layer comprising about 59.5 wt % of customizable thermoplastic polyurethanes with durometer range from 62 A to 83 D, such as Pathway™ TPU polymers (The Lubrizol Corporation), such as (PY-PT72AE). In some embodiments, the gastric residence system comprises a first inactive layer comprising about 0.5 wt % of colloidal silicon dioxide. In some embodiments, the gastric residence system comprises a first inactive layer comprising about 0.1 wt % of iron oxide, such as E172. In some embodiments, the gastric residence system comprises a second inactive layer comprising about 30 wt % of polycaprolactone (PCL), such as PCL having a viscosity midpoint between about 1.5 dl/g to about 2.1 dl/g, such as Corbion PC17. In some embodiments, the gastric residence system comprises a second inactive layer comprising about 64.9 wt % of hypromellose acetate succinate, such as HPMCAS-MG. In some embodiments, the gastric residence system comprises a second inactive layer comprising about 2.5 wt % of stearic acid 50. In some embodiments, the gastric residence system comprises a second inactive layer comprising about 2.5 wt % of prop. Glycol. In some embodiments, the gastric residence system comprises a second inactive layer comprising about 0.025 wt % of iron oxide, such as E172. In some embodiments, the gastric residence system comprises a second inactive layer comprising about 0.075 wt % of a pigment. In some embodiments, the pigment comprises FD&C Red 40 A1 Lake. In some embodiments, the amount of dye in FD&C Yellow 5 Red 40 A1 Lake is about 14-16% by weight. In some embodiments, the dosage form for administration of dapagliflozin comprises a gastric residence system, wherein the gastric residence system comprises one or two inactive layers. In some embodiments, the gastric residence system comprises a first inactive layer comprising about 39.9 wt % of Corbion PC17, about 59.5 wt % of TPU (PY-PT72AE), about 0.5 wt % of colloidal silicon dioxide and about 0.1 wt % of E172. In some embodiments, the gastric residence system comprises a second inactive layer comprising about 30 wt % of Corbion PC17, about 64.9 wt % of HPMCAS-MG, about 2.5 wt % of stearic acid 50, about 2.5 wt % of prop. Glycol, about 0.025 wt % of E172, and about 0.075 wt % of a pigment. In some embodiments, the pigment comprises FD&C Red 40 A1 Lake. In some embodiments, the amount of dye in FD&C Yellow 5 Red 40 A1 Lake is about 14-16% by weight.

In some embodiments, a dosage form for administration of one or more agents comprises a gastric residence system, wherein the gastric residence system comprises an opaque layer comprising about 70 wt % of the gastric residence system further comprises a pH-dependent disintegrating matrix comprising about 33.95 wt % of polycaprolactone (PCL), such as PCL having a viscosity midpoint between about 1.5 dl/g to about 2.1 dl/g, such as Corbion PC17. In some embodiments, the gastric residence system comprises an opaque layer comprising about 30 wt % of $(BiO)_2CO$. In some embodiments, a dosage form for administration of one or more agents comprises a gastric residence system, wherein the gastric residence system comprises an opaque layer comprising about 70 wt % of Corbion PC17, and about 30 wt % of $(BiO)_2CO_3$.

In some embodiments, a dosage form for administration of memantine and donepezil comprises a gastric residence system, wherein the gastric residence system comprises a central elastomer, a first drug-eluting segment comprising about 40 mg of memantine HCl, and a second drug-eluting segment comprising about 38 mg of donepezil HCl. In some embodiments, the gastric residence system further comprises a release rate-modulating film comprising about 73.5 wt % of polycaprolactone (PCL), such as PCL having a viscosity midpoint between about 1.5 dl/g to about 2.1 dl/g, such as Corbion PC17. In some embodiments, the release rate-modulating film comprises about 24.5 wt % of copovidone, such as VA 64. In some embodiments, the release rate-modulating film comprises about 2.0 wt % of Mg stearate. In some embodiments, the gastric residence system further comprises a time-dependent disintegrating matrix comprising about 44.95 wt % of polycaprolactone (PCL), such as PCL having a viscosity midpoint between about 1.5 dl/g to about 2.1 dl/g, such as Corbion PC17. In some embodiments, the time-dependent disintegrating matrix comprises about 35.0 wt % of an acid terminated copolymer of DL-lactide and glycolide (50/50 molar ratio) having a viscosity midpoint of viscosity midpoint between about 0.32 dl/g to about 0.48 dl/g (such as about 0.4 dl/g), such as PDLG 5004 A. In some embodiments, the time-dependent disintegrating matrix comprises about 18.0 wt % of a copolymer of DL-lactide and glycolide (50/50 molar ratio) having a viscosity midpoint of viscosity midpoint between about 0.32 dl/g to about 0.48 dl/g (such as about 0.4 dl/g), such as PDLG 5004. In some embodiments, the time-dependent disintegrating matrix comprises about 2.0 wt % of polyethylene glycol, such as polyethylene glycol with average molecular weight of 100,000, such as $PEO_{100K}$. In some embodiments, the time-dependent disintegrating matrix comprises about 0.05 wt % of iron oxide, such as E172. In some embodiments, the gastric residence system further comprises a pH-dependent disintegrating matrix comprising about 33.95 wt % of polycaprolactone (PCL), such as PCL having a viscosity midpoint between about 1.5 dl/g to about 2.1 dl/g, such as Corbion PC17. In some embodiments, the pH-dependent disintegrating matrix comprises about 63.95 wt % of hypromellose acetate succinate, such as HPMCAS-MG. In some embodiments, the pH-dependent disintegrating matrix comprises about 2.0 wt % of poly(ethylene glycol)-block-poly(propylene glycol)-block-poly(ethylene glycol) polymers, such as H—(OCH2CH2)x-(O—CH(CH3)CH2)y-(OCH2CH2)z-OH where x and z are about 101 and y is about 56, such as Poloxamer 407 (P407). In some embodiments, the pH-dependent disintegrating matrix comprises about 0.1 wt % of iron oxide, such as E172. In some embodiments, the gastric residence system further comprises one or more inactive layers. In some embodiments, the gastric residence system further comprises an opaque layer comprising about 70 wt % of polycaprolactone (PCL), such as PCL having a viscosity midpoint between about 1.5 dl/g to about 2.1 dl/g, such as Corbion PC17. In some embodiments, the opaque layer comprises about 30 wt % of $(BiO)_2CO_3$. In some embodiments, a dosage form for administration of memantine and donepezil comprises a gastric residence system, wherein the gastric residence system comprises a central elastomer, a first drug-eluting segment comprising about 40 mg of memantine HCl, and a second drug-eluting segment comprising about 38 mg of donepezil HCl. In some embodiments, the gastric residence system further comprises a release rate-modulating film comprising about 73.5 wt % of Corbion PC17, about 24.5 wt % of VA 64, and about 2.0 wt % of Mg stearate. In some embodiments, the gastric residence system further comprises a time-dependent disintegrating matrix comprising about 44.95 wt % of Corbion PC17, about 35.0 wt % of PDLG 5004 A, about 18.0 wt % of PDLG 5004, about 2.0 wt % of $PEO_{100K}$, and about 0.05 wt % of E172. In some embodiments, the gastric residence system further comprises a pH-dependent disintegrating matrix comprising about 33.95 wt % of Corbion PC17, about 63.95 wt % of HPMCAS-MG, about 2.0 wt % of P407, and about 0.1 wt % of E172. In some embodiments, the gastric residence system further comprises one or more inactive layers. In some embodiments, the gastric residence system further comprises an opaque layer comprising about 70 wt % of Corbion PC17, and about 30 wt % of $(BiO)_2CO_3$.

In some embodiments, a dosage form for administration of memantine and donepezil comprises a gastric residence system, wherein the gastric residence system comprises a central elastomer, and a drug-eluting segment comprising about 170 mg of memantine HCl and about 70 mg of donepezil HCl. In some embodiments, the gastric residence system further comprises a release rate-modulating film comprising about 88.2 wt % of polycaprolactone (PCL), such as PCL having a viscosity midpoint between about 1.5 dl/g to about 2.1 dl/g, such as Corbion PC17. In some embodiments, the release rate-modulating film comprises about 9.8 wt % of polycaprolactone (PCL), such as a low molecular weight PCL with an inherent viscosity midpoint between about 0.35 dl/g to about 0.43 dl/g, such as Corbion PC04. In some embodiments, the release rate-modulating film comprises about 2.0 wt % of Mg stearate. In some embodiments, the gastric residence system further comprises a time-dependent disintegrating matrix comprising about 44.95 wt % of polycaprolactone (PCL), such as PCL having a viscosity midpoint between about 1.5 dl/g to about 2.1 dl/g, such as Corbion PC17. In some embodiments, the time-dependent disintegrating matrix comprises about 35.0 wt % of an acid terminated copolymer of DL-lactide and glycolide (50/50 molar ratio) having a viscosity midpoint between about 0.32 dl/g to about 0.48 dl/g (such as about 0.4 dl/g), such as PDLG 5004 A. In some embodiments, the time-dependent disintegrating matrix comprises about 18.0 wt % of a copolymer of DL-lactide and glycolide (50/50 molar ratio) having a viscosity midpoint between about 0.32 dl/g to about 0.48 dl/g (such as about 0.4 dl/g), such as PDLG 5004. In some embodiments, the time-dependent disintegrating matrix comprises about 2.0 wt % of polyethylene glycol, such as polyethylene glycol with average molecular weight of 100,000, such as $PEO_{100K}$. In some embodiments, the time-dependent disintegrating matrix comprises about 0.05 wt % of iron oxide, such as E172. In some embodiments, the gastric residence system further comprises a pH-dependent disintegrating matrix comprising about 33.95 wt % of polycaprolactone (PCL), such as PCL having a viscosity midpoint between about 1.5 dl/g to about 2.1 dl/g, such as Corbion PC17. In some embodiments, the pH-dependent disintegrating matrix comprises about 63.95 wt % of hypromellose acetate succinate, such as HPMCAS-MG. In some embodiments, the pH-dependent disintegrating matrix comprises about 2.0 wt % of poly(ethylene glycol)-block-poly(propylene glycol)-block-poly(ethylene glycol) polymers, such as H—(OCH2CH2)x-(O—CH(CH3)CH2)y-(OCH2CH2)z-OH where x and z are about 101 and y is about 56, such as Poloxamer 407 (P407). In some embodiments, the pH-dependent disintegrating matrix comprises about 0.1 wt % of iron oxide, such as E172. In some embodiments, the gastric residence system further comprises an opaque layer comprising about 70 wt % of polycaprolactone (PCL), such as PCL having a viscosity midpoint between about 1.5 dl/g to about 2.1 dl/g, such as Corbion PC17. In some embodiments, the opaque layer comprises about 30 wt % of $(BiO)_2CO_3$. In some embodiments, a dosage form for administration of memantine and donepezil comprises a gastric residence system, wherein the gastric residence system comprises a central elastomer, and a drug-eluting segment comprising about 170 mg of memantine HCl and about 70 mg of donepezil HCl. In some embodiments, the gastric residence system further comprises a release rate-modulating film comprising about 88.2 wt % of Corbion PC17, about 9.8 wt % of Corbion PC04, and about 2.0 wt % of Mg stearate. In some embodiments, the gastric residence system further comprises a time-dependent disintegrating matrix comprising about 44.95 wt % of Corbion PC17, about 35.0 wt % of PDLG 5004 A, about 18.0 wt % of PDLG 5004, about 2.0 wt % of $PEO_{100K}$, and about 0.05 wt % of E172. In some embodiments, the gastric residence system further comprises a pH-dependent disintegrating matrix comprising about 33.95 wt % of Corbion PC17, about 63.95 wt % of HPMCAS-MG, about 2.0 wt % of P407, and about 0.1 wt % of E172. In some embodiments, the gastric residence system further comprises an opaque layer comprising about 70 wt % of Corbion PC17, and about 30 wt % of $(BiO)_2CO_3$.

In some embodiments, a dosage form for administration of risperidone comprises a gastric residence system, wherein the gastric residence system comprises a central elastomer, and a drug-eluting segment comprising about 14 mg of risperidone. In some embodiments, the gastric residence system further comprises a release rate-modulating film comprising about 73.5 wt % of polycaprolactone (PCL), such as PCL having a viscosity midpoint between about 1.5 dl/g to about 2.1 dl/g, such as Corbion PC17. In some embodiments, the release rate-modulating film comprises about 24.5 wt % of copovidone, such as VA64. In some embodiments, the release rate-modulating film comprises about 2.0 wt % of Mg stearate. In some embodiments, the gastric residence system further comprises a time-dependent disintegrating matrix comprising about 44.95 wt % of polycaprolactone (PCL), such as PCL having a viscosity midpoint between about 1.5 dl/g to about 2.1 dl/g, such as Corbion PC17. In some embodiments, the time-dependent disintegrating matrix comprises about 35.0 wt % of an acid terminated copolymer of DL-lactide and glycolide (50/50 molar ratio) having a viscosity midpoint between about 0.32 dl/g to about 0.48 dl/g (such as about 0.4 dl/g), such as PDLG 5004 A. In some embodiments, the time-dependent disintegrating matrix comprises about 18.0 wt % of a copolymer of DL-lactide and glycolide (50/50 molar ratio) having a viscosity midpoint between about 0.32 dl/g to about 0.48 dl/g (such as about 0.4 dl/g), such as PDLG 5004. In some embodiments, the time-dependent disintegrating matrix comprises about 2.0 wt % of polyethylene glycol, such as polyethylene glycol with average molecular weight of 100,000, such as $PEO_{100K}$. In some embodiments, the time-dependent disintegrating matrix comprises about 0.05 wt % of iron oxide, such as E172. In some embodiments, the gastric residence system further comprises a pH-dependent disintegrating matrix comprising about 33.95 wt % of polycaprolactone (PCL), such as PCL having a viscosity midpoint between about 1.5 dl/g to about 2.1 dl/g, such as Corbion PC17. In some embodiments, the pH-dependent disintegrating matrix comprises about 63.95 wt % of hypromellose acetate succinate, such as HPMCAS-MG. In some embodiments, the pH-dependent disintegrating matrix comprises about 2.0 wt % of poly(ethylene glycol)-block-poly(propylene glycol)-block-poly(ethylene glycol) polymers, such as H—(OCH2CH2)x-(O—CH(CH3)CH2)y-(OCH2CH2)z-OH where x and z are about 101 and y is about 56, such as Poloxamer 407 (P407). In some embodiments, the pH-dependent disintegrating matrix comprises about 0.1 wt % of iron oxide, such as E172. In some embodiments, the gastric residence system further comprises one or more inactive layers. In some embodiments, the gastric residence system further comprises an opaque layer comprising about 70 wt % of polycaprolactone (PCL), such as PCL having a viscosity midpoint between about 1.5 dl/g to about 2.1 dl/g, such as Corbion PC17. In some embodiments, the opaque layer comprises about 30 wt % of $(BiO)_2CO_3$. In some embodiments, a dosage form for administration of risperidone comprises a gastric residence system, wherein the gastric residence system comprises a central elastomer, and a drug-eluting segment comprising about 14 mg of risperidone. In some embodiments, the gastric residence system further comprises a release rate-modulating film comprising about 73.5 wt % of Corbion PC17, about 24.5 wt % of VA64, and about 2.0 wt % of Mg stearate. In some embodiments, the gastric residence system further comprises a time-dependent disintegrating matrix comprising about 44.95 wt % of Corbion PC17, about 35.0 wt % of PDLG 5004 A, about 18.0 wt % of PDLG 5004, about 2.0 wt % of $PEO_{100K}$, and about 0.05 wt % of E172. In some embodiments, the gastric residence system further comprises a pH-dependent disintegrating matrix comprising about 33.95 wt % of Corbion PC17, about 63.95 wt % of HPMCAS-MG, about 2.0 wt % of P407, and about 0.1 wt % of E172. In some embodiments, the gastric residence system further comprises one or more inactive layers. In some embodiments, the gastric residence system further comprises an opaque layer comprising about 70 wt % of Corbion PC17, and about 30 wt % of $(BiO)_2CO_3$.

In some embodiments, a dosage form for administration of dapagliflozin comprises a gastric residence system, wherein the gastric residence system comprises a central elastomer, a first drug-eluting segment comprising about 35 mg of dapagliflozin. In some embodiments, the gastric residence system further comprises a release rate-modulating film comprising about 49 wt % of PDL20, about 49 wt % of Corbion 5002 A, and about 2 wt % of Mg stearate. In some embodiments, the gastric residence system further comprises a time-dependent disintegrating matrix comprising about 44.95 wt % of Corbion PC17, about 35.0 wt % of PDLG 5004 A, about 18.0 wt % of PDLG 5004, about 2.0 wt % of $PEO_{100K}$, and about 0.05 wt % of E172. In some embodiments, the gastric residence system further comprises a pH-dependent disintegrating matrix comprising about 33.95 wt % of Corbion PC17, about 63.95 wt % of HPMCAS-MG, about 2.0 wt % of P407, and about 0.1 wt % of E172. In some embodiments, the gastric residence system further comprises one or more inactive layers. In some embodiments, the gastric residence system further comprises an opaque layer comprising about 70 wt % of Corbion PC17, and about 30 wt % of $(BiO)_2CO_3$.

EXAMPLES

The disclosure is further illustrated by the following non-limiting examples.

Testing Methods Used in Examples

3-Point Bending Test: A "flexural modulus" of a material is an intrinsic property of a material computed as the ratio of stress to strain in flexural deformation of the material as measured by a 3-point bending test. Although the linkers are described herein as being components of the gastric residence system, the flexural modulus of the material of the polymeric material may be measured in isolation. For example, the polymeric linker in the gastric residence system may be too short to measure the flexural modulus, but a longer sample of the same material may be used to accurately determine the flexural modulus. The longer sample used to measure the flexural modulus should have the same cross-sectional dimensions (shape and size) as the polymeric linker used in the gastric residence system. The flexural modulus is measured using a 3-point bending test in accordance with the ASTM standard 3-point bending test (ASTM D790) using a 10 mm distance between supports and further modified to accommodate materials with non-rectangular cross-sections. The longest line of symmetry for the cross section of the polymeric linker should be positioned vertically, and the flexural modulus should be measured by applying force downward. If the longest line of symmetry for the cross section of the polymeric linker is perpendicular to a single flat edge, the single flat edge should be positioned upward. If the cross-section of the polymeric linker is triangular, the apex of the triangle should be faced downward. As force is applied downward, force and displacement are measured, and the slope at the linear region is obtained to calculate the flexural modulus.

Figure 15:
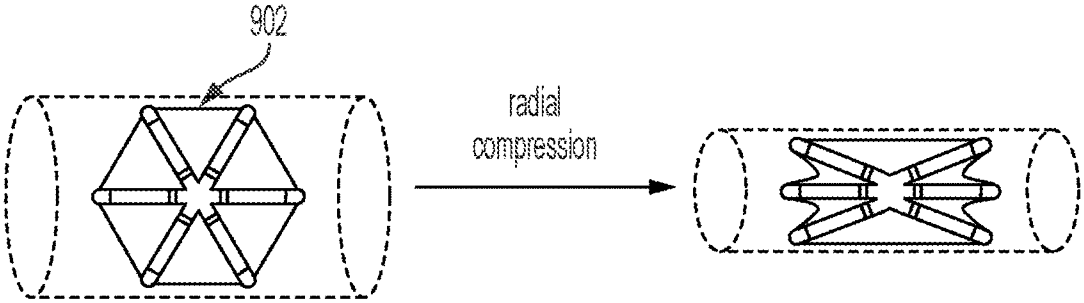
FIG. 15 shows a method of testing radial compression using an iris mechanism, according to some embodiments.

Radial Force Compression Test: A radial force compression test using an iris mechanism may be used to quantify the force required to compress an intact gastric residence system into a configuration small enough to pass through a pylorus. The instrument (i.e., iris tester; see FIG. 15) used to measure radial force compression is a Blockwise Model TTR2 Tensile Testing Machine with Model RLU124 Twin-Cam™ Radial Compression Station, 60 mm D×124 mm L.

The gastric residence system to be measured should be placed in the iris tester such that the plane of the gastric residence system is parallel to the axis of the iris cylinder. In cases where a stellate-shaped gastric residence system comprising six arms is tested, four arm tips should be placed in contact with the interior wall of the iris tester, where two arms are angled upwards and two arms are angled downwards. Two additional arms should be oriented parallel to the axis of the iris cylinder.

As the diameter of the iris mechanism decreases, a radial force is applied to the gastric residence system. A given force measurement is the force required to compress the gastric residence system to the corresponding iris mechanism diameter.

Figure 16A:
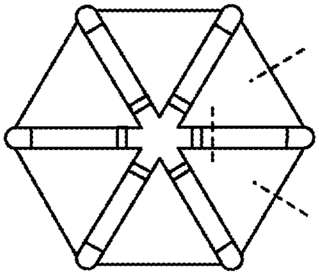
FIGS. 16A-16B show a pullout force test of a gastric residence system having a filament, according to some embodiments.
Figure 16B:
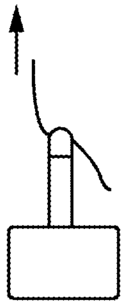
Figure 17:
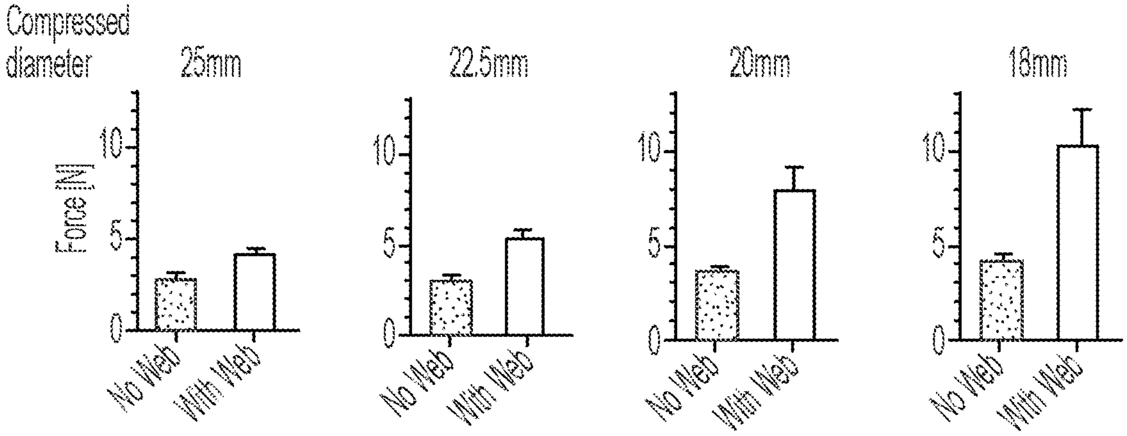
FIG. 17 shows radial force data for gastric residence systems without a filament and gastric residence systems having filament, according to some embodiments.

Pullout Force Test: The adhesion strength of a filament for a gastric residence system can be tested using a pullout force test (see FIG. 16A and FIG. 16B). As described previously, the filament may be attached to a distal end of an arm. In cases where a single filament connects more than two arms, the filament may be connected to the distal end of each arm to prevent translation of the arm along the filament when the gastric residence system is bent by gastric forces. Thus, the pullout force test described herein can quantify the amount of force required to separate the filament from the distal end of an arm.

Gastric residence systems having six arms and a filament were prepared and the arms were isolated by cutting the elastomeric core into six parts. The filament was cut between each arm. The tensile force required to pull the filament out of each arm tip was measured using an Instron 3340 Series Universal Testing System by gripping the base of the arm and one end of the filament.

Double Funnel Durability Test: A double funnel test may be used to quantify the durability and/or failure mode of a gastric residence system. The durability of a gastric residence system can help prevent the premature breaking or weakening due to repeated gastric wave/forces (and early passage through the pylorus) of a gastric residence system. To test a gastric residence system using a double funnel test, the system to be tested is gripped at its center (i.e., core) by a ring attached to a linear actuator. The gastric residence system is repeatedly moved upwards and downwards into facing cone-shaped cavities, causing the arms of gastric residence system to bend back and forth with reference to the core. The cone-shaped cavities are facing each other such that the vertex of the cones are opposite each other and the bases of each cone are proximate one another. This upwards and downwards motion is repeated for hundreds of cycles or until the gastric residence system breaks. Different specific failure modes may include a breakage at a connection point (e.g., arm-to-core or first segment-to-second segment) or tearing of the silicone core. The number of cycles to failure and the force required to bend the gastric residence system may be quantified. The test may be performed with the gastric residence system submerged in aqueous media (e.g., simulated gastric fluid) and at body temperature.

Planar Circumferential Bend Durability Test: A planar circumferential test may be used to quantify the durability and/or failure mode of a gastric residence system. In particular, the planar circumferential bend durability test can test a gastric residence system by positioning it onto a puck having four grips each in contact with arms of the gastric residence system. The grips are connected to a rotational actuator that applies force to the arms in a circumferential motion. This motion causes the arms to spread within the plane of the gastric residence system. The motion is repeated for hundreds of cycles or until the gastric residence system breaks. Different specific failure modes may include a breakage at a connection point (e.g., arm-to-core or first segment-to-second segment) or tearing of the silicone core. The number of cycles to failure and the force required to bend the gastric residence system may be quantified. The test may be performed with the gastric residence system submerged in aqueous media (e.g., simulated gastric fluid) and at body temperature.

Melt Flow Index (MFI): The melt flow index (MFI) is a measurement of viscosity at low shear, measured in grams of material that flow through a die in 10 minutes at a set temperature and applied weight. These measurements are performed using a Ray-Ran 6MPCA Advanced Melt Flow System, with a weight of 2.16 kg (but can be with a range of standardized weights) and following Procedure A of ASTM D1238 "Standard Test Method for Melt Flow Rates of Thermoplastics by Extrusion Plastometer."

Tensile Test: An Instron machine having custom-made grips can be used to evaluate the ultimate tensile strength (UTS) of the bond between any combination of stellate components: (1) in a variety of incubation media; (2) at several times of incubation; and (3) at room temperature or body temperature (37-40° C.). A low ultimate tensile strength indicates a potential failure point in the stellate. Using formulation and process optimization, tensile strength can be maximized for ideal stellate performance.

For testing stellate arms with a triangular cross-section, custom-made grips can be used having one flat plate and one notched plate. The apex of the triangular arm sits in the notch, in order to distribute the pressure from the plates more evenly across the three lengthwise faces of the triangular arm.

Tensile testing was performed using an Instron 3342 Series. A series of hot-melt extruded, thermally bonded equilateral triangular prisms with a 3.33 mm triangular base is gripped using pneumatic actuation. The crosshead moves upward at 5-500 mm/minute depending on the elasticity of the materials tested. The instrument records Force (N) v. Displacement (mm), and the maximum force is divided by the cross-sectional area at the interface to calculate ultimate tensile strength (stress).

Drug Release Rate Test: Release rate of drug is tested in fasted-state simulated gastric fluid (FaSSGF). FaSSGF was prepared as follows, according to the manufacturer's instructions (biorelevant.com). 975 mL deionized water and 25 mL of 1N hydrochloric acid were mixed in a 1 L glass media bottle. The pH was adjusted to 1.6 using 1N HCl or NaOH as needed. 2.0 grams of NaCl was added and mixed in. Just before use, 60 mg of Biorelevant powder was mixed into the solution. The composition of FaSSGF was taurocholate (0.08 mM), phospholipids (0.02 mM), sodium (34 mM), chloride (59 mM). Carrier polymer-agent compositions were formed into drug-loaded polymer arms by blending polymer powder and active pharmaceutical ingredient, and extruding. Arms were coated with release rate-modulating polymer films by dissolving the film polymer in an appropriate solvent, typically ethyl acetate or acetone, and pan-coating or dip-coating the arm in the solution of film polymer. Coated arms are then placed in a vessel containing FaSSGF, incubated at 37° C., and typically sampled at least four times over a seven-day period. Drug content was measured by HPLC. Samples were stored for no more than 3 days at 4° C. prior to analysis. At each measurement time point, in order to maintain sink conditions, the entire volume of release media was replaced with fresh solution pre-equilibrated to 37° C.

Example 1

In this Example, a dosage form according to the present invention includes a gastric residence system, wherein the gastric residence system is formulated to include both memantine HCl and donepezil HCl.

The gastric residence system includes a central elastomer that provides the gastric residence system with the ability to be compacted into a compressed configuration. The gastric residence system illustrated in this Example is an arrangement of the "star" configuration.

FIG. 1 is labelled to show the various elements of this configuration. The system 1000 comprises a central elastomeric core 1110 which is in the shape of an "asterisk" having six short branches. That is, the asterisk shape has a round central portion with six short branches protruding from the central portion, where the central portion and branches lie in the same plane. There are six arms comprising drugs. The proximal end of each arm is attached to the central elastomeric core and projects radially from it, and the distal end not attached to the central elastomeric core is located at a larger radial distance from the central elastomeric core than the proximal end. A segment 1160 of the arm is attached to one short asterisk branch. A segment 1170 is positioned between the segment 1160 and a segment 1150, followed by another segment 1170. The distal end of the arm has a segment 1120 or 1130, along with a segment 1140.

The gastric residence system has an average size of about 46 mm and each segment has a length ranging from about 0.5 mm to about 5.0 mm. Table 1 below provides a listing of the length of each segment in the gastric residence system. Each range or value below can be considered to be "about" the range or value indicated, or exactly the range or value indicated.

TABLE 1

| Segment | Length |
|---|---|
| 120 | 4.8 mm |
| 130 | 5.0 mm |
| 140 | 4.5-4.8 mm |
| 150 | 1.85 mm |
| 160 | 1.85 mm |
| 170 | 0.5 mm |

The central elastomeric core 1110 comprises a liquid silicone rubber (LSR) having a hardness of 60 durometer.

Each dosage form provided here comprises about 40 mg of memantine HCl and about 38 mg of donepezil HCl for administration. Memantine HCl is included in a first carrier polymer-agent segment 1120 (e.g., a first drug-eluting segment), and donepezil HCl is included in a second carrier polymer-agent segment 1130 (e.g., a second drug-eluting segment).

The first drug-eluting segment comprises about 45.0 wt % of memantine HCl, about 41.9 wt % of Corbion PC17, about 10.0 wt % of PDL 20, about 2.0 wt % of P407, about 0.5 wt % of Vitamin E succinate, about 0.5 wt % of $SiO_2$, and about 0.1 wt % of Sunset yellow. The second drug-eluting segment comprises about 40.0 wt % of donepezil HCl, about 44.0 wt % of Corbion PC17, about 10.0 wt % of PDL 20, about 5.0 wt % of P407, about 0.5 wt % of Vitamin E succinate, and about 0.5 wt % of $SiO_2$. Moreover, the first and second drug-eluting segments are separated from the rest of the drug arms by an inactive segment 1140, comprising about 66.495 wt % of Corbion PC17, about 32.0 wt % of VA 64, about 1.5 wt % of P407 and about 0.005 wt % of E172.

The gastric residence system further includes a time-dependent disintegrating matrix or linker, referred as the segment 1160, as well as a pH-dependent disintegrating matrix or linker, referred as the segment 1150. In addition, the gastric residence system includes a structural segment 1170 to provide radiopaque. Listed below in Table 2 are various materials used in the time-dependent disintegrating matrix, the pH-dependent disintegrating matrix, and the structural segment along with weight percentages. Each range or value below can be considered to be "about" the range or value indicated, or exactly the range or value indicated.

TABLE 2

| pH-dependent disintegrating matrix (wt %) | | Time-dependent disintegrating matrix (wt %) | | Structural segment (wt %) | |
|---|---|---|---|---|---|
| Corbion PC17 | 33.95 | Corbion PC17 | 44.95 | Corbion PC17 | 70 |
| HPMCAS-MG | 63.95 | PDLG 5004A | 35.0 | $(BiO)_2CO_3$ | 30 |
| P407 | 2.0 | PDLG 5004 | 18.0 | — | — |
| E172 | 0.1 | $PEO_{100K}$ | 2.0 | — | — |
| — | — | E172 | 0.05 | — | — |

In the gastric residence system, each drug arm is coated by a release rate-modulating film. Specifically, the coating comprises about 73.5 wt % of Corbion PC17, about 24.5 wt % of VA 64, and about 2.0 wt % of Mg stearate. The coating on the drug arm comprising memantine HCl is applied in an amount of about 4.0 wt % of the pre-coating weight of the first drug-eluting segment and the inactive segment (i.e., segments 1140, 1120 and 1140), while that on the drug arm comprising donepezil HCl is applied in an amount of about 3.0 wt % of the total pre-coating weight of the second drug-eluting segment and the inactive segment (i.e., segments 1140, 1130 and 1140).

Figure 2:
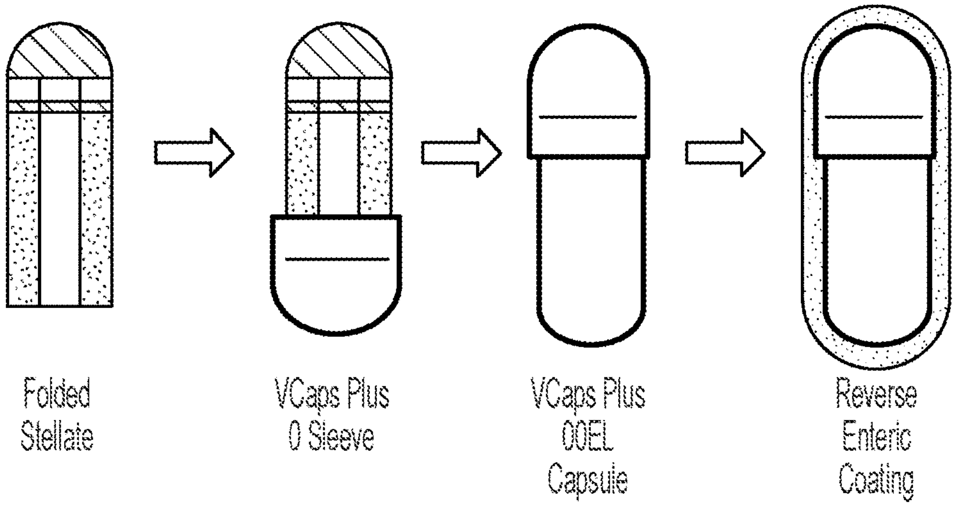
FIG. 2 shows the encapsulation process for the dosage form of Example 1.

The gastric residence system is assembled and then placed into an appropriate sized capsule. FIG. 2 illustrates the encapsulation of the gastric residence system of in this Example. The capsule is made with 32 mg of a coating, which comprises 90.9 wt % of Eudragit E, 4.55 wt % of Mg Stearate as an anti-tack agent, and 4.55 wt % of dibutyl sebacate as a plasticizer.

Figure 3:
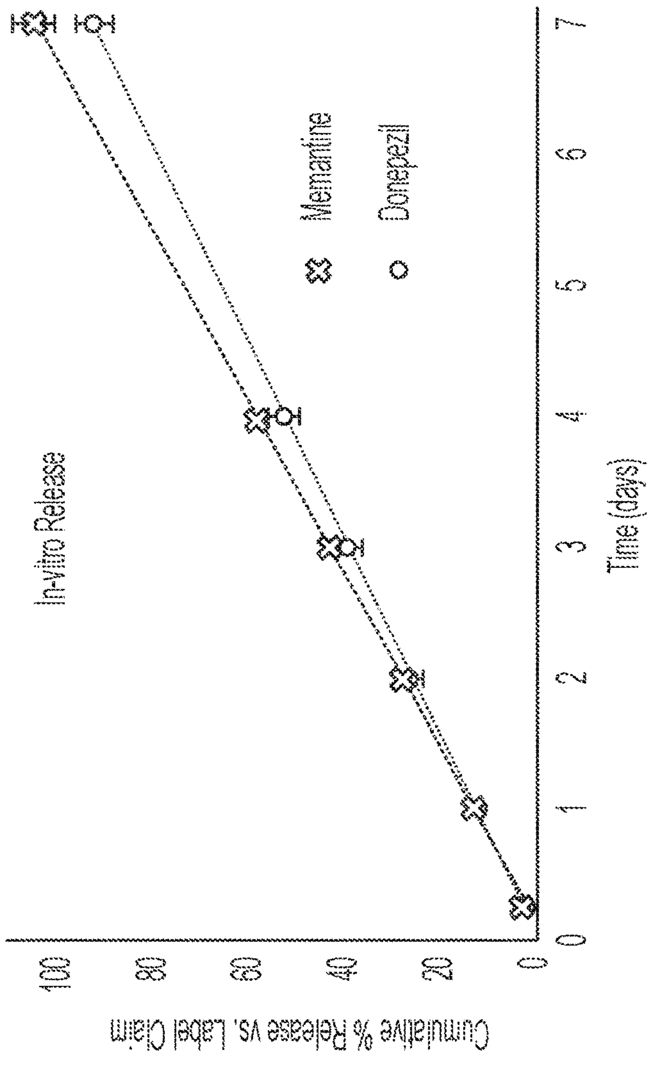
FIG. 3 shows the in-vitro release of memantine and donepezil from the dosage form of Example 1.

The release characteristics of both memantine and donepezil from the dosage form provided here were evaluated. FIG. 3 shows the in-vitro release of memantine and donepezil from the dosage form.

Figure 71:
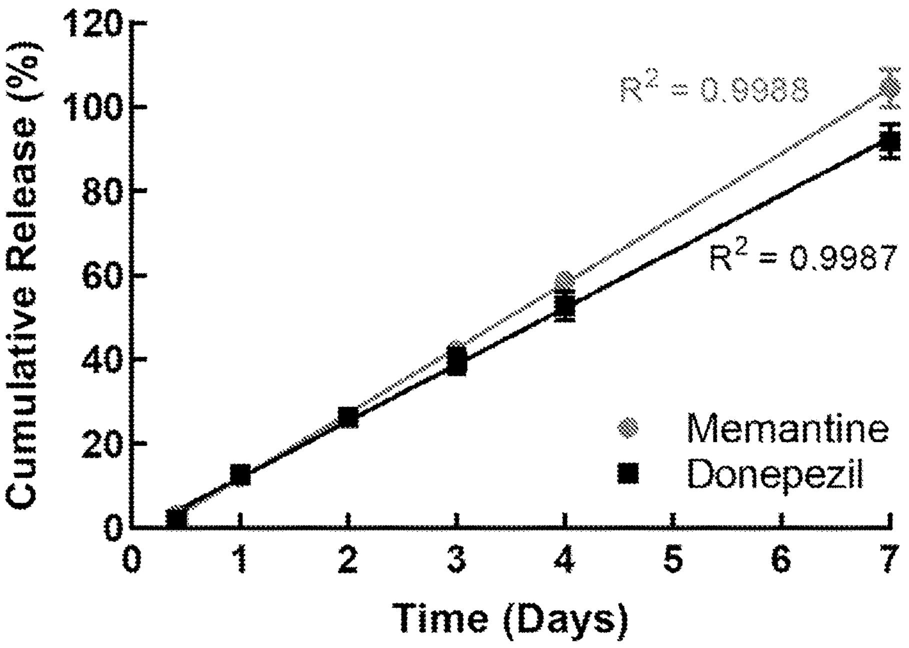
FIG. 71 depicts linear release of both memantine and donepezil of the formulation of Example 1 over seven days in vitro (mean±sd).
Figure 72:
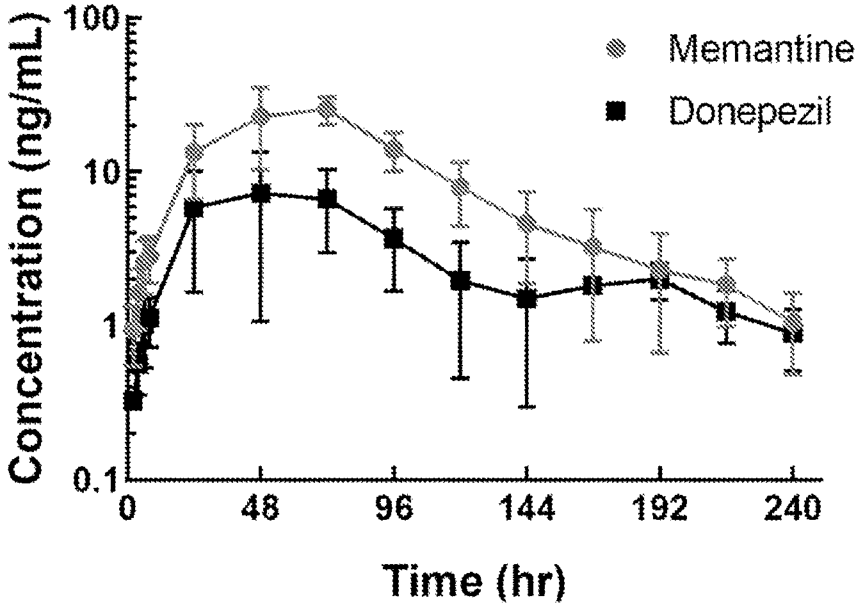
FIG. 72 depicts pharmacokinetics of the formulation of Example 1 in beagles, showing sustained plasma levels consistent with linear drug release (n=5 dogs, mean±sd).
Figures 73, 74:
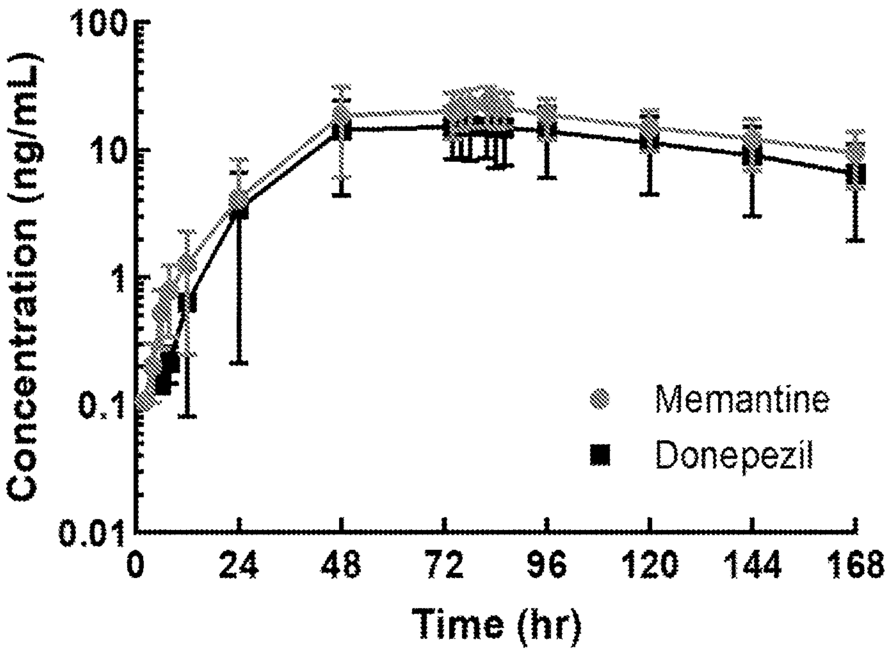
FIG. 73 depicts plasma pharmacokinetic parameters for the formulation of Example 1 in beagles (n=5).
FIG. 74 depicts pharmacokinetics of the formulation of Example 1 in human subjects in a Phase I study (n=8 healthy volunteers, mean±sd).
Figures 75, 76:
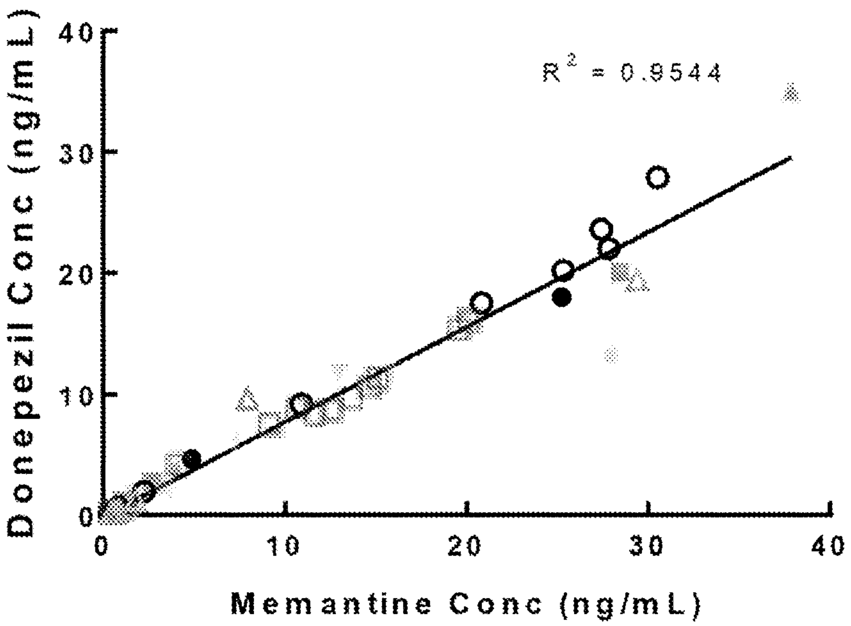
FIG. 75 depicts plasma pharmacokinetic parameters for the formulation of Example 1 in human subjects in a Phase I study (n=8). Tmax is reported as Median (nominal range), all other parameters are reported as mean (% CV).
FIG. 76 depicts plasma concentration of memantine and donepezil for each human subject at each timepoint through Cmax in a Phase I study. Linear correlation reflects consistent release from separate memantine- and donepezil-loaded arms.
Figure 77A:
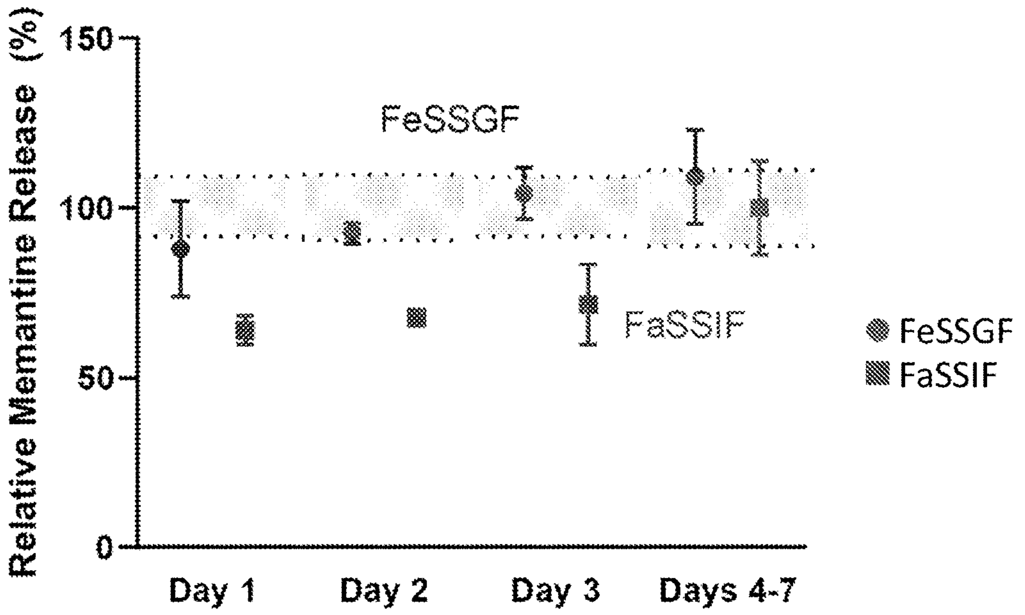
FIGS. 77A-77D depict preliminary evaluation of food effects on drug release.
Figure 77B:
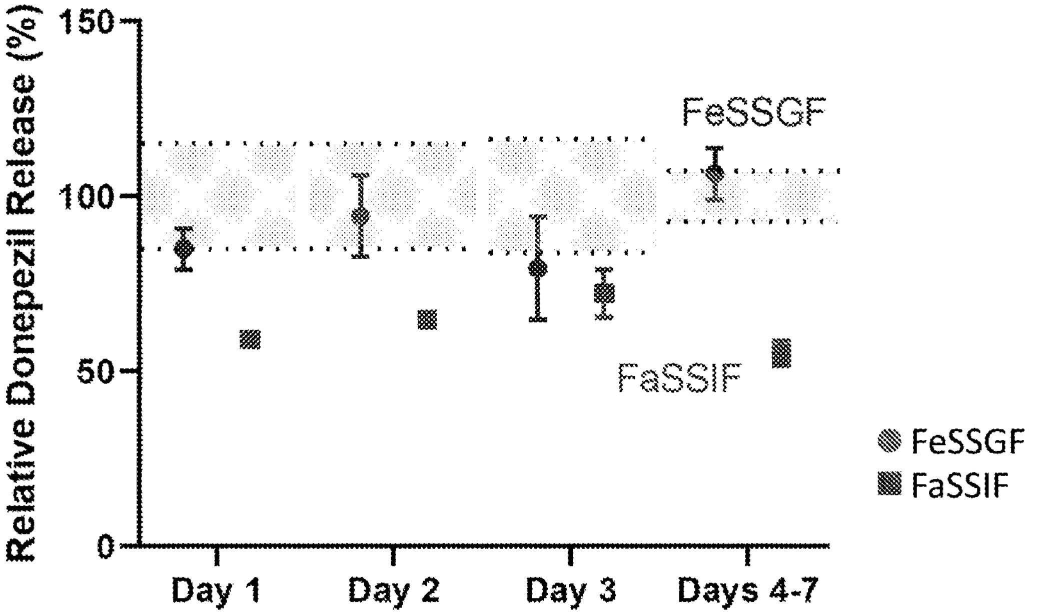
Figure 77C:
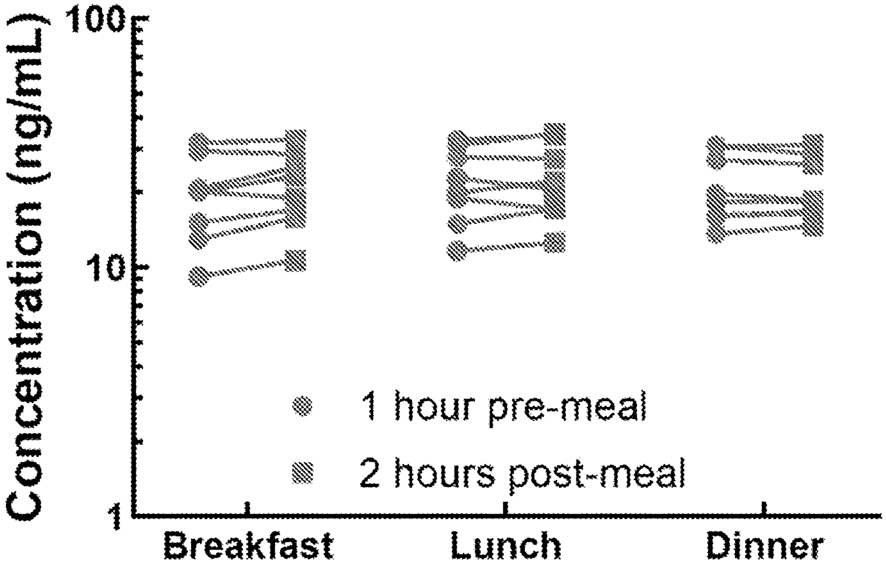
Figure 77D:
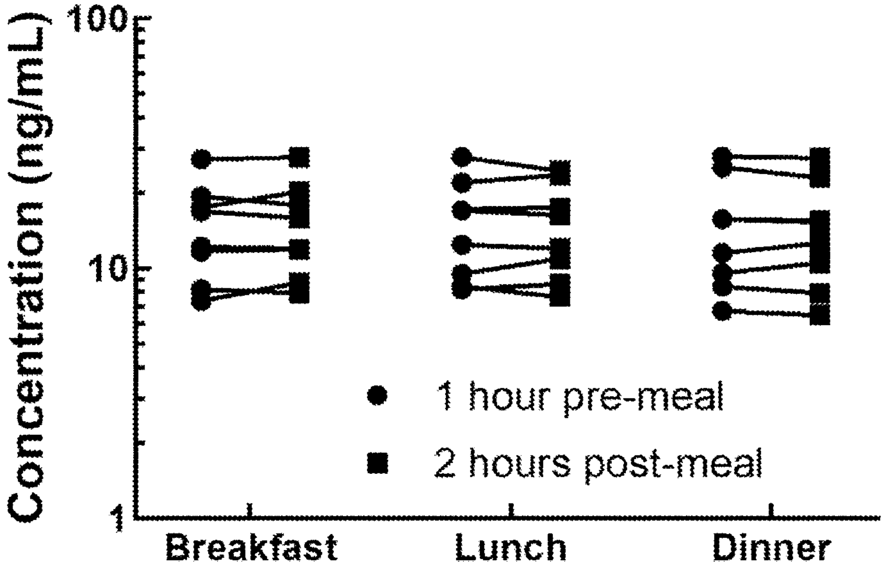
Figures 78, 79:
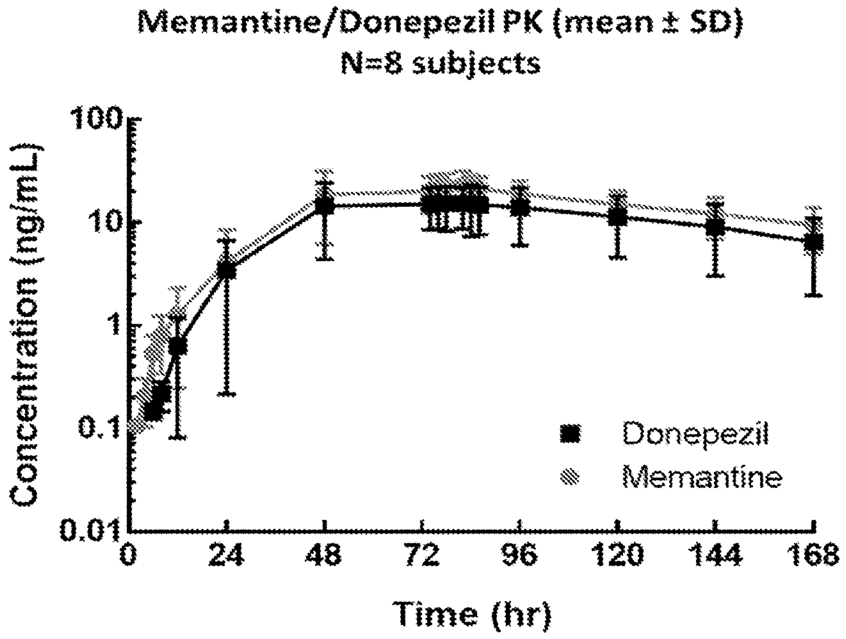
FIG. 78 depicts a logarithmic graph of the pharmacokinetics of the formulation of Example 1 in human subjects in a Phase 1 study (n=8 healthy volunteers, mean±SD).
FIG. 79 depicts pharmacokinetic parameters of memantine and donepezil, demonstrating that Formulation of Example 1 achieved drug release similar to published values of seven daily doses of extended-release memantine (Namenda XR®) and immediate-release donepezil (Aricept®).

Additional characteristics are shown in FIG. 71 (in vitro release), FIG. 72 and FIG. 73 (studies in beagle dogs).

Phase 1 Study in Humans: Low Dose

The human studies were a phase 1, open-label, single-dose study to evaluate safety, tolerability, and PK properties of the gastric residence system dosage form described in this Example 1 in eight healthy male and female participants without known GI disorders. The sample size of eight subjects was considered adequate for providing descriptive data in the evaluation of the endpoints. Participants were excluded with a history or presence of GI, hepatic, or renal disease or any other condition known to interfere with absorption, distribution, metabolism, or excretion of drugs. Other general medical exclusions included cataracts, seizures and positive screening tests for HIV, hepatitis B or hepatitis C or fecal occult blood. Each participant received a single dose of the dosage form and were monitored for safety and intensive PK sampling during a one-week stay in a clinical research unit. Primary endpoints included safety and tolerability assessed from a combination of AE reporting and examinations specified per protocol, and PK parameters for memantine and donepezil after oral administration of dosage form capsules by validated assay (e.g., $C_{max}$, $T_{max}$, $AUC_{0\text{-}last}$, $AUC_{0\text{-}t}$, $AUC_{0\text{-}168}$, $AUC_{0\text{-}\infty}$). Additionally, exploratory endpoints included pre- and post-prandial PK analysis to assess the impact of food consumption on the formulation. Plasma samples were collected from participants pre-dose and 2, 4, 6, 8, 12, 24, 48, 72, 96, 120, 144, 168 hours after dosing while inpatient for seven days, and at a single time point at each subsequent outpatient visit on Days 10, 15, 22, and 29. Safety monitoring included serial exams and assessments for AE monitoring, concomitant medication use, physical examinations, measurement of vital signs, ECGs, safety laboratories (clinical chemistry panel, liver function tests, hematology panel, urinalysis), and faecal collection (for bowel movement characterisation, formulation assessment and visual inspection of blood). Safety data were summarised by participant, by endpoint, by timepoint, and overall. GI transit data, including fecal assessment and magnetic resonance imaging (MRI) and X-ray imaging results, were summarised by participant, by timepoint, and overall. A total of eight participants received a dosage form, participated in required assessments through end of study visit, and were included in the safety population for this trial. Results are shown in FIG. 74, FIG. 75, FIG. 76, FIG. 77, FIG. 78, and FIG. 79.

This low-dose combination formulation of memantine HCl and donepezil HCl extended-release gastric residence system demonstrated consistent and linear drug release over seven days for both drugs.

Example 2

In this Example, a dosage form according to the present invention includes a gastric residence system, the gastric residence system is formulated to include both memantine HCl and donepezil HCl.

The gastric residence system includes a central elastomer that provides the gastric residence system with the ability to be compacted into a compressed configuration. The gastric residence system illustrated in this Example is a different arrangement of the “star” configuration.

Figure 4:
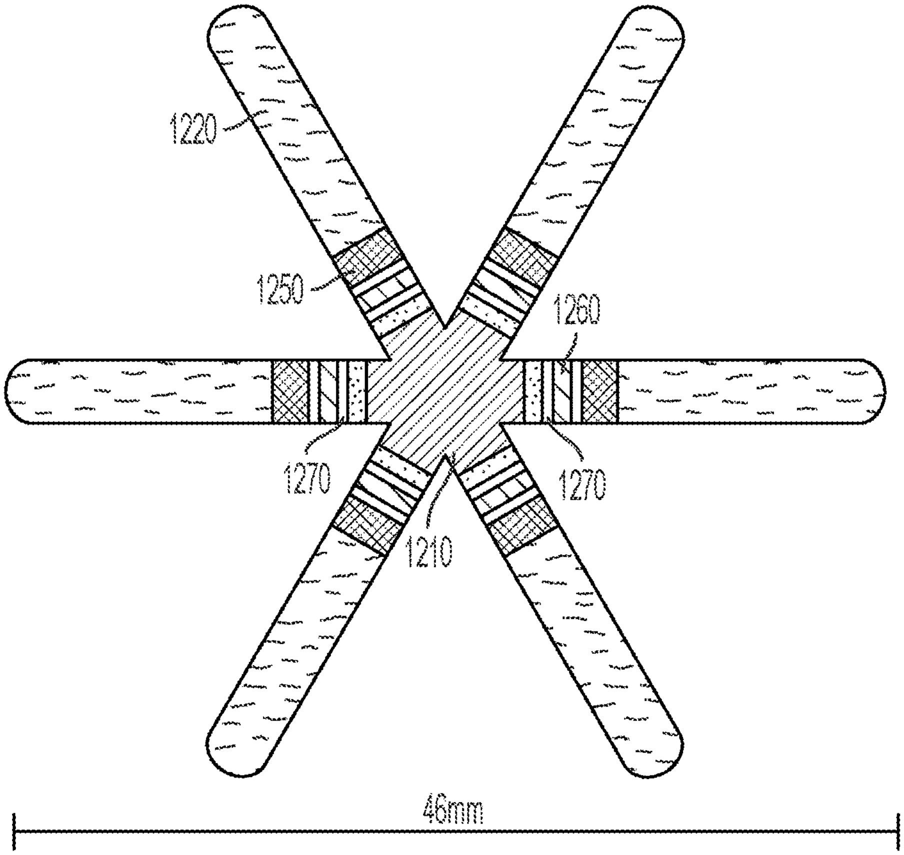
FIG. 4 shows the gastric residence system dosage form of Example 2.

FIG. 4 is labelled to show the various elements of this configuration. The system 1200 comprises a central elastomeric core 1210 which is in the shape of an “asterisk” having six short branches. A segment 1260 of the arm is attached to one short asterisk branch. The segment 1260 is positioned next to a segment 1270 followed by a segment 1250. The distal end of the arm has a segment 1220. There is an additional segment 2270 between the core and the segment 1260 on one of the six arms.

The gastric residence system has an average size of about 46 mm and each segment has a length ranging from about 0.5 mm to about 14.0 mm. Table 3 below provides a listing of the length of each segment in the gastric residence system. Each range or value below can be considered to be “about” the range or value indicated, or exactly the range or value indicated.

TABLE 3

| Segment | Length |
|---|---|
| 120 | 14 mm |
| 150 | 1.85 mm |
| 160 | 1 mm |
| 170 | 0.5 mm |

The central elastomeric core 1210 comprises a liquid silicone rubber (LSR) having a hardness of 50 durometer.

Each dosage form provided here comprises about 170 mg of memantine HCl and about 70 mg of donepezil HCl for administration. Both memantine HCl and donepezil HCl are included in a carrier polymer-agent segment 1220 (e.g., a drug-eluting segment). The drug-eluting segment comprises about 35.5 wt % of memantine HCl, about 14.5 wt % of donepezil HCl, about 43.97 wt % of Corbion PC17, about 5.0 wt % of Kollidon SR, about 0.5 wt % of Vitamin E succinate, about 0.5 wt % of $SiO_2$, and about 0.03 wt % of Sunset yellow.

The gastric residence system further includes a time-dependent disintegrating matrix or linker, referred as the segment 1260, as well as a pH-dependent disintegrating matrix or linker, referred as the segment 1250. In addition, the gastric residence system includes a structural segment 1270. The compositions of the time-dependent disintegrating matrix, the pH-dependent disintegrating matrix, and the structural segment used here are the same as those listed in Table 2 of Example 1.

In the gastric residence system, each drug arm is coated by a release rate-modulating film. Specifically, the single phase coating comprises about 88.2 wt % of Corbion PC17, about 9.8 wt % of Corbion PC04, and about 2.0 wt % of Mg stearate, and is applied in an amount of about 5 wt % of the total pre-coating weight of the drug-eluting segment (i.e., segment 1220).

The gastric residence system is assembled and then placed into an appropriate sized capsule. The capsule used here is the same as the one used in Example 1.

Phase 1 Study in Humans: High Dose

A study was done with this gastric residence system. The dose given was a single Size 00EL capsule containing about 170 mg memantine HCl and about 70 mg donepezil HCl within the ER formulation (stellate). One capsule was administered to each participant. Prior to administration of the gastric residence system, dose titration over 28 days of the combination of a daily memantine HCl extended release oral capsule to 28 mg and a donepezil HCl oral tablet to 10 mg, was accomplished according to the following regimen as oral administration:

Regimen 1: Day 1-3 (7 mg memantine, 5 mg donepezil)

Regimen 2: Day 4-7 (14 mg memantine, 5 mg donepezil)

Regimen 3: Day 8-14 (21 mg memantine, 10 mg donepezil)

Regimen 4: Day 15-28 (28 mg memantine, 10 mg donepezil).

Each participant had a clinic visit on the first day of each of the dosing regimens (and Day 22), where the respective doses were self-administered with a trained nurse (at a minimum) present. Until the remainder of the regimen, the participants orally self-administered daily at home, with calls from the clinic to verify adherence, then returned to the clinic for the next scheduled regimen (also Day 22) or entry to the inpatient unit.

Following the completion of the dose titration regimens, all participants received a single capsule dose, administered (after fasting, a low fat meal or a high fat meal) by a trained nurse (at a minimum). Participants were randomised at the time of admission to the inpatient clinic (Day 27). Block randomisation was associated with the administration condition (fasted, low- or high-fat meal) pre-dose and defined by the electronic data capture system.

Figure 80:
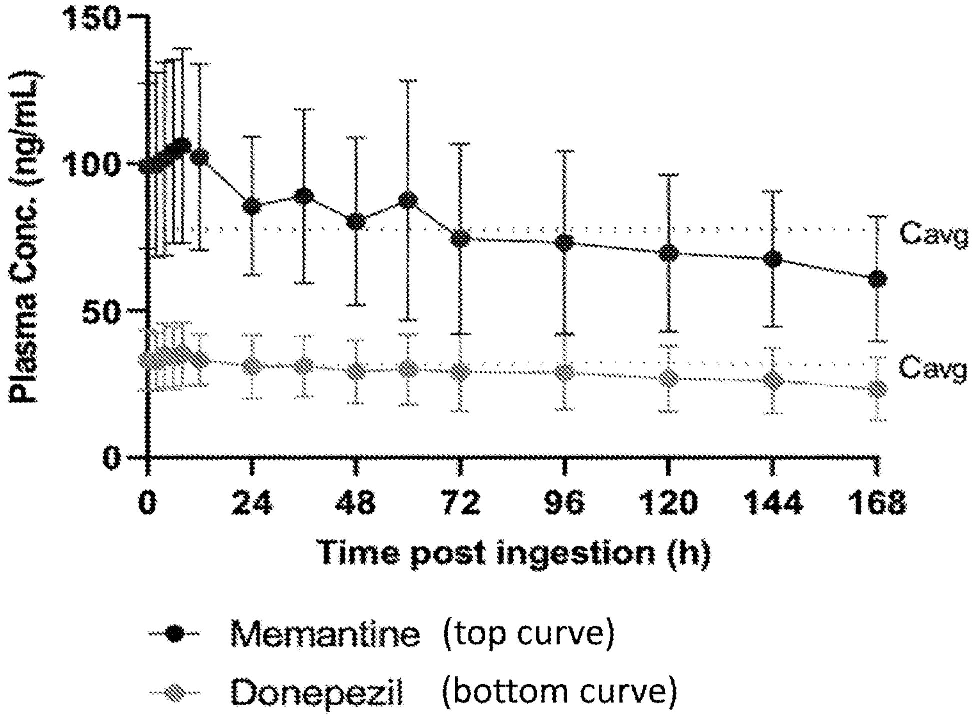
FIG. 80 depicts a linear graph of the pharmacokinetics of a higher dose formulation in human subjects in a Phase I study (n=12 healthy participants, mean±SD). $C_{avg}$ is calculated at steady state for daily IR dosing (28 mg memantine/10 mg donepezil).

Results are shown in FIG. 80.

This high-dose combination formulation of memantine HCl and donepezil HCl extended-release gastric residence system demonstrated consistent and linear drug release over seven days for both drugs.

Example 3

In this Example, a dosage form according to the present invention includes a gastric residence system, the gastric residence system is formulated to include risperidone.

The gastric residence system includes a central elastomer that provides the gastric residence system with the ability to be compacted into a compressed configuration. The gastric residence system illustrated in this Example is another different arrangement of the "star" configuration.

Figure 5:
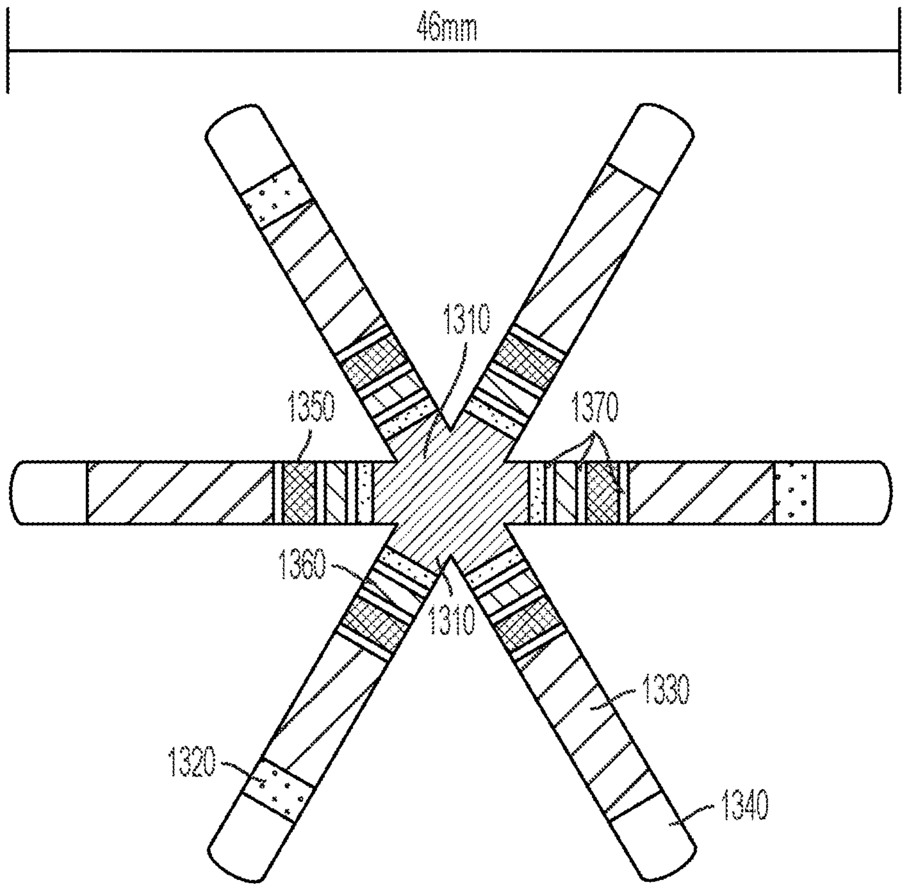
FIG. 5 shows the gastric residence system dosage form of Example 3.

FIG. 5 is labelled to show the various elements of this configuration. The system 1300 comprises a central elastomeric core 1310 which is in the shape of an "asterisk" having six short branches. A segment 1370 of the arm is attached to one short asterisk branch. The segment 1370 is followed by a segment 1360, a second segment 1370, a segment 1350 and a third segment 1370 in sequence. The distal end of each arm has segments 1330 and 1340. Half of the arms further comprise a segment 1320 between the segments 1330 and 1340.

The gastric residence system has an average size of about 46 mm and each segment has a length ranging from about 0.5 mm to about 8.0 mm. Table 4 below provides a listing of the length of each segment in the gastric residence system. Each range or value below can be considered to be "about" the range or value indicated, or exactly the range or value indicated.

TABLE 4

| Segment | Length |
|---|---|
| 120 | 2.4 mm |
| 130 | ~8 mm |
| 140 | 4 mm |
| 150 | 1.85 mm |
| 160 | 1.0 mm |
| 170 | 0.5 mm |

The central elastomeric core 1310 comprises a liquid silicone rubber (LSR) having a hardness of 50 durometer.

Each dosage form provided here comprises about 14 mg of risperidone for administration. Risperidone is included in a carrier polymer-agent segment 1320 (e.g., a drug-eluting segment). The drug-eluting segment comprises about 35.0 wt % of risperidone, about 55.9 wt % of Corbion PC17, about 5.0 wt % of VA64, about 3.0 wt % of P407, about 0.5 wt % of Vitamin E succinate, about 0.5 wt % of $SiO_2$, and about 0.1 wt % of pigment. The pigment includes about 0.05% of FD&C Yellow 5 Alum lake (14-16%) and about 0.05% of FD&C Blue 1 Alum lake (11-13%). Also contemplated in the present application are variations of this dosage form with increased numbers and/or lengths of the drug-eluting segments to achieve higher doses of the drug, for example, risperidone.

Moreover, each arm comprises two different inactive segments 1330 and 1340. A first inactive segment 1330 comprises about 66.45 wt % of Corbion PC17, about 32.0 wt % of VA 64, about 1.5 wt % of P407 and about 0.05 wt % of FD&C Blue 1 Aluminum lake. A second inactive segment 1340 comprises about 39.995 wt % of Corbion PC17, about 42.0 wt % of VA 64, about 15.0 wt % of $PEO_{100K}$, about 3.0 wt % of P407 and about 0.005 wt % of E172.

The gastric residence system further includes a time-dependent disintegrating matrix or linker, referred as the segment 1360, as well as a pH-dependent disintegrating matrix or linker, referred as the segment 1350. In addition, the gastric residence system includes a structural segment 1370. The compositions of the time-dependent disintegrating matrix, the pH-dependent disintegrating matrix, and the structural segment used here are the same as those listed in Table 2 of Example 1.

In the gastric residence system, each drug arm is coated by a release rate-modulating film. Specifically, the coating comprises about 73.5 wt % of Corbion PC17, about 24.5 wt % of VA64, and about 2.0 wt % of Mg stearate, and is applied in an amount of about 4.5% of the pre-coating weight of the segment (i.e., segments 1330, 1320 and 1340).

The gastric residence system is assembled and then placed into an appropriate sized capsule. The capsule used here is the same as the one used in Example 1.

Example 4

In this Example, a dosage form according to the present invention includes a gastric residence system, the gastric residence system is formulated to include dapagliflozin.

The gastric residence system includes a central elastomer that provides the gastric residence system with the ability to be compacted into a compressed configuration. The gastric residence system illustrated in this Example is another different arrangement of the "star" configuration.

Figure 6:
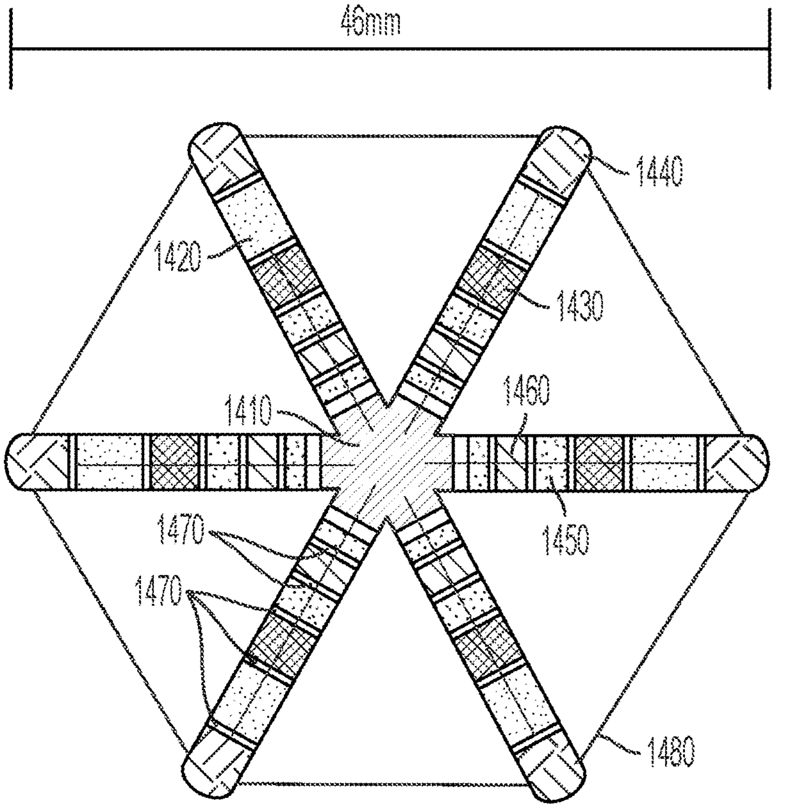
FIG. 6 shows the gastric residence system dosage form of Example 4.

FIG. 6 is labelled to show the various elements of this configuration. The system 100 comprises a central elastomeric core 1410 which is in the shape of an "asterisk" having six short branches. Segment 1470 of the arm is attached to one short asterisk branch. The segment 1470 is followed by a segment 1460, a second segment 1470, a segment 1450 and a third segment 1470 in sequence. The distal end of each arm has a segment 1430 and a segment 1440 at the top. Each of the arms further comprise a segment 1420 and another two segments 1470 between the segment 1430 and the segment 1440. Connecting the segments 1440 at the tips of each arm is a segment 1480.

The gastric residence system has an average size of about 46 mm and each segment has a length ranging from about 0.5 mm to about 4.3 mm. Table 5 below provides a listing of the length of each segment in the gastric residence system. Each range or value below can be considered to be "about" the range or value indicated, or exactly the range or value indicated.

TABLE 5

| Segment | Length |
|---|---|
| 120 | 4.3 mm |
| 130 | 3.2 mm |
| 140 | 4 mm |
| 150 | 1.85 mm |
| 160 | 1.0 mm |
| 170 | 0.5 mm |

The central elastomeric core 1410 comprises a liquid silicone rubber (LSR) having a hardness of 50 durometer.

Each dosage form provided here comprises about 35 mg of dapagliflozin for administration. Dapagliflozin is included in a carrier polymer-agent segment 1420 (e.g., a drug-eluting segment). The drug-eluting segment comprises about 20 wt % of dapagliflozin (amorphous), about 33.99 wt % of Corbion PC17, about 30 wt % of Kollidon VA64, about 10 wt % of PDL20, about 5 wt % of Span60, about 0.5 wt % of Vitamin E succinate, about 0.5 wt % of colloidal silicon dioxide, and about 0.01 wt % of pigment. The pigment includes about 17% wt of FD&C Yellow 5 Alum lake LL.

Moreover, each arm comprises two different inactive segments 1430 and 1440. A first inactive segment 1430 comprises about 39.9 wt % of Corbion PC17, about 59.5 wt % of TPU (PY-PT72AE), about 0.5 wt % of colloidal silicon dioxide and about 0.1 wt % of E172. A second inactive segment 1440 located at the tip of each arm comprises about 30 wt % of Corbion PC17, about 64.9 wt % of HPMCAS-MG, about 2.5 wt % of stearic acid 50, about 2.5 wt % of prop. Glycol, about 0.025 wt % of E172, and about 0.075 wt % of a pigment. The pigment comprises about 14-16% of FD&C Red 40 A1 Lake.

The gastric residence system further includes a time-dependent disintegrating matrix or linker, referred as the segment 1460, as well as a pH-dependent disintegrating matrix or linker, referred as the segment 1450. In addition, the gastric residence system includes a structural segment 1470. The compositions of the time-dependent disintegrating matrix, the pH-dependent disintegrating matrix, and the structural segment used here are the same as those listed in Table E2 of Example 1.

In the gastric residence system, each drug arm is coated by a release rate-modulating film. Specifically, the coating comprises about 49 wt % of PDL20, about 49 wt % of Corbion 5002A, and about 2 wt % of Mg stearate, and is applied in an amount of about 2 wt % of the total pre-coating weight of the drug-eluting segment and the two inactive segments (i.e., segments 1430, 1420 and 1440). In a variation, the drug arm has a trim coating from weld surface prior to assembly.

The gastric residence system is assembled and then placed into an appropriate sized capsule. In addition, there is a pellethane tubing, referred as the segment 1480, on the outside of the gastric residence system. The capsule used here has an inverted-sleeve orientation and is a variation of the one used in Example 1. Specifically in this Example, the core was inserted into the sleeve instead of the ends of the arms.

Example 5

The radial force required to compress gastric residence systems to various iris diameters was tested using the radial force test described in detail previously. As shown in FIG. 11, a gastric residence system with a filament and a gastric residence system without a filament were tested. As shown, the discrepancy between the force required to compress the gastric residence system with a filament and the gastric residence system without a filament increases as the compressed diameter decreases. The results demonstrate that at compressed diameters small enough for the gastric residence system to prematurely pass through the pylorus (i.e., diameters of 20 mm and less), the force required to compress the gastric residence system with a filament is at least two times greater than the force required to compress the gastric residence system without a filament.

Example 6

Figure 18:
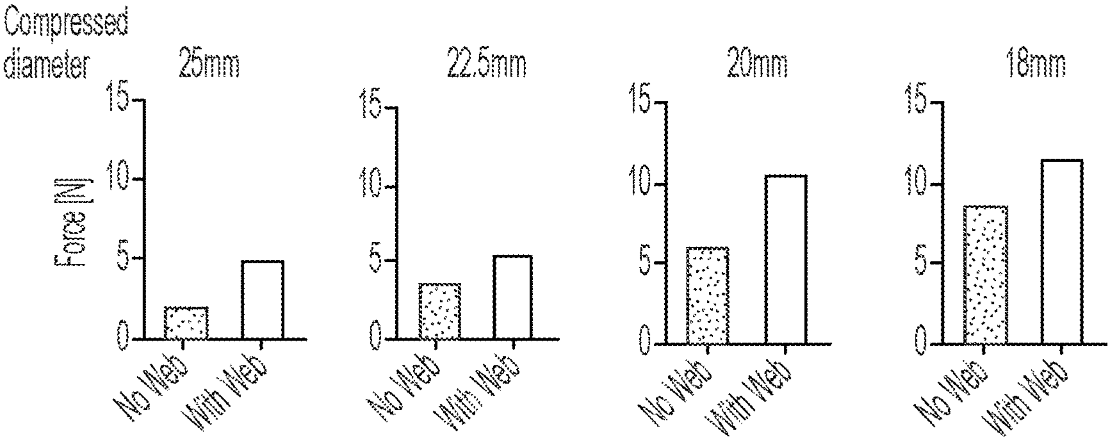
FIG. 18 shows radial force data for gastric residence systems without a filament and comprising flexible arms and gastric residence systems having filament and stiff arms, according to some embodiments.

The radial force required to compress gastric residence systems to various iris diameters was tested using the radial force test described in detail previously. In particular, a gastric residence systems having relatively flexible arms (compared to the gastric residence systems tested in Example 5) with and without a filament were tested. Like the gastric residence systems tested in Example 5, FIG. 18 shows that the discrepancy between the force required to compress the gastric residence system with a filament and the gastric residence system without a filament increases as the compressed diameter decreases. Further, as shown in the figure, the force required to compress the gastric residence system with the filament to a compressed diameter small enough to prematurely pass through the pylorus (i.e., diameters of 20 mm and less) is approximately one and a half times greater than the force required to compress the gastric residence system without a filament to the same compressed diameter.

Example 7

Figure 19:
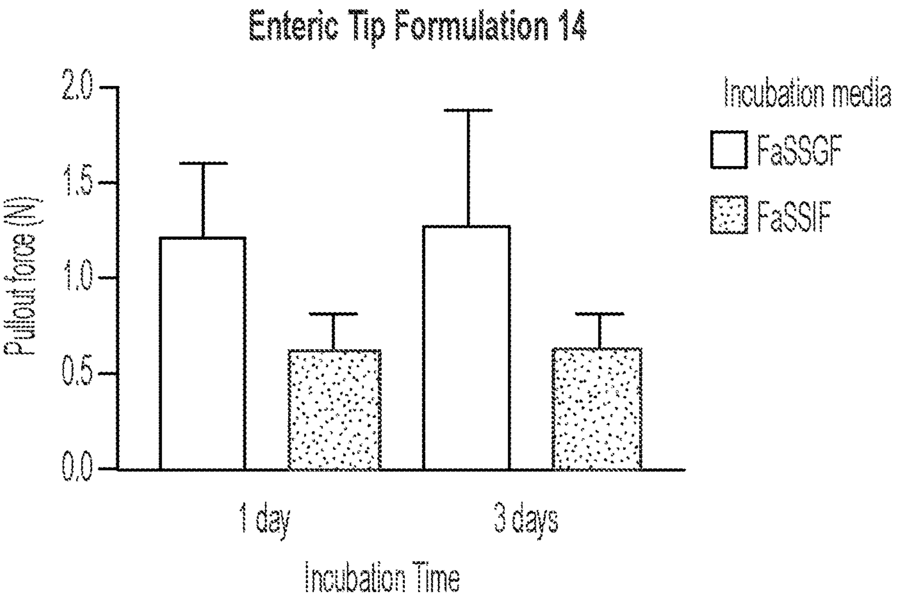
FIG. 19 shows pullout force data for gastric residence systems comprising filament and enteric tips (formulation 14), according to some embodiments.

The pullout force required to separate a filament from an arm tip was tested at various incubation settings. As shown in FIG. 19, the pullout force was tested for filaments connected to arm tips having formulation 14 (shown in Table 6) using the pullout force testing procedure described in detail previously. Tips comprising this formulation are designed to remain connected to the filament in a highly acidic, or gastric environment, and separate or slip from the filament in an intestinal environment as the gastric residence system components pass through the intestine of a patient. Adhesion force was measured after samples were incubated in fasted state simulated gastric fluid (FaSSGF, pH 1.6) or fasted state simulated intestinal fluid (FaSSIF, pH 6.5) for both 1 and 3 days. As shown in the Figure, the length of incubation (i.e., 1 day or 3 days) only marginally affected the pullout force of samples incubated in the fasted state simulated gastric fluid and the fasted state simulated intestinal fluid. However, the pullout force between the two simulated fluids varied significantly. The pullout force of the samples incubated in fasted state simulated gastric fluid was approximately twice that of the pullout force of the samples incubated in fasted state simulated intestinal fluid.

TABLE 6

Arm tip formulation compositions.

| | Formulation 1 | Formulation 6 | Formulation 14 | Formulation 15 |
|---|---|---|---|---|
| PCL (wt. %) | 30 | 30 | 30 | 30 |
| HPMC AS MG (wt. %) | 64.9 | 49.9 | 64.9 | 59.9 |
| Plasticizer (wt. %) | Propylene Glycol, 5 | P407, 10 | Propylene Glycol, 2.5 | Propylene Glycol, 5 |
| Stearic Acid (wt. %) | 0 | 0 | 2.5 | 5 |

Example 8

Figure 20:
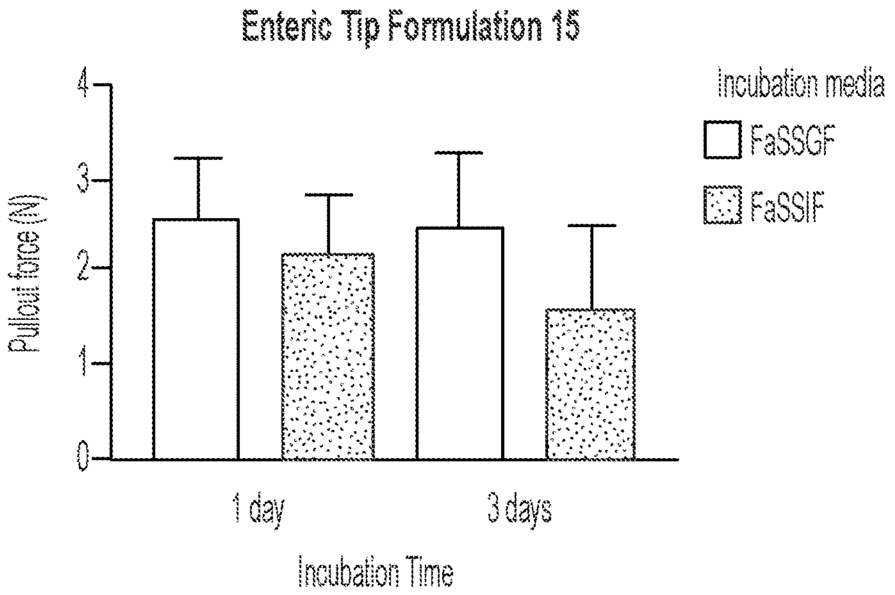
FIG. 20 shows pullout force data for gastric residence systems comprising filament and enteric tips (formulation 15), according to some embodiments.

The pullout force required to separate a filament from an arm tip was tested at various incubation settings. As shown in FIG. 20, the pullout force was tested for filaments connected to arm tips having formulation 15 (shown in Table 6) using the pullout force testing procedure described in detail previously. Tips comprising this formulation are designed to remain connected to the filament in a highly acidic, or gastric environment, and separate or slip from the filament in an intestinal environment as the gastric residence system components pass through the intestine of a patient. Adhesion force was measured after samples were incubated in fasted state simulated gastric fluid (FaSSGF, pH 1.6) or fasted state simulated intestinal fluid (FaSSIF, pH 6.5) for both 1 and 3 days. As shown in the Figure, the length of incubation (i.e., 1 day or 3 days) only marginally affected the pullout force of samples incubated in the fasted state simulated gastric fluid. However, the pullout force of samples incubated for 3 days was approximately 75% that of the pullout force of samples incubated only 1 day in the fasted state simulated intestinal fluid. Additionally, the pullout force of the samples incubated in fasted state simulated gastric fluid was approximately at least 20% more than that of the pullout force of the samples incubated in fasted state simulated intestinal fluid.

Example 9

Figure 21:
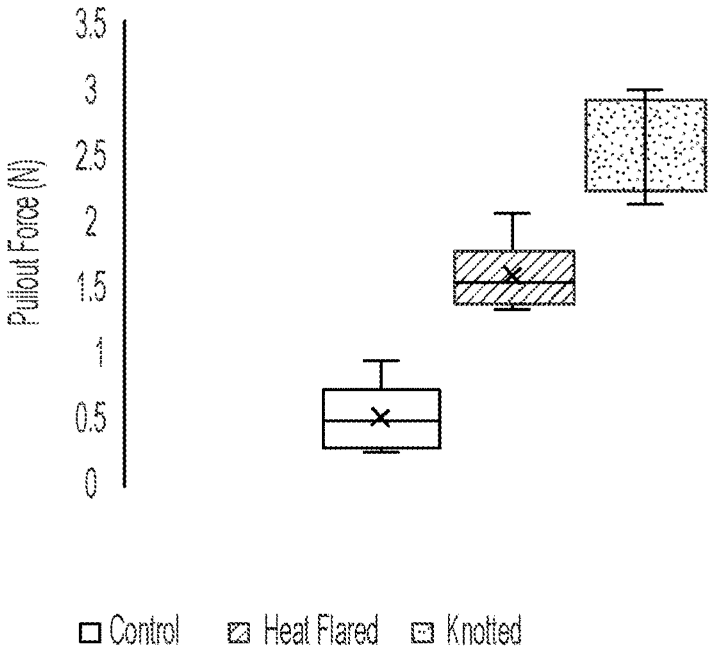
FIG. 21 shows pullout force data for filaments of gastric residence systems having filament of different securing methods, according to some embodiments.

The pullout force required to separate a filament from an arm tip was tested for both knotted and heated filament ends. FIG. 21 shows the results of this test. The samples were incubated in fasted state simulated gastric fluid for three days. As shown in the Figure, the samples having knotted filament ends required the most force to separate the filament from the arm tip. The samples with heat-flared filament ends required less force to separate the filament from the arm tip than the knotted filament ends, but more force than the control samples (neither knotted nor heated). As shown in the Figure, the pullout force required to separate the knotted filament ends was approximately at least one and a half times that of the pullout force required to separate the heated filament ends from the arm tip, and approximately five times that of the pullout force required to separate the control (i.e., unknotted, unheated) filament ends from the arm tip.

Example 10

Figure 22:
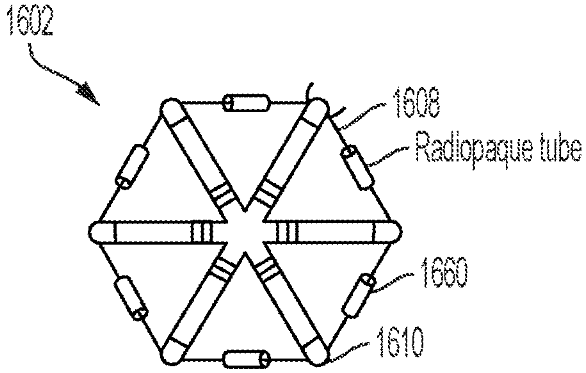
FIG. 22 shows a gastric residence system having filament that has been prepared for visualization when in a dog's stomach, according to some embodiments.
Figure 23A:
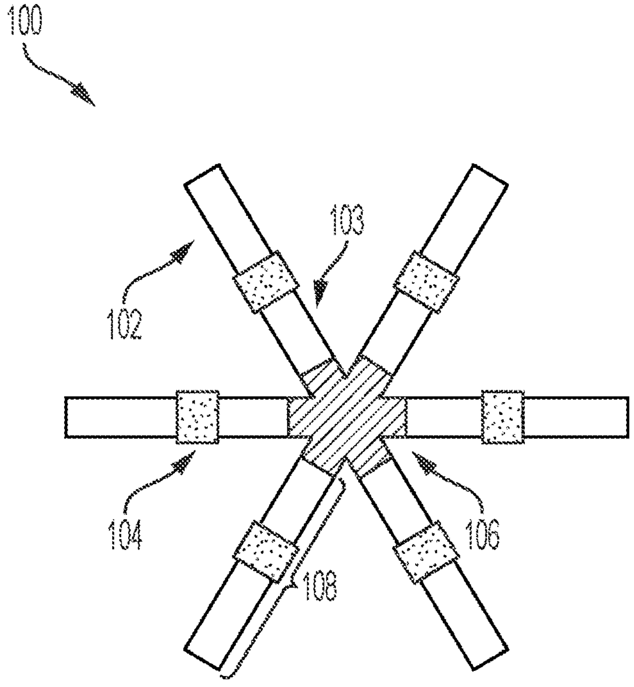
FIG. 23A, FIG. 23B, and FIG. 23C show various gastric residence system configurations, according to some embodiments.
Figure 23B:
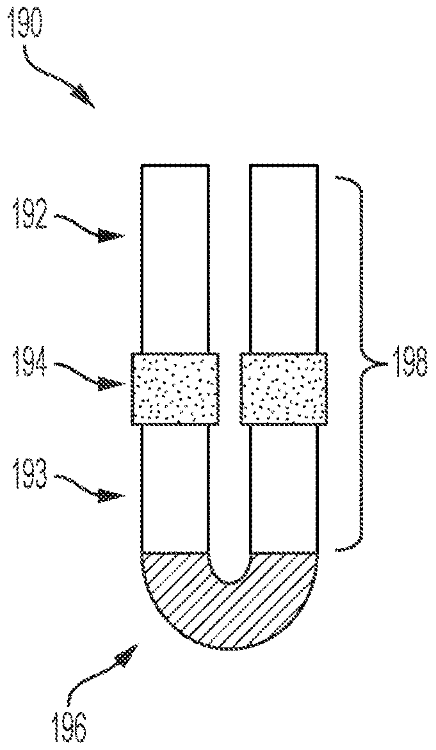
Figure 23C:
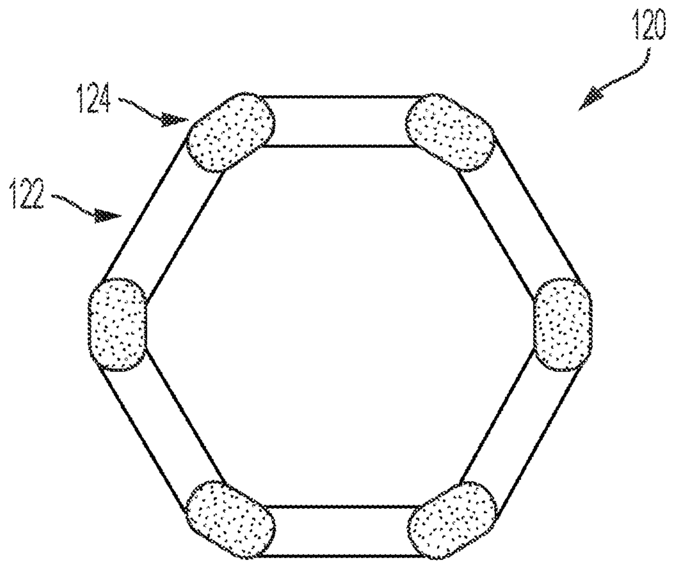

Gastric residence of gastric residence systems comprising a filament were tested in dogs. FIG. 22 shows gastric residence system 1602 comprising filament 1608 having knotted ends. A radiopaque tube/marker 1660 was placed on filament 1608 between each arm tip 1610. Two or more radiopaque tube/marker 1660 can be used to identify the location and intactness of the gastric residence system in vivo via X-ray imaging. The radiopaque tube/marker 1660 comprised bismuth blended into a polymeric matrix. Specifically, bismuth-loaded polycaprolactone was formed into tubes, and the tubes were fed onto the filament between each arm during filament assembly. The radiopaque tubes could slide freely along the filament and could slide off the filament if filament ends slipped free from the stellate. During animal studies, filament intactness was tracked on X-rays by observing the number and orientation of radiopaque tubes visible.

Gastric residence systems were assembled with arm tips 1610 comprising enteric formulation 14 (see Table 6) via notching, wrapping, and rounding as shown in FIG. 22. Arm tips 1610 were notched with a circular saw. Pellethane filaments were cut to length, radiopaque tubes were fed onto filaments, and filament ends were knotted. Filaments were added to gastric residence systems by feeding through the notches at the ends of the arms such that one radiopaque marker was located between each arm. The notches were then closed by applying pressure from a heated die (85° C., 25 psi, for 30 sec). Gastric residence systems were loaded into hydroxypropyl methylcellulose capsules and dosed orally in beagles. Gastric residence systems were visualized daily by X-ray for one week. The number of polycaprolactone tubes visible in X-rays is shown in Table 7. In two of the three dogs, webs remained intact for greater than one week. In the third gastric residence system, two radiopaque tubes separated from the stellate by day 7, and the stellate passed from the body by day 8. The data indicate that filaments comprising of these materials are sufficiently durable to support weeklong gastric residence.

TABLE 7

Gastric residence in beagle dogs, tested using gastric residence systems having a filament.

| Animal # | Day 1 | Day 2 | Day 3 | Day 4 | Day 5 | Day 6 | Day 7 | Day 8 |
|---|---|---|---|---|---|---|---|---|
| 1005 | 6/6 | 6/6 | 6/6 | 6/6 | 6/6 | 6/6 | 6/6 | 6/6 |
| 1006 | 6/6 | 6/6 | 6/6 | 6/6 | 6/6 | 6/6 | 6/6 | 6/6 |
| 1007 | 6/6 | 6/6 | 6/6 | 6/6 | 6/6 | 6/6 | 4/6 | 0/6 |

Example 11

Figure 28:
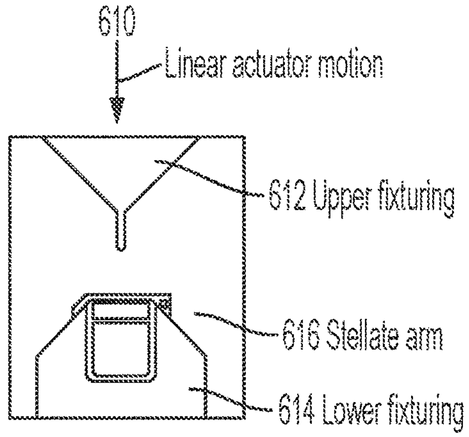
FIG. 28 shows a method of measuring stiffness of a gastric residence system using a 3-point being test, according to some embodiments.
Figure 29:
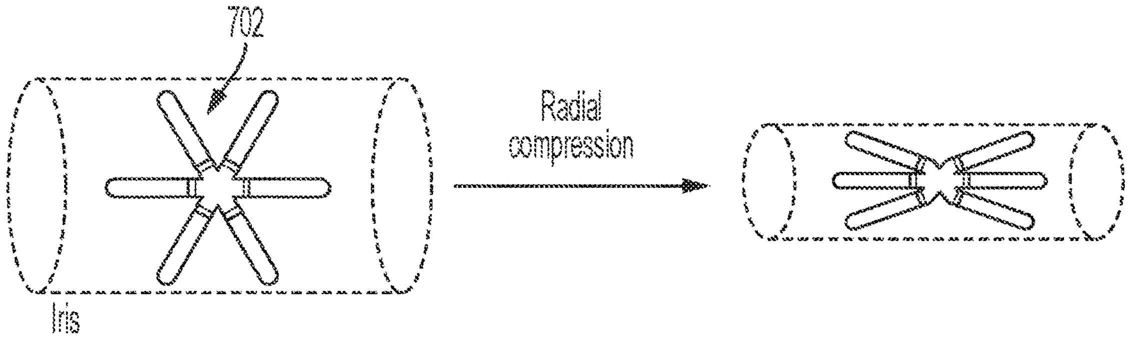
FIG. 29 shows an iris mechanism measuring radial force of a gastric residence system, according to some embodiments.
Figure 30:
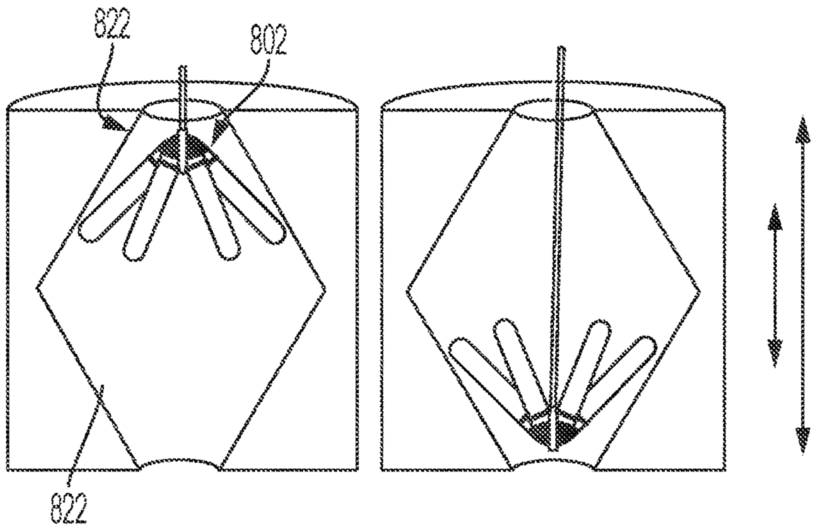
FIG. 30 shows a method of measuring the durability of a gastric residence system using cyclic loading in a double funnel, according to some embodiments.
Figure 31:
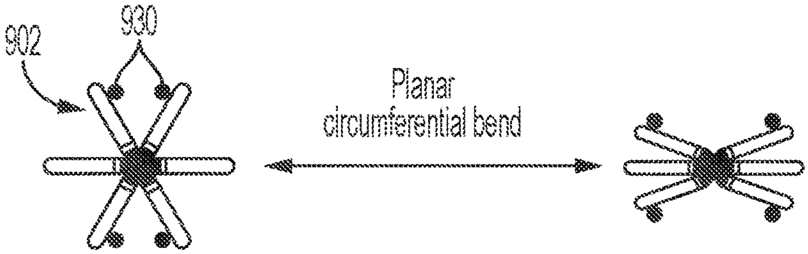
FIG. 31 shows a method of measuring the durability of a gastric residence system using cyclic loading of a planar circumferential bend, according to some embodiments.
Figure 32:
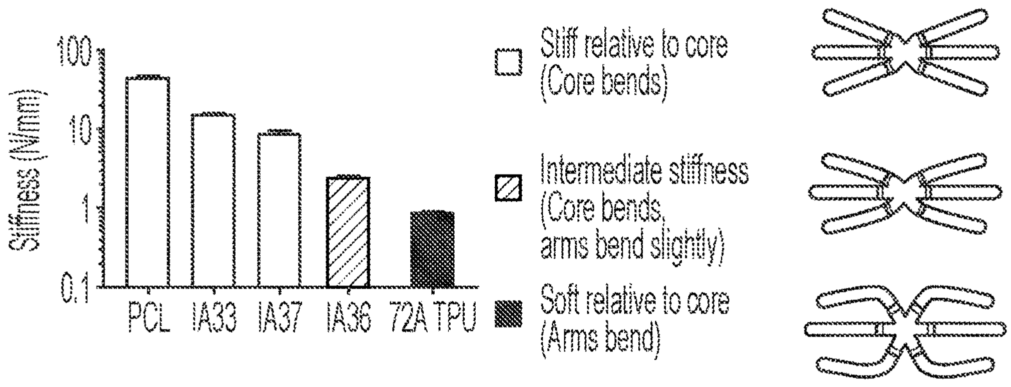
FIG. 32 shows material stiffness data of different gastric residence systems, according to some embodiments.

FIG. 32 shows stiffness data of five different arms as measured using the 3-point bending test described in detail above and depicted in FIG. 28. The five different arms tested include arms comprising polycaprolactone, (PCL), polycaprolactone combined with soluble materials (IA33, IA27, and IA36), and thermoplastic polyurethane having a durometer of 72 A (72 A TPU). The formulations of the different arms are provided in Table 8, below:

| Formulation or Material Name | Composition | Hydrated Stiffness (N/mm) |
|---|---|---|
| SS09 | 30% Mannitol, 70% PCL | 21.8 |
| IA30 | 35% VA64, 1.5% P407, 63.5% PCL | 7.0 |
| IA33 | 20% VA64, 1.5% P407, 78.5% PCL | 14.4 |
| IA36 | 42% VA64, 15% PEO, 3% P407, 40% PCL | 3.0 |
| IA37 | 32% VA64, 1.5% P407, 66.5% PCL | 10.3 |

Table 8, above, includes the following materials: mannitol, polycaprolactone (PCL), copovidone (VA64, Kollidon VA64), poloxamer P407 (P407), and polyethylene oxide 100 kDa (PEO).

As shown in the figure, the pure polycaprolactone arms exhibited the greatest stiffness and the thermoplastic polyurethane arms exhibited the least stiffness values. The three arms comprising polycaprolactone and soluble materials showed a moderate level of stiffness in comparison. As discussed above, these materials (polycaprolactone mixed with soluble materials) lose stiffness when exposed to an aqueous environment and the soluble materials are hydrated.

Additionally, the relative stiffness of each material tested was reported. This was determined using an eyeball test (i.e., how easily the arms bend when the gastric residence system is compressed). As shown, the white bars represent relatively stiff arms (when the gastric residence system is compressed, the core bends and the arms remain straight), the hatched bar represents an arm of intermediate stiffness (core bends and arms bend slightly), and the shaded bar represents relatively soft or flexible arms (arms bend before the core bends).

Example 12

Figure 33:
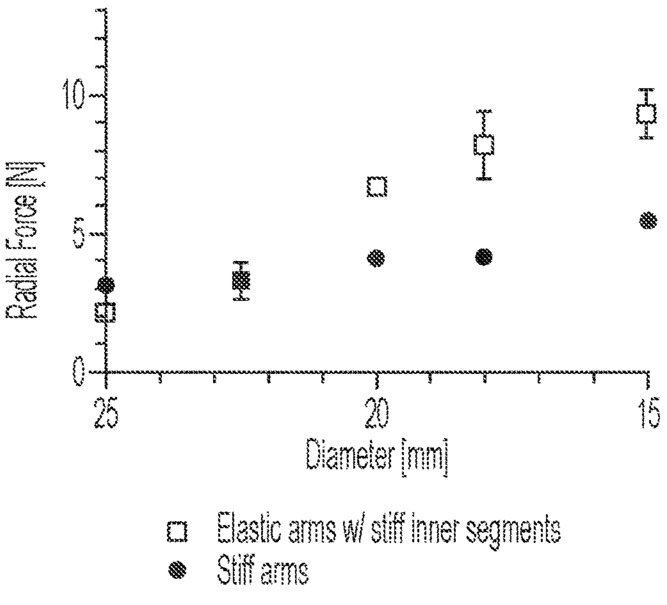
FIG. 33 shows the radial force of various iris diameters for a gastric residence system having relatively stiff arms and a gastric residence system having relatively flexible arms (i.e., a first segment and a second segment), according to some embodiments.

FIG. 33 shows radial force data for two different types of gastric residence systems. Both gastric residence systems having flexible arms (comprising a first segment and a second segment) and gastric residence systems having stiff arms were tested using the radial force compression test depicted in FIG. 26 and described in detail above. In particular, the gastric residence systems that were tested comprised 50 A silicone cores. The gastric residence system having stiff arms comprised arms made of polycaprolactone. The gastric residence system comprising flexible arms comprised arms made of a stiff blend of PLGA, PLA, HPMCAS, and TPU (first segment) and TPU (Pathways 72A) (second segment).

As shown, for both types of gastric residence systems that were tested, the force increased as the diameter of the iris tester decreased. At relatively large iris tester diameters (i.e., compression diameters of 20 mm and greater), the gastric residence system having flexible arms compressed with less force.

However, the results also reveal that the force required to compress the gastric residence system having the flexible arms to an iris tester diameter of 20 mm and less was markedly greater than the force required to compress the gastric residence system having stiff arms to an iris tester diameter of 20 mm or less. Accordingly, this indicates that the force required to compress a gastric residence system having flexible arms to a bended configuration small enough to pass through a pylorus (i.e., an opening having a diameter of 20 mm) is greater than the force required to compress a gastric residence system having stiff arms to a bending configuration small enough to pass through a pylorus (i.e., an opening having a diameter of 20 mm). Thus, the radial force test results suggest that a gastric residence system having flexible arms is more able to resist premature passage through a patient's pylorus.

Example 13

Figure 34:
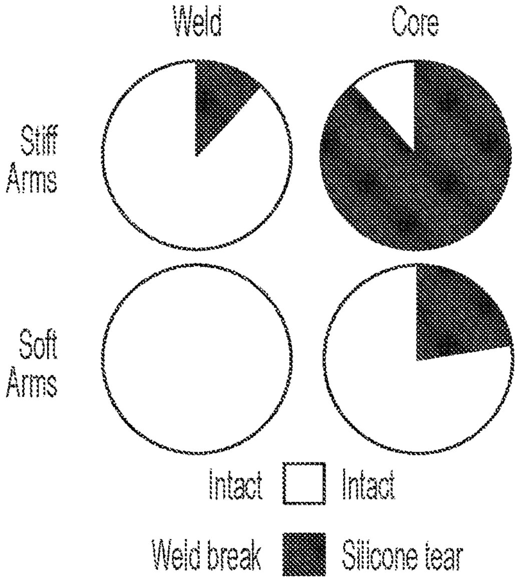
FIG. 34 shows failure mode analysis data of gastric residence systems having relatively stiff arms and gastric residence systems having relatively flexible arms, according to some embodiments.

FIG. 34 shows results of a double funnel durability test of two different gastric residence systems. In particular, FIG. 34 shows gastric residence system condition after 200 cycles in the double funnel test (described in detail above). This test was not performed in an aqueous environment.

As shown in the figure, a gastric residence system with stiff arms and a gastric residence system with flexible arms were tested. The gastric residence system with flexible arms comprised formula IA36 (see Table 8, above). The gastric residence system with stiff arms comprised formula IA37 (see Table 8, above). As shown, gastric residence systems with flexible arms resisted a connection failure (i.e., weld break) entirely, and greater than 75% resisted a silicone core tear failure. However, gastric residence systems with stiff arms showed some connection failures (i.e., weld break) (less than 12%) and greater than 85% silicone core tear failure. Accordingly, this test demonstrates that gastric residence systems comprising flexible arms may more effectively resist breaking and/or weakening (and thus, early pylorus passage) due to repeated gastric waves/forces in the stomach.

Figure 35:
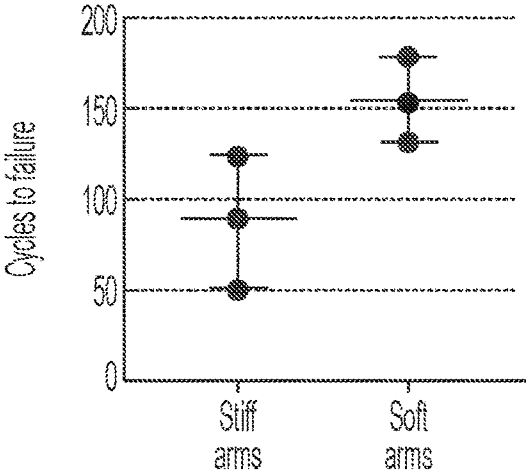
FIG. 35 shows the number of cycles to failure for gastric residence systems having relatively stiff arms and gastric residence systems having relatively flexible arms, according to some embodiments.

FIG. 35 shows the results of a double funnel test quantifying the number of cycles to failure. The gastric residence systems tested comprised of stiff arm materials (90 wt. % PCL, 10 wt. % sucrose) or flexible arm materials (29 wt. % PCL, 71 wt. % soluble materials, with soluble materials removed by solvent extraction prior to testing) joined to a silicone core with a disintegrating matrix. (Specifically, the 71 wt. % soluble materials comprised IVM119 (40% IVM, 20% Soluplus, 5% P407, 5% SSG, 0.5% Silica, 0.5% a-tocopherol, Balance PCL), incubated in ethanol prior to stellate assembly. Ethanol removes the ivermectin and excipients quickly, leaving a soft porous PCL arm.)

The disintegrating matrix comprised 15 wt. % polycaprolactone and 85 wt. % HPMCAS (hydroxypropyl methylcellulose acetate succinate). Three gastric residence systems of each formulation were subjected to repeated upwards and downwards motion in a double funnel test until two arms broke. The number of cycles was recorded. In each case of failure, breakage occurred at the joint between the disintegrating matrix and a neighboring material (i.e., core or arm). As shown in the Figure, gastric residence systems comprising flexible arms withstood more cycles prior to failure than gastric residence systems with stiff arms. This demonstrates that gastric residence systems having flexible arms may withstand more gastric compression waves before failure than gastric residence systems with stiff arms. Thus, gastric residence systems having flexible arms may be more effective at resisting premature failure and passage through a patient's pylorus.

Example 14

Figure 36:
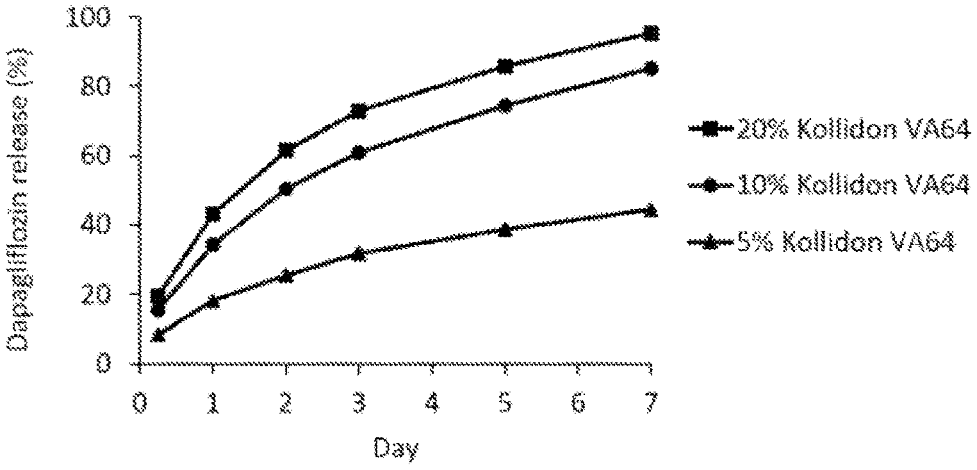
FIG. 36 shows the release profile of dapagliflozin for gastric residence systems having a PCL coating, according to some embodiments.

FIG. 36 shows the release of the water-soluble API dapagliflozin from elastic TPU-based matrices (i.e., materials that may be used for flexible arms). Drug release rate can be modulated by varying the content of soluble excipient (Kollidon VA64) in the formulation. Higher excipient content facilitates greater water entry into the matrix and faster drug release. Similarly, varying drug load within the matrix is expected to impact release rate, with higher drug loading creating greater porosity for accelerated release.

Dapagliflozin, TPU, and soluble excipients were combined in a hot melt extrusion process. Extrudates were shaped into triangular rods (representing gastric residence system arms, comprising an equilateral triangular cross-section having sides measuring 3.3 mm and a rod length measuring 15-20 mm) by compression molding or profile extrusion. Drug release from the matrix was measured by incubating the formulation in fasted state simulated gastric fluid (FaSSGF powder from BioRelevant) and measuring drug concentration in the release media over time. Release media was replaced at each sampling time point in order to maintain sink conditions based on drug solubility. Drug concentration in solution was measured by high performance liquid chromatography. Drug release is plotted as percent of loaded drug in the formulation. The specific formulation composition tested is as follows: 20% Amorphous dapagliflozin, 20% Bismuth subcarbonate, 0.5% silica, 0.5% vitamin E succinate, 0.1% iron oxide, Kollidon VA64, balance Pathways 72AE TPU.

Example 15

Figure 37:
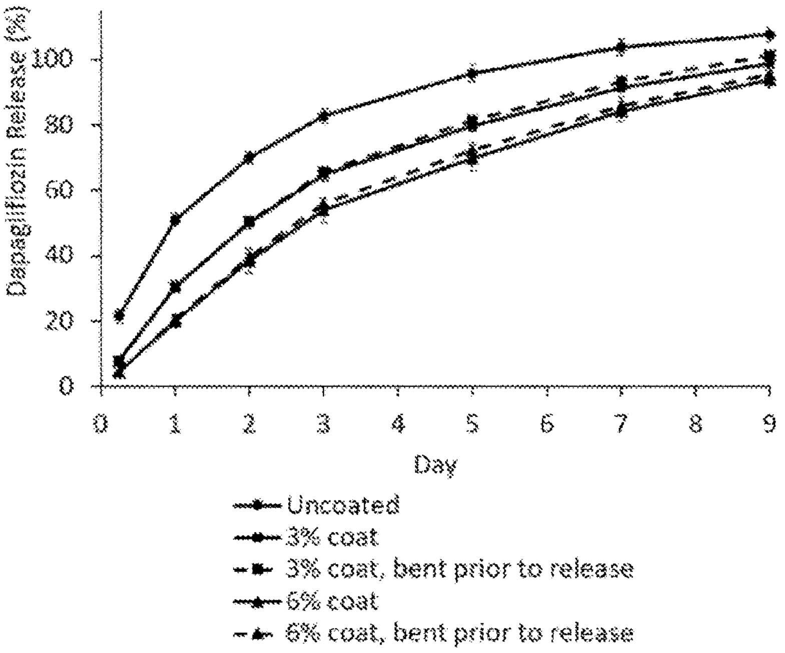
FIG. 37 shows the amount of dapagliflozin per day for uncoated gastric residence systems and coated gastric residence systems, according to some embodiments.

FIG. 37 shows dapagliflozin release from TPU-based matrices with and without a release-rate modulating polymer film. Drug polymer matrices were prepared by hot melt extrusion as described above with reference to FIG. 13. Extruded rods were cut into segments and coated with a polycaprolactone-based film using a pan coating process. In particular, coating components were dissolved in ethyl acetate and pan coating was performed using a Freund-Vector LDCS Hi-Coater Lab Coater.

As shown in the Figure, addition of the coating reduced initial burst release from the formulation and improved linearity of release overall. In particular, a greater coating weight provides a thicker diffusion barrier for slower release (see the 6% coating results as compared to the 3% coating results). It is expected that release rate may be further tuned by varying coating porosity, which may be achieved by changing the content of soluble excipient (Kollidon VA64) in the coating, with higher porosity leading to faster release.

As the underlying TPU matrices are flexible, it is feasible that bending of the matrix could cause coating disruption and loss of control over drug release. To evaluate this, a set of coated matrices were bent to a greater than 90-degree bend prior to the drug release assay (3% coat, bent prior to release and 6% coat, bent prior to release data points). Release data show that this bending had little to no impact on subsequent drug release, suggesting that the coating remained an intact diffusion barrier.

The formulation compositions used in this example are as follows:

Matrix (DaEX18): 20% Dapagliflozin Amorphous, 20% Bismuth subcarbonate, 0.5% silica, 0.5% vitamin E succinate, 0.1% iron oxide, 20% Kollidon VA64, balance Pathways 72AE TPU.

Coating: 73.5% PCL, 25% Kollidon VA64, 1.5% magnesium stearate

Example 16

Figure 38:
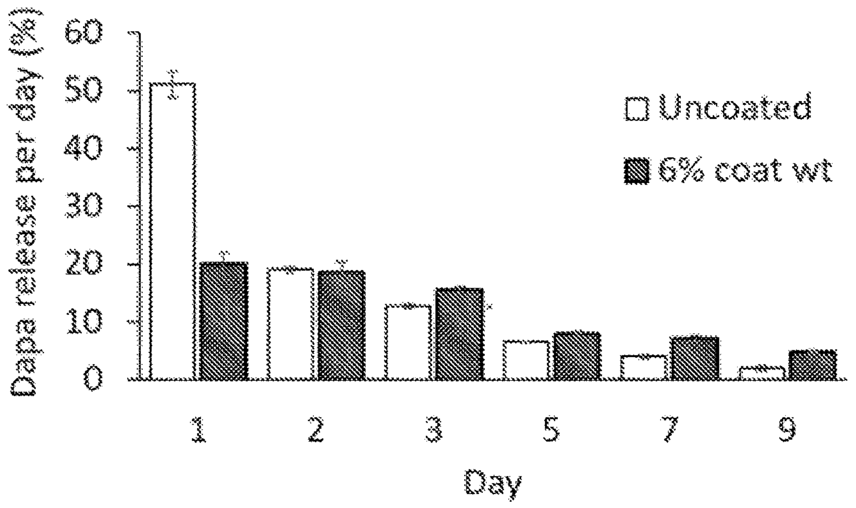
FIG. 38 shows the linearity of dapagliflozin release per day for coated and uncoated gastric residence systems, according to some embodiments.

FIG. 38 shows an alternate analysis of drug release from two of the formulations described above with respect to FIG. 36 (i.e., uncoated gastric residence system arms and 6% coat weight gastric residence arms). Specifically, the daily release of drug for the uncoated matrix and the matrix with a 6% coat weight of the PCL/copovidone blend was tested. For the uncoated matrix, the amount of drug delivered on Day 7 was less than 10% of the amount of drug delivered on Day 1. However, the amount of drug release for the coated arms was approximately 25% on Day 7 as compared to the amount of drug release on Day 1. Thus, the amount of drug release each day for the coated arms is more consistent and stable than that of the uncoated arms. This demonstrates that the addition of the coating on the loaded arms of a gastric residence system limits burst release on Day 1 and also helps to maintain sustained release at later time points.

Example 17

Figure 39:
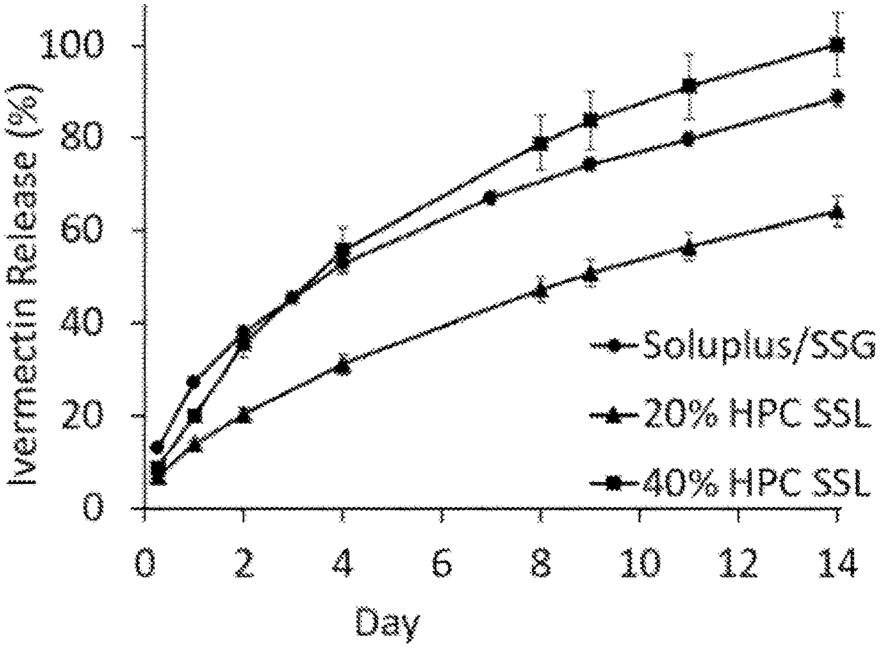
FIG. 39 shows the release profile of ivermectin from gastric residence systems having elastic TPU-based matrices, according to some embodiments.

FIG. 39 shows release of the hydrophobic drug ivermectin from elastic TPU-based matrices. These matrices were prepared using the same methods as described above with reference to FIG. 14. The drug release rate can be modulated by varying the content and type of soluble excipients (in this case, Soluplus, sodium starch glycolate (SSG), and hydroxypropyl cellulose (HPC)) in the formulation. Higher excipient content can facilitate greater water entry into the matrix and faster drug release. Similarly, the amount of drug loading within the matrix is expected to impact release rate. Specifically, a higher drug loading can create greater porosity and an accelerated release.

The formulation compositions used to obtain the data provided in FIG. 39 include:

Soluplus/sodium starch glycolate (SSG): 20% ivermectin 40% Soluplus, 5% SSG, 5% P407, 0.5% Silica, 0.5% α-tocopherol succinate, Balance 72ATPU 20% hydroxypropylcellulose (HPC) SSL: 20% ivermectin, 20% HPC SSL, 5% P407, 0.5% Silica, 0.5% α-tocopherol succinate, Balance 72ATPU 40% HPC SSL: 20% ivermectin, 40% HPC SSL, 5% P407, 0.5% Silica, 0.5% a-tocopherol succinate, Balance 72ATPU Example 18

Figure 40:
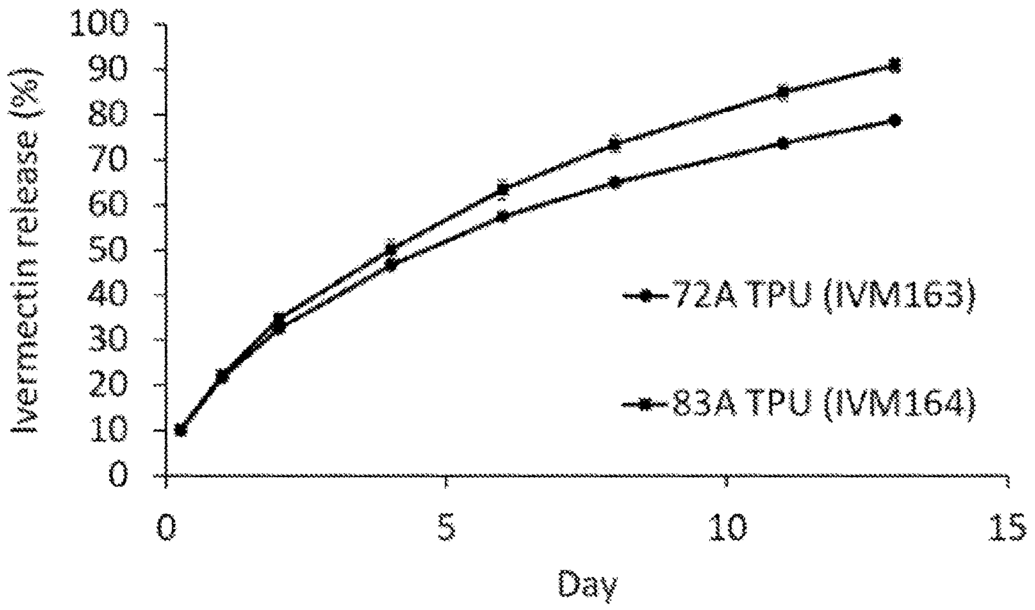
FIG. 40 shows the ivermectin release profile for gastric residence forms made with TPU of different durometers, according to some embodiments.

FIG. 40 shows release of ivermectin from similar formulations (of those describe immediately above with reference to FIG. 38) prepared using different durometers of Pathways TPU. As shown in the figure, the release rate is similar for the two formulations. This suggests that TPU in varying durometers has a similar impact on controlling water entry and drug release. By varying TPU durometer, the overall stiffness of the gastric residence system arm may be modulated to meet targets for gastric retention. The data also suggest that durometer changes may be made with minimal impact to drug release profiles.

The formulation compositions used to obtain the results of depicted in FIG. 40 include 40% ivermectin, 20% Soluplus, 5% P407, 5% SSG, 0.5% Silica, 0.5% α-tocopherol, Balance TPU (83 A or 72 A durometer, Pathway PY-PT72AE or PY-PT83AL).

Example 19

To evaluate shape retention of PCL and TPU at elevated temperatures, extruded rods (triangular cross section, 3.3 mm/side) were placed on two supports across an unsupported 10-cm span in a controlled temperature oven. The center point of the rod was marked and its height was measured as the rods were exposed to increasing temperature as noted in the table below (Table 9). PCL rods melted completely upon exposure to 60° C. and TPU rods maintained their shape at 75° C. At temperatures of 85-105° C., TPU appeared to soften slightly as the center point had lowered by ~0.3 cm. TPU softened more rapidly at temperatures>105° C. The data suggest that TPU based gastric residence systems may have superior temperature stability when compared to PCL-based systems.

Shape retention of encapsulated PCL- and TPU-based gastric residence systems was evaluated at excursion temperatures. Placebo arms made of PCL or TPU were assembled with silicone-based elastomeric cores to create stellate gastric residence systems. The stellates were folded and stored in 00EL HPMC capsules in an oven at 65° C. for 8 h, then cooled and removed from capsules. The PCL arms melted and adhered to one another and the stellate was not able to open. The TPU (Pathway PY-PT72AE) arms remained separated triangular rods and the stellate unfolded intact. The table below shows the results of this test.

TABLE 9

| Temperature, Exposure Time | PCL | TPU |
|---|---|---|
| RT-50° C., days | Solid | Solid |
| 60° C.,30 min | Melted | No Change |
| 65° C., 1 h | Melted | No Change |
| 75° C., 1 h | Melted | No Change |
| 85° C., 1 h | Melted | 0.3 cm Sagging |
| 95° C., 1 h | Melted | 0.3 cm Sagging |
| 105° C., 1 h | Melted | 0.3 cm Sagging |
| 115° C., 1 h | Melted | 1.2 cm Sagging |
| 125° C., 1 h | Melted | 2.2 cm Sagging |
| 125° C., overnight | Melted | Melted |

Figure 45:
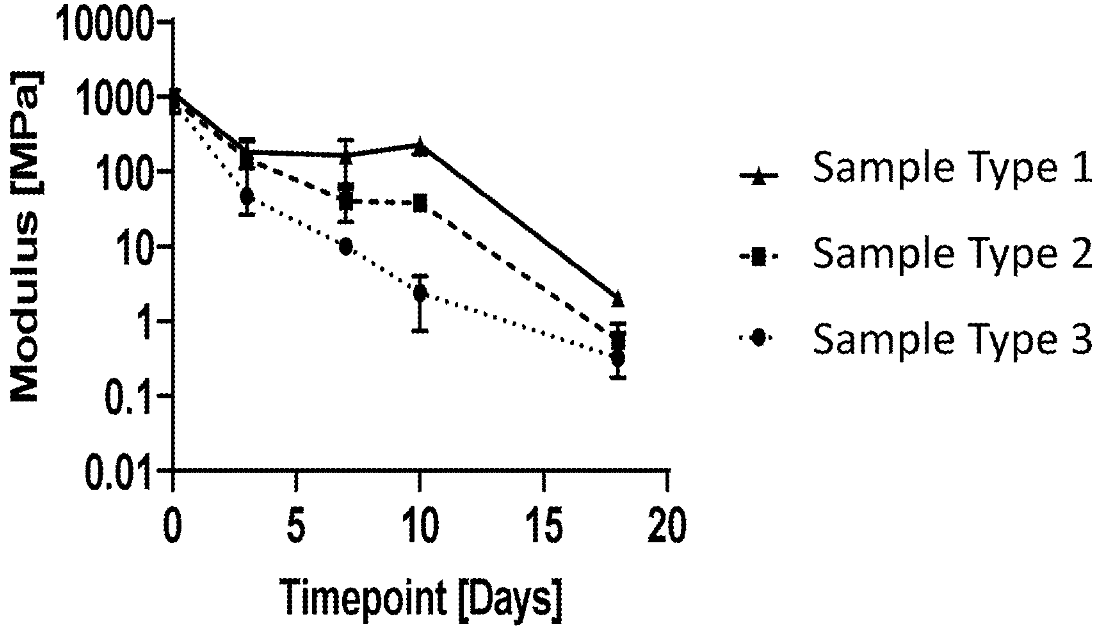
FIG. 45 shows the flexural modulus results after incubation various time-dependent polymeric linkers in a fasted state simulated gastric fluid (FaSSGF) at various time points.

Physical stability of polycaprolactone and Pathway PY-PT72AE TPU at elevated temperatures Example 20: Time Dependent Polymeric Linkers Samples of three time-dependent polymeric linker types containing 85% PLGA and 15% PLA were formed as listed in Table 10. The samples were incubated in FaSSGF at about 37-40° C. for 3, 5, 10, or 18 days before the flexural modulus was measured using a 3-point bending test. Results are shown in FIG. 45, which shows that the sample type 3 degrades faster than sample type 2, which degrades faster than sample type 1, in the FaSSGF.

TABLE 10

| Sample Type No. | 15% PLA | 85% PLGA |
|---|---|---|
| 1 | Purasorb ® PLDL 7024 | Resomer ® RG 653H |
| 2 | Purasorb ® PDL 20 | Resomer ® RG 653H |
| 3 | Purasorb ® PDL 05 | Resomer ® RG 653H |

Figure 46:
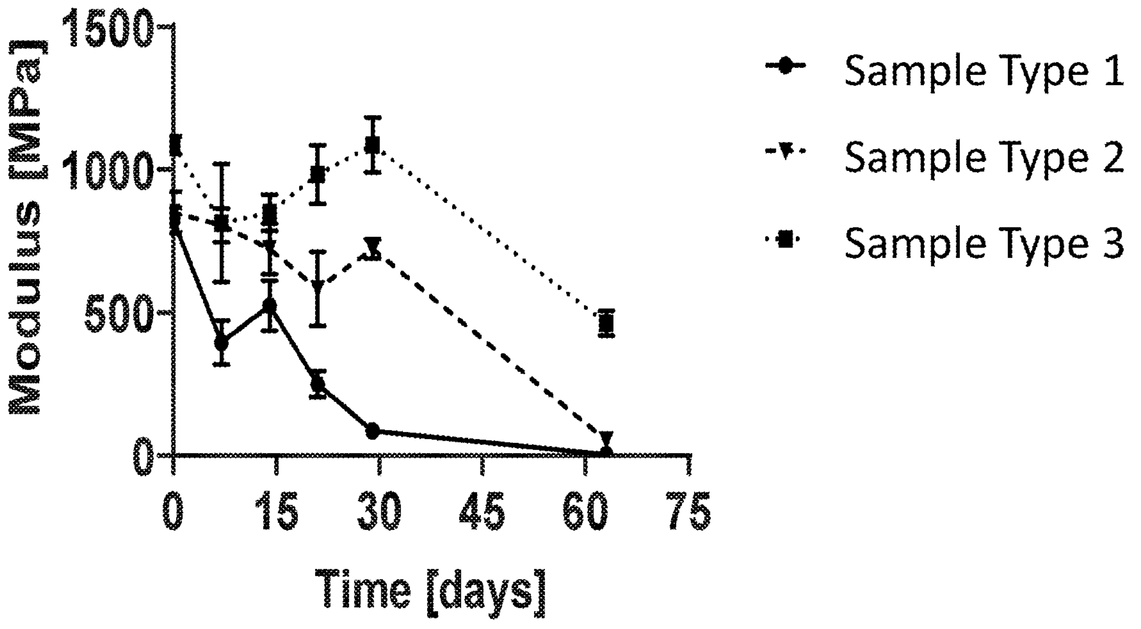
FIG. 46 shows the flexural modulus results after incubation various additional time-dependent polymeric linkers in a FaSSGF at various time points.

Also tested were time-dependent polymeric linker samples containing 55% PLGA and 45% PCL, as listed in Table 11. The samples were incubated in FaSSGF at about 37-40° C. for 7, 14, 21, 29, or 63 days before the flexural modulus was measured using a 3-point bending test. Results are shown in FIG. 46, which shows that the sample type 1 degrades faster than sample type 2, which degrades faster than sample type 3, in the FaSSGF.

TABLE 11

| Sample Type No. | 55% PLGA | 45% PCL |
|---|---|---|
| 1 | Purasorb ® PDLG 7502 | Purasorb ® PC 17 |
| 2 | Purasorb ® PDLG 5010 | Purasorb ® PC 17 |
| 3 | Purasorb ® PDLG 7507 | Purasorb ® PC 17 |

Figure 47:
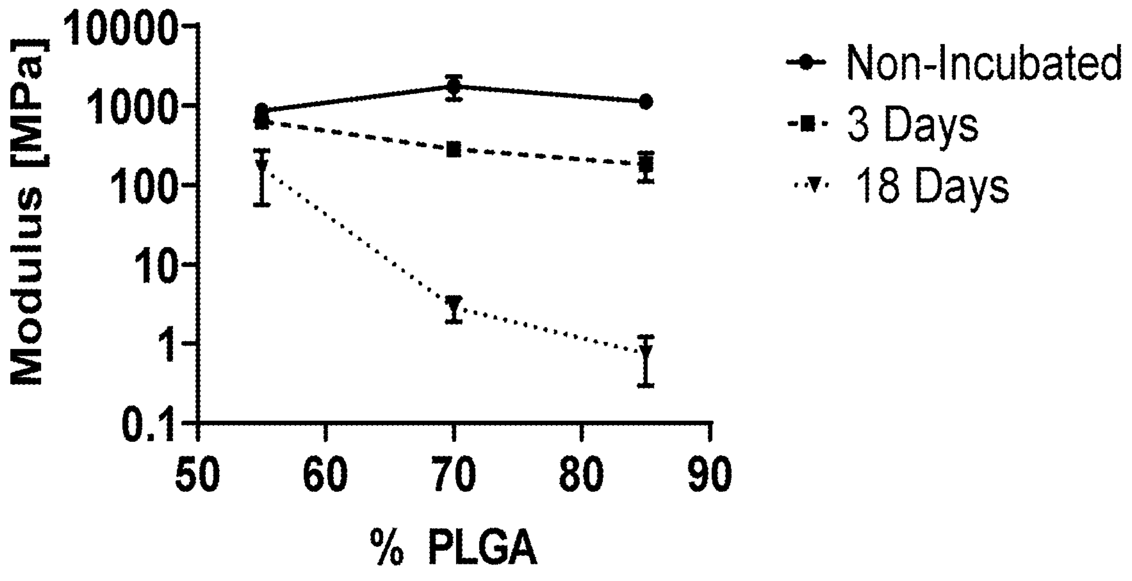
FIG. 47 shows the flexural modulus results after incubation a time-dependent polymeric linkers containing different amounts of PLGA in a FaSSGF after 3 days and after 18 days.

Loss of flexural modulus of the time-dependent polymeric linkers can be adjusted by increasing or decreasing the amount of PLGA polymer in the linker. A higher amount of PLGA results in faster degradation of the sample. Samples containing 55%, 70%, or 85% Resomer® RG 653H (with the balance being Purasorb® PLDL 7024) were incubated for 3 or 18 days in FaSSGF before measuring the flexural modulus. The Results are shown in FIG. 47, which shows that the higher percentage of PLGA in the polymeric linker results in faster degradation under simulated gastric conditions.

Figure 48:
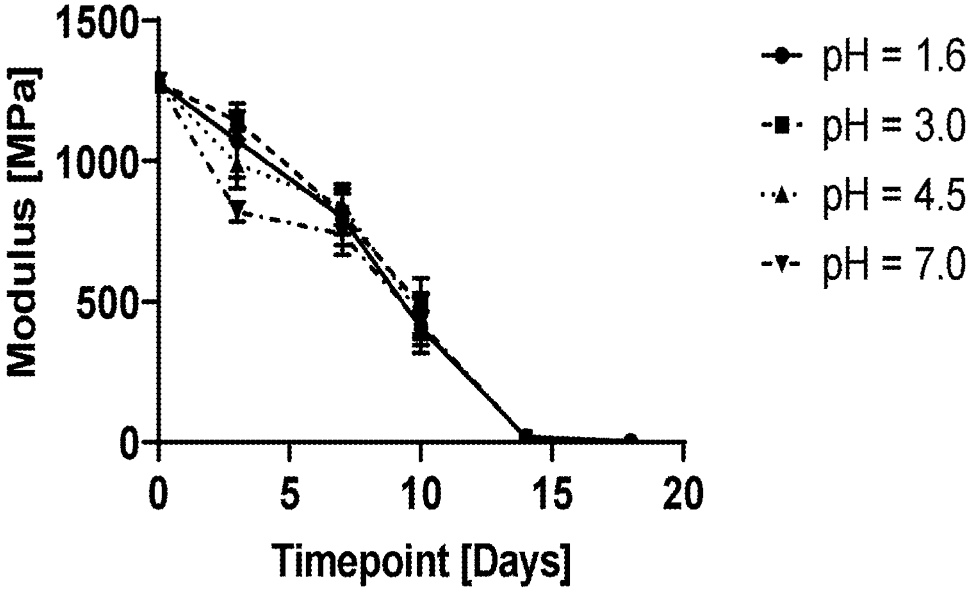
FIG. 48 shows the flexural modulus results after incubating pH-independent time-dependent polymeric linker in aqueous solutions having different pH values over time.

The pH independence for the time-dependent polymeric linker was tested by incubating samples of a time-dependent polymeric linker containing PLGA and PCL in an aqueous solution at pH 1.6, 3.0, 4.5, or 7.0 for 3, 7, 10, 14, or 18 days. An exemplary sample contained 44.95% PCL, 53% Purasorb® PDLG 5004 A, 2% 100K polyethylene glycol, and 0.05% iron oxide, and the flexural modulus of the sample after incubation at various pH conditions and lengths of time are shown in FIG. 48. As shown in FIG. 48, the degradation of the sample time-dependent polymeric linker was generally independent of pH, indicating that the PLGA degrades in an aqueous condition independently of the pH and in a time-dependent manner.

Example 21: Enteric Polymeric Linkers

Enteric polymeric linkers were designed to quickly degrade in the intestine with no or limited degradation in the stomach. An enteric polymer was used to obtain the desired result of the enteric polymeric linker.

Figure 49:
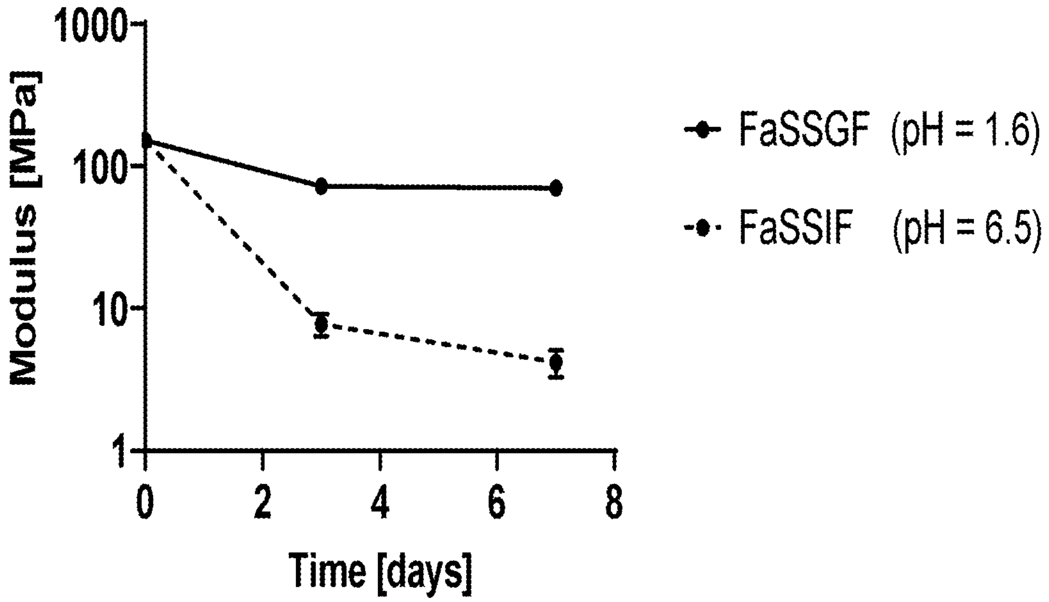
FIG. 49 compares the flexural modulus of an enteric polymeric linker incubated over time in FaSSGF or a fasted state simulated intestinal fluid (FaSSIF).

An exemplary enteric polymeric linker was formed by hot melt extrusion of a polymer blend containing 60% HPMCAS MG and 40% Pathways™ 72AE TPU. The flexural modulus o the sample was measured before incubation or after incubation for 3 days or 7 days in either FaSSGF (pH 1.6) or FaSSIF (pH 6.5). The enteric polymeric linker sample substantially degraded in the simulated intestinal conditions (FaSSIF), but did not significantly degrade in the simulated gastric conditions (FaSSGF), as shown in FIG. 49.

Figure 50:
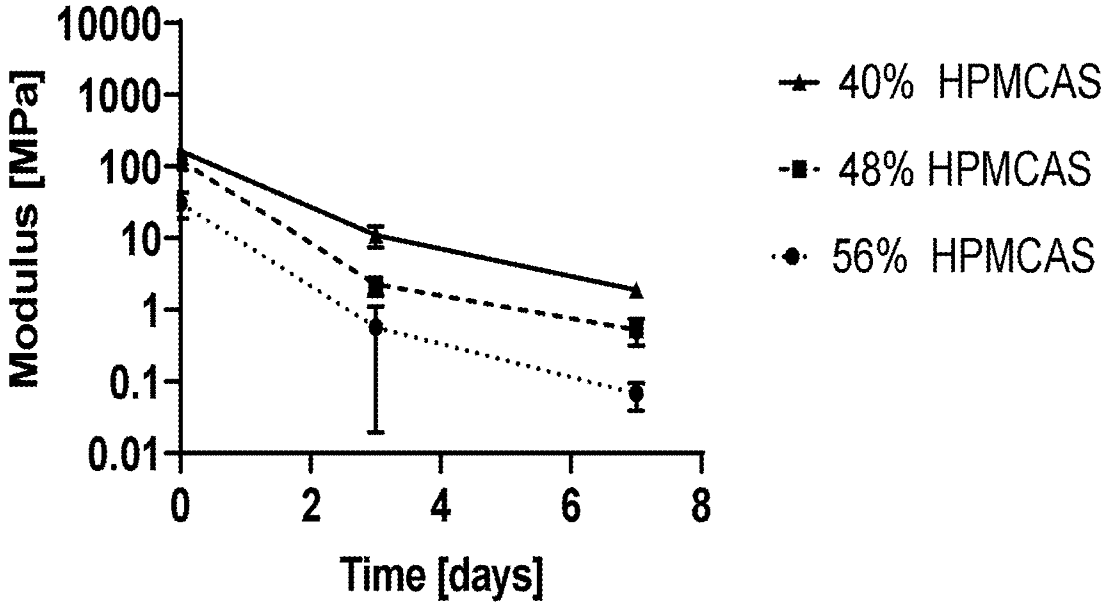
FIG. 50 compares the flexural modulus of an enteric polymeric linker containing different amounts of HPMCAS after incubating in FaSSIF over time.

Rate of enteric polymeric linker degradation as function of enteric polymer amount in the polymeric linker was tested by forming samples with varying amounts of enteric polymer, as shown in Table 12. The samples were incubated in FaSSIF, and flexural modulus was measured prior to incubation, 3 days after incubation or 7 days after incubation. As shown in FIG. 50, higher amounts of enteric polymer, namely HPMCAS, resulted in faster degradation of the enteric polymeric linker sample in simulated intestinal conditions.

TABLE 12

| Sample Type No. | Enteric Polymer | Carrier Polymer | Additional Components |
|---|---|---|---|
| 1 | 40% HPMCAS MG | 50% Pathways ™ 72AE TPU | 10% Propylene Glycol |
| 2 | 48% HPMCAS MG | 40% Pathways ™ 72AE TPU | 12% Propylene Glycol |
| 3 | 56% HPMCAS MG | 30% Pathways ™ 72AE TPU | 14% Propylene Glycol |

Figure 51:
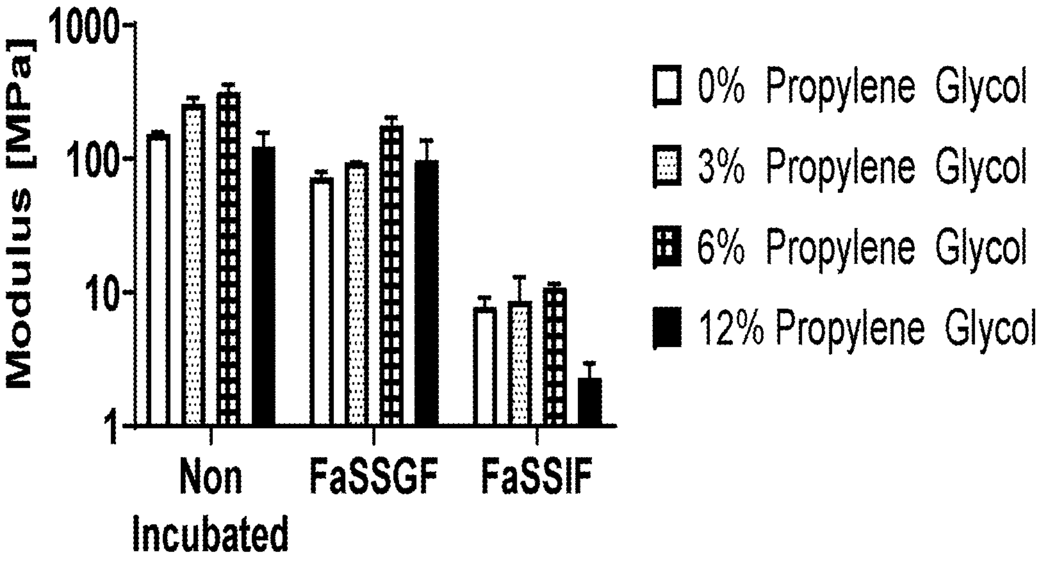
FIG. 51 compares the flexural modulus of an enteric polymeric linker containing different amounts of propylene glycol after incubating in FaSSGF or FaSSIF.

The effect of propylene glycol in the enteric polymeric linker, and its effect on pH dependence, was tested by varying the amount of propylene glycol in the enteric polymeric linker samples, as shone in Table 6, and measuring the change in flexural modulus after incubation for 3 days in simulated gastric conditions (FaSSGF) or simulated intestinal conditions (FaSSIF). Results are shown in FIG. 51, which shows that higher amounts of propylene glycol can enhance degradation of the enteric polymeric linker under simulated intestinal conditions but does not affect the rate of degradation under simulated gastric conditions, even though the samples with higher propylene glycol concentration had lower amounts of enteric polymer (HPMCAS).

TABLE 13

| Sample Type No. | Enteric Polymer | Carrier Polymer | Additional Components |
|---|---|---|---|
| 1 | 60% HPMCAS MG | 40% Pathways ™ 72AE TPU | None |
| 1 | 57% HPMCAS MG | 40% Pathways ™ 72AE TPU | 3% Propylene Glycol |
| 2 | 54% HPMCAS MG | 40% Pathways ™ 72AE TPU | 6% Propylene Glycol |
| 3 | 48% HPMCAS MG | 40% Pathways ™ 72AE TPU | 12% Propylene Glycol |

Example 22: Dual Time-Dependent and Enteric Polymeric Linkers

A dual time-dependent and enteric polymeric linker was formed by including a pH-independent degradable polymer, namely PLGA, with an enteric polymer, namely HPMCAS in a polymeric linker sample. The pH-independent degradable polymer allows for weakening of the polymeric linker at any pH, including gastric conditions, and the enteric polymer allows for accelerated degradation under intestinal conditions.

Figure 52:
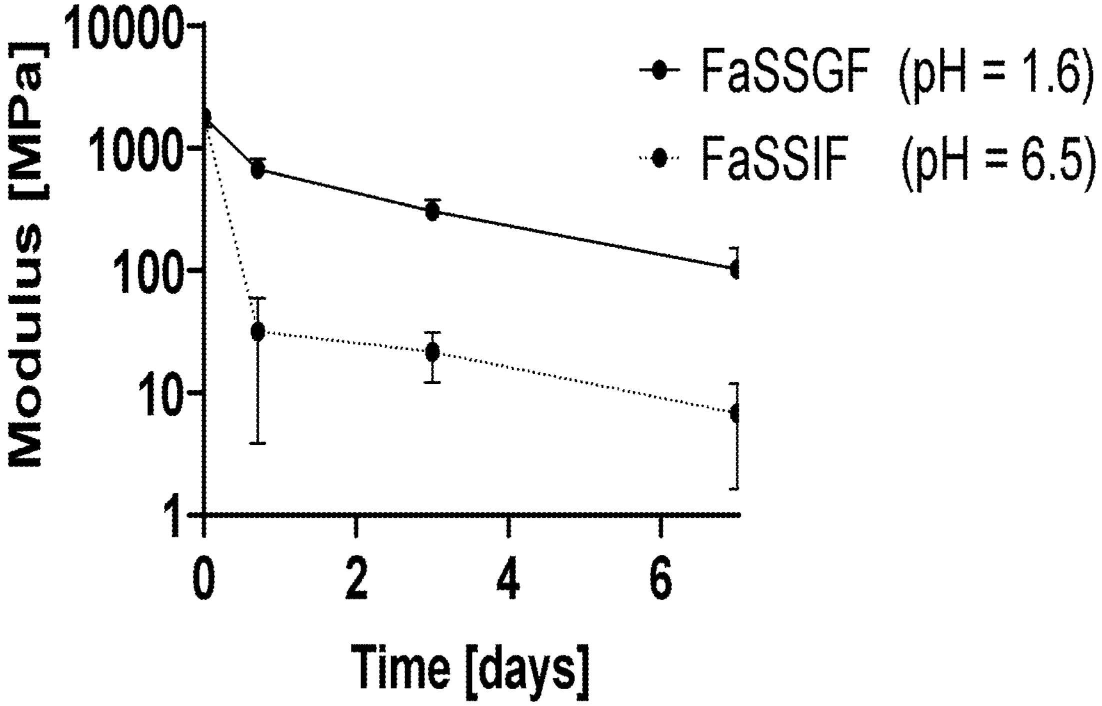
FIG. 52 compares the flexural modulus of a dual time-dependent and enteric polymeric linker containing an enteric polymer (HPMCAS) and a pH-independent degradable polymer (PLGA) after incubation in FaSSGF or FaSSIF over time.

A dual time-dependent and enteric polymeric linker was formed by hold melt extruding a homogenous mixture of 60% HPMCAS MG and 40% PLGA (namely, Resomer® RG 653H). The flexural modulus of the samples were measured prior to incubation or after incubation for 3 days, 5 days, or 7 days in FaSSGF or FaSSIF. Results are shown in FIG. 52, which demonstrates that the dual time-dependent and enteric polymeric linker degrades slowly in simulated gastric conditions, but quickly in simulated intestinal conditions.

Example 23: Weld Strength of Linker Materials Joined to Base Polymer

Components of the gastric residence system dosage form were produced through hot melt extrusion, cut to size, and joined together using thermal bonding. The thermal bonding process included loading the selected components into a nest in the desired configuration, applying radial pressure such that all interfaces make contact, and subjecting the exposed side of the components to infrared (IR) radiation. Strong thermal bonds are created when polymer chains are heated to the point at which they can flow across the joint interface and intermingle with chains from the adjacent component. The temperature reached by materials under IR exposure varies between different materials because each polymer blend has its own absorptive and conductive properties. The average process temperature was measured using thermocouples inserted directly into the interface between the two materials.

The material properties were evaluated using a capillary rheometer to determine the melt viscosities in a relevant temperature range. The preliminary viscosity data was used to drive layer reformulation, including adding plasticizers to lower melt viscosity as well as colorants to change IR absorption properties. Bond strength between the layers was evaluated using tensile testing to measure the force required to pull the components apart. This testing was performed on an Instron universal test system using custom grips.

The average peak temperature reached during the process was about 110 degrees Celsius. Variability in these measurements comes from a variety of factors including precise thermocouple positioning—the materials are exposed to IR from one side, so the conductivity of the materials affects how quickly the temperature equilibrates.

Figure 53A:
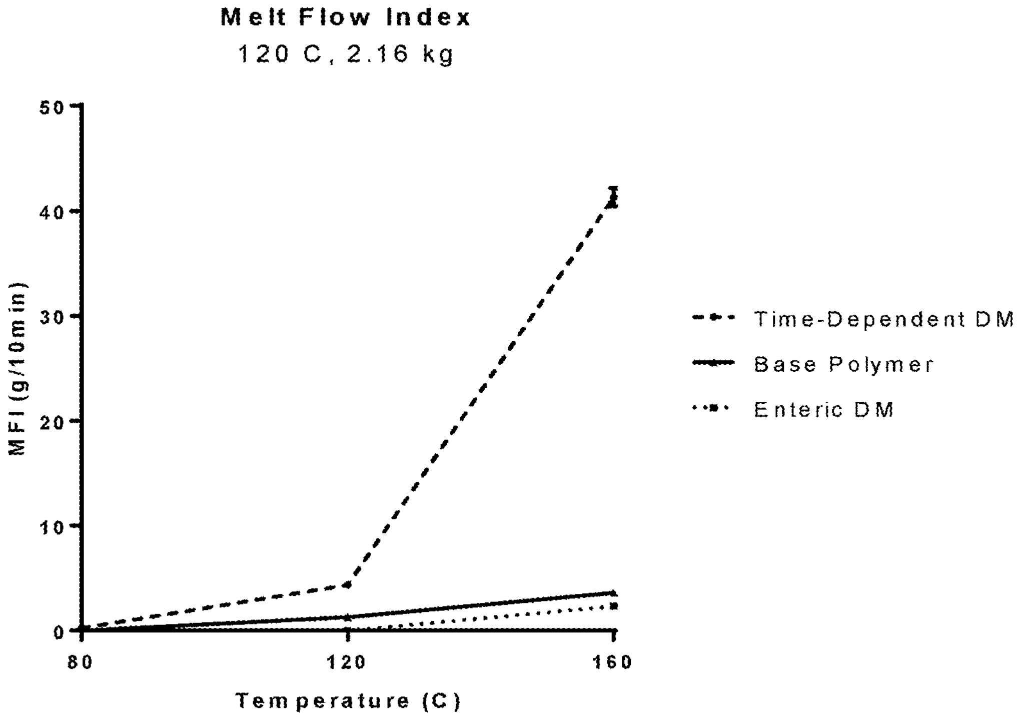
FIG. 53A shows the melt flow index over various materials, including a carrier polymer (base polymer), a time-dependent polymeric linker, and an enteric linker with or within a plasticizer.
Figure 53B:
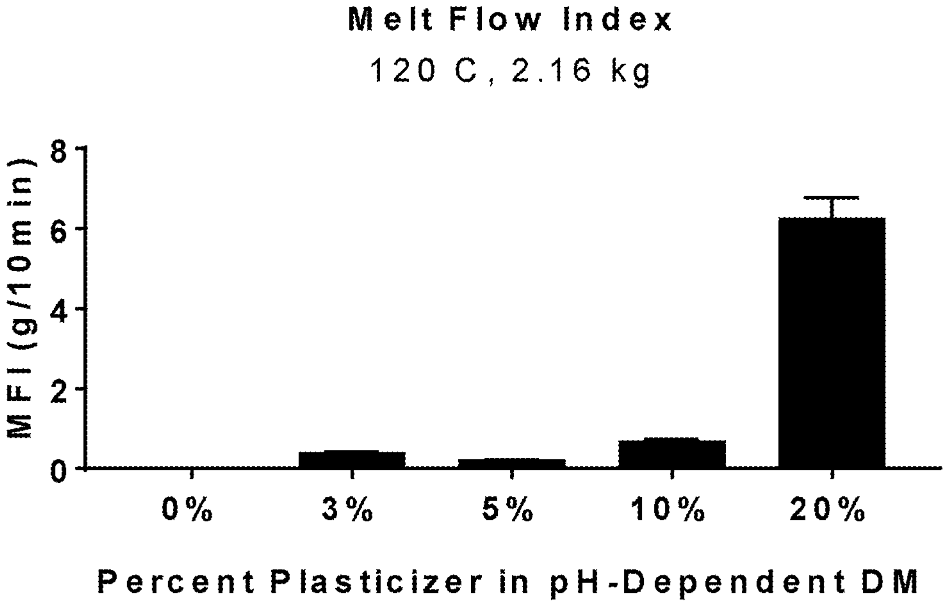
FIG. 53B shows the melt flow index of enteric polymeric linker materials with different amounts of plasticizer, as measured at 120° C. and a 2.16 kg load.

Melt Flow Index. The melt flow index (MFI) is a measurement of viscosity determined by the grams of material that flow through a specific capillary in 10 minutes at a certain temperature and load. Thermal bonds are formed by the intermingling of polymer chains at the layer interfaces, so achieving similar melt flow indices is important for promoting this interaction and creating strong bonds. The two polymeric linker formulations have very different MFIs. An exemplary tested enteric polymeric linker (34% PCL, 64% HPMCAS, 2% P407) does not flow under the 2.16 kg load at all until it is heated to 120° C., whereas an exemplary time-dependent polymeric linker (45% PCL, 35% Purasorb® PDLG 5004 A, 18% Purasorb® PDLG 5004, 2% 100K polyethylene glycol) and the pure carrier polymer (100% PCL) flow significantly more (FIG. 53A). The formulation of the enteric polymeric linker was adjusted as shown in Table 14 to alter the amount of polyethylene glycol, and the melt flow index was measured at 120° C. (FIG. 53B, showing Samples 1-5 of Table 14). As the amount of polyethylene glycol (plasticizer) is increased, so too did the melt flow index.

TABLE 14

| Sample No. | % PCL | % HPMCAS | % P407 | % polyethylene glycol 100K |
|---|---|---|---|---|
| 1 | 34.00 | 64.00 | 2.00 | 0.00 |
| 2 | 32.98 | 62.08 | 1.94 | 3.00 |
| 3 | 32.30 | 60.80 | 1.90 | 5.00 |
| 4 | 30.60 | 57.60 | 1.80 | 10.00 |
| 5 | 27.20 | 51.20 | 1.60 | 20.00 |
| 6 | 34.00 | 54.30 | 1.70 | 10.00 |
| 7 | 34.00 | 44.61 | 1.39 | 20.00 |

Figure 54A:
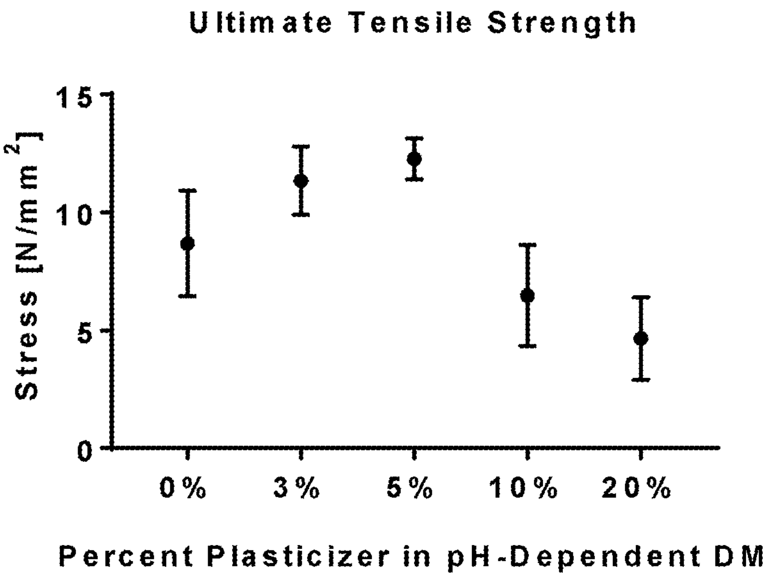
FIG. 54A show the change of the tensile strength of a bond after joining an enteric polymeric linker with differing amounts of plasticizer to a time-dependent linker.

Tensile Strength. An Instron machine and custom-made grips were used to evaluate the ultimate tensile strength (UTS) of the bond between welded materials. The crosshead moves upward at 5-500 mm/minute depending on the elasticity of the materials tested. The instrument records Force (N) v. Displacement (mm), and the maximum force is divided by the cross-sectional area at the interface to calculate ultimate tensile strength (stress). A low ultimate tensile strength indicates a potential failure point in the gastric residence system. The tensile strength of the bond between the enteric polymeric materials listed in Table 14 and the time-dependent linker was measured, as shown in FIG. 54A.

Figure 54B:
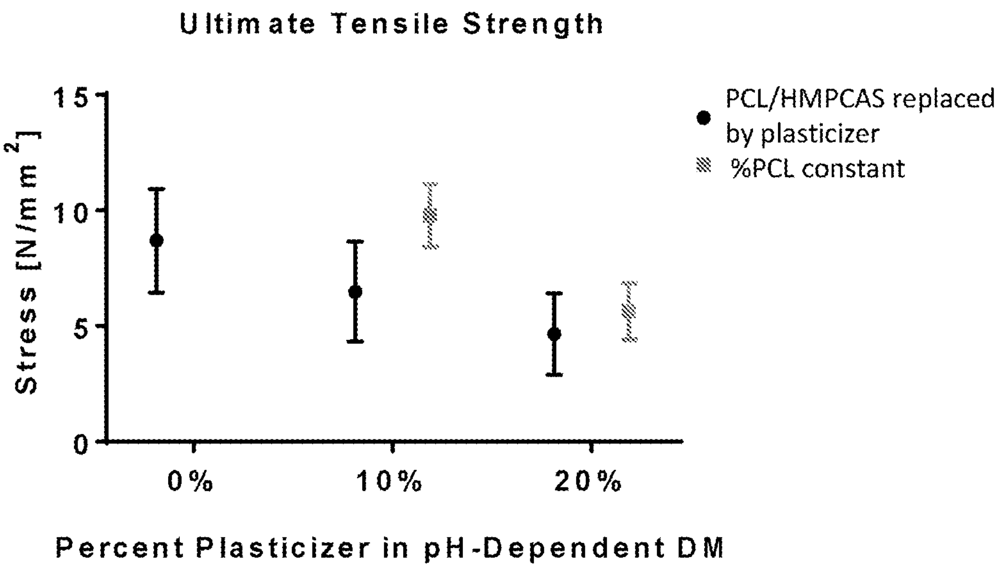
FIG. 54B shows the tensile strength of a bond joining an enteric polymeric linker with different amounts of plasticizer to a time-dependent linker. Values indicated by a circle represent materials wherein increased plasticizer replaces both PCL and HPMCAS, and valued indicated by a square represent materials with constant amounts of PCL.

Including a plasticizer in the enteric polymeric linker formulation increased flow at process-relevant temperatures (FIG. 53B) and tensile strength (FIG. 54A) of the bond between the enteric polymeric linker and a joined time-dependent linker. Although including higher amounts of plasticizer in the enteric polymeric linker resulted in a drop in the tensile strength of the bond, this drop can be somewhat recovered by increasing the amount of carrier polymer (e.g., PCL) common to both the enteric polymeric linker and the joined time dependent linker (see FIG. 54B, showing the tensile strength of samples 1, 6 and 7 of Table 14, each having 34% PCL, next to samples 4 and 5 of Table 14 having varying amounts of PCL).

Example 24: Enteric Polymeric Linkers

Figure 55A:
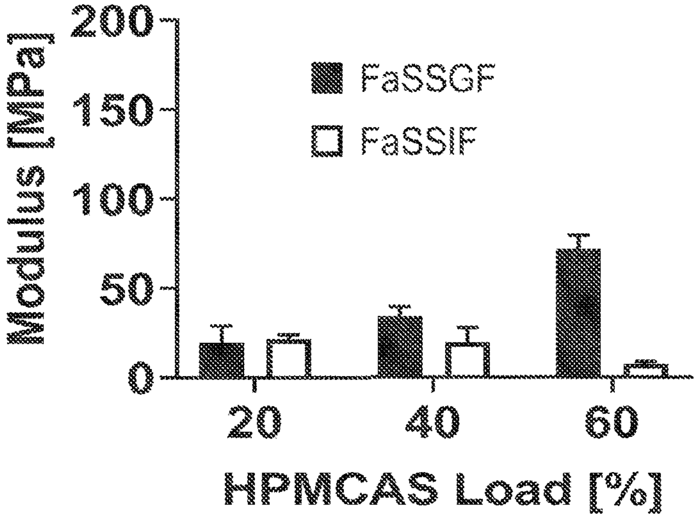
FIG. 55A shows the flexural modulus of various enteric polymeric linker materials after incubating in FaSSGF or FaSSIF.
Figure 55B:
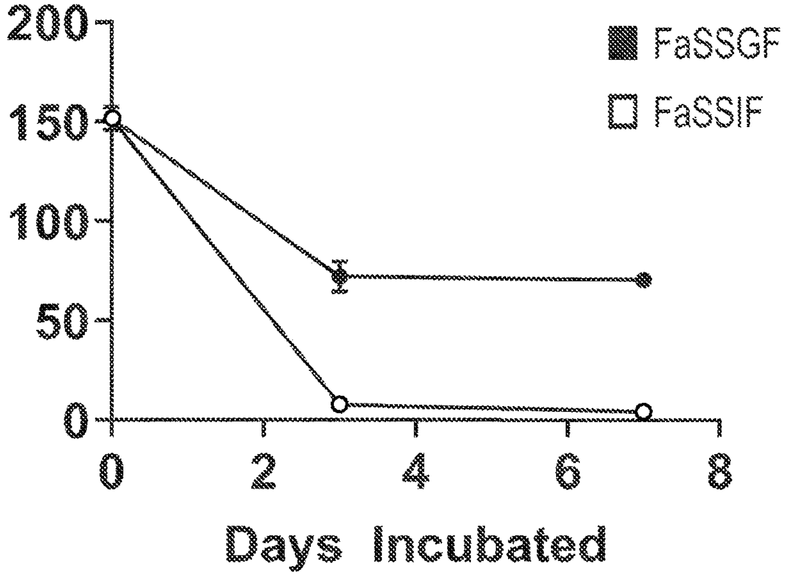
FIG. 55B shows the flexural modulus of an enteric polymeric linker material containing 60% HPMCAS and 40% TPU after incubating in FaSSGF or FaSSIF as a function of time.

Enteric polymeric linker materials were formed using 20%, 40%, or 60% HPMCAS mixed with 80%, 60%, or 40% Pathways™ 72AE TPU. The polymeric materials were incubated in FaSSIF or FaSSGF at 37° C. for 3 days. The flexural modulus of the materials was measured, which is shown in FIG. 55A. The flexural modulus of the material containing 60% HPMCAS and 40% TPU was measured at 0 days and after 3 days or 7 days incubation in FaSSIF or FaSSGF at 37° C., as shown in FIG. 55B.

The enteric polymeric linker material samples were also cryogenically fractured and incubated in FaSSIF to solubilize the HPMCAS. Scanning electron microscopy (SEM) was performed on samples, and the domains left by the leaching HPMCAS were sized as circles using ImageJ and reported as an Average Domain Size (um), as shown in Table 15. At HPMCAS load 60%, an order of magnitude increase of HPMCAS domain size was observed, leading to improved elution of HPMCAS from the matrix.

TABLE 15

| % HPMCAS | Average Domain Size (um) |
|---|---|
| 20% HPMCAS | 7.68 ± 2.52 |
| 40% HPMCAS | 6.65 ± 3.284 |
| 60% HPMCAS | 60.83 ± 3 4.49 |

Example 25: In Vivo Performance of Polymeric Linkers

Components of the gastric residence systems can be manufactured by various methods, such as co-extrusion or three-dimensional printing, as disclosed in U.S. Pat. No. 10,182,985, and published patent applications US 2018/0311154 A1, US 2019/0262265 A1, US 2019/0231697 A1, US 2019/0254966 A1, and WO 2018/227147.

Gastric residence systems in stellate dosages forms were evaluated in a dog model, a commonly accepted model for preclinical pharmacology and toxicology evaluations. Capsules containing the stellate systems were administered to dogs after fasting for 12 hours. Gastric residence systems were placed in the back of the throat and followed with a food chase. Ventrodorsal X-rays were collected within an hour after dosing and daily for one week. If gastric residence systems were retained in the body longer than one week, X-rays were taken three times per week until the gastric residence systems passed. Six steel fiducials embedded in the gastric residence system enabled analysis of the location (stomach or lower GI tract) and intactness of each gastric residence system.

Figure 56:
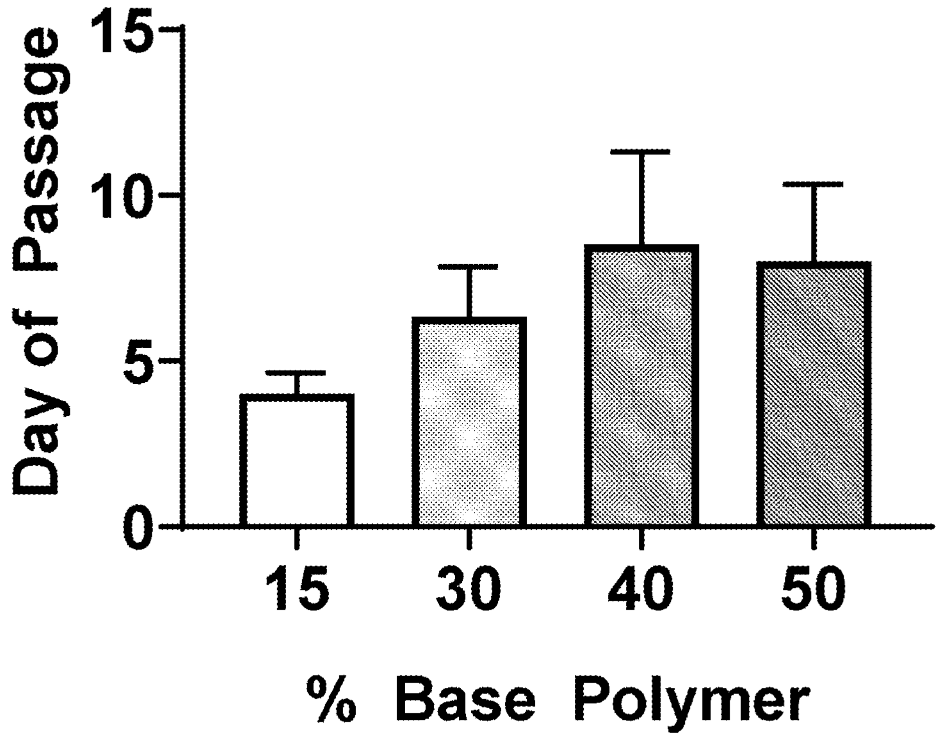
FIG. 56 shows the gastric retention time of a gastric residence system with an enteric polymer mixed with a carrier (i.e., base) polymer at different amounts.

Enteric polymeric linkers containing (a) 15% PCL and 85% HPMCAS, (b) 30% PCL and 70% HPMCAS, (c) 40% PCL and 50% HPMCAS, or (d) 50% PCL and 50% HPMCAS in the stellate dosage forms were tested in the dog model. The enteric polymeric linkers were welded to PCL coupling members of the gastric residence system in the stellate dosage form. Gastric retention in the dog models is shown in FIG. 56, which demonstrates that the dosage forms containing 40% or 50% PCL endured gastric residence for a longer period than enteric linkers with smaller amounts of PCL. The higher amounts of PCL in the enteric polymeric linker enhanced the weld strength of the polymeric linker to the PCL coupling member, which resulted in the longer gastric residence.

Gastric retention in dog models was also tested for additional polymeric linkers using a PCL-based gastric residence system (that is, the polymeric linkers were welded to gastric residence system components containing PCL). The weldability of linker materials to PCL drug arms were determined based on the tensile strength of the bonds, while the gastric retention in a dog model was examined as described above using ventrodorsal X-rays. Enteric characters was measured in vitro by incubating polymeric linker materials in FaSSIF and FaSSGF. If the flexural modulus decreases after incubation in FaSSIF but not in FaSSGF, the enteric character for that material was qualitatively characterized as good (+++ or ++++). If the flexural modulus did not decrease or decreased only slightly, the enteric character for the material was qualitatively characterized as poor (+ or ++). Tested enteric polymeric linkers and results are shown in Table 16, and tested time-dependent polymeric linkers and results are shown in Table 17.

TABLE 16

| | Formulation | | | Gastric Residence in Dogs | Weldability | |
|---|---|---|---|---|---|---|
| Sample | PCL (wt %) | HPMCAS (wt %) | Additives (wt %) | (average days (StDev)) | & Adhesion | Enteric Character |
| 1 | 49.90 | 50 | 0.1% iron oxide | 8.5 (1.2) | +++ | + |
| 2 | 39.90 | 60 | 0.1% iron oxide | 8.5 (2.8) | +++ | + |
| 3 | 38 | 58 | 4% PEO 100K | 9.5 (3.4) | +++ | + |
| 4 | 35.90 | 36 | 28% TEC<br>0.1% iron oxide | 4.2 (0.8) | +++ | + |
| 5 | 33.90 | 64 | 2% P407<br>0.1% iron oxide | 10.0 (2.2) | +++ | ++ |
| 6 | 33.90 | 64 | 2% PEO 100K<br>0.1% iron oxide | 6.8 (2.6) | +++ | ++ |
| 7 | 29.90 | 70 | 0.1% iron oxide | 6.0 (1.6) | ++ | +++ |
| 8 | 14.90 | 85 | 0.1% iron oxide | 4.0 (0.6) | + | ++++ |
| 9 | 13.9 | 84 | 2% PEO 100K<br>0.1% iron oxide | 4.5 (1.6) | + | ++++ |
| 10 | 14.90 | 75 | 10% TEC<br>0.1% iron oxide | 2.7 (0.5) | + | ++++ |

High amounts of HPMCAS in the enteric polymeric linker (samples 8-10 in Table 16) provided very good enteric character, but the weld between the enteric polymeric linker and the PCL component was weak, risking breakage and premature gastric exit. The addition of plasticizer in samples with a moderate amount of PCL (samples 3-6 in Table 16) increased the weldability of the polymeric linker to the PCL component. Inclusion of P407 in sample 5 improved cutting of the polymeric linker during product manufacture.

TABLE 17

| | Formulation | | | | Gastric Residence in | |
|---|---|---|---|---|---|---|
| Sample | PCL (wt %) | Acid-terminated PLGA (wt %) | Ester-terminated PLGA (wt %) | Additives (wt %) | Dogs (average days (StDev)) | Weldability & Adhesion |
| 2 | 44.95 | 53 | 0 | 2% PEO 100K 0.05% iron oxide | 7.6 (0.5) | +++ |
| 3 | 44.95 | 35 | 18 | 2% PEO 100K 0.05% iron oxide | 8.0 (2.4) | +++ |
| 4 | 50 | 50 | 0 | N/A | 8.5 (2.3) | +++ |
| 5 | 49.95 | 45 | 0 | 5% PEO 100K 0.05% iron oxide | 4.0 (1.9) | +++ |
| 6 | 50 | 45 | 0 | 5% PEO 100K | 17.0 (5.9) | N/A |

For the time-dependent polymeric linkers listed in Table 17, all polymeric linkers welded with good strength to the PCL components of the gastric residence system. Addition of 2% PEO resulted in increased flowability of the polymeric mixture during manufacture (sample 2 in Table 17), although adding too much PEO resulted in shortened gastric residence time (sample 5 in Table 17).

Gastric residence systems with one enteric polymeric linker and one time-dependent linker were also tested in dog models. Combination System 1 included a time-dependent polymeric linker according to Sample 2 of Table 17 (average gastric residence of 7.6 days alone), and an enteric polymeric linker according to Sample 3 of Table 16 (average gastric residence of 9.5 days alone), and had an average gastric residence of 8.3 days (2.1 days standard deviation). Combination System 2 included a time-dependent polymeric linker according to Sample 3 of Table 17 (average gastric residence of 8 days) and an enteric polymeric linker according to Sample 5 of Table 16, and had an average gastric residence of 8.5 days (standard deviation 1.5 days). Combination System 3 included a time-dependent polymeric linker according to Sample 2 of Table 17 (average gastric residence of 7.6 days) and an enteric polymeric linker according to Sample 5 of Table 16 (average gastric residence of 4.0 days), and had an average gastric residence of 3.7 days (1.2 days standard deviation).

Example 26: FaSSGF Preparation

FaSSGF was prepared as follows, according to the manufacturer's instructions (biorelevant.com). 975 mL deionized water and 25 mL of 1N hydrochloric acid were mixed in a 1 L glass media bottle. The pH was adjusted to 1.6 using 1N HCl or NaOH as needed. 2.0 grams of NaCl was added and mixed in. Just before use, 60 mg of Biorelevant powder was mixed into the solution. The composition of FaSSGF is taurocholate (0.08 mM), phospholipids (0.02 mM), sodium (34 mM), chloride (59 mM).

Example 27: Dip Coating Provides Release Rate Control for High and Low Drug Load Formulations Drug Arm Formulation Preparation:

All non-PCL powders were blended and wet granulated with water. The dried granules were then blended with PCL powder and compounding extrusion was performed using a twin screw extruder. Profile extrusion was subsequently performed using a twin screw extruder. DNP34 and M116 arm formulations were used for dip coating experiments.

TABLE 18

| Name | Composition | Function |
|---|---|---|
| MEM116 | 45% MEM, 41.9% PCL, 10% PDL20, 2% P407, 0.5% Vit. E Succinate, 0.5% SiO2, 0.1% pigment | memantine formulation |
| MEM122 | 50% MEM, 43.97% PCL, 5% Kollidon SR, 0.5% Vit E Succinate, 0.5% SiO2, 0.03% pigment | memantine formulation |
| DNP34 | 40% DNP, 44% PCL, 10% PDL20, 5% P407, 0.5% Vit. E Succinate, 0.5% SiO2 | donepezil formulation |
| MD01 | 35% MEM, 14.5% DNP, 43.97% PCL, 5% Kollidon SR, 0.5% Vit E Succinate, 0.5% SiO2, 0.03% pigment | memantine + donepezil formulation |
| RSP49 | 35% RSP, 55.9% PCL, 5% VA64, 3% P407, 0.5% Vit. E Succinate, 0.5% SiO2, 0.1% pigment | risperidone formulation |
| D138 | 20% dapagliflozin, 33.99% PCL, 30% VA64, 10% PDL20, 5% Sorbitan monostearate (Span60), 0.5% Vit. E Succinate, 0.5% Colloidal silicon dioxide (M5P), 0.01% pigment | dapagliflozin formulation |

Dip coating: Dip coating solutions were prepared as follows: the solid contents of each coating solution were weighed directly into a glass vial. Solvent was added to reach the appropriate solids content (% w/v). The solutions were stirred at 65° C. and 300 rpm until solids were solubilized or uniformly suspended. Exemplary compositions of coating solutions are listed in Table 19. All dip coating formulations were prepared in ethyl acetate either as a solution or as a stable suspension (for coating formulations with insoluble ingredients such as porogens). All solutions were prepared at 8% w/v solid content, except for solutions containing PEG 10K, which were prepared at 5% w/v solid content and suspensions containing K90F at 6-8 w/v. Drug arms were gripped with forceps, completely submerged in the coating solution, and immediately removed. Coated arms were dried in a fume hood overnight. In all dip-coating experiments, the PDL used was Corbion Purasorb PDL20, a PDL having 2.0 dl/g intrinsic viscosity (range 1.6 dl/g to 2.4 dl/g). In all dip-coating experiments, the PDLG used was Corbion Purasorb PDLG 5004 A, an acid terminated copolymer of DL-lactide and glycolide (50/50 molar ratio) having an inherent viscosity midpoint of 0.4 dl/g. For dip coating, PCL HMW was 80 kD or 2.07 dL/g in $CHCl_3$ and PCL LMW was 14 kD. PDL-PCL2575 used was Lactel® 25:75 poly(DL-lactide-co-ε-caprolactone) with inherent viscosity 0.70-0.90 dl/g, while PDL-PCL8020 was Lactel® 80:20 poly(DL-lactide-co-ε-caprolactone) with inherent viscosity 0.70-0.90 dl/g.

TABLE 19

Coating formulations for dip coating.

| Formulation No. | Coating Formulation |
|---|---|
| 1 | PDL |
| 2 | PCL HMW |
| 3 | 1:1 PCL HMW:PCL LMW |
| 4 | 3:1, PDL:VA64 |
| 5 | 3:1, PCL HMW:K90F |
| 6 | 9:1, PDL:PEG1 |
| 7 | 9:1, PDL:L31 |
| 8 | 27:2:1, PDL:PEG1:PPG |
| 9 | 9:1, PCL HMW:PG |
| 10 | 9:1, PCL HMW:PPG |
| 11 | 9:1, PCL HMW:L-31 |
| 12 | 9:1, PCL HMW:F-108 |
| 13 | 27:2:1, PCL HMW:PEG1:PPG |
| 14 | 9:1, PCL HMW:PCL triol |
| 15 | 9:1, PDL:PG |
| 16 | 9:1, PDL:PPG |
| 17 | 9:1, PDL:L-31 |
| 18 | 9:1, PDL:F-108 |
| 19 | 27:2:1, PDL:PEG1:PPG |
| 20 | 4:1, PDL:K90F |
| 21 | 4:1, PDL:PVPP |
| 22 | 9:27:4 PDL:PCL:PEG |
| 23 | 36:9:5 PDL:PCL:PEG |
| 24 | 9:1, PDL-PCL2575:PEG1 |
| 25 | 9:l, PDL-PCL8020:PEGl |
| 26 | PDLG 5004A |
| 27 | 3:1, PDLG:VA64 |
| 28 | 3:1, PCL HMW:PVPP |
| 29 | 4:1, PDL:K90F |
| 30 | 3:1, PDL:PVPP |
| 31 | 3:1, PDL-PCL2575:K90F |
| 32 | 3:1, PDL-PCL2575:PVPP |
| 33 | 3:1, PDL-PCL8020:K90F |
| 34 | 3:1, PDL-PCL8020:PVPP |
| 35 | PVAc |
| 36 | PDL-PCL2575 |
| 37 | PDL-PCL8020 |
| 38 | 3:1, PVAc:VA64 |
| 39 | 3:1, PDL-PCL2575:VA64 |
| 40 | 3:1, PDL-PCL8020:VA64 |
| 41 | 2:1, PCL HMW:PCL LMW |
| 42 | 1:2, PCL HMW:PCL LMW |
| 43 | 9:1, PCL HMW:PEG10 |
| 44 | 9:1, PDL:PEG1 |
| 45 | 9:1, PDL:PEG10 |
| 46 | 9:1, PCL HMW:PEG1 |
| 47 | 9:1, PVAc:PEG1 |
| 48 | 9:1, PVAc:PEG10 |
| 49 | 9:1, PDL-PCL2575:PEG10 |
| 50 | 9:1, PDL-PCL8020:PPEG10 |
| 64 | 9:1, PCL HMW:mannitol |

In Vitro Release: Each formulation was applied to DN34 drug arms and evaluated for release in fasted state simulated gastric fluid (FaSSGF) for seven days. Release rates were evaluated using the procedures provided below for dapagliflozin, donepezil, and memantine.

Example 28: Pan Coating Provides Release Rate Control for High and Low Drug Load Formulations Drug Arm Formulation Preparation: The underlined drugs as indicated in Table 18 were respectively blended into drug-loaded arms using one of the following procedures.

Procedure #1: All non-API powders were bag blended by hand until a visually uniform mixture was achieved. API was added and the mixture bag blended further until a visually uniform mixture was again achieved. Compounding extrusion was performed using a twin screw extruder at 140° C. Profile extrusion was performed using a twin screw extruder and a temperature gradient of 120° C. to 100° C. to maintain the desired shape.

Procedure #2: All non-API powders were bag blended by hand until a visually uniform mixture was achieved. API was added and the mixture bag blended further until a visually uniform mixture was again achieved. Compounding extrusion was performed using a twin screw extruder and temperature gradient of 115-130° C. Profile extrusion was performed using a single screw extruder and a temperature gradient of 50-80° C.

Procedure #3: All non-PCL powders were blended and wet granulated with water. The dried granules were then blended with PCL powder and compounding extrusion was performed using a twin screw extruder. Profile extrusion was subsequently performed using a twin screw extruder.

Procedure #4: Each API was granulated independently with all other non-PCL powders. The powder mixes were blended wet granulated with water. The dried granules containing memantine, dried granules containing donepezil, and PCL powder were then blended and compounding extrusion was performed using a twin screw extruder. Profile extrusion was subsequently performed using a single screw extruder. Arm formulations used are listed in Table 1.

Exemplary compositions of pan coating solutions are listed in Table 20. Pan-coating procedures were carried out as described below.

Poly-Lactide-Based Films

Solutions of poly-lactide-based polymers were prepared in neat and dry acetone with solid concentrations of 1.5-3.3% w/v. Solutions were prepared in one of two methods described below, with each method demonstrating comparable performance in both the film coating process and in drug release.

Method 1: PDL20 was removed from −20° C. freezer and equilibrated to room temperature for at least 2 hours. A stir bar and glass bottle for solution preparation were triple rinsed with acetone. The wash solvent was decanted and evaporated. Half of the desired mass of acetone was placed in the glass bottle with the stir bar and set to stir at 180-200 RPM at room temperature. The entire mass of PDL20 required in formulation was slowly added to the stirring acetone. The glass bottle was then capped, sealed with parafilm, and left to stir overnight. Subsequently, the solution was allowed to settle. If any particulates were observed, the solution was decanted and re-weighed. The additional desired mass of acetone was then added to the solution. PDLG5002 A was removed from −20° C. freezer and equilibrated to room temperature for at least 2 hours. The entire mass of PDLG5002 A required in formulation was slowly added to the stirring solution containing PDL20 and acetone. The solution was then set to stir at room temperature at 180-200 RPM for at least 30 minutes. Magnesium stearate was added in one portion to the stirring solution and allowed to stir at 180-200 RPM under room temperature for at least 10 minutes to achieve a homogenous dispersion. The suspension was weighed and filled to mass with acetone if needed.

Method 2: PDL20 was removed from −20° C. freezer and equilibrated to room temperature for at least 2 hours. A glass bottle and impeller for solution preparation were triple rinsed with acetone. The wash solvent was decanted and evaporated. The desired mass of acetone was placed in the glass bottle and set to stir at 500 RPM at room temperature. The entire mass of PDL20 required in formulation was slowly added to the stirring acetone. The glass bottle was then capped, sealed with parafilm, and left to stir for at least 2 hours. Subsequently, the solution was allowed to settle. If any particulates were observed, the solution was decanted, re-weighed, and filled to mass with acetone if needed.

PDLG5002 A was removed from −20° C. freezer and equilibrated to room temperature for at least 2 hours. The entire mass of PDLG5002 A required in formulation was slowly added to the stirring solution containing PDL20 and acetone. The solution was allowed to stir at 500 RPM under room temperature for at least an additional 30 minutes. Magnesium stearate was added into one portion of the solution with continued stirring. The resulting suspension was stirred for at least 5 minutes to achieve a homogenous dispersion. The suspension was then weighed and filled to mass with acetone if needed.

Procedures similar to Method 1 and Method 2 were used for preparation of PDL20 coating solutions using other additional polymers instead of PDLG5002 A. Separately, a mixture of placebo arms and drug arms totaling 480 g was prepared. The quantity of drug-containing arms was approximately 1% to 25% by weight.

The coating solution, maintained under agitation with a stir bar during spraying, was then applied to the mixture of placebo and drug loaded arms using a LDCS Hi-Coater pharmaceutical pan coater with manufacturer-supplied spray nozzle (Freund-Vector, Marion, Iowa, USA). The following parameters were used: inlet air temperature (48° C.), exhaust air temperature (36-38° C.), airflow (50 CFM), pan run speed (22 RPM), atomization pressure (20 PSI), pattern pressure (18 PSI). A-Pharm-Line acetone-resistant tubing was used with the built-in peristaltic pump and was pre-washed with 50 g of neat and dry acetone. The mixture of placebo and drug arms was then loaded into the pan. Solution was applied in 12 minute intervals followed by 5 minutes of tumbling. This procedure was repeated until a desired mass gain of approximately 1-6% (w/w) was achieved. Mass gain was determined based on the amount of solution sprayed. After the desired quantity of solution was sprayed, arms were dried for at least 2 hours at ambient condition to drive off any residual acetone. After evaporation, arms were stored sealed with desiccant until use in drug release studies.

In all pan-coating experiments, the PDL used was Corbion Purasorb PDL20, a PDL having 2.0 dl/g intrinsic viscosity (range 1.6 dl/g to 2.4 dl/g). In all pan-coating experiments, the PDLG used was either Corbion Purasorb PDLG 5004 A (an acid terminated copolymer of DL-lactide and glycolide in 50/50 molar ratio, having an inherent viscosity midpoint of 0.4 dl/g), or Corbion Purasorb PDLG 5002 A (an acid terminated copolymer of DL-lactide and glycolide in a 50/50 molar ratio, having an inherent viscosity midpoint of 0.2 dl/g).

Polycaprolactone-Based Films

Solutions containing polycaprolactone-based polymers were prepared in neat and dry ethyl acetate with solid concentration of 3.3% w/v.

A glass bottle and impeller for solution preparation were triple rinsed with ethyl acetate. The wash solvent was decanted and evaporated. The desired mass of ethyl acetate was weighed in the glass bottle. The solid PCL was weighed and added to the glass bottle containing ethyl acetate. The bottle was then placed on a hot plate set at approximately 45° C. and set to stir at between 500-550 RPM using an overhead stirrer (IKA Works Inc., Wilmington, NC, USA). The bottle was then capped and left to stir for approximately 30 minutes. Once PCL was fully dissolved, Kollidon VA64 was added to it with continued stirring. Once the VA64 was solubilized, heating was stopped, and the hot plate was removed. Magnesium stearate was added, and the suspension was continually stirred until cooled to room temperature. Procedures similar to this method were used for preparation of PCL coating solutions using other ethyl acetate-soluble ingredients instead of VA64.

Separately, a mixture of placebo arms and drug arms totaling approximately 485 g was prepared. The quantity of drug-containing arms was approximately 1% to 25% by weight.

The coating solution, maintained under agitation with a stir bar during spraying, was then applied to mixture of placebo and drug loaded arms using a LDCS Hi-Coater pharmaceutical pan coater with manufacturer-supplied spray nozzle (Freund-Vector, Marion, Iowa, USA). The following parameters were used: inlet air temperature (50° C.), exhaust air temperature (40-42° C.), airflow (50 CFM), pan run speed (22 RPM), atomization pressure (20-22 PSI), pattern pressure (18-20 PSI). Ethyl acetate-resistant tubing was used with the built-in peristaltic pump and was pre-washed with approximately 50 ml of neat solvent. The mixture of placebo and drug arms were then loaded into the pan. Solution was applied in 5-minute intervals followed by 3 minutes of tumbling. This procedure was repeated until a desired mass gain of approximately 1-6% (w/w) was achieved. Mass gain was determined based on solution sprayed on the placebo and drug arms in the pan. After coating, arms were stored at ambient conditions until used in drug release studies. For PCL used in pan coating, high molecular weight PCL (PCL HMW) had intrinsic viscosity of 1.7 dl/g, while low molecular weight PCL (PCL LMW) had intrinsic viscosity less than or equal to 0.8 dl/g, most typically less than 0.4 dl/g.

TABLE 20

Coating formulations for pan coating.

| Formulation Code | Coating Formulation | Coating Solvent | Coating Solution Concentration (% w/v) |
|---|---|---|---|
| 51 | 9:1, PDL:PEG1; 2% Mg stearate by weight of solids | Ethyl acetate | 2.6 |
| 52 | 1:1, PDL:PDLG; 2% Mg stearate by weight of solids | Acetone | 1.5 |
| 53 | 3:1, PCL HMW:VA64; 2% Mg stearate by weight of solids | Ethyl Acetate | 3.3 |
| 54 | PDLG5004; 2% Mg stearate by weight of solids | Acetone | 1.5 |
| 55 | 1:1, PDL:PDLG; 2% Mg stearate by weight of solids | Acetone | 1.5 |
| 56 | 9:1, PCL HMW:P407; 2% Mg stearate by weight of solids | Ethyl Acetate | 3.3 |

TABLE 20-continued

Coating formulations for pan coating.

| Formulation Code | Coating Formulation | Coating Solvent | Coating Solution Concentration (% w/v) |
|---|---|---|---|
| 57 | PCL midMW; 2% Mg stearate by weight of solids | Ethyl Acetate | 3.3 |
| 58 | 1:3, PCL HMW:PCL LMW; 2% Mg stearate by weight of solids | Ethyl Acetate | 3.3 |
| 59 | 4:6, PCL HMW:PCL LMW; 2% Mg stearate by weight of solids | Ethyl Acetate | 3.3 |
| 60 | 1:1, PCL HMW:PCL LMW; 2% Mg stearate by weight of solids | Ethyl Acetate | 3.3 |
| 61 | 3:1, PCL HMW:PCL LMW; 2% Mg stearate by weight of solids | Ethyl Acetate | 3.3 |
| 62 | 85:15, PCL HMW:PCL LMW; 2% Mg stearate by weight of solids | Ethyl Acetate | 3.3 |
| 63 | 9:1, PCL HMW:PCL LMW; 2% Mg stearate by weight of solids | Ethyl Acetate | 3.3 |

Example 29: In Vitro Drug Release Assay and Exposure to Welding Conditions for Pan-Coated or Dip-Coated Drug Arms In Vitro release: In vitro release of drugs for coated drug arms was conducted as follows for the various drugs.

To measure dapagliflozin release, fasted state simulated gastric fluid (FaSSGF; biorelevant.com LTD, London, UK) was prepared per the manufacturer's instructions. Individual coated drug arms were placed in flat bottom 20 mL glass scintillation vials with 10 mL FaSSGF. Each vial was placed upright in an Innova43 shaking incubator (Eppendorf AG, Hamburg, Germany) at 200 RPM and 37° C. Drug content in the FaSSGF was analyzed by HPLC at least four times over at least seven days. Samples were stored for no more than 3 days at 4° C. prior to analysis. At each measurement time point, in order to maintain sink conditions, the entire volume of release media was replaced with fresh solution pre-equilibrated to 37° C.

To measure donepezil release, fasted state simulated gastric fluid (FaSSGF; biorelevant.com LTD, London, UK) was prepared per the manufacturer's instructions. Individual coated drug arms were placed in conical bottom 15 mL polypropylene tubes with 10 mL FaSSGF. Each tube was placed upright in an Innova43 shaking incubator (Eppendorf AG, Hamburg, Germany) at 200 RPM and 37° C. Drug content in the FaSSGF was analyzed by HPLC at least four times over at least seven days. Samples were stored for no more than 3 days at 4° C. prior to analysis. At each measurement time point, in order to maintain sink conditions, the entire volume of release media was replaced with fresh solution pre-equilibrated to 37° C.

To measure memantine release, fasted state simulated gastric fluid (FaSSGF; biorelevant.com LTD, London, UK) was prepared per the manufacturer's instructions. Individual coated drug arms were placed in in conical bottom 15 mL polypropylene tubes with 10 mL FaSSGF. Each tube was placed upright in an Innova43 shaking incubator (Eppendorf AG, Hamburg, Germany) at 200 RPM and 37 C. Drug content in the FaSSGF was analyzed by HPLC with pre-column derivatization at least four times over at least seven days. Samples were stored for no more than 3 days at 4° C. prior to analysis. At each measurement time point, in order to maintain sink conditions, the entire volume of release media was replaced with fresh solution pre-equilibrated to 37° C.

Thermal exposure: To test the effect of residence system assembly on the coating, drug-loaded arms were thermally exposed to the same process or a similar process used to assemble dosage forms and dosage form components (i.e., composite arms). Welding operations were performed using a custom fixture that enables control of weld temperature, applied pressure, and material alignment. In typical heat-assisted assembly, irradiation of drug-loaded arms reaches temperatures of approximately 60-160° C., most commonly below 120° C. In typical heat-assisted assembly, pressures of 15-60 psi are applied to one or both sides of an arm. Arms were exposed to IR and pressure either by a) using welding conditions identical to those used for preparation of a stellate system, by welding arms to a liquid silicone rubber (LSR) core, then cutting them from the stellate for in vitro release study or b) welding conditions identical to those used for preparation of composite arms (i.e., inactive-active-inactive segments), which are welding conditions highly similar to that used in preparation of stellate system. Alternatively, arms can be welded under the same conditions as to an LSR core, but using an aluminum core insert as a placeholder. These scenarios which are comparable to preparation of a stellate dosage form for animal or human dosing, where a drug arm is only partly exposed to IR. In scenario b) full arms can be exposed to IR and pressure without being attached to anything, which represents a "worst case" scenario where an entire arm is exposed to IR (which is not representative of stellate assembly).

After welding, all drug-loaded arms were stored at room temperature for at least overnight to facilitate complete re-crystallization before drug release was evaluated. In vitro release of drug was performed on single ("isolated") arms in individual vials.

Example 30: Effect of PC30 Coating on Drug Release Kinetics for Welded Gastric Residence System with Low Load Memantine/Donepezil Formulation (MD01)

To elucidate the effect of a candidate PCL-based coating on memantine and donepezil drug release in residence systems, drug arms for MD01 were prepared, pan-coated with PC30 (60:40 w/w, Corbion PC17:Corbion PC04+2% Mg stearate by weight of solids) using procedures as described in Example 28, subjected to IR exposure resembling typical assembly, and tested for in vitro drug release as described below. Corbion PC17 is a high molecular weight PCL with an inherent viscosity midpoint of 1.7 dl/g (range 1.5-1.9 dl/g), while Corbion PC04 is a low molecular weight PCL with an inherent viscosity midpoint of 0.4 dl/g (range 0.35 dl/g to 0.43 dl/g).

In Vitro Release: MD01 was evaluated for release in fasted state simulated gastric fluid (FaSSGF) for seven days. Drug arms weighing approximately 25-150 mg were generally used to evaluate in vitro release, most typically arms weighing approximately 100 mg. Carrier polymer-agent formulation was processed into drug arms, pan-coated with PC26 or PC30, and evaluated for drug release kinetics before and after exposure to welding conditions (IR exposure to 4 to 7 mm out of the 14 mm drug arm) according to Example 29. Coat weight gain was approximately 5.2% for PC30-coated arms. The cumulative drug release was plotted and shown in FIG. 57.

Figure 57:
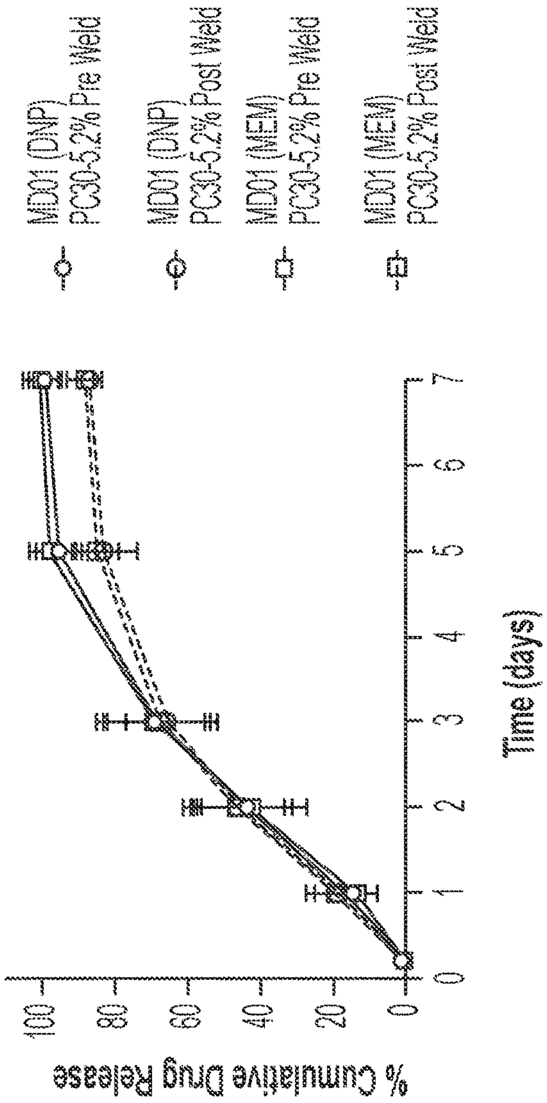
FIG. 57 shows drug release curves for donepezil (DNP) and memantine (MEM) from drug-loaded arms before and after exposure to welding conditions.

As shown in FIG. 57, release of both memantine and donepezil could be modulated and controlled by use of an appropriate release-rate modulating film, as demonstrated by the linear release rate achieved over 7 days by pan-coating MD01 drug arms with PC30 coating solution in ethyl acetate. FIG. 57 further showed that exposure of the coated arms to welding conditions did not affect the linear drug release rate over at least 7 days, indicating that the release modulation afforded by PC30 coating formulation would not be adversely affected by the welding process used in gastric residence system assembly.

Example 31: Effect of PC25 and PC26 Coating on Drug Release Kinetics for Welded Gastric Residence System with Low Load Donepezil Formulation (DNP34)

To elucidate the effect of candidate PCL-based coatings on donepezil drug release in residence systems, drug arms for DNP34 were prepared, pan-coated with either PC25 (50:50 w/w, Corbion PC17: Corbion PC02; +2% Mg stearate by weight of solids), PC26 (75:25 w/w, Corbion PC17: Corbion PC04; +2% Mg stearate by weight of solids), or control coating PC17 (75:25 w/w, Corbion PC17: VA64; +2% Mg stearate by weight of solids) as described in Example 28, subjected to IR exposure resembling typical assembly, and tested for in vitro drug release as described below. Corbion PC17 is a high molecular weight PCL with an intrinsic viscosity midpoint of 1.7 dl/g, while Corbion PC02 and Corbion PC04 are low molecular weight PCL with intrinsic viscosity midpoints of 0.2 dl/g (PC02) and 0.4 dl/g (PC04).

In Vitro Release: DNP34 was evaluated for release in fasted state simulated gastric fluid (FaSSGF) for seven days. Drug arms within a general range of approximately 25-150 mg, typically weighing approximately 100 mg, were used to evaluate in vitro release. Drug arms were pan-coated with PC25, PC26, or PC17 and evaluated for drug release kinetics before and after exposure to welding conditions (IR exposure to 4 to 7 mm out of the 14 mm drug arm) according to Example 29. The coat weight gain was approximately 2.7% for PC25, 2.5% for PC26, and 3.3% for PC17. The cumulative drug release with PC25 or P26 coating was compared to that with PC17 coating, and shown in FIGS. 2 and 3, respectively.

Figure 58:
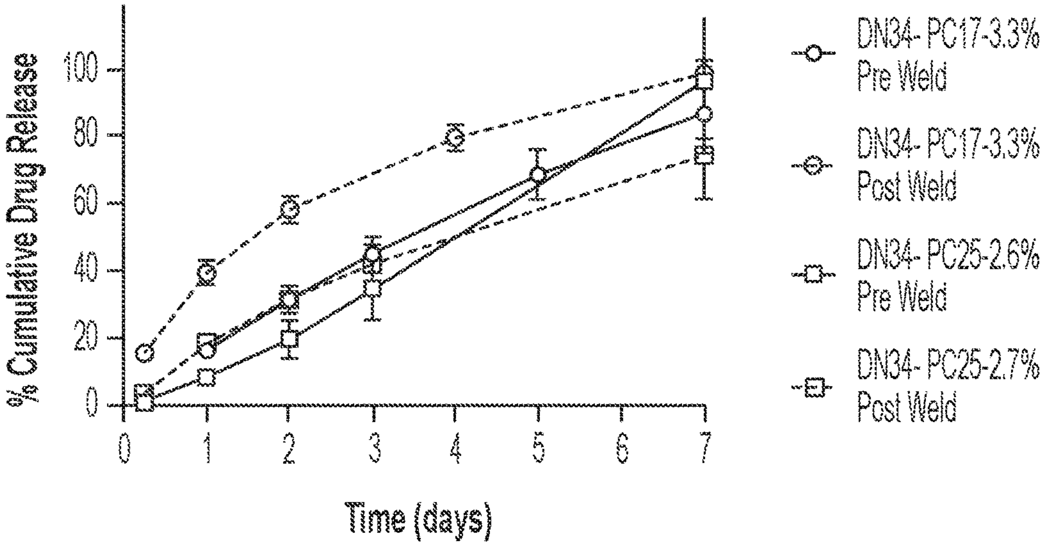
FIG. 58 shows drug release curves for donepezil from donepezil-loaded arms (DN34) before and after exposure to welding conditions.
Figure 59:
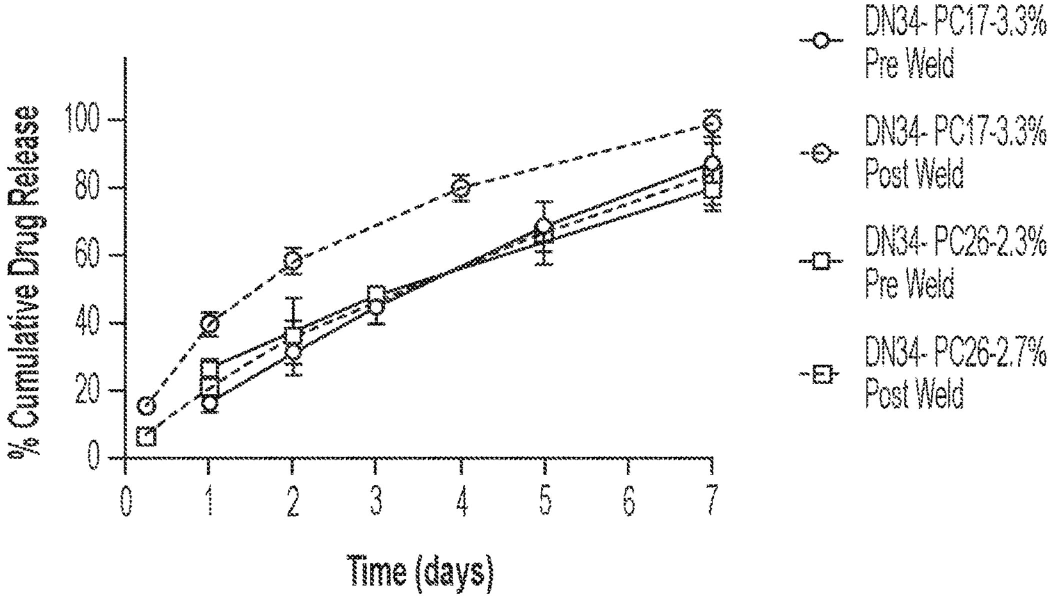
FIG. 59 shows drug release curves for donepezil from donepezil-loaded arms (DN34) before and after exposure to welding conditions.

As shown in FIG. 58 and FIG. 59, by pan-coating DNP34 drug arms with PC17 coating solutions in ethyl acetate, linear release of donepezil could be achieved over 7 days. However, release kinetics shifted significantly when PC17-coated DNP34 drug arms were subjected to welding conditions. In contrast, release of donepezil could be modulated and controlled by use of an appropriate release-rate modulating film, as demonstrated by the linear release rate achieved over 7 days by pan-coating DNP34 drug arms with PC25 or PC26 coating solutions in ethyl acetate (FIG. 58, FIG. 59 respectively), where exposure of the coated arms to welding conditions did not affect the linear drug release rate over at least 7 days, indicating that the release modulation afforded by PC25 or PC26 coating formulations would not be adversely affected by the welding process used in gastric residence system assembly (FIG. 58, FIG. 59, respectively).

The PC17 coating contains the pore-forming agent VA64 (copovidone; vinylpyrrolidone-vinyl acetate copolymer), and is believed to form non-homogeneous coatings. The non-homogeneous coatings are disrupted during heat-assisted assembly or procedures similar to heat exposure during heat-assisted assembly, leading to large differences between the release rate from coated drug arms before heat exposure as compared to coated drug arms after heat exposure. These results demonstrate the advantage of using homogeneous release-rate modulating films, without porogens or other elements that result in a non-homogeneous coating.

Example 32: Effect of PC28 Coating on Drug Release Kinetics for Welded Gastric Residence System with Low Load Memantine Formulation (MEM116)

To elucidate the effect of a candidate PCL-based coatings on memantine drug release in residence systems, drug arms for MEM116 were prepared, pan-coated with either PC28 (50:50 w/w, Corbion PC17: Corbion PC04; +2% Mg stearate by weight of solids), or control coating PC17 (75:25 w/w, Corbion PC17: VA64; +2% Mg stearate by weight of solids) as described in Example 28, subjected to IR exposure resembling typical assembly, and tested for in vitro drug release as described below. Corbion PC17 is a high molecular weight PCL while Corbion PC04 is a low molecular weight PCL.

In Vitro Release: MEM116 was evaluated for release in fasted state simulated gastric fluid (FaSSGF) for seven days. Drug arms within a general range of approximately 25-150 mg, typically weighing approximately 100 mg, were used to evaluate in vitro release. Drug arms were pan-coated with PC17 or PC28, and evaluated for drug release kinetics before and after exposure to welding conditions (IR exposure to 4 to 7 mm out of the 14 mm drug arm) according to Example 29. The coat weight gain was 3% for PC28. The cumulative drug release with PC28 coating was compared to that with PC17 coating, and shown in FIG. 60.

Figure 60:
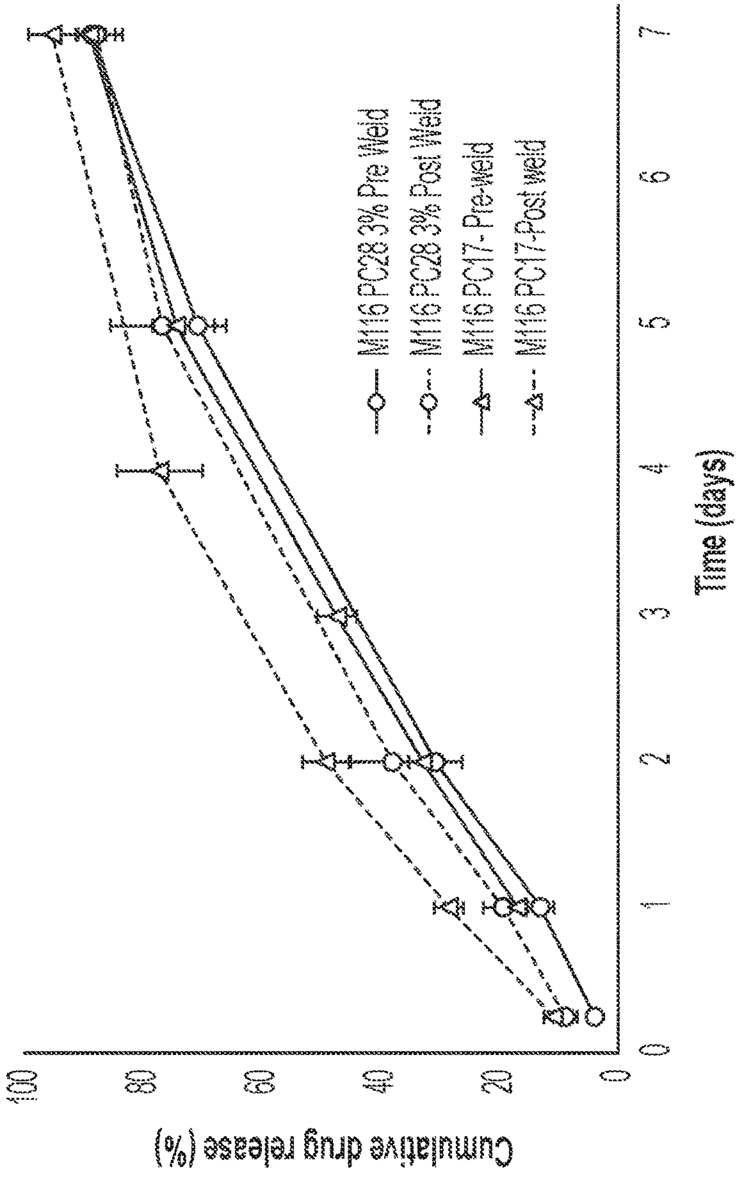
FIG. 60 shows drug release curves for memantine from memantine-loaded arms (M116) before and after exposure to welding conditions.

As shown in FIG. 60, by pan-coating M116 drug arms with PC17 coating solutions in ethyl acetate, linear release of memantine could be achieved over 7 days. However, the release kinetics shifted significantly when PC17-coated M116 drug arms were subjected to welding conditions. In contrast, release of memantine could be modulated and controlled by use of an appropriate release-rate modulating film, as demonstrated by the linear release rate achieved over 7 days by pan-coating MEM116 drug arms with PC28 coating solutions in ethyl acetate (FIG. 60), where exposure of the coated arms to welding conditions had very little effect on the linear drug release rate over at least 7 days, indicating that the release modulation afforded by PC28 coating formulation would not be adversely affected by the welding process used in gastric residence system assembly (FIG. 60).

Example 33: Effect of PC25 and PC28 Coating on Drug Release Kinetics for Welded Gastric Residence System with High Load Memantine Formulation (MEM122)

To elucidate the effect of a candidate PCL-based coating on memantine and donepezil drug release in residence systems, drug arms for MEM122 were prepared, pan-coated with either PC25 (50:50 w/w, Corbion PC17: Corbion PC02; +2% Mg stearate by weight of solids) or PC28 (50:50 w/w, Corbion PC17: Corbion PC04; +2% Mg stearate by weight of solids) using procedures as described in Example 28, subjected to IR exposure resembling typical assembly, and tested for in vitro drug release as described below.

In Vitro Release: MEM122 was evaluated for release in fasted state simulated gastric fluid (FaSSGF) for seven days. Drug arms within a general range of approximately 25-150 mg, typically weighing approximately 100 mg, were used to evaluate in vitro release. Drug arms were pan-coated with PC25 or PC28, and evaluated for drug release kinetics before and after exposure to welding conditions (IR exposure to 4 to 7 mm out of the 14 mm drug arm) according to Example 29. Coating weight gain was approximately 4.5% for both PC25 and PC28. The cumulative drug release was plotted and shown in FIG. 61 and FIG. 62, respectively.

Figure 61:
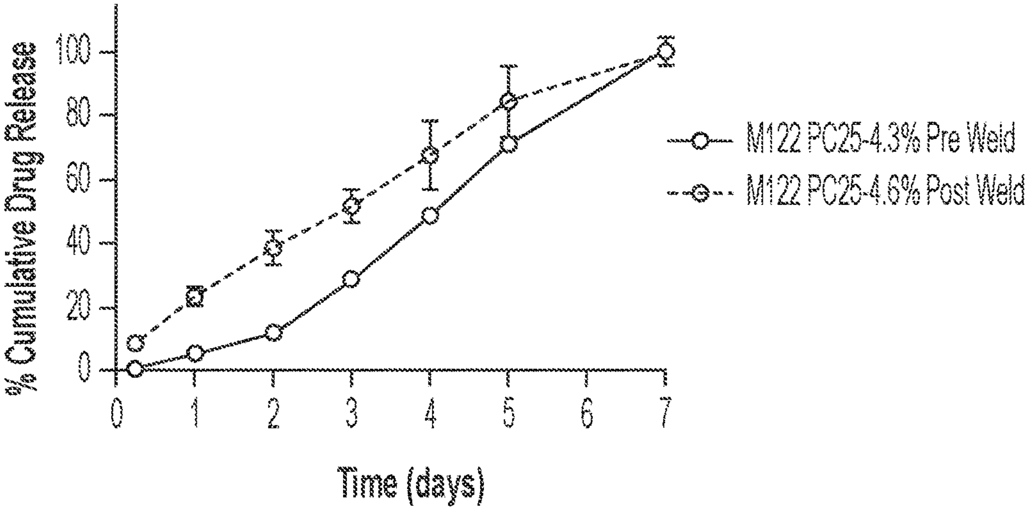
FIG. 61 shows drug release curves for memantine from memantine-loaded arms (M122) before and after exposure to welding conditions.
Figure 62:
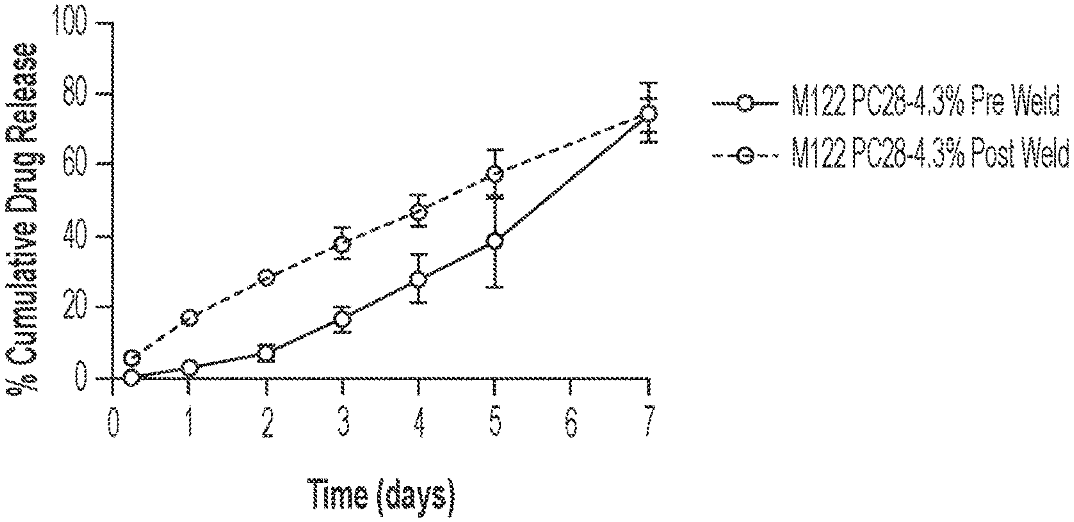
FIG. 62 shows drug release curves for memantine from memantine-loaded arms (M122) before and after exposure to welding conditions.

As shown in FIG. 61 and FIG. 62, release of memantine could be modulated and controlled by use of an appropriate release-rate modulating film.

Example 34: Effect of PC26 Coating on Drug Release Kinetics for Welded Gastric Residence System with Low Load Memantine/Donepezil Formulation (MD01)

To elucidate the effect of a candidate PCL-based coatings on memantine and donepezil drug release in residence systems, drug arms for MD01 were prepared, pan-coated with PC26 (75:25 w/w, Corbion PC17: Corbion PC04; +2% Mg stearate by weight of solids) using procedures as described in Example 28, subjected to IR exposure resembling typical assembly, and tested for in vitro drug release as described below. Corbion PC17 is a high molecular weight PCL while Corbion PC04 is a low molecular weight PCL.

In Vitro Release: MD01 was evaluated for release in fasted state simulated gastric fluid (FaSSGF) for seven days. Drug arms within a general range of approximately 25-150 mg, typically weighing approximately 100 mg, were used to evaluate in vitro release. Drug arms were pan-coated with PC26, and evaluated for drug release kinetics before and after exposure to welding conditions (IR exposure to 4 to 7 mm out of the 14 mm drug arm) according to Example 29. The cumulative drug release was plotted and shown in FIG. 63.

Figure 63:
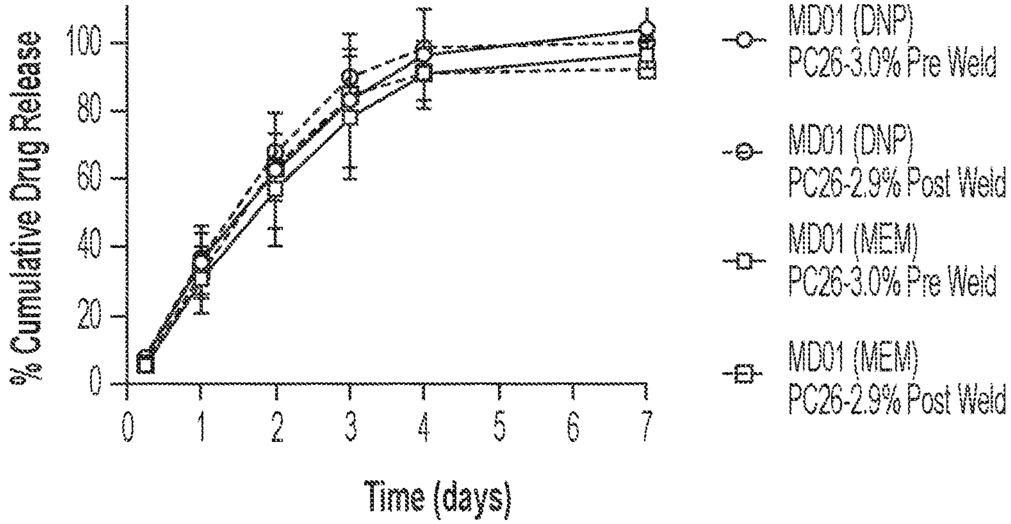
FIG. 63 shows drug release curves for donepezil (DNP) and memantine (MEM) from drug-loaded arms before and after exposure to welding conditions.

As shown in FIG. 63, release of both memantine and donepezil could be modulated and controlled by use of an appropriate release-rate modulating film. FIG. 63 further shows that exposure of the coated arms to welding conditions did not affect the drug release rate over at least 7 days, indicating that the release modulation afforded by PC26 coating formulation would not be adversely affected by the welding process used in gastric residence system assembly.

Example 35: Effect of Incremental Coating with PC26 on Drug Release Kinetics for Welded Gastric Residence System with Low Load Memantine/Donepezil Formulation (MD01)

To elucidate how incremental PC26 coating (75:25 w/w, Corbion PC17: Corbion PC04; +2% Mg stearate by weight of solids) affects memantine and donepezil drug release in residence systems, drug arms for MD01 were prepared, pan-coated with PC26 as described in Example 28 to achieve a coat weight gain of approximately 3%, 3.5%, 5.5% or 7% to 7.5%, subjected to IR exposure resembling that in typical assembly, and subsequently tested for in vitro drug release as described below.

In Vitro Release: MD01 was evaluated for release in fasted state simulated gastric fluid (FaSSGF) for seven days. Drug arms within a general range of approximately 25-150 mg, typically weighing approximately 100 mg, were used to evaluate in vitro release. Drug arms were pan-coated with PC26, and evaluated for drug release kinetics before and after exposure to welding conditions (IR exposure to 4 to 7 mm out of the 14 mm drug arm) according to Example 29. The average coat wait gain for the respective groups of drug arms were as displayed in FIG. 64A and FIG. 64B. The cumulative drug release with PC26 coating at the indicated coat weight gains was compared, and shown in FIG. 64A (memantine release) and FIG. 64B (donepezil release).

Figure 64A:
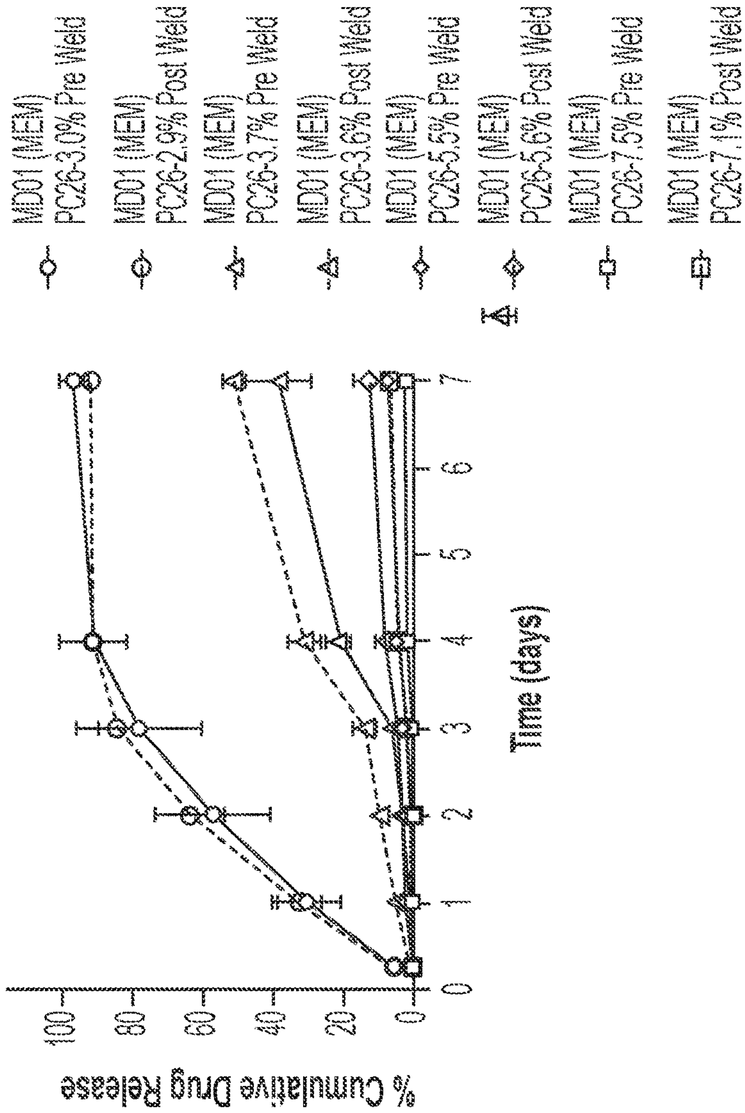
FIG. 64A shows drug release curves for memantine (MEM) from drug-loaded arms before and after exposure to welding conditions.
Figure 64B:
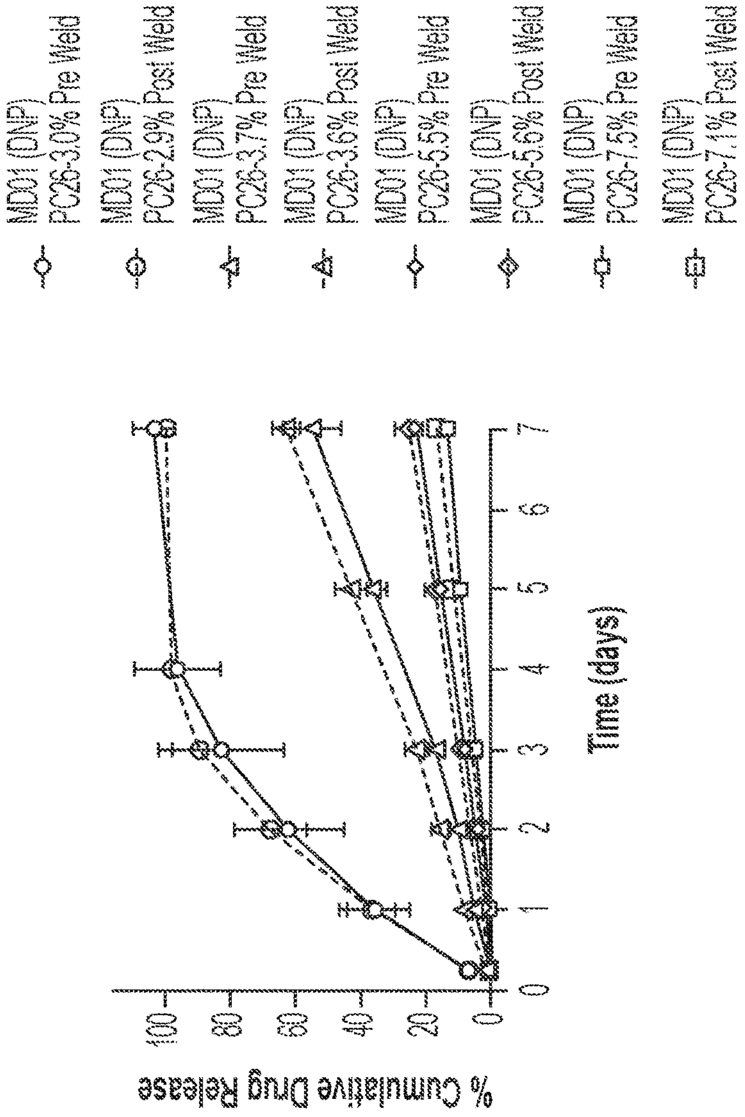
FIG. 64B shows drug release curves for donepezil (DNP) from drug-loaded arms before and after exposure to welding conditions.

As shown in FIG. 64A and FIG. 64B, release of both memantine and donepezil could be modulated and controlled by use of an appropriate release-rate modulating film at a selected coating mass. PC26 coating at 3% mass gain afforded linear release kinetics through day 4, at which point most of the drugs had been released. Coating at 3.5% mass gain afforded a more gradual release of both drugs. Coating at 5.5% and 7% mass gain resulted in linear release kinetics for both memantine and donepezil, but also resulted in relatively low cumulative drug release (FIG. 64A and FIG. 64B, respectively). FIG. 64A and FIG. 64B further showed that heat exposure of the coated arms did not substantially affect the drug release rates over at least 7 days, indicating that the release modulation afforded by PC26 coating formulation (at 3% to 7.5% coat weight gain) would not be adversely affected by the welding process used in gastric residence system assembly.

Example 36: Effect of Incremental Coating with PC27 on Drug Release Kinetics for Welded Gastric Residence System with Low Load Memantine Formulation (MEM116)

To elucidate how incremental coating with PC27 formulation (40:60 w/w, Corbion PC17: Corbion PC02; +2% Mg stearate by weight of solids) affects memantine drug release in residence systems, drug arms for MEM116 was prepared, pan-coated with PC27 as described in Example 28 to achieve a coat weight gain of approximately 2%, 3%, or 4.5%, subjected to IR exposure resembling typical assembly, and subsequently tested for in vitro drug release as described below.

In Vitro Release: MEM116 was evaluated for release in fasted state simulated gastric fluid (FaSSGF) for seven days. Drug arms within a general range of approximately 25-150 mg, typically weighing approximately 100 mg, were used to evaluate in vitro release. Drug arms were pan-coated with PC27, and evaluated for drug release kinetics before and after exposure to welding conditions (IR exposure to 4 to 7 mm out of the 14 mm drug arm) according to Example 29.

Figure 65:
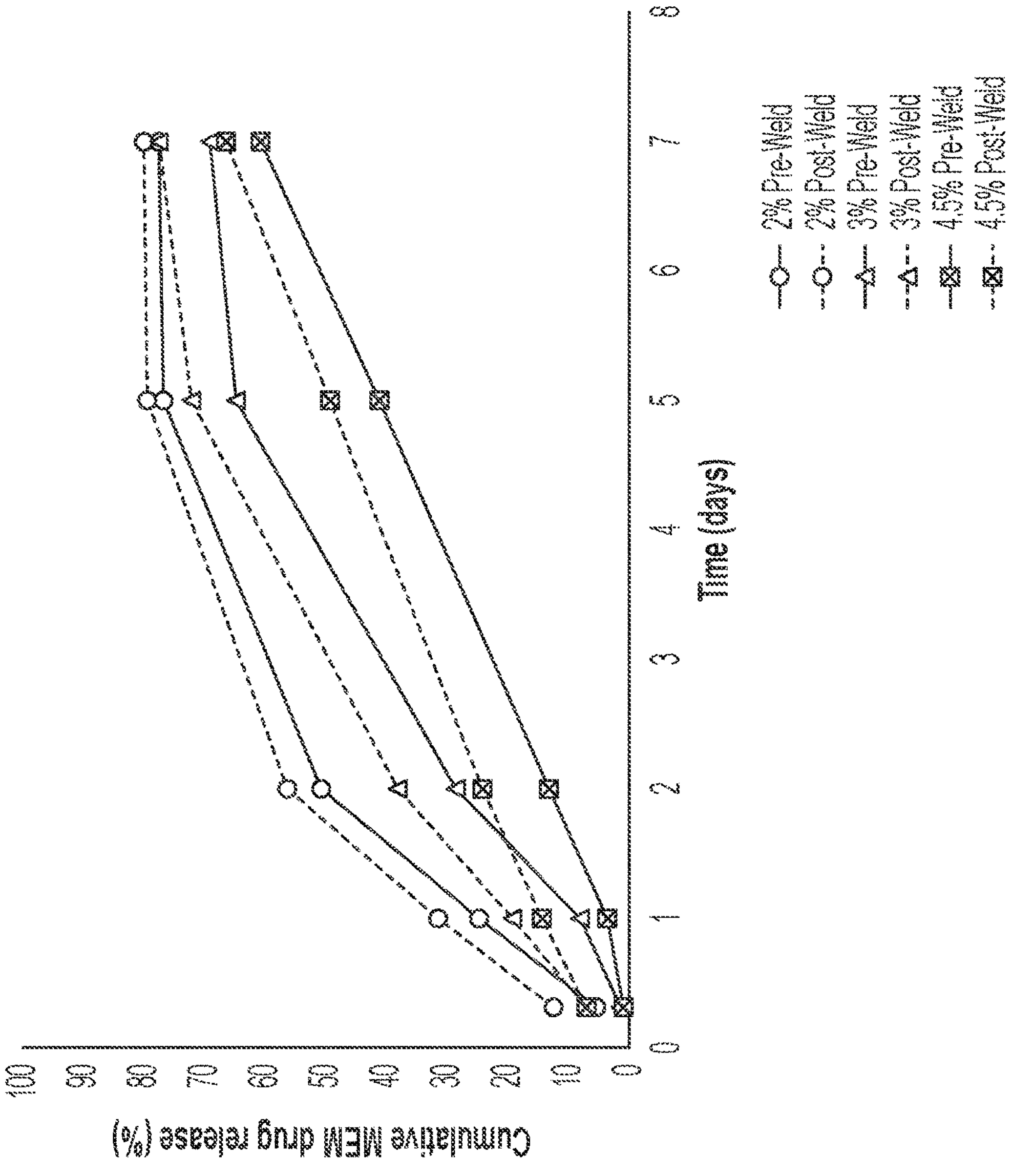
FIG. 65 shows drug release curves for memantine from drug-loaded arms before and after exposure to welding conditions, at different coat weights.

The average coat weight gains for the respective groups of drug arms were as displayed in FIG. 65. The cumulative drug release with PC27 coating at the indicated coat weight gains is shown in FIG. 65.

As shown in FIG. 65, release of memantine could be modulated and controlled by use of an appropriate release-rate modulating film at a selected coating mass. PC27 coating at 4.5% mass gain resulted in linear release kinetics for memantine.

Example 37: Effect of PDL/PDLG5002 A Coating on Drug Release Kinetics for Welded Gastric Residence System with Dapagliflozin Formulation (D138)

To elucidate the effect of a candidate PDL-based coating on dapagliflozin drug release in residence systems, drug formulation rods (monoliths) for D138 were prepared, pan-coated with PDL/PDLG5002 A (1:1 w/w, PDL20: PDLG5002 A; +2% Mg stearate by weight of solids) using procedures as described in Example 28, subjected to IR exposure resembling typical assembly, and tested for in vitro drug release as described below.

In Vitro Release: D138 was evaluated for release in fasted state simulated gastric fluid (FaSSGF) for seven days. Drug arms within a general range of approximately 25-150 mg, typically weighing approximately 100 mg, were used to evaluate in vitro release. Drug arms were prepared (i) with or without coating, and (ii) before and after exposure to welding conditions (IR exposure to 4 mm out of the 10 mm drug arm), and evaluated for drug release kinetics according to Example 29. The cumulative drug release was plotted and shown in FIG. C-66 (UNC-NW mono=uncoated, non-welded monoliths; C-NW mono=coated, non-welded monoliths; UNC-W mono=uncoated, welded monoliths; C-W mono=coated, welded monoliths).

Figure 66:
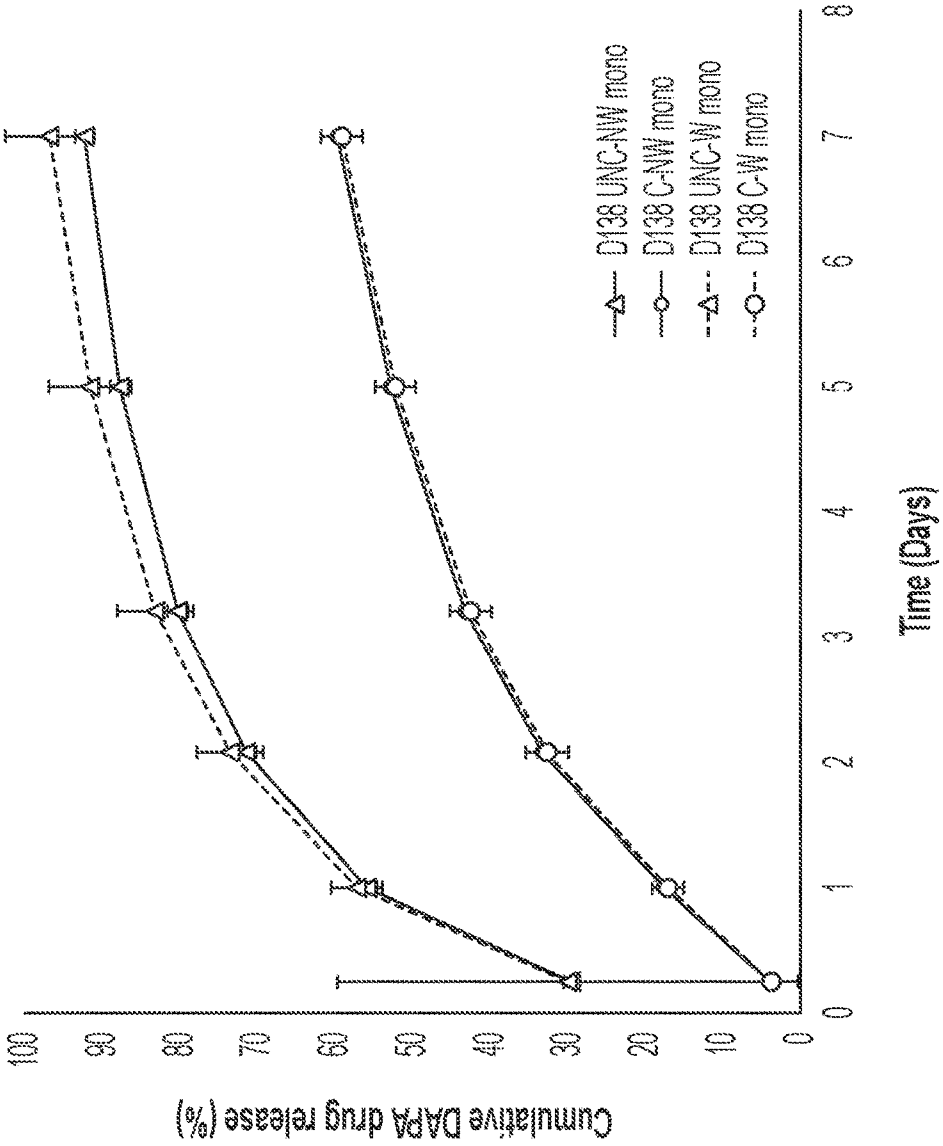
FIG. 66 shows drug release curves for dapagliflozin (DAPA) from coated and uncoated drug-loaded arms before and after exposure to welding conditions, with IR exposure to 4 mm out of 10 mm of the drug-loaded arm.

FIG. 66 further showed that exposure of the coated monoliths to welding conditions did not affect drug release rate over at least 7 days as compared to the coated monoliths not exposed to welding conditions, indicating that the release modulation afforded by the PDL/PDLG5002 A coating formulation would not be adversely affected by the welding process used in gastric residence system assembly.

Example 38: Effect of PDL/PDLG5002 A Coating on Drug Release Kinetics for Welded Gastric Residence System with Dapagliflozin Formulation (D138)

To determine whether PDL/PDLG5002 A coating could withstand excessive exposure to heat and still retain a dapagliflozin drug release profile similar to the pre-exposure drug release profile, drug monoliths for D138 were prepared, pan-coated with PDL/PDLG5002 A (1:1 w/w, PDL20: PDLG5002 A; +2% Mg stearate by weight of solids) using procedures as described in Example 28, subjected to IR exposure exceeding that experienced in a typical assembly process, and tested for in vitro drug release as described below.

In Vitro Release: D138 was evaluated for release in fasted state simulated gastric fluid (FaSSGF) for seven days. Drug arms within a general range of approximately 25-150 mg, typically weighing approximately 100 mg, were used to evaluate in vitro release. Drug arms were prepared, pan-coated with PDL/PDLG5002 A with or without IR exposure exceeding that in welding for typical assembly (IR exposure to 15 mm out of the 15 mm drug arm), and evaluated for drug release kinetics according to Example 29. The cumulative drug release was plotted and shown in FIG. 67.

Figure 67:
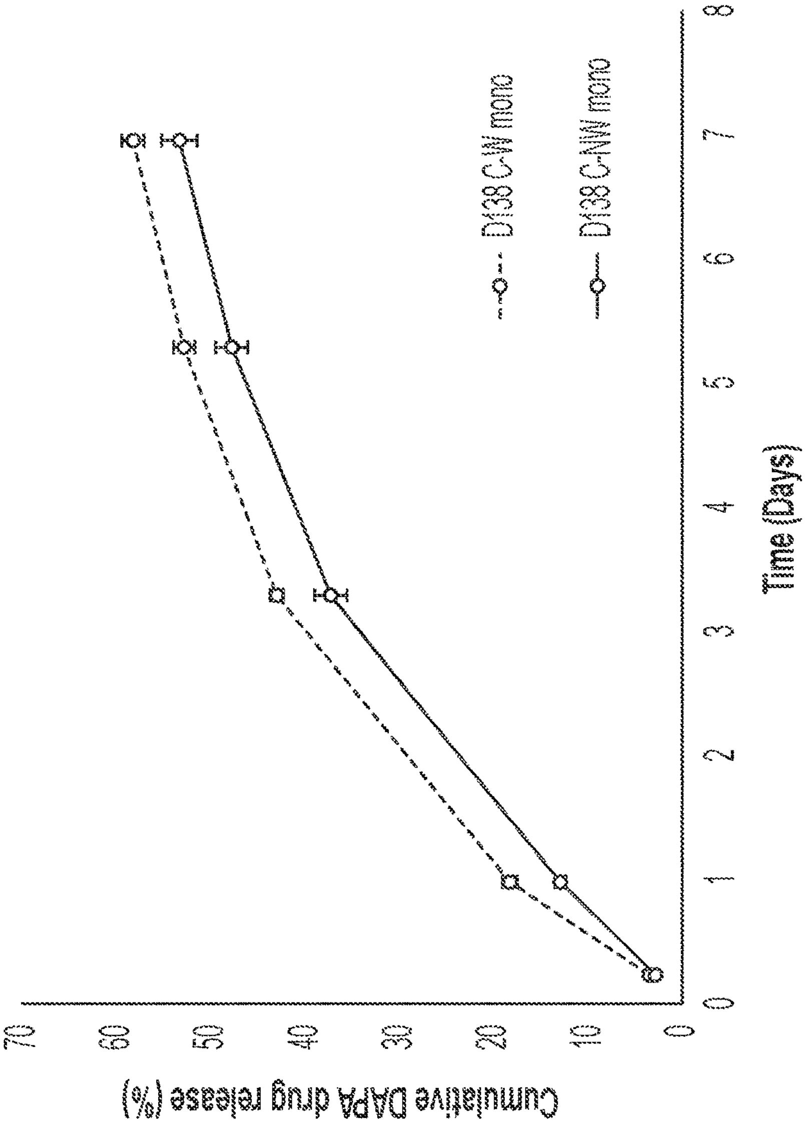
FIG. 67 shows drug release curves for dapagliflozin (DAPA) from coated drug-loaded arms before and after exposure to welding conditions, with IR exposure to 15 mm out of 15 mm of the drug-loaded arm.

FIG. 67 shows that exposure to welding conditions, with IR exposure exceeding that experienced during typical assembly of the coated monoliths, did not substantially affect the drug release rate over at least 7 days, indicating that the release modulation afforded by PDL/PDLG5002 A coating formulation would not be adversely affected by the welding process in a typical gastric residence system assembly process, or an assembly procedure where even more exposure to IR irradiation occurs than the exposure that occurs during the typical assembly process.

Example 39: Effect of PDL/PDLG5002 A Coating on Drug Release Kinetics for Gastric Residence System with Dapagliflozin Formulation (D138) Receiving Overexposure to Welding To determine whether PDL/PDLG5002 A coating could withstand excessive exposure to welding in drug arm assembly and still retain a drug release profile similar to the pre-exposure drug release profile, composite drug arms containing D138 as well as inactive arm-parts were prepared, pan-coated with PDL/PDLG5002 A (1:1 w/w, PDL20: PDLG5002 A; +2% Mg stearate by weight of solids) using procedures as described in Example 28, subjected to IR exposure exceeding that in typical assembly and tested for in vitro drug release as described below.

In Vitro Release: D138 was evaluated for release in fasted state simulated gastric fluid (FaSSGF) for seven days. Drug arms within a general range of approximately 25-150 mg, typically weighing approximately 100 mg, were used to evaluate in vitro release. D138-containing composite drug arms were prepared, pan-coated with PDL/PDLG5002 A with or without IR exposure exceeding that in welding for typical assembly (IR exposure to 15 mm out of the 15 mm drug arm), and evaluated for drug release kinetics according to Example 29. The cumulative drug release was plotted and shown in FIG. 68 (C-W comp=coated, welded composite arm; C-NW comp=coated, non-welded composite arm).

Figure 68:
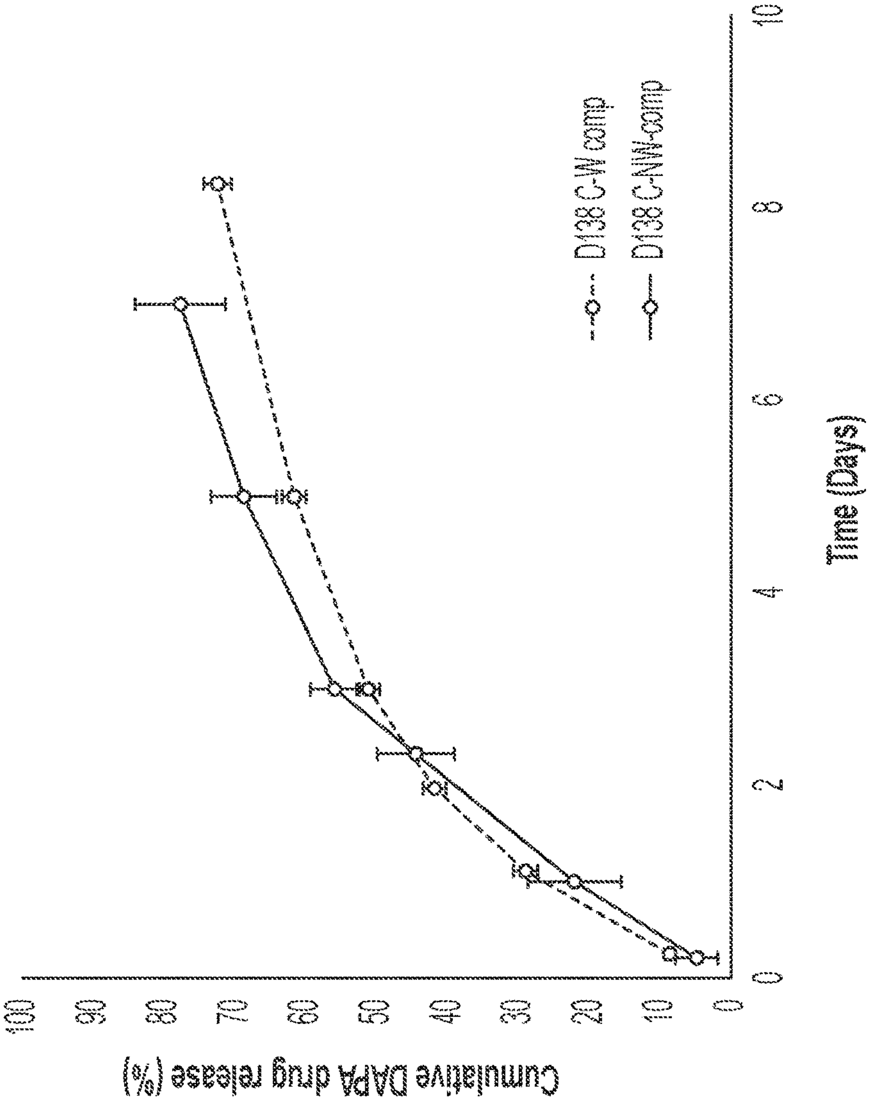
FIG. 68 shows drug release curves for dapagliflozin (DAPA) from coated drug-loaded arms before and after welding, where inactive segments are welded to either end of the drug-loaded arm, with IR exposure to 15 mm out of 15 mm of the arm, including 4 mm out of 4 mm of the drug-containing arm segment.

FIG. 68 shows that exposure to welding conditions, with IR exposure exceeding that in typical assembly of the coated composite arms, did not significantly affect drug release rate, indicating that the release modulation afforded by PDL/PDLG5002 A coating formulation would not be adversely affected by the welding process in a typical gastric residence system, or an assembly procedure where even more exposure to IR irradiation occurs than the exposure that occurs during the typical assembly process.

Example 40: Effect of Filaments on Improving Resistance of Gastric Resident System to Compression Degradable sutures can be used as filaments to enhance gastric residence properties of the gastric residence systems. The degradable sutures can be elastic or inelastic. Further, the degradable sutures can be bioresorbable. In some instances, the degradable sutures were attached to the enteric tips of the stellate arms.

To evaluate the effect of elasticity of the outer filament on the stellate resistance to compression to a size that can pass through the pylorus, stellate gastric residence systems were assembled using filaments of varying elasticity. Polyurethane elastomer (Pellethane tubing) was used as an elastic filament material, and poly(glyclolic acid) sutures were used as inelastic filaments. Filaments were attached to enteric tips of stellate arms via notching, spooling, and rounding. Radial force required to compress the stellates to a diameter of 20 mm was then measured using an iris tester.

Figure 88A:
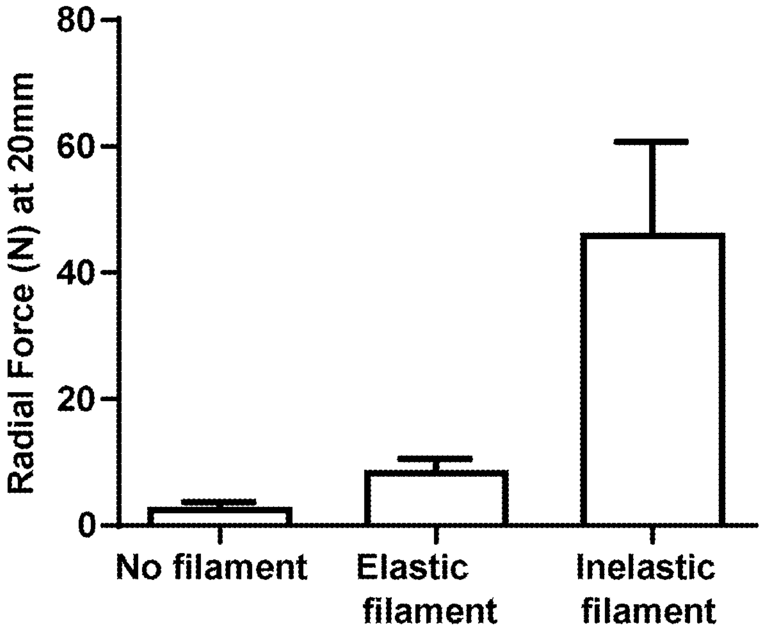
FIG. 88A shows the ability of elastic or inelastic filaments in increasing the resistance of a stellate gastric residence system to compression.

A shown in FIG. 88A, both filament materials increased the stellate's resistance to compression compared to stellates with no filament. In addition, stellates with inelastic webs had greater resistance to compression than stellates with elastic webs.

In addition, adhesion strength of PLGA sutures to stellate arms with enteric tips was evaluated by measuring pullout force after incubation. Stellate gastric residence systems were assembled with enteric tips and with filaments, made from either polyurethane elastomer (Pellethane) or PLGA sutures. The filaments were attached to enteric tips of stellate arms via notching, spooling, and rounding. Adhesion of the filament to stellate arms was measured before and after incubation in fasted state simulated gastric fluid for the indicated periods of time (0 day, 1 day, 4 days or 7 days).

Figure 88B:
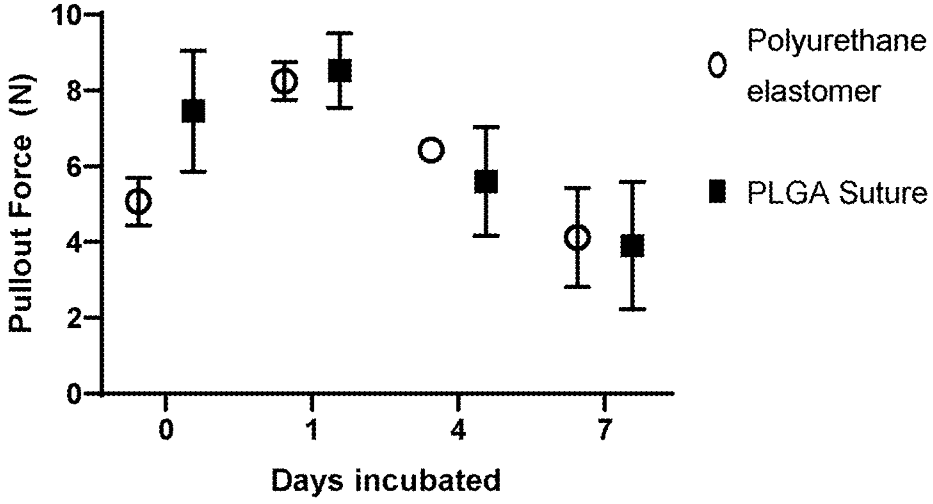
FIG. 88B shows the adhesion strength of degradable sutures to the enteric tips of gastric residence systems over time in a simulated gastric environment.

As shown in FIG. 88B, adhesion of both types of filaments was strongest at early timepoints and reduced at later timepoints, consistent with observed hydration and softening of the enteric tip material. More importantly, both the polyurethane elastomer and PLGA filament materials maintained an adhesion strength above the 1N target for at least 7 days.

Figure 81A:
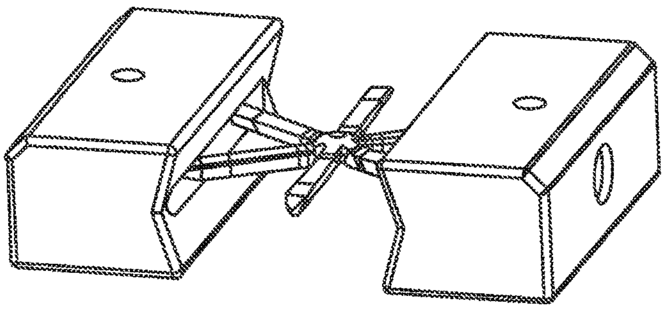
FIG. 81A shows the cyclic incubated nonplanar compressive (CINC) test apparatus holding a stellate gastric residence system.
Figure 81B:
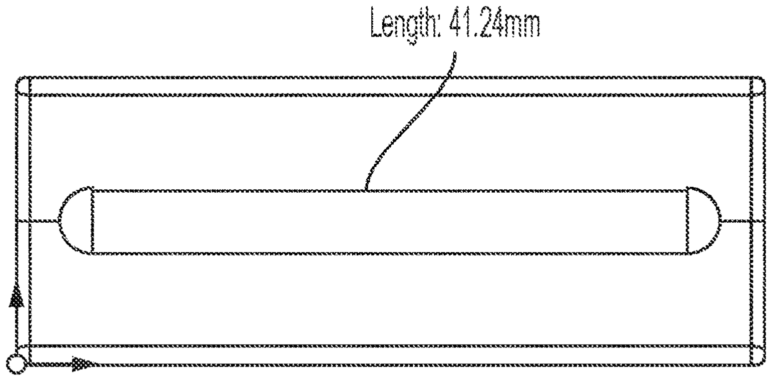
FIG. 81B illustrates an internal side view of the cyclic incubated nonplanar compressive (CINC) test apparatus, showing the slot into which the stellate arms are placed.

Example 41: Mechanical Testing of Disintegrating Matrices Under Various Conditions Cyclic Incubated Nonplanar Compressive (CINC) Testing of Disintegrating Matrices: The cyclic incubated nonplanar compressive (CINC) test apparatus was designed to hold stellates submerged in heated aqueous fluid. While submerged, the stellates are compressed by means of two opposing holders, as shown in FIG. 81A. Each of these holders consists of a channel 41.24 mm in length (see FIG. 81B). Both channels are in the horizontal plane, facing each other. The stellate is placed in the apparatus with the ends of two arms in each holder, supporting the stellate with four opposing arms, leaving two arms unsupported. While the holders are fully open, the stellate is in the same (horizontal) plane as the holder channels. During actuation one holder is moved toward the other, causing the stellate to be compressed. The force of the stellate core holds the stellate in the channel as the holders reciprocate. The tips of the arms are free to move within the channels, allowing the angle between the arms to change. With the exception of the tips of the arms, the stellate is not constrained in the vertical plane.

Stellates were incubated in jars that contained fasted state simulated gastric fluid (FaSSGF) at 37° C. At each timepoint stellates were removed from the jars, blotted dry, then photographed. The CINC test apparatus was filled with FaSSGF and preheated to 37° C. Stellates were placed in the CINC test apparatus and allowed to equilibrate for 10 minutes. Stellates were then run in the CINC test apparatus for 50 cycles. Each cycle consisted of a 1.88 second hold with the holders in the open position, a 0.85 second move to the closed position, a 1.88 second hold in the closed position, then 0.85 seconds to return to the open position. In the open position the deepest point of the channels was 38.64 mm apart, and in the closed position the channels were 21.64 mm apart. Immediately following CINC testing, stellates were blotted dry and photographed. Stellates are observed for signs of failure (bending, weld separation, arm breakage) before and after each compression cycle. Stellates were then returned to the jars of FaSSGF incubated at 37° C. until the next timepoint. Stellates are tested by the same procedure until they fail or become too damaged to be held by the fixture. Failure modes and timing of failures (day, number of compression cycles) are reported.

Table 21 shows the results of representative linkers upon testing in CINC. Qualitative results can rank expected gastric residency.

TABLE 21

| Stellate with: | Day Linker failed in CINC Test | Failure mode |
|---|---|---|
| Timing Linker 1 | 2 | Linker bent irreversibly |
| Timing Linker 2 | 14 | Linker bent irreversibly |
| Timing Linker 3 | 30 | Arm broke at linker interface |

Stress Relaxation "Window" Testing: Stress relaxation of linkers within stellates was evaluated using "window" testing, which measures material deformation and recovery of stellate arms after prolonged compression with incubation biorelevant media.

Figure 82:
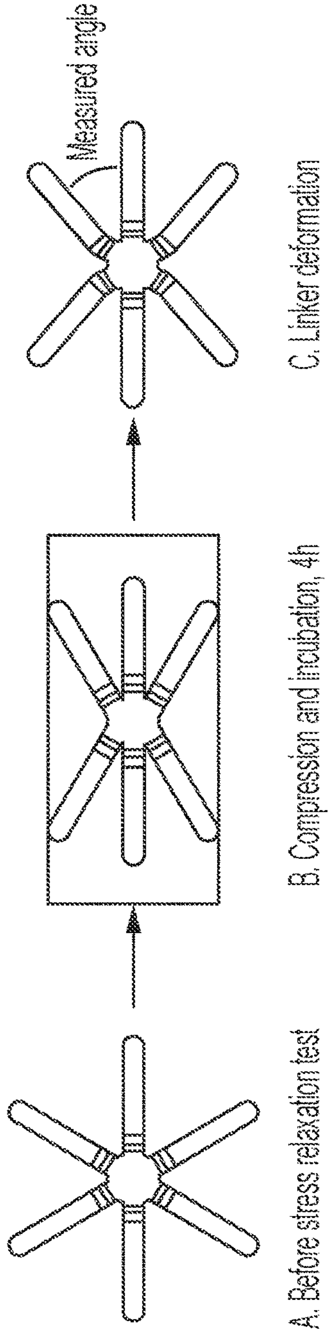
FIG. 82 shows a schematic summarizing the stress relaxation test procedure, indicating the angle that may be measured to track extent of linker deformation. Panel A: before stress relaxation test; Panel B: compression and incubation (for 4 hours); Panel C: measured angle for linker deformation after test.

Stellates assembled with linkers (see FIG. 82, panel A) were incubated in biorelevant media (FaSSGF or FaSSIF) at 37° C. prior to testing. At each time point, stellates were photographed and then manually compressed and placed within a compartment of the plastic "window" fixture, which holds stellates in a compressed position during incubation (as in FIG. 82, panel B). The fixtures containing compressed stellates were placed within a sealed container containing biorelevant media at 37° C. for four hours (see again FIG. 82, panel B). Stellates were then removed from the fixture, photographed, and returned to biorelevant media for incubation (without compression) until the next time point. Arm angle change was measured using image analysis software such as ImageJ and was reported as the angle between a bent arm and the neighboring unstressed arm (see FIG. 82, panel C). Results for three different linkers are shown in FIG. 83A and FIG. 83B.

The window fixture used included an array of compartments that were each 50 mm long×15 mm wide×15 mm deep. The fixture was 3D-printed with a clear photopolymer resin using a Formlabs Form 2 printer but can be made of any durable material.

Figure 83A:
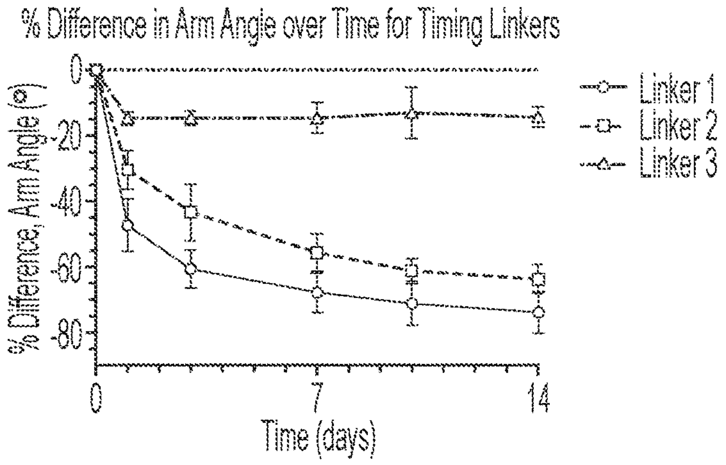
FIG. 83A and FIG. 83B show stress relaxation "window" test results. For three different linkers described in Table 10, FIG. 19A displays the % difference in arm angle post-window test over time in the stellate arms, while FIG. 19B also includes the % difference in arm angle after recovery. This data demonstrates clear distinctions in stellate and thus linker behavior.
Figure 83B:
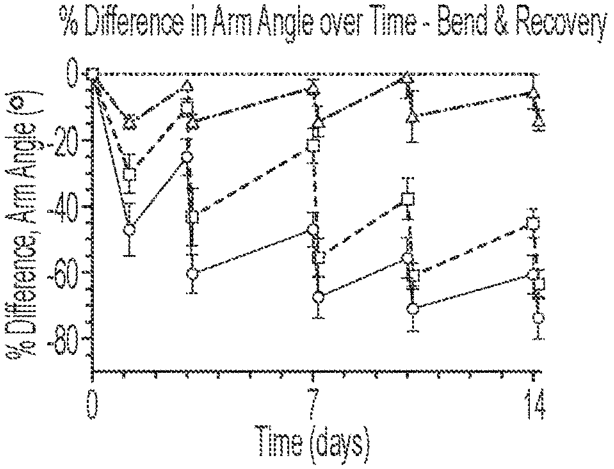

For the three different linkers described in Table 23, FIG. 83A displays the % difference in arm angle post-window test over time in the stellate arms, while FIG. 83B also includes the % difference in arm angle after recovery. This data demonstrates clear distinctions in stellate and thus linker behavior.

Figure 84:
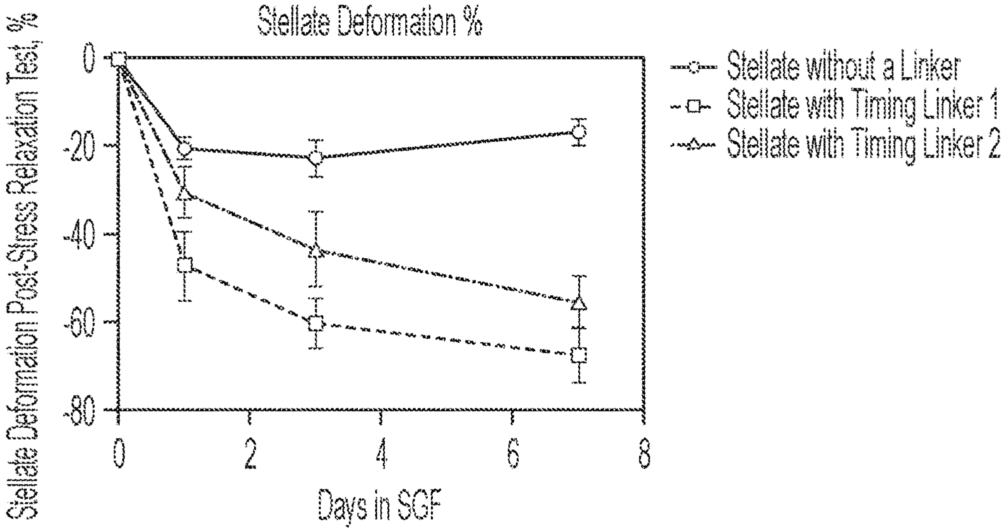
FIG. 84 shows that stellates with a timing linker demonstrate a time-dependent, tunable stress-relaxation behavior. The profile outlined for Timing Linker 1 is associated with a gastric residence of 7.2±3.2 days, and the profile outlined for Timing Linker 2 is associated with a gastric residence of 19.3±3.9 days.
Figure 85:
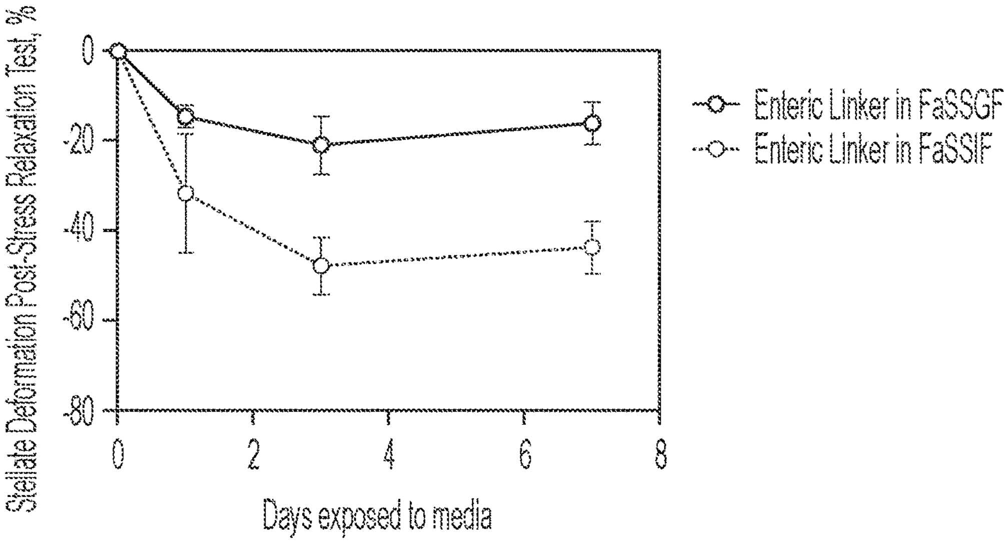
FIG. 85 shows the results of a Stellate Deformation post-Stress Relaxation Test over days in FaSSGF vs. FaSSIF. This data was collected with representative Enteric Linker 1.

Stellate Deformation Post Stress Relaxation: Stellate Deformation Post Stress Relaxation Time over days is shown in FIG. 84. Stellates with a timing linker demonstrate a time-dependent, tunable stress-relaxation behavior. The profile outlined for Timing Linker 1 is associated with a gastric residence of 7.2±3.2 days, and the profile outlined for Timing Linker 2 is associated with a gastric residence of 19.3±3.9 days. FIG. 85 shows a Stellate Deformation Post-Stress Relaxation Test over days in FaSSGF vs. FaSSIF. This data was collected with representative Enteric Linker 1.

Figure 86A:
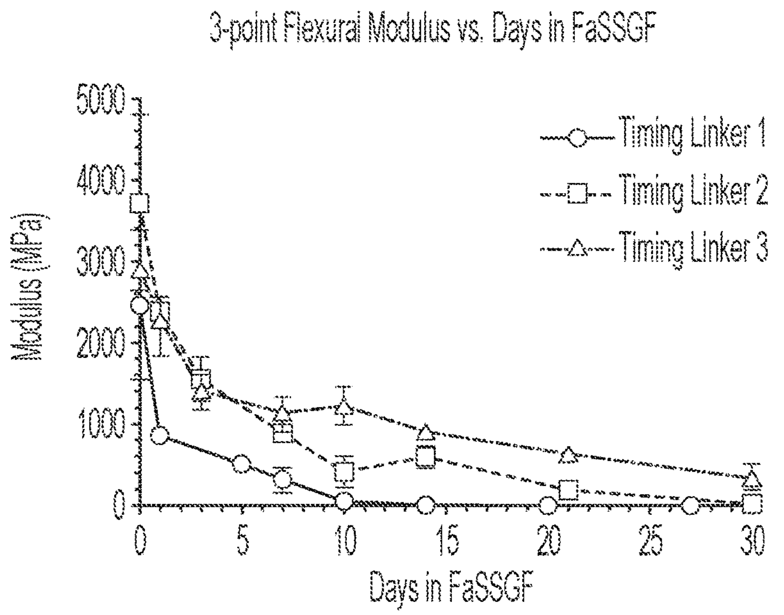
FIG. 86A and FIG. 86B illustrate the decay of representative timing and enteric linkers in relevant media.
Figure 86B:
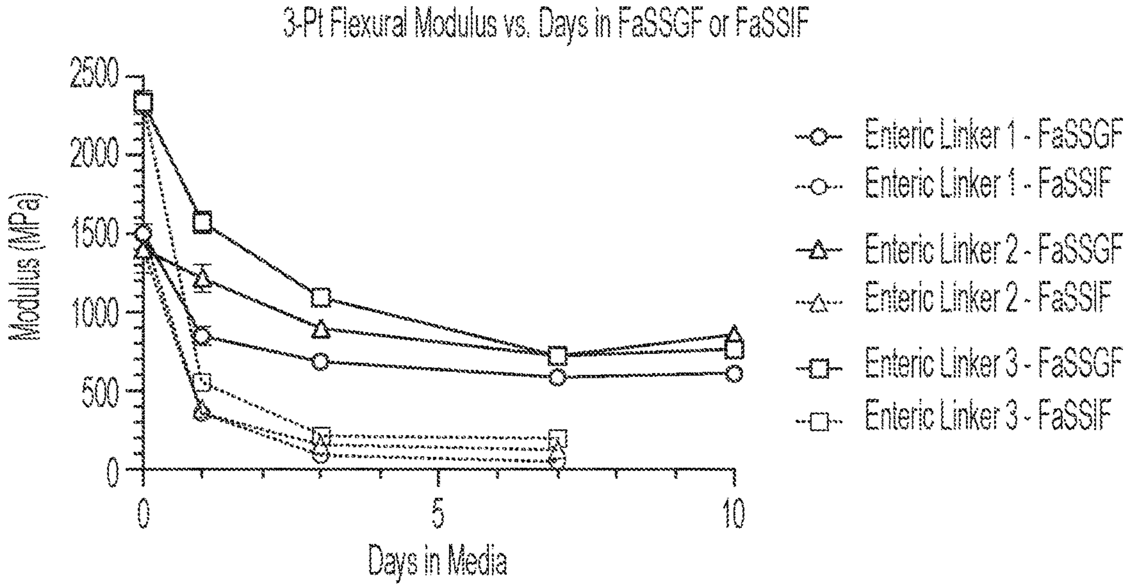

3-Point Bending Test: Tests of 3-Pt of Bending of Enteric and Timing Matrices, which demonstrate the decay of representative timing and enteric linkers in relevant media, are shown in FIG. 86A (timing linkers) and FIG. 86B (enteric linkers).

Table 22 shows a comparison of representative timing linkers in the 3-Pt Bending test, stress relaxation test, CINC test, and their relationship of these parameters with gastric residence. Mechanical tests that capture bending, deformation, and failure of linkers are analyzed together to predict rank order of duration of gastric residence for stellates incorporating different linker formulations.

TABLE 22

| Component | IV [dl/g] | End-cap | DL:G Ratio | Timing Linker 1 | Timing Linker 2 | Timing Linker 3 |
|---|---|---|---|---|---|---|
| PDLG 1 | 0.3 | Acid | 65:35 | 70% | — | — |
| PDLG 2 | 0.3 | Acid | 75:25 | — | 70% | 50% |
| PLDL | 2.4 | Acid | n/a | 30% | 30% | 50% |
| Test | | | | — | — | — |
| Flexural Modulus (3-Point Bend): Days until strength drops below 200MPa | | | | 7-10 | 10-14 | >30 |
| Stress Relaxation Test: Days into the test that stellate is deformed to > 65% | | | | 3-7 | 14-17 | >30 |
| Performance under Cyclic Stress (CINCT): Days until DM failure | | | | 2 | 14 | 30 |
| Gastric residence time in dogs (Days) | | | | 7.2 ± 3.2 | 19.3 ± 3.9 | 25.3 ± 5.2 |

Table 23 shows data for a representative enteric linker in the 3-Pt bending and stress relaxation test. Mechanical tests that capture softening and deformation of enteric linkers in different pH media are used to evaluate pH responsiveness. While all three linkers described maintain stiffness at gastric pH for >10 days, enteric linkers 1 and 2 soften more readily at intestinal pH than enteric linker 3, and therefore may be expected to soften more readily in the intestine.

TABLE 23

| Test | Enteric Linker 1 | Enteric Linker 2 | Enteric Linker 3 |
|---|---|---|---|
| Formulation | 34% PCL<br>64% HPMCAS<br>2% P-407 | 40% PDL 20<br>40% HPMCAS<br>20% TPU | 55% PDL 20<br>40% HPMCAS<br>5% TPU |
| Flexural Modulus (3-Point Bend): Days until strength drops below 200 MPa in FaSSGF | >10 | >10 | >10 |
| Flexural Modulus (3-Point Bend): Days until strength drops below 200 MPa in FaSSIF | 1-3 | 1-3 | 3-7 |

Example 42

The deployment time of gastric residence systems comprising a filament and sleeved on the arm-side of and the deployment time of gastric residence systems comprising a filament and sleeved on the core side was tested. Specifically, some gastric residence systems, such as stellate-shaped gastric residence systems, are configured to compact/fold at the core. Thus, when compacted/folded, the gastric residence system has an arm side (e.g., the side indicated by the arrow in FIG. 87A) and a core side (e.g., the side indicated by the arrow in FIG. 87C). The example described herein tests the deployment time for gastric residence systems that are compacted and sleeved on an arm side and gastric residence systems that are compacted and sleeved on a core side.

Figure 87A:
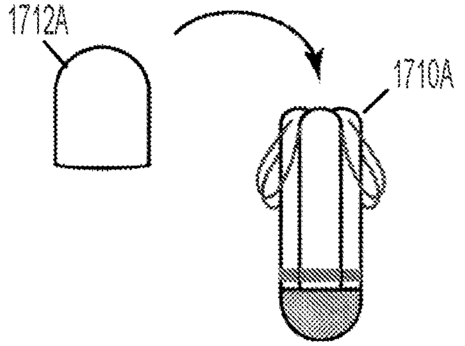
FIG. 87A shows a compacted/folded gastric residence system comprising a filament being sleeved on an arm side, according to some embodiments.
Figure 87B:
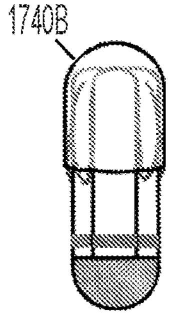
FIG. 87B shows a sleeved compacted/folded gastric residence system comprising a filament, according to some embodiments.
Figure 87C:
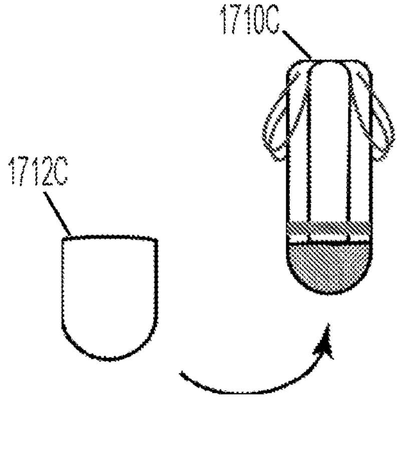
FIG. 87C shows a compacted/folded gastric residence system comprising a filament being sleeved on a core side, according to some embodiments.
Figure 87D:
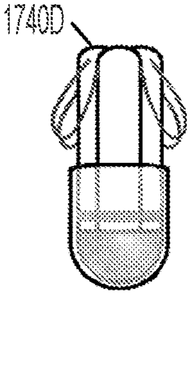
FIG. 87D shows a sleeved compacted/folded gastric residence system comprising a filament, according to some embodiments.

FIGS. 87A-87G shows different sleeving and encapsulation configurations for gastric residence systems comprising a filament. Specifically, FIG. 87A shows a compacted/folded gastric residence system 1710A that is being sleeved on an arm side with sleeve 1712A. Compacted/folded gastric residence system 1710A comprises a filament between each arm of the gastric residence system. Thus, the filament of the gastric residence system is covered by sleeve 1712A. FIG. 87B shows gastric residence system 1710A sleeved with sleeve 1712A on the arm side of the gastric residence system to form sleeved compacted/folded gastric residence system 1740B. FIG. 87C shows a compacted/folded gastric residence system 1710C. However, compacted/folded gastric residence system 1710C is shown being sleeved on the core side of the gastric residence system with sleeve 1712C. FIG. 87D shows compacted/folded gastric residence system 1710D sleeved with sleeve 1712C on the core side of the gastric residence system. Thus, unlike sleeved compacted/folded gastric residence system 1740B of FIG. 87B, the webbing of compacted/folded gastric residence system 1710C is not covered by sleeve 1712C in sleeved compacted/folded gastric residence system 1740D.

Figure 87E:
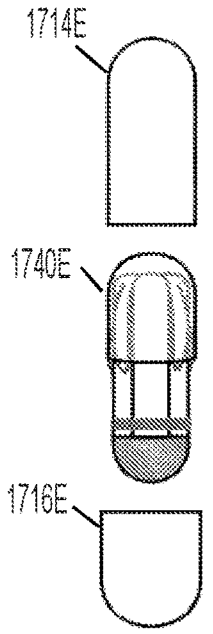
FIG. 87E shows a compacted/folded gastric residence system comprising a filament and sleeved on an arm side being encapsulated with a two-piece capsule, according to some embodiments.
Figure 87F:
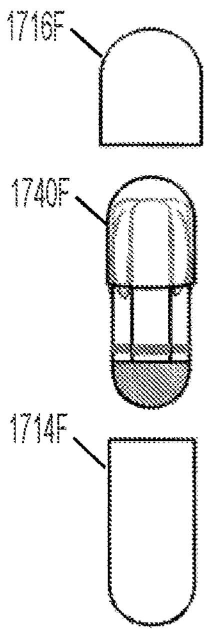
FIG. 87F shows a compacted/folded gastric residence system comprising a filament and sleeved on an arm side being encapsulated with a two-piece capsule, according to some embodiments.

FIGS. 87E and 87F show different encapsulation configurations for sleeved compacted/folded gastric residence systems. Both sleeved compacted/folded gastric residence system 1740E of FIG. 87E and sleeved compacted/folded gastric residence system 1740F of FIG. 87F are sleeved on an arm side of the gastric residence system. Further, FIG. 87E shows sleeved gastric residence system 1740E being encapsulated with a two-piece capsule. The cap of the two-piece capsule, cap 1716E, is shown encapsulating the sleeved gastric residence system on its core side, and the body of the two-piece capsule, body 1714E, is shown encapsulating the sleeved gastric residence system on its sleeved arm side. FIG. 87F shows sleeved gastric residence system 1740F being encapsulating with a two-piece capsule. However, unlike that of FIG. 87E, the sleeved compacted/folded gastric residence system 1740F of FIG. 87F is being encapsulated with the body of the two-piece capsule, body 1714F, encapsulating the core side, and the cap of the two-piece capsule, cap 1716F encapsulating the sleeved arm side of the gastric residence system.

Figure 87G:
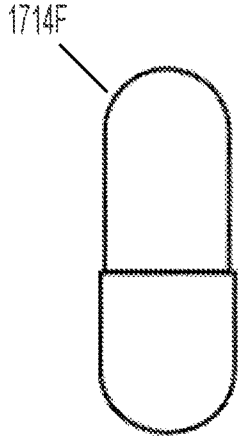
FIG. 87G shows an encapsulated compacted/folded gastric residence system, according to some embodiments.

FIG. 87G shows an encapsulated sleeved compacted/folded gastric residence system 1742G.

The sleeve used in these trials were VCaps Plus HPMC size 0. The sleeved gastric residence systems were then encapsulated in VCaps Plus HPMC capsules. Below, Table 24 shows deployment time data for arm-side sleeved gastric residence systems, and Table 25 shows deployment time data for core-side sleeved gastric residence systems. The data of both Tables 24 and 25 was obtained using the Deployment (Rocker) test at pH 7, described in further detail below.

TABLE 24

Arm-side sleeve deployment results.

| Capsule # | Deployment time (min) |
|---|---|
| 1 | 95.3 |
| 2 | 78.7 |
| 3 | 83.6 |
| 4 | 68.6 |
| 5 | 67.0 |
| Average | 78.6 |
| StDev | 11.6 |

TABLE 25

Core-side sleeve deployment results.

| Capsule # | Deployment time (min) |
|---|---|
| 1 | 87.8 |
| 2 | 130.2 |
| 3 | 107.7 |
| 4 | 81.9 |
| 5 | 55.6 |
| 6 | 71.0 |
| 7 | 101.0 |
| 8 | 84.8 |
| 9 | 85.7 |
| 10 | 59.0 |
| Average | 86.5 |
| StDev | 22.5 |

As shown in Tables 24 and 25, the deployment time of core-side sleeved gastric residence systems and arm-side sleeved gastric residence systems are similar. Although the average deployment time of core-side sleeved gastric residence systems is slightly greater than that of arm-side sleeved gastric residence systems, the difference is not enough to be statistically significant. Thus, the deployment time of arm-side gastric residence systems and the deployment time of core-side gastric residence systems, based on the data of Tables 24 and 25, are arguably the same.

Example 43

Degradable sutures can be used as filaments to enhance gastric residence properties of the gastric residence systems. The degradable sutures can be elastic or inelastic. Further, the degradable sutures can be bioresorbable. In some instances, the degradable sutures were attached to the enteric tips of the stellate arms.

To evaluate the effect of elasticity of the outer filament on the stellate resistance to compression to a size that can pass through the pylorus, stellate gastric residence systems were assembled using filaments of varying elasticity. Polyurethane elastomer (Pellethane tubing) was used as an elastic filament material, and poly(glyclolic acid) sutures were used as inelastic filaments. Filaments were attached to enteric tips of stellate arms via notching, spooling, and rounding. Radial force required to compress the stellates to a diameter of 20 mm was then measured using an iris tester.

A shown in FIG. 88A, both filament materials increased the stellate's resistance to compression compared to stellates with no filament. In addition, stellates with inelastic webs had greater resistance to compression than stellates with elastic webs.

In addition, adhesion strength of PLGA sutures to stellate arms with enteric tips was evaluated by measuring pullout force after incubation. Stellate gastric residence systems were assembled with enteric tips and with filaments, made from either polyurethane elastomer (Pellethane) or PLGA sutures. The filaments were attached to enteric tips of stellate arms via notching, spooling, and rounding. Adhesion of the filament to stellate arms was measured before and after incubation in fasted state simulated gastric fluid for the indicated periods of time (0 day, 1 day, 4 days or 7 days).

As shown in FIG. 88B, adhesion of both types of filaments was strongest at early timepoints and reduced at later timepoints, consistent with observed hydration and softening of the enteric tip material. More importantly, both the polyurethane elastomer and PLGA filament materials maintained an adhesion strength above the 1N target for at least 7 days.

EXEMPLARY EMBODIMENTS

Embodiment 1. A gastric residence system, comprising:

one or more first arms comprising a carrier polymer and an agent, the one or more first arms attached to a second arm through a polymeric linker comprising:

i) poly(lactic-co-glycolide) (PLGA) and at least one additional linker polymer;

ii) poly(lactic-co-glycolide) (PLGA) and polylactic acid (PLA);

iii) poly(lactic-co-glycolide) (PLGA) and polycaprolactone (PCL);

iv) poly(lactic-co-glycolide) (PLGA) and a thermoplastic polyurethane (TPU);

v) a thermoplastic polyurethane (TPU) and an enteric polymer;

vi) poly(lactic-co-glycolide) (PLGA) and an enteric polymer;

vii) polylactic acid (PLA) and a plasticizer;

viii) polycaprolactone (PCL) and a plasticizer;

ix) a thermoplastic polyurethane (TPU) and a plasticizer; or x) a pH-independent degradable polymer and an enteric polymer;

wherein the polymeric linker loses 20% or more of its flexural modulus or breaks after incubation in an aqueous solution at pH 1.6 for 21 days at 37° C.;

wherein the gastric residence system is retained in the stomach for a period of at least 24 hours; and wherein the arm comprising a carrier polymer-agent further comprises a release rate-modulating film coated on the arm;

wherein the release rate-modulating film comprises:

a) poly-D,L-lactide (PDL) and poly-D,L-lactide/glycolide (PDLG);

b) high molecular weight polycaprolactone (PCL-HMW) and low molecular weight polycaprolactone (PCL-LMW);

c) poly-D,L-lactide (PDL);

d) poly-D,L-lactide (PDL) and polyethylene glycol-polypropylene glycol-polyethylene glycol (PEG-PPG-PEG) block copolymer;

e) poly-D,L-lactide (PDL) and polyethylene glycol (PEG);

f) poly-D,L-lactide (PDL), polyethylene glycol-polypropylene glycol-polyethylene glycol (PEG-PPG-PEG) block copolymer, and polyethylene glycol (PEG); or g) poly-D-lactide-polycaprolactone co-polymer (PDL-PCL copolymer).

Embodiment 2. The gastric residence system of embodiment 1, comprising a core; a plurality of arms connected to the core at a proximal end through a plurality of linker components, one linker component of the plurality of the plurality of linker components corresponding to each arm of the plurality of arms, and the plurality of arms extending radially from the proximal end; and a filament circumferentially connecting each arm of the plurality of arms.

Embodiment 3. The gastric residence system of embodiment 1 or 2, comprising one or more arms extending radially, wherein the one or more arms comprises a first portion comprising a first polymer composition and a second portion comprising a second polymer composition, wherein the first portion has a stiffness greater than a stiffness of the second portion, as measured using a 3-point bending test per ASTM D790.

Embodiment 4. A gastric residence system comprising:

a core; a plurality of arms connected to the core at a proximal end through a plurality of linker components, one linker component of the plurality of the plurality of linker components corresponding to each arm of the plurality of arms, and the plurality of arms extending radially from the proximal end; and a filament circumferentially connecting each arm of the plurality of arms;

wherein at least one linker component comprises:

i) poly(lactic-co-glycolide) (PLGA) and at least one additional linker polymer;

ii) poly(lactic-co-glycolide) (PLGA) and polylactic acid (PLA);

iii) poly(lactic-co-glycolide) (PLGA) and polycaprolactone (PCL);

iv) poly(lactic-co-glycolide) (PLGA) and a thermoplastic polyurethane (TPU);

v) a thermoplastic polyurethane (TPU) and an enteric polymer;

vi) poly(lactic-co-glycolide) (PLGA) and an enteric polymer;

vii) polylactic acid (PLA) and a plasticizer;

viii) polycaprolactone (PCL) and a plasticizer;

ix) a thermoplastic polyurethane (TPU) and a plasticizer; or x) a pH-independent degradable polymer and an enteric polymer;

wherein the at least one linker loses 80% or more of its flexural modulus or breaks after incubation in an aqueous solution at pH 1.6 for 14 days at 37° C.

Embodiment 5. The gastric residence system of embodiment 4, wherein the arm comprising a carrier polymer-agent further comprises a release rate-modulating film coated on the arm;

wherein the release rate-modulating film comprises:

a) poly-D,L-lactide (PDL) and poly-D,L-lactide/glycolide (PDLG);

b) high molecular weight polycaprolactone (PCL-HMW) and low molecular weight polycaprolactone (PCL-LMW);

c) poly-D,L-lactide (PDL);

d) poly-D,L-lactide (PDL) and polyethylene glycol-polypropylene glycol-polyethylene glycol (PEG-PPG-PEG) block copolymer;

e) poly-D,L-lactide (PDL) and polyethylene glycol (PEG);

f) poly-D,L-lactide (PDL), polyethylene glycol-polypropylene glycol-polyethylene glycol (PEG-PPG-PEG) block copolymer, and polyethylene glycol (PEG); or g) poly-D-lactide-polycaprolactone co-polymer (PDL-PCL copolymer).

Embodiment 6. The gastric residence system of embodiment 4 or 5, comprising one or more arms extending radially, wherein the one or more arms comprises a first portion comprising a first polymer composition and a second portion comprising a second polymer composition, wherein the first portion has a stiffness greater than a stiffness of the second portion, as measured using a 3-point bending test per ASTM D790.

Embodiment 7. A gastric residence system comprising:

a core; a plurality of arms connected to the core at a proximal end through a plurality of linker components, one linker component of the plurality of linker components corresponding to each arm of the plurality of arms, and the plurality of arms extending radially from the proximal end; and a filament circumferentially connecting each arm of the plurality of arms;

wherein the arms comprise a carrier polymer-agent segment, wherein a release rate-modulating film is coated on the carrier polymer-agent segment;

wherein the release rate-modulating film comprises:

a) poly-D,L-lactide (PDL) and poly-D,L-lactide/glycolide (PDLG);

b) high molecular weight polycaprolactone (PCL-HMW) and low molecular weight polycaprolactone (PCL-LMW);

c) poly-D,L-lactide (PDL);

d) poly-D,L-lactide (PDL) and polyethylene glycol-polypropylene glycol-polyethylene glycol (PEG-PPG-PEG) block copolymer;

e) poly-D,L-lactide (PDL) and polyethylene glycol (PEG);

f) poly-D,L-lactide (PDL), polyethylene glycol-polypropylene glycol-polyethylene glycol (PEG-PPG-PEG) block copolymer, and polyethylene glycol (PEG); or g) poly-D-lactide-polycaprolactone co-polymer (PDL-PCL copolymer).

Embodiment 8. The gastric residence system of embodiment 7, wherein at least one linker component comprises:

i) poly(lactic-co-glycolide) (PLGA) and at least one additional linker polymer;

ii) poly(lactic-co-glycolide) (PLGA) and polylactic acid (PLA);

iii) poly(lactic-co-glycolide) (PLGA) and polycaprolactone (PCL);

iv) poly(lactic-co-glycolide) (PLGA) and a thermoplastic polyurethane (TPU);

v) a thermoplastic polyurethane (TPU) and an enteric polymer;

vi) poly(lactic-co-glycolide) (PLGA) and an enteric polymer;

vii) polylactic acid (PLA) and a plasticizer;

viii) polycaprolactone (PCL) and a plasticizer;

ix) a thermoplastic polyurethane (TPU) and a plasticizer; or x) a pH-independent degradable polymer and an enteric polymer;

wherein the at least one linker loses 80% or more of its flexural modulus or breaks after incubation in an aqueous solution at pH 1.6 for 14 days at 37° C.

Embodiment 9. The gastric residence system of embodiment 7 or 8, comprising one or more arms extending radially, wherein the one or more arms comprises a first portion comprising a first polymer composition and a second portion comprising a second polymer composition, wherein the first portion has a stiffness greater than a stiffness of the second portion, as measured using a 3-point bending test per ASTM D790.

Embodiment 10. A gastric residence system comprising:

one or more arms extending radially, wherein the one or more arms comprises a first portion comprising a first polymer composition and a second portion comprising a second polymer composition, wherein the first portion has a stiffness greater than a stiffness of the second portion, as measured using a 3-point bending test per ASTM D790;

wherein the arms further comprise a carrier polymer-agent segment, wherein a release rate-modulating film is coated on the carrier polymer-agent segment;

wherein the release rate-modulating film comprises:

a) poly-D,L-lactide (PDL) and poly-D,L-lactide/glycolide (PDLG);

b) high molecular weight polycaprolactone (PCL-HMW) and low molecular weight polycaprolactone (PCL-LMW);

c) poly-D,L-lactide (PDL);

d) poly-D,L-lactide (PDL) and polyethylene glycol-polypropylene glycol-polyethylene glycol (PEG-PPG-PEG) block copolymer;

e) poly-D,L-lactide (PDL) and polyethylene glycol (PEG);

f) poly-D,L-lactide (PDL), polyethylene glycol-polypropylene glycol-polyethylene glycol (PEG-PPG-PEG) block copolymer, and polyethylene glycol (PEG); or g) poly-D-lactide-polycaprolactone co-polymer (PDL-PCL copolymer).

Embodiment 11. The gastric residence system of embodiment 10, wherein at least one linker component comprises:

i) poly(lactic-co-glycolide) (PLGA) and at least one additional linker polymer;

ii) poly(lactic-co-glycolide) (PLGA) and polylactic acid (PLA);

iii) poly(lactic-co-glycolide) (PLGA) and polycaprolactone (PCL);

iv) poly(lactic-co-glycolide) (PLGA) and a thermoplastic polyurethane (TPU);

v) a thermoplastic polyurethane (TPU) and an enteric polymer;

vi) poly(lactic-co-glycolide) (PLGA) and an enteric polymer;

vii) polylactic acid (PLA) and a plasticizer;

viii) polycaprolactone (PCL) and a plasticizer;

ix) a thermoplastic polyurethane (TPU) and a plasticizer; or x) a pH-independent degradable polymer and an enteric polymer;

wherein the at least one linker loses 80% or more of its flexural modulus or breaks after incubation in an aqueous solution at pH 1.6 for 14 days at 37° C.

Embodiment 12. The gastric residence system of embodiment 10 or 11, comprising a core; a plurality of arms connected to the core at a proximal end through a plurality of linker components, one linker component of the plurality of the plurality of linker components corresponding to each arm of the plurality of arms, and the plurality of arms extending radially from the proximal end; and a filament circumferentially connecting each arm of the plurality of arms.

Embodiment 13. A gastric residence system comprising:

a plurality of arms extending radially, wherein the plurality of arms comprises a first portion comprising a first polymer composition and a second portion comprising a second polymer composition, wherein the first portion has a stiffness greater than a stiffness of the second portion, as measured using a 3-point bending test per ASTM D790;

wherein the plurality of arms are connected to a core at a proximal end through a plurality of linker components, one linker component of the plurality of linker components corresponding to each arm of the plurality of arms, and the plurality of arms extending radially from the proximal end; and a filament circumferentially connecting each arm of the plurality of arms.

Embodiment 14. The gastric residence system of embodiment 13, wherein at least one linker component comprises:

i) poly(lactic-co-glycolide) (PLGA) and at least one additional linker polymer;

ii) poly(lactic-co-glycolide) (PLGA) and polylactic acid (PLA);

iii) poly(lactic-co-glycolide) (PLGA) and polycaprolactone (PCL);

iv) poly(lactic-co-glycolide) (PLGA) and a thermoplastic polyurethane (TPU);

v) a thermoplastic polyurethane (TPU) and an enteric polymer;

vi) poly(lactic-co-glycolide) (PLGA) and an enteric polymer;

vii) polylactic acid (PLA) and a plasticizer;

viii) polycaprolactone (PCL) and a plasticizer;

ix) a thermoplastic polyurethane (TPU) and a plasticizer; or x) a pH-independent degradable polymer and an enteric polymer;

wherein the at least one linker loses 80% or more of its flexural modulus or breaks after incubation in an aqueous solution at pH 1.6 for 14 days at 37° C.

Embodiment 15. The gastric residence system of embodiment 13 or 14, wherein the arm comprising a carrier polymer-agent further comprises a release rate-modulating film coated on the arm;

wherein the release rate-modulating film comprises:

a) poly-D,L-lactide (PDL) and poly-D,L-lactide/glycolide (PDLG);

b) high molecular weight polycaprolactone (PCL-HMW) and low molecular weight polycaprolactone (PCL-LMW);

c) poly-D,L-lactide (PDL);

d) poly-D,L-lactide (PDL) and polyethylene glycol-polypropylene glycol-polyethylene glycol (PEG-PPG-PEG) block copolymer;

e) poly-D,L-lactide (PDL) and polyethylene glycol (PEG);

f) poly-D,L-lactide (PDL), polyethylene glycol-polypropylene glycol-polyethylene glycol (PEG-PPG-PEG) block copolymer, and polyethylene glycol (PEG); or g) poly-D-lactide-polycaprolactone co-polymer (PDL-PCL copolymer).

Embodiment 16. A gastric residence system comprising:

one or more arms extending radially, wherein the one or more arms comprises a first portion comprising a first polymer composition and a second portion comprising a second polymer composition, wherein the first portion has a stiffness greater than a stiffness of the second portion, as measured using a 3-point bending test per ASTM D790;

wherein the arms further comprise at least one linker, the at least one linker comprising:

i) poly(lactic-co-glycolide) (PLGA) and at least one additional linker polymer;

ii) poly(lactic-co-glycolide) (PLGA) and polylactic acid (PLA);

iii) poly(lactic-co-glycolide) (PLGA) and polycaprolactone (PCL);

iv) poly(lactic-co-glycolide) (PLGA) and a thermoplastic polyurethane (TPU);

v) a thermoplastic polyurethane (TPU) and an enteric polymer;

vi) poly(lactic-co-glycolide) (PLGA) and an enteric polymer;

vii) polylactic acid (PLA) and a plasticizer;

viii) polycaprolactone (PCL) and a plasticizer;

ix) a thermoplastic polyurethane (TPU) and a plasticizer; or x) a pH-independent degradable polymer and an enteric polymer;

wherein the at least one linker loses 80% or more of its flexural modulus or breaks after incubation in an aqueous solution at pH 1.6 for 14 days at 37° C.

Embodiment 17. The gastric residence system of embodiment 16, wherein the arm comprising a carrier polymer-agent further comprises a release rate-modulating film coated on the arm;

wherein the release rate-modulating film comprises:

a) poly-D,L-lactide (PDL) and poly-D,L-lactide/glycolide (PDLG);

b) high molecular weight polycaprolactone (PCL-HMW) and low molecular weight polycaprolactone (PCL-LMW);

c) poly-D,L-lactide (PDL);

d) poly-D,L-lactide (PDL) and polyethylene glycol-polypropylene glycol-polyethylene glycol (PEG-PPG-PEG) block copolymer;

e) poly-D,L-lactide (PDL) and polyethylene glycol (PEG);

f) poly-D,L-lactide (PDL), polyethylene glycol-polypropylene glycol-polyethylene glycol (PEG-PPG-PEG) block copolymer, and polyethylene glycol (PEG); or g) poly-D-lactide-polycaprolactone co-polymer (PDL-PCL copolymer).

Embodiment 18. The gastric residence system of embodiment 16 or 17, comprising a core; a plurality of arms connected to the core at a proximal end through a plurality of linker components, one linker component of the plurality of the plurality of linker components corresponding to each arm of the plurality of arms, and the plurality of arms extending radially from the proximal end; and a filament circumferentially connecting each arm of the plurality of arms.

Embodiment 19. A gastric residence system, comprising:

a plurality of first arms comprising a carrier polymer and an agent, the plurality of first arms attached to second arms through a polymeric linker comprising:

i) poly(lactic-co-glycolide) (PLGA) and at least one additional linker polymer;

ii) poly(lactic-co-glycolide) (PLGA) and polylactic acid (PLA);

iii) poly(lactic-co-glycolide) (PLGA) and polycaprolactone (PCL);

iv) poly(lactic-co-glycolide) (PLGA) and a thermoplastic polyurethane (TPU);

v) a thermoplastic polyurethane (TPU) and an enteric polymer;

vi) poly(lactic-co-glycolide) (PLGA) and an enteric polymer;

vii) polylactic acid (PLA) and a plasticizer;

viii) polycaprolactone (PCL) and a plasticizer;

ix) a thermoplastic polyurethane (TPU) and a plasticizer; or x) a pH-independent degradable polymer and an enteric polymer;

wherein the polymeric linker loses 80% or more of its flexural modulus or breaks after incubation in an aqueous solution at pH 1.6 for 14 days at 37° C.;

wherein the gastric residence system is retained in the stomach for a period of at least 24 hours;

and wherein the plurality of arms comprising a carrier polymer-agent further comprise a release rate-modulating film coated on the arms;

wherein the release rate-modulating film comprises:

a) poly-D,L-lactide (PDL) and poly-D,L-lactide/glycolide (PDLG);

b) high molecular weight polycaprolactone (PCL-HMW) and low molecular weight polycaprolactone (PCL-LMW);

c) poly-D,L-lactide (PDL);

d) poly-D,L-lactide (PDL) and polyethylene glycol-polypropylene glycol-polyethylene glycol (PEG-PPG-PEG) block copolymer;

e) poly-D,L-lactide (PDL) and polyethylene glycol (PEG);

f) poly-D,L-lactide (PDL), polyethylene glycol-polypropylene glycol-polyethylene glycol (PEG-PPG-PEG) block copolymer, and polyethylene glycol (PEG); or g) poly-D-lactide-polycaprolactone co-polymer (PDL-PCL copolymer);

and wherein the plurality of arms further comprises a first portion comprising a first polymer composition and a second portion comprising a second polymer composition, wherein the first portion has a stiffness greater than a stiffness of the second portion, as measured using a 3-point bending test per ASTM D790;

and wherein the plurality of arms are connected to a core at a proximal end through a plurality of linker components, one linker component of the plurality of linker components corresponding to each arm of the plurality of arms, and the plurality of arms extending radially from the proximal end; and a filament circumferentially connecting each arm of the plurality of arms.

Embodiment 20. The gastric residence system of any one of embodiments 1, 4, 8, 11, 14, 16 and 19, wherein the polymeric linker comprises poly(lactic-co-glycolide) (PLGA) and at least one additional linker polymer.

Embodiment 21. The gastric residence system of any one of embodiments 1, 4, 8, 11, 14, 16 and 19-20, wherein the polymeric linker loses 40% or more of its flexural modulus or breaks after incubation in an aqueous solution at pH 1.6 for 21 days at 37° C.

Embodiment 22. The gastric residence system of any one of embodiments 1, 4, 8, 11, 14, 16 and 19-20, wherein the polymeric linker loses 60% or more of its flexural modulus or breaks after incubation in an aqueous solution at pH 1.6 for 21 days at 37° C.

Embodiment 23. The gastric residence system of any one of embodiments 1, 4, 8, 11, 14, 16 and 19-20, wherein the polymeric linker loses 80% or more of its flexural modulus or breaks after incubation in an aqueous solution at pH 1.6 for 21 days at 37° C.

Embodiment 24. The gastric residence system of any one of embodiments 1, 4, 8, 11, 14, 16 and 19-20, wherein the polymeric linker loses 90% or more of its flexural modulus or breaks after incubation in an aqueous solution at pH 1.6 for 21 days at 37° C.

Embodiment 25. The gastric residence system of any one of embodiments 1, 4, 8, 11, 14, 16 and 19-24, wherein the polymeric linker loses 20% or more of its flexural modulus or breaks after incubation in an aqueous solution at pH 1.6 for 14 days at 37° C.

Embodiment 26. The gastric residence system of any one of embodiments 1, 4, 8, 11, 14, 16 and 19-24, wherein the polymeric linker loses 40% or more of its flexural modulus or breaks after incubation in an aqueous solution at pH 1.6 for 14 days at 37° C.

Embodiment 27. The gastric residence system of any one of embodiments 1, 4, 8, 11, 14, 16 and 19-24, wherein the polymeric linker loses 60% or more of its flexural modulus or breaks after incubation in an aqueous solution at pH 1.6 for 14 days at 37° C.

Embodiment 28. The gastric residence system of any one of embodiments 1, 4, 8, 11, 14, 16 and 19-24, wherein the polymeric linker loses 80% or more of its flexural modulus or breaks after incubation in an aqueous solution at pH 1.6 for 14 days at 37° C.

Embodiment 29. The gastric residence system of any one of embodiments 1, 4, 8, 11, 14, 16 and 19-24, wherein the polymeric linker loses 90% or more of its flexural modulus or breaks after incubation in an aqueous solution at pH 1.6 for 14 days at 37° C.

Embodiment 30. The gastric residence system of any one of embodiments 1, 4, 8, 11, 14, 16 and 19-29, wherein the polymeric linker loses 20% or more of its flexural modulus or breaks after incubation in an aqueous solution at pH 1.6 for 7 days at 37° C.

Embodiment 31. The gastric residence system of any one of embodiments 1, 4, 8, 11, 14, 16 and 19-29, wherein the polymeric linker loses 40% or more of its flexural modulus or breaks after incubation in an aqueous solution at pH 1.6 for 7 days at 37° C.

Embodiment 32. The gastric residence system of any one of embodiments 1, 4, 8, 11, 14, 16 and 19-29, wherein the polymeric linker loses 60% or more of its flexural modulus or breaks after incubation in an aqueous solution at pH 1.6 for 7 days at 37° C.

Embodiment 33. The gastric residence system of any one of embodiments 1, 4, 8, 11, 14, 16 and 19-29, wherein the polymeric linker loses 80% or more of its flexural modulus or breaks after incubation in an aqueous solution at pH 1.6 for 7 days at 37° C.

Embodiment 34. The gastric residence system of any one of embodiments 1, 4, 8, 11, 14, 16 and 19-29, wherein the polymeric linker loses 90% or more of its flexural modulus or breaks after incubation in an aqueous solution at pH 1.6 for 7 days at 37° C.

Embodiment 35. The gastric residence system of any one of embodiments 1, 4, 8, 11, 14, 16 and 19-34, wherein the polymeric linker loses 20% or more of its flexural modulus or breaks after incubation in an aqueous solution at pH 1.6 for 3 days at 37° C.

Embodiment 36. The gastric residence system of any one of embodiments 1, 4, 8, 11, 14, 16 and 19-34, wherein the polymeric linker loses 40% or more of its flexural modulus or breaks after incubation in an aqueous solution at pH 1.6 for 3 days at 37° C.

Embodiment 37. The gastric residence system of any one of embodiments 1, 4, 8, 11, 14, 16 and 19-34, wherein the polymeric linker loses 60% or more of its flexural modulus or breaks after incubation in an aqueous solution at pH 1.6 for 3 days at 37° C.

Embodiment 38. The gastric residence system of any one of embodiments 1, 4, 8, 11, 14, 16 and 19-34, wherein the polymeric linker loses 80% or more of its flexural modulus or breaks after incubation in an aqueous solution at pH 1.6 for 3 days at 37° C.

Embodiment 39. The gastric residence system of any one of embodiments 1, 4, 8, 11, 14, 16 and 19-34, wherein the polymeric linker loses 90% or more of its flexural modulus or breaks after incubation in an aqueous solution at pH 1.6 for 3 days at 37° C.

Embodiment 40. The gastric residence system of any one of embodiments 1, 4, 8, 11, 14, 16 and 19-39, wherein the at least one additional linker polymer comprises polylactic acid (PLA), the carrier polymer, polycaprolactone (PCL), or a thermoplastic polyurethane (TPU).

Embodiment 41. The gastric residence system of any one of embodiments 1, 4, 8, 11, 14, 16 and 19-39, wherein the carrier polymer comprises PCL and the at least one additional linker polymer comprises PCL.

Embodiment 42. The gastric residence system of any one of embodiments 1, 4, 8, 11, 14, 16 and 19-39, wherein the carrier polymer comprises TPU and the at least one additional linker polymer comprises a TPU.

Embodiment 43. The gastric residence system of any one of embodiments 1, 4, 8, 11, 14, 16 and 19-39, wherein the at least one additional linker polymer comprises PLA.

Embodiment 44. The gastric residence system of embodiment 43, wherein the carrier polymer comprises PCL or TPU.

Embodiment 45. The gastric residence system of any one of embodiments 1, 4, 8, 11, 14, 16 and 19, wherein the polymeric linker comprises (a) poly(lactic-co-glycolide) (PLGA), and (b) polylactic acid (PLA), polycaprolactone (PCL), or a thermoplastic polyurethane (TPU).

Embodiment 46. The gastric residence system of embodiment 45, wherein the carrier polymer comprises PCL and the polymeric linker comprises the PLGA and the PCL.

Embodiment 47. The gastric residence system of embodiment 45, wherein the carrier polymer comprises the TPU and the polymeric linker comprises the PLGA and the TPU.

Embodiment 48. The gastric residence system of embodiment 45, wherein the polymeric linker comprises the PLGA and the PLA.

Embodiment 49. The gastric residence system of embodiment 45, wherein the carrier polymer comprises the TPU or the PCL.

Embodiment 50. The gastric residence system of any one of embodiments 1, 4, 8, 11, 14, 16 and 19-49, wherein the PLGA comprises poly(D,L-lactic-co-glycolide) (PDLG).

Embodiment 51. The gastric residence system of any one of embodiments 1, 4, 8, 11, 14, 16 and 19-50, wherein the PLGA comprises acid-terminated PLGA.

Embodiment 52. The gastric residence system of any one of embodiments 1, 4, 8, 11, 14, 16 and 19-51, wherein the PLGA comprises ester-terminated PLGA.

Embodiment 53. The gastric residence system of any one of embodiments 1, 4, 8, 11, 14, 16 and 19-52, wherein the PLGA comprises acid-terminated PLGA and ester-terminated PLGA at a ratio of about 1:9 to about 9:1.

Embodiment 54. The gastric residence system of any one of embodiments 1, 4, 8, 11, 14, 16 and 19-53, wherein the polymeric linker comprises about 70 wt % or less PLGA.

Embodiment 55. The gastric residence system of any one of embodiments 1, 4, 8, 11, 14, 16 and 19-54, wherein the polymeric linker comprises between about 30 wt % and about 70 wt % PLGA.

Embodiment 56. The gastric residence system of any one of embodiments 1, 4, 8, 11, 14, 16 and 19-55, wherein the polymeric linker further comprises an enteric polymer.

Embodiment 57. The gastric residence system of embodiment 56, wherein the enteric polymer comprises hydroxypropyl methylcellulose acetate succinate (HPMCAS).

Embodiment 58. The gastric residence system of any one of embodiments 1, 4, 8, 11, 14, 16 and 19-56, wherein the one or more first arms are attached to the second arm through the polymeric linker and a second polymeric linker, the second polymeric linker comprising an enteric polymer.

Embodiment 59. The gastric residence system of embodiment 58, wherein the second polymeric linker further comprises TPU, PCL or PLGA.

Embodiment 60. The gastric residence system of any one of embodiments 1, 4, 8, 11, 14, 16 and 19-59, wherein the polymeric linker further loses 80% or more of its flexural modulus or breaks after incubation in an aqueous solution at pH 6.5 for 3 days at 37° C.

Embodiment 61. The gastric residence system of any one of embodiments 1, 4, 8, 11, 14, 16 and 19-59, wherein the polymeric linker comprises:

(a) a thermoplastic polyurethane (TPU) or comprising poly(lactic-co-glycolide) (PLGA), and (b) an enteric polymer;

wherein the polymeric linker loses 80% or more of its flexural modulus or breaks after incubation in an aqueous solution at pH 6.5 for 3 days at 37° C.

Embodiment 62. The gastric residence system of embodiment 61, wherein the carrier polymer comprises TPU and the one or more polymeric linkers comprises TPU.

Embodiment 63. The gastric residence system of embodiment 62, wherein the polymeric linker comprises PLGA.

Embodiment 64. The gastric residence system of embodiment 63, wherein the polymeric linker further comprises polylactic acid (PLA).

Embodiment 65. The gastric residence system of embodiment 63 or 64, wherein the PLGA is poly(D,L-lactic-co-glycolide) (PDLG).

Embodiment 66. The gastric residence system of any one of embodiments 63-65, wherein the PLGA comprises acid-terminated PLGA.

Embodiment 67. The gastric residence system of any one of embodiments 63-66, wherein the PLGA comprises ester-terminated PLGA.

Embodiment 68. The gastric residence system of any one of embodiments 63-67, wherein the PLGA comprises acid-terminated PLGA and ester-terminated PLGA at a ratio of about 1:9 to about 9:1.

Embodiment 69. The gastric residence system of any one of embodiments 63-68, wherein the polymeric linker comprises about 70 wt % or less PLGA.

Embodiment 70. The gastric residence system of any one of embodiments 63-69, wherein the polymeric linker comprises between about 30 wt % and about 70% PLGA.

Embodiment 71. The gastric residence system of any one of embodiments 61-70, wherein the enteric polymer comprises hydroxypropyl methylcellulose acetate succinate (HPMCAS).

Embodiment 72. The gastric residence system of any one of embodiments 61-71, wherein the polymeric linker comprises about 20 wt % to about 80 wt % enteric polymer.

Embodiment 73. The gastric residence system of any one of embodiments 1, 4, 8, 11, 14, 16 and 19-72, wherein the polymeric linker comprises about 0.5 wt % to about 20 wt % plasticizer.

Embodiment 74. The gastric residence system of embodiment 73, wherein the plasticizer comprises propylene glycol, polyethylene glycol (PEG), triethyl butyl citrate (TBC), dibutyl sebacate (DBS), triacetin, triethyl citrate (TEC), a poloxamer, or D-α-tocopheryl polyethylene glycol succinate.

Embodiment 75. The gastric residence system of any one of embodiments 1, 4, 8, 11, 14, 16 and 19-74 wherein the polymeric linker comprises a linker polymer and about 0.5 wt % to about 20 wt % plasticizer.

Embodiment 76. The gastric residence system of embodiment 75, wherein the polymeric linker comprises about 0.5% to about 12% plasticizer.

Embodiment 77. The gastric residence system of embodiment 75 or 76, wherein the linker polymer comprises an enteric polymer.

Embodiment 78. The gastric residence system of embodiment 77, wherein the one or more polymeric linkers lose 80% or more of their flexural modulus or breaks after incubation in an aqueous solution at pH 6.5 for 3 days at 37° C.

Embodiment 79. The gastric residence system of embodiment 77 or 78, wherein the enteric polymer comprises hydroxypropyl methylcellulose acetate succinate (HPMCAS).

Embodiment 80. The gastric residence system of any one of embodiments 77-79, wherein the polymeric linker comprises about 20 wt % to about 80 wt % enteric polymer.

Embodiment 81. The gastric residence system of any one of embodiments 75-80, wherein the linker polymer comprises the carrier polymer.

Embodiment 82. The gastric residence system of any one of embodiments 75-81, wherein the carrier polymer is polycaprolactone (PCL) or a thermoplastic polyurethane (TPU).

Embodiment 83. The gastric residence system of any one of embodiments 75-82, wherein the linker polymer comprises polylactic acid (PLA), polycaprolactone (PCL), or a thermoplastic polyurethane (TPU).

Embodiment 84. The gastric residence system of any one of embodiments 75-83, wherein the linker polymer comprises a time-dependent degradable polymer.

Embodiment 85. The gastric residence system of any one of embodiments 75-84, wherein the polymeric linker loses 20% or more of its flexural modulus or breaks after incubation in an aqueous solution at pH 1.6 for 21 days at 37° C.

Embodiment 86. The gastric residence system of any one of embodiments 75-85, wherein the polymeric linker loses 40% or more of its flexural modulus or breaks after incubation in an aqueous solution at pH 1.6 for 21 days at 37° C.

Embodiment 87. The gastric residence system of any one of embodiments 75-86, wherein the polymeric linker loses 60% or more of its flexural modulus or breaks after incubation in an aqueous solution at pH 1.6 for 21 days at 37° C.

Embodiment 88. The gastric residence system of any one of embodiments 75-87, wherein the polymeric linker loses 80% or more of its flexural modulus or breaks after incubation in an aqueous solution at pH 1.6 for 21 days at 37° C.

Embodiment 89. The gastric residence system of any one of embodiments 75-88, wherein the polymeric linker loses 90% or more of its flexural modulus or breaks after incubation in an aqueous solution at pH 1.6 for 21 days at 37° C.

Embodiment 90. The gastric residence system of any one of embodiments 75-89, wherein the polymeric linker loses 20% or more of its flexural modulus or breaks after incubation in an aqueous solution at pH 1.6 for 14 days at 37° C.

Embodiment 91. The gastric residence system of any one of embodiments 75-89, wherein the polymeric linker loses 40% or more of its flexural modulus or breaks after incubation in an aqueous solution at pH 1.6 for 14 days at 37° C.

Embodiment 92. The gastric residence system of any one of embodiments 75-89, wherein the polymeric linker loses 60% or more of its flexural modulus or breaks after incubation in an aqueous solution at pH 1.6 for 14 days at 37° C.

Embodiment 93. The gastric residence system of any one of embodiments 75-89, wherein the polymeric linker loses 80% or more of its flexural modulus or breaks after incubation in an aqueous solution at pH 1.6 for 14 days at 37° C.

Embodiment 94. The gastric residence system of any one of embodiments 75-89, wherein the polymeric linker loses 90% or more of its flexural modulus or breaks after incubation in an aqueous solution at pH 1.6 for 14 days at 37° C.

Embodiment 95. The gastric residence system of any one of embodiments 75-94, wherein the polymeric linker loses 20% or more of its flexural modulus or breaks after incubation in an aqueous solution at pH 1.6 for 7 days at 37° C.

Embodiment 96. The gastric residence system of any one of embodiments 75-94, wherein the polymeric linker loses 40% or more of its flexural modulus or breaks after incubation in an aqueous solution at pH 1.6 for 7 days at 37° C.

Embodiment 97. The gastric residence system of any one of embodiments 75-94, wherein the polymeric linker loses 60% or more of its flexural modulus or breaks after incubation in an aqueous solution at pH 1.6 for 7 days at 37° C.

Embodiment 98. The gastric residence system of any one of embodiments 75-94, wherein the polymeric linker loses 80% or more of its flexural modulus or breaks after incubation in an aqueous solution at pH 1.6 for 7 days at 37° C.

Embodiment 99. The gastric residence system of any one of embodiments 75-94, wherein the polymeric linker loses 90% or more of its flexural modulus or breaks after incubation in an aqueous solution at pH 1.6 for 7 days at 37° C.

Embodiment 100. The gastric residence system of any one of embodiments 75-99, wherein the polymeric linker loses 20% or more of its flexural modulus or breaks after incubation in an aqueous solution at pH 1.6 for 3 days at 37° C.

Embodiment 101. The gastric residence system of any one of embodiments 75-99, wherein the polymeric linker loses 40% or more of its flexural modulus or breaks after incubation in an aqueous solution at pH 1.6 for 3 days at 37° C.

Embodiment 102. The gastric residence system of any one of embodiments 75-99, wherein the polymeric linker loses 60% or more of its flexural modulus or breaks after incubation in an aqueous solution at pH 1.6 for 3 days at 37° C.

Embodiment 103. The gastric residence system of any one of embodiments 75-99, wherein the polymeric linker loses 80% or more of its flexural modulus or breaks after incubation in an aqueous solution at pH 1.6 for 3 days at 37° C.

Embodiment 104. The gastric residence system of any one of embodiments 75-99, wherein the polymeric linker loses 90% or more of its flexural modulus or breaks after incubation in an aqueous solution at pH 1.6 for 3 days at 37° C.

Embodiment 105. The gastric residence system of any one of embodiments 75-104, wherein the time-dependent degradable polymer comprises poly(lactic-co-glycolide) (PLGA).

Embodiment 106. The gastric residence system of embodiment 105, wherein the PLGA comprises poly(D,L-lactic-co-glycolide) (PDLG).

Embodiment 107. The gastric residence system of embodiment 105 or 106, wherein the PLGA comprises acid-terminated PLGA.

Embodiment 108. The gastric residence system of any one of embodiments 105-107, wherein the PLGA comprises ester-terminated PLGA.

Embodiment 109. The gastric residence system of any one of embodiments 105-108, wherein the PLGA comprises acid-terminated PLGA and ester-terminated PLGA at a ratio of about 1:9 to about 9:1.

Embodiment 110. The gastric residence system of any one of embodiments 105-109, wherein the polymeric linker comprises about 70 wt % or less PLGA.

Embodiment 111. The gastric residence system of any one of embodiments 105-110, wherein the polymeric linker comprises between about 30% and about 70% PLGA.

Embodiment 112. The gastric residence system of any one of embodiments 105-111, wherein the plasticizer comprises propylene glycol, polyethylene glycol (PEG), triethyl butyl citrate (TBC), dibutyl sebacate (DBS), triacetin, triethyl citrate (TEC), a poloxamer, or D-α-tocopheryl polyethylene glycol succinate.

Embodiment 113. The gastric residence system of any one of embodiments 1, 4, 8, 11, 14, 16 and 19, wherein the polymeric linker comprises:

(a) a pH-independent degradable polymer, and (b) an enteric polymer.

Embodiment 114. The gastric residence system of embodiment 113, wherein the polymeric linker further comprises the carrier polymer.

Embodiment 115. The gastric residence system of embodiment 113 or 114, wherein the carrier polymer is a TPU or a PCL.

Embodiment 116. The gastric residence system of any one of embodiments 113-115, wherein the pH-independent degradable polymer comprises PLGA.

Embodiment 117. The gastric residence system of embodiment 116, wherein the PLGA is poly(D,L-lactic-co-glycolide) (PDLG).

Embodiment 118. The gastric residence system of embodiment 116 or 117, wherein the PLGA comprises acid-terminated PLGA.

Embodiment 119. The gastric residence system of any one of embodiments 116-118, wherein the PLGA comprises ester-terminated PLGA.

Embodiment 120. The gastric residence system of any one of embodiments 116-119, wherein the PLGA comprises acid-terminated PLGA and ester-terminated PLGA at a ratio of about 1:9 to about 9:1.

Embodiment 121. The gastric residence system of any one of embodiments 116-120, wherein the polymeric linker comprises about 70 wt % or less PLGA.

Embodiment 122. The gastric residence system of any one of embodiments 116-121, wherein the polymeric linker comprises between about 30 wt % and about 70% PLGA.

Embodiment 123. The gastric residence system of any one of embodiments 116-122, wherein the enteric polymer comprises hydroxypropyl methylcellulose acetate succinate (HPMCAS).

Embodiment 124. The gastric residence system of any one of embodiments 116-123, wherein the polymeric linker comprises about 20 wt % to about 80 wt % enteric polymer.

Embodiment 125. The gastric residence system of any one of embodiments 116-124, wherein the polymeric linker comprises about 0.5 wt % to about 20 wt % plasticizer.

Embodiment 126. The gastric residence system of embodiment 125, wherein the plasticizer comprises propylene glycol, polyethylene glycol (PEG), triethyl butyl citrate (TBC), dibutyl sebacate (DBS), triacetin, triethyl citrate (TEC), a poloxamer, or D-α-tocopheryl polyethylene glycol succinate.

Embodiment 127. The gastric residence system of any one of embodiments 1, 4, 8, 11, 14, 16 and 19-126, wherein materials in the polymeric linker is homogenously blended.

Embodiment 128. The gastric residence system of any one of embodiments 1, 4, 8, 11, 14, 16 and 19-127, wherein the polymeric linker is substantially free of the agent.

Embodiment 129. The gastric residence system of any one of embodiments 1, 4, 8, 11, 14, 16 and 19-128, wherein the polymeric linker further comprises a color-absorbing dye.

Embodiment 130. The gastric residence system of embodiment 129, wherein the color-absorbing dye comprises iron oxide.

Embodiment 131. The gastric residence system of any one of embodiments 1, 4, 8, 11, 14, 16 and 19-130, comprising a plurality of first arms, wherein:

each first arm is attached to the second arm through a separate polymeric linker;

the second arm is an elastic central member;

the gastric residence system is configured to be folded and physically constrained during administration and is configured to assume an open retention shape upon removal of a constraint; and change between the folded shape and the open retention shape is mediated by the elastic central member that undergoes elastic deformation when the residence structure is in the folded shape and recoils when the gastric residence structure assumes the open retention shape.

Embodiment 132. The gastric system of embodiment 131, wherein the gastric residence system is constrained within a capsule configured to degrade with the stomach.

Embodiment 133. The gastric residence system of any one of embodiments 1, 4, 8, 11, 14, 16 and 19-132, wherein the agent is a drug.

Embodiment 134. The gastric residence system of any one of embodiments 1, 4, 8, 11, 14, 16 and 19-133, wherein the second arm is an elastomer.

Embodiment 135. The gastric residence system of any one of embodiments 1, 4, 8, 11, 14, 16 and 19-134, wherein the second arm is a central elastomer, and wherein the one or more first arms are arms that radially project from the central elastomer.

Embodiment 136. A method of delivering an agent to an individual, comprising deploying the gastric residence system of any one of embodiments 1, 4, 8, 11, 14, 16 and 19-135, within the stomach of the individual.

Embodiment 137. The method of embodiment 136, wherein the individual is a human.

Embodiment 138. The arm of any one of embodiments 1, 4, 7, 10, 13, 16 and 19, wherein the PDL comprises PDL having an intrinsic viscosity of about 1.6 dl/g to about 2.4 dl/g.

Embodiment 139. The arm of any one of embodiments 1, 4, 7, 10, 13, 16 and 19, wherein the PDLG comprises PDLG having an intrinsic viscosity of about 0.1 dl/g to about 0.5 dl/g.

Embodiment 140. The arm of any one of embodiments 1, 4, 7, 10, 13, 16 and 138-139, wherein the PDL:PDLG ratio is between about 2:1 to about 1:2 (weight/weight).

Embodiment 141. The arm of any one of embodiments 1, 4, 7, 10, 13, 16 and 138-140, wherein the PDL:PDLG ratio is between about 1.25:1 to about 1:1.25 (w/w).

Embodiment 142. The arm of any one of embodiments 1, 4, 7, 10, 13, 16 and 138-141, wherein the PDL:PDLG ratio is about 1:1 (w/w).

Embodiment 143. The arm of any one of embodiments 1, 4, 7, 10, 13, 16 and 138-142, wherein the release rate-modulating film is substantially free of porogen.

Embodiment 144. The arm of any one of embodiments 1, 4, 7, 10, 13, 16 and 138-143, wherein the increase in the weight of the arm due to addition of the release rate-modulating film is about 2% to about 6% of the weight of the uncoated arm.

Embodiment 145. The arm of any one of embodiments 1, 4, 7, 10, 13, 16 and 138-144, wherein the release rate of agent from the arm in aqueous media is substantially linear over at least a 96-hour period.

Embodiment 146. The arm of any one of embodiments 1, 4, 7, 10, 13, 16 and 138-145, wherein the release rate of agent from the arm is substantially the same before and after thermal cycling.

Embodiment 147. A gastric residence system comprising an arm of any one of embodiments 1, 4, 7, 10, 13, 16 and 138-146

Embodiment 148. A gastric residence system comprising:

one or more arms of any one of embodiments 1, 4, 7, 10, 13, 16 and 138-147; and a central elastic polymeric component;

wherein the one or more arms are each connected to the central elastic polymeric component via a separate linker component;

wherein the gastric residence system is configured to be folded and physically constrained during administration and is configured to assume an open retention shape upon removal of a constraint;

wherein change between the folded shape and the open retention shape is mediated by the elastic polymeric component that undergoes elastic deformation when the residence system is in the folded shape and recoils when the gastric residence system assumes the open retention shape; and wherein said linker degrades, dissolves, disassociates, or mechanically weakens in a gastric environment which results in loss of retention shape integrity and passage out of a gastric cavity.

Embodiment 149. An arm for use in the gastric residence system of any of embodiments 1, 4, 7, 10, 13, 16 and 138-148, comprising:

a carrier polymer, at least one agent or a pharmaceutically acceptable salt thereof, and a release rate-modulating film coated on at least a portion of the surface of the arm;

wherein the release rate-modulating film comprises high molecular weight polycaprolactone (PCL-HMW) and low molecular weight polycaprolactone (PCL-LMW).

Embodiment 150. The arm of embodiment 149, wherein the PCL-HMW comprises PCL of about $M_n$ 750,000 to about $M_n$ 250,000; or PCL having an intrinsic viscosity of about 1.6 dl/g to about 2.4 dl/g.

Embodiment 151. The arm of embodiment 149 or 150, wherein the PCL-LMW comprises PCL of about $M_n$ 10,000 to about $M_n$ 20,000; or PCL having an intrinsic viscosity of about 0.1 dl/g to about 0.8 dl/g.

Embodiment 152. The arm of embodiment 149 or 150, wherein the PCL-HMW comprises PCL of about $M_n$ 75,000 to about $M_n$ 250,000, or PCL having an intrinsic viscosity of about 1.6 dl/g to about 2.4 dl/g; and the PCL-LMW comprises PCL of about $M_n$ 10,000 to about $M_n$ 20,000, or PCL having an intrinsic viscosity of about 0.1 dl/g to about 0.8 dl/g.

Embodiment 153. The arm of any one of embodiments 149-152, wherein the (PCL-HMW):(PCL-LMW) ratio is between about 1:4 to about 95:5 (weight/weight).

Embodiment 154. The arm of any one of embodiments 149-152, wherein the (PCL-HMW):(PCL-LMW) ratio is between about 2:3 to about 95:5 (weight/weight).

Embodiment 155. The arm of any one of embodiments 149-152, wherein the (PCL-HMW):(PCL-LMW) ratio is between about 3:1 to about 95:5 (weight/weight).

Embodiment 156. The arm of any one of embodiments 149-152, wherein the (PCL-HMW):(PCL-LMW) ratio is about 9:1 (w/w).

Embodiment 157. The arm of any one of embodiments 149-152, wherein the release rate-modulating film is substantially free of porogen.

Embodiment 158. The arm of any one of embodiments 149-157, wherein the increase in the weight of the arm due to addition of the release rate-modulating film is about 2% to about 6% of the weight of the uncoated arm.

Embodiment 159. The arm of any one of embodiments 149-158, wherein the release rate of agent from the arm in aqueous media is substantially linear over at least a 96-hour period.

Embodiment 160. The arm of any one of embodiments 149-160, wherein the release rate of agent from the arm is substantially the same before and after thermal cycling.

Embodiment 161. A gastric residence system comprising an arm of any one of embodiments 149-160.

Embodiment 162. A gastric residence system comprising:

one or more arms of any one of embodiments 149-160; and a central elastic polymeric component;

wherein the one or more arms are each connected to the central elastic polymeric component via a separate linker component;

wherein the gastric residence system is configured to be folded and physically constrained during administration and is configured to assume an open retention shape upon removal of a constraint;

wherein change between the folded shape and the open retention shape is mediated by the elastic polymeric component that undergoes elastic deformation when the residence system is in the folded shape and recoils when the gastric residence system assumes the open retention shape; and wherein said linker degrades, dissolves, disassociates, or mechanically weakens in a gastric environment which results in loss of retention shape integrity and passage out of a gastric cavity.

Embodiment 163. An arm for use in the gastric residence system of any of embodiments 1, 4, 7, 10, 13, 16 and 138-148, comprising:

a carrier polymer, at least one agent or a pharmaceutically acceptable salt thereof, and a release rate-modulating film coated on at least a portion of the surface of the arm;

wherein the release rate-modulating film comprises poly-D, L-lactide (PDL).

Embodiment 164. The arm of embodiment 163, wherein the PDL comprises PDL having an intrinsic viscosity of about 1.6 dl/g to about 2.4 dl/g Embodiment 165. The arm of embodiment 163 or 164, wherein the release rate-modulating film further comprises polycaprolactone (PCL) and polyethylene glycol (PEG).

Embodiment 166. The arm of embodiment 165, wherein the PCL comprises PCL of about $M_n$ 75,000 to about $M_n$ 250,000.

Embodiment 167. The arm of embodiment 165 or 166, wherein the PEG comprises PEG of about $M_n$ 800 to about $M_n$ 10,000.

Embodiment 168. The arm of any one of embodiments 165-167, wherein the PDL comprises between about 15% to about 80% of the release rate-modulating film, the PCL comprises between about 15% to about 75% of the release rate-modulating film, and the PEG comprises between about 5% to about 15% of the release rate-modulating film, by weight.

Embodiment 169. The arm of any one of embodiments 165-167, wherein the PDL:PCL:PEG ratio is about 9:27:4 (w/w/w).

Embodiment 170. The arm of any one of embodiments 165-167, wherein the PDL:PCL:PEG ratio is about 36:9:5 (w/w/w).

Embodiment 171. The arm of any one of embodiments 163-170, wherein the release rate-modulating film is substantially free of porogen.

Embodiment 172. The arm of any one of embodiments 163-171, wherein the increase in the weight of the arm due to addition of the release rate-modulating film is about 2% to about 6% of the weight of the uncoated arm.

Embodiment 173. The arm of any one of embodiments 163-172, wherein the release rate of agent from the arm in aqueous media is substantially linear over at least a 96-hour period.

Embodiment 174. The arm of any one of embodiments 163-173, wherein the release rate of agent from the arm is substantially the same before and after thermal cycling.

Embodiment 175. A gastric residence system comprising an arm of any one of embodiments 163-174.

Embodiment 176. A gastric residence system comprising:

one or more arms of any one of embodiments 163-174; and a central elastic polymeric component;

wherein the one or more arms are each connected to the central elastic polymeric component via a separate linker component;

wherein the gastric residence system is configured to be folded and physically constrained during administration and is configured to assume an open retention shape upon removal of a constraint;

wherein change between the folded shape and the open retention shape is mediated by the elastic polymeric component that undergoes elastic deformation when the residence system is in the folded shape and recoils when the gastric residence system assumes the open retention shape; and wherein said linker degrades, dissolves, disassociates, or mechanically weakens in a gastric environment which results in loss of retention shape integrity and passage out of a gastric cavity.

Embodiment 177. The arm of embodiment 163, wherein the release rate-modulating film further comprises a polyethylene glycol-polypropylene glycol-polyethylene glycol (PEG-PPG-PEG) block copolymer.

Embodiment 178. The arm of embodiment 177, wherein the PEG-PPG-PEG block copolymer comprises PEG-PPG-PEG block copolymer of $M_n$ about 14,000 to about 15,000.

Embodiment 179. The arm of embodiment 177 or embodiment 178, wherein the PEG-PPG-PEG block copolymer comprises about 75% to about 90% ethylene glycol.

Embodiment 180. The arm of any one of embodiments 177-179, wherein the (PDL):(PEG-PPG-PEG block copolymer) ratio is between about 85:15 to about 95:5 (w/w).

Embodiment 181. The arm of any one of embodiments 177-179, wherein the (PDL):(PEG-PPG-PEG block copolymer) ratio is about 9:1 (w/w).

Embodiment 182. The arm of any one of embodiments 177-181, wherein the release rate-modulating film is substantially free of porogen.

Embodiment 183. The arm of any one of embodiments 177-182, wherein the increase in the weight of the arm due to addition of the release rate-modulating film is about 2% to about 6% of the weight of the uncoated arm.

Embodiment 184. The arm of any one of embodiments 177-183, wherein the release rate of agent from the arm in aqueous media is substantially linear over at least a 96-hour period.

Embodiment 185. The arm of any one of embodiments 177-184, wherein the release rate of agent from the arm is substantially the same before and after thermal cycling.

Embodiment 186. A gastric residence system comprising an arm of any one of embodiments 177-185.

Embodiment 187. A gastric residence system comprising:

one or more arms of any one of embodiments 177-185 and a central elastic polymeric component;

wherein the one or more arms are each connected to the central elastic polymeric component via a separate linker component;

wherein the gastric residence system is configured to be folded and physically constrained during administration and is configured to assume an open retention shape upon removal of a constraint;

wherein change between the folded shape and the open retention shape is mediated by the elastic polymeric component that undergoes elastic deformation when the residence system is in the folded shape and recoils when the gastric residence system assumes the open retention shape; and wherein said linker degrades, dissolves, disassociates, or mechanically weakens in a gastric environment which results in loss of retention shape integrity and passage out of a gastric cavity.

Embodiment 188. The arm of embodiment 163, wherein the release rate-modulating film further comprises polyethylene glycol (PEG).

Embodiment 189. The arm of embodiment 163, wherein the release rate-modulating film further comprises polypropylene glycol (PPG).

Embodiment 190. The arm of embodiment 163, wherein the release rate-modulating film further comprises polyethylene glycol (PEG) and polypropylene glycol (PPG).

Embodiment 191. The arm of embodiment 190, wherein the PDL comprises between about 75% to about 95% of the release rate-modulating film, the PEG comprises between about 3% to about 10% of the release rate-modulating film, and the PPG comprises between about 1% to about 7% of the release rate-modulating film, by weight.

Embodiment 192. The arm of embodiment 190, wherein the (PDL):(PEG):(PPG) ratio is about 90:(six and two-thirds):(three and one-third) by weight.

Embodiment 193. The arm of any one of embodiments 188 and 190-192, wherein the PEG comprises PEG of molecular weight about 800 to about 1,200.

Embodiment 194. The arm of any one of embodiments 189-192, wherein the PPG comprises PPG of about $M_n$ 2,500 to about $M_n$ 6,000.

Embodiment 195. The arm of any one of embodiments 188-194, wherein the release rate-modulating film is substantially free of porogen.

Embodiment 196. The arm of any one of embodiments 188-195, wherein the increase in the weight of the arm due to addition of the release rate-modulating film is about 2% to about 6% of the weight of the uncoated arm.

Embodiment 197. The arm of any one of embodiments 188-196, wherein the release rate of agent from the arm in aqueous media is substantially linear over at least a 96-hour period.

Embodiment 198. The arm of any one of embodiments 188-197, wherein the release rate of agent from the arm is substantially the same before and after thermal cycling.

Embodiment 199. A gastric residence system comprising an arm of any one of embodiments 188-198.

Embodiment 200. A gastric residence system comprising:

one or more arms of any one of embodiments 188-198; and a central elastic polymeric component;

wherein the one or more arms are each connected to the central elastic polymeric component via a separate linker component;

wherein the gastric residence system is configured to be folded and physically constrained during administration and is configured to assume an open retention shape upon removal of a constraint;

wherein change between the folded shape and the open retention shape is mediated by the elastic polymeric component that undergoes elastic deformation when the residence system is in the folded shape and recoils when the gastric residence system assumes the open retention shape; and wherein said linker degrades, dissolves, disassociates, or mechanically weakens in a gastric environment which results in loss of retention shape integrity and passage out of a gastric cavity.

Embodiment 201. An arm for use in the gastric residence system of any of embodiments 1, 4, 7, 10, 13, 16, 19 and 138-148, comprising:

a carrier polymer, at least one agent or a pharmaceutically acceptable salt thereof, and a release rate-modulating film coated on at least a portion of the surface of the arm;

wherein the release rate-modulating film comprises poly-D-lactide-polycaprolactone co-polymer (PDL-PCL copolymer).

Embodiment 202. The arm of embodiment 201, wherein PDL comprises between about 15% to about 90% of the PDL-PCL copolymer.

Embodiment 203. The arm of embodiment 201, wherein PDL comprises between about 15% to about 35% of the PDL-PCL copolymer.

Embodiment 204. The arm of embodiment 201, wherein PDL comprises between about 70% to about 90% of the PDL-PCL copolymer.

Embodiment 205. The arm of any one of embodiments 201-204, wherein the PDL-PCL copolymer comprises PDL-PCL copolymer having intrinsic viscosity of about 0.6 dl/g to about 1 dl/g.

Embodiment 206. The arm of any one of embodiments 201-205, wherein the release rate-modulating film further comprises PEG.

Embodiment 207. The arm of embodiment 206, wherein the PEG comprises PEG of average molecular weight between about 800 and about 1,200.

Embodiment 208. The arm of embodiment 206 or 207, wherein the PDL-PCL copolymer comprises about 75% to about 95% of the release rate modulating film by weight and the PEG comprises about 5% to about 25% of the release rate modulating film by weight.

Embodiment 209. The arm of embodiment 206 or 207, wherein the PDL-PCL copolymer comprises about 90% of the release rate modulating film by weight and the PEG comprises about 10% of the release rate modulating film by weight.

Embodiment 210. The arm of any one of embodiments 201-209, wherein the release rate-modulating film is substantially free of porogen.

Embodiment 211. The arm of any one of embodiments 201-210, wherein the increase in the weight of the arm due to addition of the release rate-modulating film is about 2% to about 6% of the weight of the uncoated arm.

Embodiment 212. The arm of any one of embodiments 201-211, wherein the release rate of agent from the arm in aqueous media is substantially linear over at least a 96-hour period.

Embodiment 213. The arm of any one of embodiments 201-212, wherein the release rate of agent from the arm is substantially the same before and after thermal cycling.

Embodiment 214. A gastric residence system comprising an arm of any one of embodiments 201-213.

Embodiment 215. A gastric residence system comprising:

one or more arms of any one of embodiments 201-213; and a central elastic polymeric component;

wherein the one or more arms are each connected to the central elastic polymeric component via a separate linker component;

wherein the gastric residence system is configured to be folded and physically constrained during administration and is configured to assume an open retention shape upon removal of a constraint;

wherein change between the folded shape and the open retention shape is mediated by the elastic polymeric component that undergoes elastic deformation when the residence system is in the folded shape and recoils when the gastric residence system assumes the open retention shape; and wherein said linker degrades, dissolves, disassociates, or mechanically weakens in a gastric environment which results in loss of retention shape integrity and passage out of a gastric cavity.

Embodiment 216. The arm or gastric residence system of any one of embodiments 1, 4, 7, 10, 13, 16 and 138-215, wherein the release rate-modulating film is applied by pan coating.

Embodiment 217. The arm or gastric residence system of any one of embodiments 1, 4, 7, 10, 13, 16 and 138-215, wherein the release rate-modulating film is applied by dip coating.

Embodiment 218. The arm or gastric residence system of any one of embodiments 1, 4, 7, 10, 13, 16 and 138-217, wherein the at least one agent or a pharmaceutically acceptable salt thereof comprises one or more of drug, a pro-drug, a biologic, a statin, rosuvastatin, a nonsteroidal anti-inflammatory drug (NSAID), meloxicam, a selective serotonin reuptake inhibitor (SSRs), escitalopram, citalopram, a blood thinner, clopidogrel, a steroid, prednisone, an antipsychotic, aripiprazole, risperidone, an analgesic, buprenorphine, an opioid antagonist, naloxone, an anti-asthmatic, montelukast, an anti-dementia drug, memantine, a cardiac glycoside, digoxin, an alpha blocker, tamsulosin, a cholesterol absorption inhibitor, ezetimibe, an anti-gout treatment, colchicine, an antihistamine, loratadine, cetirizine, an opioid, loperamide, a proton-pump inhibitor, omeprazole, an antiviral agent, entecavir, an antibiotic, doxycycline, ciprofloxacin, azithromycin, an anti-malarial agent, levothyroxine, a substance abuse treatment, methadone, varenicline, a contraceptive, a stimulant, caffeine, a nutrient, folic acid, calcium, iodine, iron, zinc, thiamine, niacin, vitamin C, vitamin D, biotin, a plant extract, a phytohormone, a vitamin, a mineral, a protein, a polypeptide, a polynucleotide, a hormone, an anti-inflammatory drug, an antipyretic, an antidepressant, an antiepileptic, an antipsychotic agent, a neuroprotective agent, an anti-proliferative, an anti-cancer agent, an antimigraine drug, a prostaglandin, an antimicrobial, an antifungals, an antiparasitic, an anti-muscarinic, an anxiolytic, a bacteriostatic, an immunosuppressant agent, a sedative, a hypnotic, a bronchodilator, a cardiovascular drug, an anesthetic, an anti-coagulant, an enzyme inhibitor, a corticosteroid, a dopaminergic, an electrolyte, a gastro-intestinal drug, a muscle relaxant, a parasympathomimetic, an anorectic, an anti-narcoleptics, quinine, lumefantrine, chloroquine, amodiaquine, pyrimethamine, proguanil, chlorproguanil-dapsone, a sulfonamide, sulfadoxine, sulfamethoxypyridazine, mefloquine, atovaquone, primaquine, halofantrine, doxycycline, clindamycin, artemisinin, an artemisinin derivative, artemether, dihydroartemisinin, arteether, or artesunate.

Embodiment 219. The arm or gastric residence system of any one of embodiments 1, 4, 7, 10, 13, 16 and 138-217, wherein the at least one agent or a pharmaceutically acceptable salt thereof comprises memantine.

Embodiment 220. The arm or gastric residence system of any one of embodiments 1, 4, 7, 10, 13, 16 and 138-217, wherein the at least one agent or a pharmaceutically acceptable salt thereof comprises donepezil.

Embodiment 221. The arm or gastric residence system of any one of embodiments 1, 4, 7, 10, 13, 16 and 138-217, wherein the at least one agent or a pharmaceutically acceptable salt thereof comprises memantine and donepezil.

Embodiment 222. The arm or gastric residence system of any one of embodiments 1, 4, 7, 10, 13, 16 and 138-217, wherein the at least one agent or a pharmaceutically acceptable salt thereof comprises risperidone.

Embodiment 223. The arm or gastric residence system of any one of embodiments 1, 4, 7, 10, 13, 16 and 138-217, wherein the at least one agent or a pharmaceutically acceptable salt thereof comprises dapagliflozin.

Embodiment 224. The gastric residence system of any one of embodiments 2, 4, 7, 12, 13, 18 and 19, wherein the filament circumferentially connects a distal end of each arm of the plurality of arms.

Embodiment 225. The gastric residence system of any one of embodiments 2, 4, 7, 12, 13, 18, 19 and 224, wherein the plurality of arms comprises at least three arms.

Embodiment 226. The gastric residence system of any of embodiments 2, 4, 7, 12, 13, 18, 19 and 224-225, wherein the plurality of arms is configured to be loaded with an active pharmaceutical ingredient.

Embodiment 227. The gastric residence system of any of embodiments 2, 4, 7, 12, 13, 18, 19 and 224-226, wherein the plurality of arms comprises 40-60% loading of an active pharmaceutical ingredient.

Embodiment 228. The gastric residence system of any of embodiments 2, 4, 7, 12, 13, 18, 19 and 224-227, wherein the linker component degrades, dissolves, disassociates, or mechanically weakens in a gastric environment.

Embodiment 229. The gastric residence system of any of embodiments 2, 4, 7, 12, 13, 18, 19 and 224-228, wherein the gastric residence system is configured to be folded during administration and is configured to assume an open configuration when in a patient's stomach.

Embodiment 230. The gastric residence system of embodiment 229, wherein the core undergoes elastic deformation when the gastric residence system is in the folded configuration and recoils when the gastric residence system assumes the open configuration.

Embodiment 231. The gastric residence system of any of embodiments 2, 4, 7, 12, 13, 18, 19 and 224-230, wherein the gastric residence system has a multi-armed star shape in the open configuration.

Embodiment 232. The gastric residence system of any of embodiments 2, 4, 7, 12, 13, 18, 19 and 224-231, wherein the force required to compress the gastric residence system into a configuration small enough to pass through an opening having a diameter of 20 mm is at least one and a half times greater than the force required to compress a gastric residence system without a filament into a configuration small enough to pass through the opening, as measured using a radial test.

Embodiment 233. The gastric residence system of any of embodiments 2, 4, 7, 12, 13, 18, 19 and 224-232, wherein the pullout force required to separate the filament from the distal end of a first arm of the plurality of arms is greater than 1N when measured after incubating the gastric residence system in an environment of pH 1.6 for 3 days.

Embodiment 234. The gastric residence system of any of embodiments 2, 4, 7, 12, 13, 18, 19 and 224-233, wherein the pullout force required to separate the filament from the distal end of the first arm of the plurality of arms is less than 2N when measured after incubating the gastric residence system in an environment of pH 6.5 for 3 days.

Embodiment 235. The gastric residence system of any of embodiments 2, 4, 7, 12, 13, 18, 19 and 224-234, wherein the distal end of each arm of the plurality of arms comprises an enteric material.

Embodiment 236. The gastric residence system of any of embodiments 2, 4, 7, 12, 13, 18, 19 and 224-235, wherein the filament comprises one or more of an elastic polymer, a biosorbable polymer, and a plasticizer.

Embodiment 237. The gastric residence system of embodiment 235 or 236, wherein the enteric material of the distal end of each arm comprises a polymer, an enteric polymer, a plasticizer, and an acid.

Embodiment 238. The gastric residence system of embodiment 237, wherein the biodegradable polymer comprises polycaprolactone.

Embodiment 239. The gastric residence system of embodiment 237 or 238, wherein the enteric polymer comprises hydroxypropylmethylcellulose acetate succinate.

Embodiment 240. The gastric residence system of any of embodiments 237-239, wherein the plasticizer comprises propylene glycol.

Embodiment 241. The gastric residence system of any of embodiments 237-240, wherein the acid comprises stearic acid.

Embodiment 242. The gastric residence system of any of embodiments 2, 4, 7, 12, 13, 18, 19 and 224-242, wherein the distal end of each arm comprises a notch and the filament is positioned within the notch of each distal end.

Embodiment 243. The gastric residence system of embodiment 242, wherein the filament is secured by overlapping a first end of the filament and a second end of the filament within a first notch, and the first end and the second end are secured by enlarging the first end and the second end of the filament.

Embodiment 244. The gastric residence system of any of embodiments 2, 4, 7, 12, 13, 18, 19 and 224-243, wherein the gastric residence system is used to treat a patient.

Embodiment 245. The gastric residence system of embodiment 244, wherein the patient is a human or a dog.

Embodiment 246. The gastric residence system of any one of embodiments 3, 6, 9, 10, 13, 16 and 19, comprising a core.

Embodiment 247. The gastric residence system of embodiment 246, comprising a plurality of arms connected to the core and extending radially from the core.

Embodiment 248. The gastric residence system of any one of embodiments 3, 6, 9, 10, 13, 16 and 19, wherein each arm of the plurality of arms comprises a first segment comprising a first polymer composition and a second segment comprising a second polymer composition.

Embodiment 249. The gastric residence system of any of embodiments 3, 6, 9, 10, 13, 16, 19 and 246-248, wherein the force required to compress the gastric residence system into a configuration small enough to pass through an opening having a diameter of 20 mm is at least 1.2 times greater than the force required to compress a gastric residence system having only a first polymer composition into a configuration small enough to pass through the opening, as measured using an iris testing mechanism.

Embodiment 250. The gastric residence system of any of embodiments 3, 6, 9, 10, 13, 16, 19 and 246-249, wherein the first polymer composition comprises one or more of PCL, PLA, PLGA, HPMCAS, and TPU.

Embodiment 251. The gastric residence system of any of embodiments 3, 6, 9, 10, 13, 16, 19 and 246-250, wherein the second polymer composition comprises one or more of a polyurethane, a polyether-polyamide copolymer, a thermoplastic elastomer, a thermoplastic polyurethane, polycaprolactone polylactic acid copolymer, a poly(trimethylene carbonate),a polyglycerol sebacate, and a silicone.

Embodiment 252. The gastric residence system of any of embodiments 3, 6, 9, 10, 13, 16, 19 and 246-251, wherein the second polymer composition comprises at least a polycaprolactone and a soluble material to form a material that softens upon exposure to an aqueous environment.

Embodiment 253. The gastric residence system of any of embodiments 3, 6, 9, 10, 13, 16, 19 and 246-252, wherein the first segment is directly connected to the second segment of the at least one arm.

Embodiment 254. The gastric residence system of any of embodiments 3, 6, 9, 10, 13, 16, 19 and 246-253, wherein the first segment is connected to the second segment via a linker.

Embodiment 255. The gastric residence system of any of embodiments 3, 6, 9, 10, 13, 16, 19 and 246-254, wherein the first segment comprises 20-50% of a length of the at least one arm, the length being measured from a proximal end of the at least one arm, the proximal end being proximate to the core or a linker connecting the at least one arm to the core, to a distal end of the at least one arm.

Embodiment 256. The gastric residence system of any of embodiments 3, 6, 9, 10, 13, 16, 19 and 246-255, wherein the second segment comprises 50-80% of a length of the at least one arm, the length being measured from a proximal end of the at least one arm, the proximal end being proximate to the core or a linker connecting the at least one arm to the core, to a distal end of the at least one arm.

Embodiment 257. The gastric residence system of any of embodiments 3, 6, 9, 10, 13, 16, 19 and 246-256, wherein a number of fatigue cycles required to break the gastric residence system is at least 25% greater than a number of fatigue cycles required to break a gastric residence system with stiff arms, as measured using a double funnel test.

Embodiment 258. A gastric residence system made using the method of any of embodiments 3, 6, 9, 10, 13, 16, 19 and 246-257, wherein the gastric residence system is used to treat a patient.

Embodiment 259. The gastric residence system of embodiment 258, wherein the patient is a human or a dog.

Embodiment 260. A gastric residence system comprising arms comprising drug-eluting segments, where the arms are affixed to a central elastomer, wherein the drug eluting segments comprise:

a carrier polymer;

memantine or a salt thereof; and donepezil or a salt thereof;

wherein the drug eluting segments further comprise a coating comprising a release rate-modulating polymer film; and wherein the gastric residence system is configured to provide a steady-state concentration $C_{ss}$ of memantine of between about 60 ng/ml and about 160 ng/ml and a steady-state concentration $C_{ss}$ of donepezil of between about 30 ng/ml and about 60 ng/ml after administration of the gastric residence system to a human; and wherein the gastric residence system is configured to remain resident in the stomach for a period of between 4 days to 14 days.

Embodiment 261. A gastric residence system comprising arms comprising drug-eluting segments, where the arms are affixed to a central elastomer, wherein the drug eluting segments comprise:

a carrier polymer;

memantine or a salt thereof; and donepezil or a salt thereof;

wherein the drug eluting segments further comprise a coating comprising a release rate-modulating polymer film; and wherein the gastric residence system is configured to provide a $C_{max}$ of memantine of between about 80 ng/ml and about 200 ng/ml and a $C_{max}$ of donepezil of between about 40 ng/ml and about 80 ng/ml after administration of the gastric residence system to a human; and wherein the gastric residence system is configured to remain resident in the stomach for a period of between 4 days to 14 days.

Embodiment 262. The gastric residence system of embodiment 260 or 261, wherein the gastric residence system comprises about 150 mg to about 200 mg of memantine or a salt thereof and about 50 to about 90 mg of donepezil or a salt thereof.

Embodiment 263. The gastric residence system of embodiment 260 or 261, wherein the gastric residence system comprises about 150 mg to about 200 mg of memantine HCl and about 50 to about 90 mg of donepezil HCl.

Embodiment 264. The gastric residence system of any one of embodiments 260-263, wherein each drug eluting segment comprises about 30 wt % to about 40 wt % of memantine or a salt thereof and about 10 wt % to about 20 wt % of donepezil or a salt thereof.

Embodiment 265. The gastric residence system of any one of embodiments 260-264, wherein the carrier polymer comprises polycaprolactone (PCL).

Embodiment 266. The gastric residence system of embodiment 265, wherein the PCL has a viscosity between about 1.5 dl/g to about 2.1 dl/g.

Embodiment 267. The gastric residence system of any one of embodiments 260-266, wherein the drug-eluting segments further comprise a mixture of polyvinyl acetate (PVAc) and povidone (PVP).

Embodiment 268. The gastric residence system of embodiment 267, wherein the mixture of PVAc and PVP has a ratio of about 3:1 PVAc:PVP to about 5:1 PVAc:PVP.

Embodiment 269. The gastric residence system of any one of embodiments 260-268, wherein the drug-eluting segments further comprise Vitamin E or an ester thereof.

Embodiment 270. The gastric residence system of any one of embodiments 260-269, wherein the drug-eluting segments further comprise $SiO_2$.

Embodiment 271. The gastric residence system of any one of embodiments 260-270, wherein the drug-eluting segments further comprise a coloring agent.

Embodiment 272. The gastric residence system of any one of embodiments 260-271, wherein the central elastomer comprises silicone rubber.

Embodiment 273. The gastric residence system of any one of embodiments 260-272, wherein the central elastomer has a durometer of about 45 A to about 65 A.

Embodiment 274. The gastric residence system of any one of embodiments 260-273, wherein the release rate-modulating polymer film comprises PCL.

Embodiment 275. The gastric residence system of embodiment 274, wherein the PCL has a viscosity between about 1.5 dl/g to about 2.1 dl/g.

Embodiment 276. The gastric residence system of embodiment 274, wherein the release rate-modulating polymer film comprises PCL having a viscosity between about 1.5 dl/g to about 2.1 dl/g and PCL having a viscosity between about 0.2 dl/g to about 0.6 dl/g.

Embodiment 277. The gastric residence system of any one of embodiments 273-276, wherein the release rate-modulating polymer film further comprises magnesium stearate.

Embodiment 278. The gastric residence system of any one of embodiments 260-277, wherein the gastric residence system is configured to provide a $T_{max}$ of memantine after administration of the gastric residence system to a human of between about 36 hours and about 160 hours.

Embodiment 279. The gastric residence system of any one of embodiments 260-277, wherein the gastric residence system is configured to provide a $T_{max}$ of memantine after administration of the gastric residence system to a human of between about 48 hours and about 144 hours.

Embodiment 280. The gastric residence system of any one of embodiments 260-277, wherein the gastric residence system is configured to provide a $T_{max}$ of memantine after administration of the gastric residence system to a human of between about 48 hours and about 96 hours.

Embodiment 281. The gastric residence system of any one of embodiments 260-280, wherein the gastric residence system is configured to provide a $T_{max}$ of donepezil after administration of the gastric residence system to a human of between about 36 hours and about 160 hours.

Embodiment 282. The gastric residence system of any one of embodiments 260-280, wherein the gastric residence system is configured to provide a $T_{max}$ of donepezil after administration of the gastric residence system to a human of between about 48 hours and about 144 hours.

Embodiment 283. The gastric residence system of any one of embodiments 260-280, wherein the gastric residence system is configured to provide a $T_{max}$ of donepezil after administration of the gastric residence system to a human of between about 48 hours and about 96 hours.

Embodiment 284. The gastric residence system of any one of embodiments 260-283, wherein the gastric residence system is configured to provide a human in vivo plasma profile at steady state having a $C_{max,ss}$ for memantine of about 140 ng/mL±50 ng/mL; or wherein the gastric residence system is configured to provide a human in vivo plasma profile at steady state having a $C_{min,ss}$ for memantine of about 90 ng/mL±40 ng/mL, with the caveat that $C_{min,ss}$ for memantine is less than $C_{max,ss}$ for memantine; or wherein the gastric residence system is configured to provide a human in vivo plasma profile at steady state having a $C_{ave,ss}$ for memantine of about 115 ng/mL±15 ng/mL, with the caveat that $C_{ave,ss}$ for memantine is greater than $C_{min,ss}$ for memantine and $C_{ave,ss}$ for memantine is less than $C_{max,ss}$ for memantine;

and wherein the gastric residence system is configured to provide a human in vivo plasma profile at steady state having a $C_{max,ss}$ for donepezil of about 60 ng/mL±20 ng/mL; or wherein the gastric residence system is configured to provide a human in vivo plasma profile at steady state having a $C_{min,ss}$ for donepezil of about 40 ng/mL±20 ng/mL, with the caveat that $C_{min,ss}$ for donepezil is less than $C_{max,ss}$ for donepezil; or wherein the gastric residence system is configured to provide a human in vivo plasma profile at steady state having a $C_{ave,ss}$ for donepezil of about 50 ng/mL±20 ng/mL, with the caveat that $C_{ave,ss}$ for donepezil is greater than $C_{min,ss}$ for donepezil and $C_{ave,ss}$ for donepezil is less than $C_{max,ss}$ for donepezil.

Embodiment 285. The gastric residence system of any one of embodiments 260-284, wherein release of memantine over the first 24 hours of gastric residence is no more than three times release of memantine over any subsequent 24 hour period of gastric residence following the first 24 hours of gastric residence.

Embodiment 286. The gastric residence system of any one of embodiments 260-285, wherein release of donepezil over the first 24 hours of gastric residence is no more than three times release of donepezil over any subsequent 24 hour period of gastric residence following the first 24 hours of gastric residence.

Embodiment 287. The arm or gastric residence system of any one of embodiments 1, 4, 7, 10, 13, 16 and 138-217, wherein the at least one agent or a pharmaceutically acceptable salt thereof comprises rosuvastatin or the calcium salt of rosuvastatin.

Embodiment 288. A gastric residence system comprising one or more first structural members attached to a second structural member through a polymeric linker, the polymeric linker comprising 68 to 72% by weight poly(lactic-co-glycolide) (PLGA) and 28 to 32% by weight polylactic acid, wherein the PLGA comprises a lactic acid to glycolic acid ratio of 65:35.

Embodiment 289. A gastric residence system comprising one or more first structural members attached to a second structural member through a polymeric linker, the polymeric linker comprising 68 to 72% poly(lactic-co-glycolide) PLGA by weight and 28 to 32% by weight polylactic acid, wherein the PLGA comprises a lactic acid to glycolic acid ratio of 75:25.

Embodiment 290. A gastric residence system comprising one or more first structural members attached to a second structural member through a polymeric linker, the polymeric linker comprising 48 to 52% poly(lactic-co-glycolide) PLGA by weight and 48 to 52% by weight polylactic acid (PLA), wherein the PLGA comprises a lactic acid to glycolic acid ratio of 75:25.

Embodiment 291. A gastric residence system comprising one or more first structural members attached to a second structural member through a polymeric linker, the polymeric linker comprising 22 to 26% poly(lactic-co-glycolide) PLGA by weight, 54 to 58% by weight polylactic acid (PLA), and 18 to 22% by weight thermoplastic polyurethane (TPU), wherein the PLGA comprises a lactic acid to glycolic acid ratio of 65:35.

Embodiment 292. A gastric residence system comprising one or more first structural members attached to a second structural member through a polymeric linker, the polymeric linker comprising 22 to 26% poly(lactic-co-glycolide) PLGA by weight, 54 to 58% by weight polylactic acid (PLA), and 18 to 22% by weight thermoplastic polyurethane (TPU), wherein the PLGA comprises a lactic acid to glycolic acid ratio of 75:25.

Embodiment 293. A gastric residence system comprising one or more first structural members attached to a second structural member through a polymeric linker, the polymeric linker comprising 38 to 42% poly(lactic-co-glycolide) PLGA by weight, 38 to 42% by weight polylactic acid (PLA), and 18 to 22% by weight TPU, wherein the PLGA comprises a lactic acid to glycolic acid ratio of 75:25.

Embodiment 294. A gastric residence system comprising one or more first structural members attached to a second structural member through a polymeric linker, wherein a glass transition temperature of the polymeric linker decreases to below body temperature after 7-14 days in an aqueous environment.

Embodiment 295. A gastric residence system comprising arms comprising drug-eluting segments, where the arms are affixed to a central elastomer, wherein the drug eluting segments comprise:

a carrier polymer;

rosuvastatin or a salt thereof;

wherein the drug eluting segments further comprise a coating comprising a release rate-modulating polymer film; and wherein the gastric residence system is configured to provide an average concentration at steady-state ($C_{ss}$) of rosuvastatin of between about 0.5 ng/ml and about 10 ng/ml after administration of the gastric residence system to a human; and wherein the gastric residence system is configured to remain resident in the stomach for a period of between 4 days to 14 days.

Embodiment 296. A gastric residence system comprising arms comprising drug-eluting segments, where the arms are affixed to a central elastomer, wherein the drug eluting segments comprise:

a carrier polymer;

rosuvastatin or a salt thereof;

wherein the drug eluting segments further comprise a coating comprising a release rate-modulating polymer film; and wherein the gastric residence system is configured to provide a Cmax of rosuvastatin of between about 1 ng/ml and about 50 ng/ml after administration of the gastric residence system to a human; and wherein the gastric residence system is configured to remain resident in the stomach for a period of between 4 days to 14 days.

Embodiment 297. The gastric residence system of embodiment 295 or 296, wherein the gastric residence system comprises about 20 mg to about 350 mg of rosuvastatin or a salt thereof.

Embodiment 298. The gastric residence system of any one of embodiments 295-297, wherein each drug eluting segment comprises about 30 wt % to about 40 wt % of rosuvastatin or a salt thereof.

Embodiment 299. The gastric residence system of any one of embodiments 295-298, wherein the carrier polymer comprises polycaprolactone (PCL).

Embodiment 300. The gastric residence system of any one of embodiments 295-299, wherein the drug-eluting segments comprise:

(a) polycaprolactone (PCL), optionally wherein the segment comprises about 35 wt % to about 45 wt % of PCL; and/or (b) polyethylene glycol-polypropylene glycol-polyethylene glycol (PEG-PPG-PEG) block copolymer, optionally wherein the segment comprises about 6 wt % to about 9 wt % of PEG-PPG-PEG block coplymer; and/or (c) polyethylene glycol, optionally wherein the segment comprises about 12 wt % to about 18 wt % of polyethylene glycol; and/or (c) Vitamin E or an ester thereof, optionally wherein the segment comprises about 0.2 wt % to about 0.8 wt % of Vitamin E; and/or (d) $SiO_2$; optionally wherein the segment comprises about 0.2 wt % to about 0.8 wt % of $SiO_2$; and/or (e) an optional coloring agent, optionally wherein the segment comprises about 0.3 wt % to about 0.9 wt % of the coloring agent.

Embodiment 301. The gastric residence system of any one of embodiments 295-300, wherein the gastric residence system comprises an inactive spacer comprising:

(a) polycaprolactone (PCL), optionally wherein the spacer comprises about 25 wt % to about 35 wt % of PCL; and/or (b) poly-D,L-lactide (PDL), optionally wherein the spacer comprises about 25 wt % to about 35 wt % of PDL; and/or (c) barium sulfate, optionally wherein the spacer comprises about 35 wt % to about 45 wt % of barium sulfate; and/or (d) an optional coloring agent, optionally wherein the spacer comprises about 0.05 wt % to about 0.15 wt % of the coloring agent.

Embodiment 302. The gastric residence system of any one of embodiments 295-301, wherein the gastric residence system comprises polymeric linkers comprising a time-dependent degradable polymer and/or an enteric polymer.

Embodiment 303. The gastric residence system of embodiment 302, wherein the enteric linker comprises:

(a) polycaprolactone (PCL), optionally wherein the enteric linker comprises about 25 wt % to about 35 wt % of PCL; and/or (b) hydroxypropyl methylcellulose acetate succinate (HPMCAS); optionally wherein the enteric linker comprises about 60 wt % to about 70 wt % of HPMCAS; and/or (c) polyethylene glycol-polypropylene glycol-polyethylene glycol (PEG-PPG-PEG) block copolymer, optionally wherein the enteric linker comprises about 1 wt % to about 3 wt % of PEG-PPG-PEG block coplymer; and/or (d) an optional coloring agent, optionally wherein the enteric linker comprises about 0.05 wt % to about 0.15 wt % of the coloring agent.

Embodiment 304. The gastric residence system of embodiment 302 or 303, wherein the time-dependent degradable polymer comprises:

(a) polycaprolactone (PCL), optionally wherein the time-dependent degradable polymer comprises about 40 wt % to about 60 wt % of PCL; and/or (b) polylactide (PLA); optionally wherein the PLA is PDL, further optionally wherein the time-dependent degradable polymer comprises about 40 wt % to about 60 wt % of PDL.

Embodiment 305. The gastric residence system of any one of embodiments 295-304, wherein the release rate-modulating polymer film comprises:

(a) polycaprolactone (PCL), optionally wherein the release rate-modulating polymer film comprises about 65 wt % to about 75 wt % of PCL; and/or (b) copovidone, optionally wherein the release rate-modulating polymer film comprises about 25 wt % to about 35 wt % of copovidone; and/or (c) magnesium stearate, optionally wherein the release rate-modulating polymer film comprises about 1 wt % to about 3 wt % of magnesium stearate.

Embodiment 306. The gastric residence system of any one of embodiments 295-305, wherein the PCL has a viscosity between about 1.5 dl/g to about 2.1 dl/g.

Embodiment 307. The gastric residence system of any one of embodiments 295-306, wherein the central elastomer comprises silicone rubber.

Embodiment 308. The gastric residence system of any one of embodiments 295-307, wherein the central elastomer has a durometer of about 45 A to about 55 A.

Embodiment 309. The gastric residence system of embodiment 305, wherein the release rate-modulating polymer film comprises PCL having a viscosity between about 1.5 dl/g to about 2.1 dl/g and/or PCL having a viscosity between about 0.2 dl/g to about 0.6 dl/g.

Embodiment 310. The gastric residence system of any one of embodiments 295-309, wherein the gastric residence system is configured to provide a $T_{max}$ of rosuvastatin after administration of the gastric residence system to a human of between about 3 hours and about 160 hours.

Embodiment 311. The gastric residence system of any one of embodiments 295-310, wherein release of rosuvastatin over the first 24 hours of gastric residence is no more than five times release of rosuvastatin over any 24 hour period during the subsequent 4 days of gastric residence.

Embodiment 312. A gastric residence system comprising arms comprising drug-eluting segments, where the arms are affixed to a central elastomer, wherein the drug eluting segments comprise:

a carrier polymer;

memantine or a salt thereof; and donepezil or a salt thereof;

wherein the drug eluting segments further comprise a coating comprising a release rate-modulating polymer film; and wherein the gastric residence system is configured to provide an average concentration at steady-state ($C_{ss}$) of memantine of between about 60 ng/ml and about 160 ng/ml and an average concentration at steady-state ($C_{ss}$) of donepezil of between about 30 ng/ml and about 60 ng/ml after administration of the gastric residence system to a human; and wherein the gastric residence system is configured to remain resident in the stomach for a period of between 4 days to 14 days.

Embodiment 313. The gastric residence system of any one of embodiments 260-284, wherein release of memantine over the first 24 hours of gastric residence is no more than five times release of memantine over any 24 hour period during the subsequent 4 days of gastric residence.

Embodiment 314. The gastric residence system of any one of embodiments 260-285, wherein release of donepezil over the first 24 hours of gastric residence is no more than five times release of donepezil over any 24 hour period during the subsequent 4 days of gastric residence.

Embodiment 315. The gastric residence system of any one of embodiments 260-284, wherein release of memantine over the first 24 hours of gastric residence is no more than three time release of memantine over any 24 hour period during the subsequent 4 days of gastric residence.

Embodiment 316. The gastric residence system of any one of embodiments 260-285, wherein release of donepezil over the first 24 hours of gastric residence is no more than three times release of donepezil over any 24 hour period during the subsequent 4 days of gastric residence.

The disclosures of all publications, patents, patent applications and published patent applications referred to herein by an identifying citation are hereby incorporated herein by reference in their entirety. Web sites references using "World-Wide-Web" at the beginning of the Uniform Resource Locator (URL) can be accessed by replacing "World-Wide-Web" with "www."

Although the foregoing invention has been described in some detail by way of illustration and example for purposes of clarity of understanding, it is apparent to those skilled in the art that certain changes and modifications will be practiced. Therefore, the description and examples should not be construed as limiting the scope of the invention.

What is claimed is:

1. A gastric residence system, comprising:

one or more first arms comprising a carrier polymer and an agent, the one or more first arms attached to a second arm through a polymeric linker comprising:

i) poly (lactic-co-glycolide) (PLGA) and at least one additional linker polymer;

ii) poly (lactic-co-glycolide) (PLGA) and polylactic acid (PLA);

iii) poly (lactic-co-glycolide) (PLGA) and polycaprolactone (PCL);

iv) poly (lactic-co-glycolide) (PLGA) and a thermoplastic polyurethane (TPU);

v) a thermoplastic polyurethane (TPU) and an enteric polymer;

vi) poly (lactic-co-glycolide) (PLGA) and an enteric polymer;

vii) polylactic acid (PLA) and a plasticizer;

viii) polycaprolactone (PCL) and a plasticizer;

ix) a thermoplastic polyurethane (TPU) and a plasticizer; or x) a pH-independent degradable polymer and an enteric polymer;

wherein the polymeric linker loses 20% or more of its flexural modulus or breaks after incubation in an aqueous solution at pH 1.6 for 21 days at 37° C.;

wherein the gastric residence system is retained in the stomach for a period of at least 24 hours; and wherein the one or more first arms comprising a carrier polymer-agent further comprises a release rate-modulating film coated on the arm;

wherein the release rate-modulating film comprises:

a) poly-D,L-lactide (PDL) and poly-D,L-lactide/glycolide (PDLG);

b) high molecular weight polycaprolactone (PCL-HMW) and low molecular weight polycaprolactone (PCL-LMW);

c) poly-D,L-lactide (PDL);

d) poly-D,L-lactide (PDL) and polyethylene glycol-polypropylene glycol-polyethylene glycol (PEG-PPG-PEG) block copolymer;

e) poly-D,L-lactide (PDL) and polyethylene glycol (PEG);

f) poly-D,L-lactide (PDL), polyethylene glycol-polypropylene glycol-polyethylene glycol (PEG-PPG-PEG) block copolymer, and polyethylene glycol (PEG); or g) poly-D-lactide-polycaprolactone co-polymer (PDL-PCL copolymer).

2. The gastric residence system of claim 1, comprising a core; a plurality of arms connected to the core at a proximal end through a plurality of linker components, one linker component of the plurality of the plurality of linker components corresponding to each arm of the plurality of arms, and the plurality of arms extending radially from the proximal end; and a filament circumferentially connecting each arm of the plurality of arms.

3. The gastric residence system of claim 2, wherein the filament circumferentially connects a distal end of each arm of the plurality of arms.

4. The gastric residence system of claim 1, comprising one or more arms extending radially, wherein the one or more arms comprises a first portion comprising a first polymer composition and a second portion comprising a second polymer composition, wherein the first portion has a stiffness greater than a stiffness of the second portion, as measured using a 3-point bending test per ASTM D790.

5. The gastric residence system of claim 1, wherein one or more of: the polymeric linker loses 20% or more of its flexural modulus or breaks after incubation in an aqueous solution at pH 1.6 for 14 days at 37° C.; the polymeric linker loses 20% or more of its flexural modulus or breaks after incubation in an aqueous solution at pH 1.6 for 7 days at 37° C.; or the polymeric linker loses 20% or more of its flexural modulus or breaks after incubation in an aqueous solution at pH 1.6 for 3 days at 37° C.

6. The gastric residence system of claim 1, wherein one or more of: the at least one additional linker polymer comprises polylactic acid (PLA), the carrier polymer, polycaprolactone (PCL), or a thermoplastic polyurethane (TPU); the carrier polymer comprises PCL and the at least one additional linker polymer comprises PCL; the carrier polymer comprises TPU and the at least one additional linker polymer comprises a TPU; the at least one additional linker polymer comprises PLA; the carrier polymer comprises PCL or TPU; wherein the polymeric linker comprises (a) poly (lactic-co-glycolide) (PLGA), and (b) polylactic acid (PLA), polycaprolactone (PCL), or a thermoplastic polyurethane (TPU).

7. The gastric residence system of claim 1, wherein the polymeric linker further loses 80% or more of its flexural modulus or breaks after incubation in an aqueous solution at pH 6.5 for 3 days at 37° C.

8. The gastric residence system of claim 1, wherein materials in the polymeric linker are homogenously blended.

9. The gastric residence system of claim 1, wherein the polymeric linker is substantially free of the agent.

10. The gastric residence system of claim 1, wherein the polymeric linker further comprises a color-absorbing dye comprising iron dioxide.

11. The gastric residence system of claim 1, comprising a plurality of first arms, wherein:

each first arm is attached to the second arm through a separate polymeric linker;

the second arm is an elastic central member;

the gastric residence system is configured to be folded and physically constrained during administration and is configured to assume an open retention shape upon removal of a constraint; and change between the folded shape and the open retention shape is mediated by the elastic central member that undergoes elastic deformation when the residence structure is in the folded shape and recoils when the gastric residence structure assumes the open retention shape.

12. The gastric system of claim 11, wherein the gastric residence system is constrained within a capsule configured to degrade with the stomach.

13. The gastric residence system of claim 1, wherein the release rate-modulating film is substantially free of porogen.

14. The gastric residence system of claim 1, wherein the increase in the weight of the one or more first arms comprising a carrier polymer-agent due to addition of the release rate-modulating film is about 2% to about 6% of the weight of the uncoated one or more first arms.

15. The gastric residence system of claim 1, wherein the release rate of agent from the one or more first arms comprising a carrier polymer-agent in aqueous media is substantially linear over at least a 96-hour period.

16. The gastric residence system of claim 1, wherein the release rate of agent from the one or more first arms comprising a carrier polymer-agent is substantially the same before and after thermal cycling.

17. A gastric residence system comprising an arm of claim 1.

18. The gastric residence system of claim 1, wherein the at least one agent or a pharmaceutically acceptable salt thereof comprises one or more of drug, a pro-drug, a biologic, a statin, rosuvastatin, a nonsteroidal anti-inflammatory drug (NSAID), meloxicam, a selective serotonin reuptake inhibitor (SSRs), escitalopram, citalopram, a blood thinner, clopidogrel, a steroid, prednisone, an antipsychotic, aripiprazole, risperidone, an analgesic, buprenorphine, an opioid antagonist, naloxone, an anti-asthmatic, montelukast, an anti-dementia drug, memantine, a cardiac glycoside, digoxin, an alpha blocker, tamsulosin, a cholesterol absorption inhibitor, ezetimibe, an anti-gout treatment, colchicine, an antihistamine, loratadine, cetirizine, an opioid, loperamide, a proton-pump inhibitor, omeprazole, an antiviral agent, entecavir, an antibiotic, doxycycline, ciprofloxacin, azithromycin, an anti-malarial agent, levothyroxine, a substance abuse treatment, methadone, varenicline, a contraceptive, a stimulant, caffeine, a nutrient, folic acid, calcium, iodine, iron, zinc, thiamine, niacin, vitamin C, vitamin D, biotin, a plant extract, a phytohormone, a vitamin, a mineral, a protein, a polypeptide, a polynucleotide, a hormone, an anti-inflammatory drug, an antipyretic, an antidepressant, an antiepileptic, an antipsychotic agent, a neuroprotective agent, an anti-proliferative, an anti-cancer agent, an antimigraine drug, a prostaglandin, an antimicrobial, an antifungals, an antiparasitic, an anti-muscarinic, an anxiolytic, a bacteriostatic, an immunosuppressant agent, a sedative, a hypnotic, a bronchodilator, a cardiovascular drug, an anesthetic, an anti-coagulant, an enzyme inhibitor, a corticosteroid, a dopaminergic, an electrolyte, a gastro-intestinal drug, a muscle relaxant, a parasympathomimetic, an anorectic, an anti-narcoleptics, quinine, lumefantrine, chloroquine, amodiaquine, pyrimethamine, proguanil, chlorproguanil-dapsone, a sulfonamide, sulfadoxine, sulfamethoxypyridazine, mefloquine, atovaquone, primaquine, halofantrine, doxycycline, clindamycin, artemisinin, an artemisinin derivative, artemether, dihydroartemisinin, arteether, or artesunate.

19. The gastric residence system of claim 1, wherein the second arm is a central elastomer, and wherein the one or more first arms are arms that radially project from the central elastomer.

20. A method of delivering an agent to an individual, comprising deploying the gastric residence system of claim 1, within the stomach of the individual, wherein the individual is a human.

* * * * *